US010683509B2

(12) United States Patent
Jose et al.

(10) Patent No.: US 10,683,509 B2
(45) Date of Patent: Jun. 16, 2020

(54) SURFACE DISPLAY OF FUNCTIONAL PROTEINS IN A BROAD RANGE OF GRAM NEGATIVE BACTERIA

(71) Applicant: AUTODISPLAY BIOTECH GMBH, Duesseldorf (DE)

(72) Inventors: Joachim Jose, Duesseldorf (DE); Mark George Teese, Muenster (DE); Shanna Sichwart, Muenster (DE); Iasson Tozakidis, Muenster (DE)

(73) Assignee: Autodisplay Biotech GmbH, Duesseldorf (DE)

( * ) Notice: Subject to any disclaimer, the term of this patent is extended or adjusted under 35 U.S.C. 154(b) by 200 days.

(21) Appl. No.: 14/774,973

(22) PCT Filed: Jun. 4, 2014

(86) PCT No.: PCT/EP2014/054383

§ 371 (c)(1),
(2) Date: Sep. 11, 2015

(87) PCT Pub. No.: WO2014/139862

PCT Pub. Date: Sep. 18, 2014

(65) Prior Publication Data

US 2016/0108407 A1 Apr. 21, 2016

(30) Foreign Application Priority Data

Mar. 13, 2013 (EP) .................................... 13159041

(51) Int. Cl.

| | |
|---|---|
| ***C12N 15/62*** | (2006.01) |
| ***C12N 9/42*** | (2006.01) |
| ***C12N 15/10*** | (2006.01) |
| ***C12N 15/63*** | (2006.01) |

(52) U.S. Cl.

CPC ......... *C12N 15/625* (2013.01); *C12N 9/2437* (2013.01); *C12N 9/2445* (2013.01); *C12N 15/1037* (2013.01); *C12N 15/63* (2013.01); *C07K 2319/02* (2013.01); *C07K 2319/035* (2013.01); *C07K 2319/60* (2013.01); *C12Y 302/01004* (2013.01); *C12Y 302/01021* (2013.01); *C12Y 302/01091* (2013.01)

(58) Field of Classification Search

CPC combination set(s) only.
See application file for complete search history.

(56) References Cited

U.S. PATENT DOCUMENTS

| | | | |
|---|---|---|---|
| 5,268,270 | A | 12/1993 | Meyer et al. |
| 6,040,141 | A | 3/2000 | Klauser et al. |
| 8,945,887 | B2 | 2/2015 | Jose et al. |

FOREIGN PATENT DOCUMENTS

| | | | |
|---|---|---|---|
| CN | 102791855 | A | 11/2012 |
| EP | 0 254 090 | A1 | 1/1987 |
| WO | 02070645 | A2 | 9/2002 |
| WO | 2011029881 | A2 | 3/2011 |
| WO | 2012038508 | A1 | 3/2012 |

OTHER PUBLICATIONS

Timothy J. Wells et al. Autotransporters of *Escherichia coli*: a sequence based characterization Microbiology (2010), 156, 2459-2469.*

Office Action dated Apr. 21, 2017 in the corresponding Chinese Patent Application No. 201480024033.8, 11 pages.

Valencia Salema, "Development of *Escherichia coli* cell surface display for selection of singe domain antibodies from immune libraries", University of Madrid, Jul. 11, 2011 (Abstract only).

Munoz E M: "Estudio comparativo de los dominiostransportadores de los sistemas de secrecion tipo Vde proteobacterias y su aplicacion en la presentacionde anticuerpos en la superficie de *E. coil*", Dec. 31, 2009 (Dec. 31, 2009), XP002725992, Retrieved from the Internet: URL:https://repositorio.uam.es/bitstream/handle/10486/4136/28221 marin mu%C3%Bloz el viraopt.pdf?sequence=1 [retrieved on Jun. 18, 2014] pp. 123-131; figure 43 Conclusion point 6.

Valencio Salema et al: "Selection of Single Domain Antibodies from Immune Libraries Displayed on the Surface of *E. coli* Cells with Two [beta]-Domains of Opposite Topologies", PLOS ONE, vol. 8, No. 9, Sep. 23, 2013 (Sep. 23, 2013), p. e75126, XP055123932, ISSN: 1932-6203, DOI: 10.1371/journal.pone.0075126 abstract.

Celik et al, "A Bioinformatic Strategy for the Detection, Classification and Analysis of Bacterial Autotransporters". PLoS ONE, 2012, vol. 7, issue 8, e43245.

Sichwart et al, "Maximized Autotransporter-Mediated Expression . . . ", Food Technol. Biotechnol., 2015, 53 (3) 251-260.

Tozakidis et al., "Proof of concept for the simplified breakdown of cellulose by combining Pseudomonas putida strains . . . ", Microbial Cell Factories, 2016, 15:103.

Anderson et al. "Assembly of Minicellulosomes on the surface of Bacillus subtilis", Appl Environ Microbial. 2011;77:4849-58.

Francisco et al., "Specific adhesion and hydrolysis of cellulose by intact *Escherichia coli* expressing surface anchored cellulase or cellulose binding domains", Biotechnology (NY). 1993;11:491-5.

(Continued)

*Primary Examiner* — Kagnew H Gebreyesus

(74) *Attorney, Agent, or Firm* — Rothwell, Figg, Ernst & Manbeck, P.C.

(57) ABSTRACT

The present invention relates to a method for the surface display of a recombinant polypeptide on the surface of a host cell, said method comprising the steps: (a) providing a host cell transformed with a nucleic acid fusion operatively linked with an expression control sequence, said nucleic acid fusion comprising: (i) a portion encoding a signal peptide, (ii) a portion encoding the recombinant polypeptide to be displayed, (iii) a portion encoding a transmembrane linker, and (iv) a portion encoding the trans porter domain of an EhaA protein, and (b) culturing the host cell under conditions wherein the nucleic acid fusion is expressed and the expression product comprising the recombinant polypeptide is displayed on the surface of the host cell.

31 Claims, 30 Drawing Sheets

Figure 1:
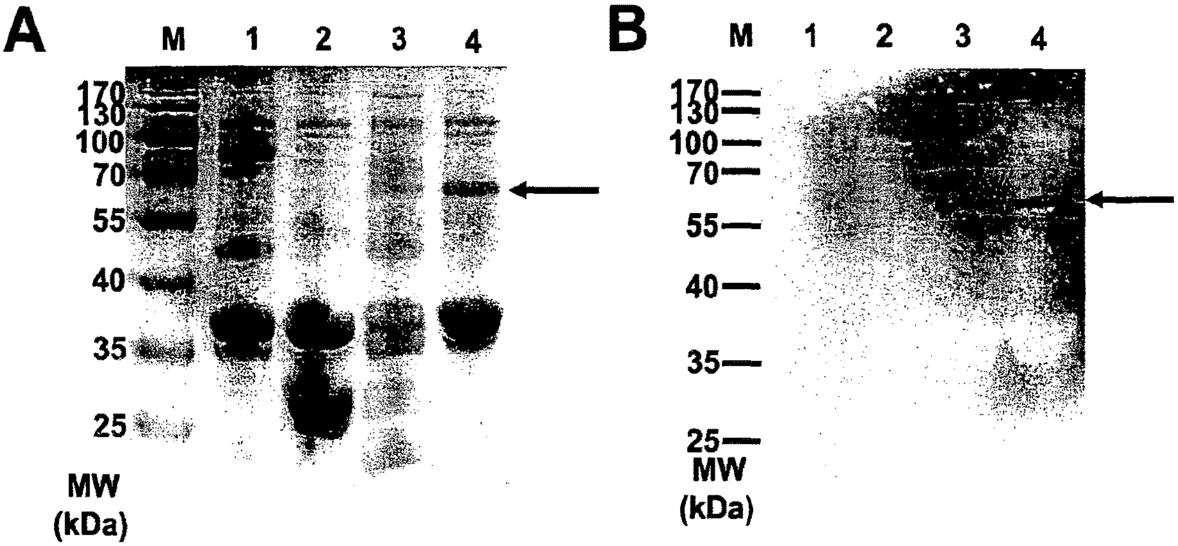

Specification includes a Sequence Listing.

(56) References Cited

OTHER PUBLICATIONS

Jung et al., “Expression of carboxymethylcellulase on the surface of *Escherichia coli* using Pseudomonas syringae ice nucleation protein”, Enzyme and Microb Technol, 1998;22:348-54.
Ko et al., “Bacterial cell surface display of a multifunctional cellulolytic enzyme screened from a bovine rumen metagenomic resource”, J Microbiol Biotechnol. 2015;25(11):1835-41.
Munoz-Gutierrez et al., “Cell surface display of a beta-glucosidase employing the type V secretion system on ethanologenic *Escherichia coli* for the fermentation of cellobiose to ethanol”, J Ind Microbiol Biotechnol., 2012;39:1141-52.
Ryu et al., A whole cell biocatalyst for cellulosic ethanol production from dilute acid-pretreated corn stover hydrolyzates, Appl Microbiol Biotechnol. 2011;91:529-42.
Tanaka et al., “Creation of a cellooligosaccharide-assimilating *Escherichia coli* strain by displaying active betaglucosidase on the cell surface via a novel anchor protein”, Appl Environ Microbiol. 2011;77:6265-70.
You C, et al. Enhanced Microbial Utilization of Recalcitrant Cellulose by an Ex Vivo Cellulosome-Microbe Complex, Applied and Environmental Microbilogy, 2011, pp. 1437-1444.
Barnard et al., “Molecular Basis for the Activation of a Catalytic Asparagine Residue in a Self-Cleaving Bacterial Autotransporter”, J. Mol_Biol., (2012) 415, 128-142.
Benz et al., “Structures and Functions of autotransporter proteins in microbial pathogens”, International Journal of Medical Microbiology, 301 (2011) 461-468.
Gentz et al., “Promoters Recognized by Escherichia coli Rna Polymerase Selected by Function: Highly Efficient Promoters from Bacteriophage T5”, Journal of Bacteriology, Oct. 1985, vol. 164, no. 1, pp. 70-77.
Ghose, “Measurement of Cellulase Activities”, Pure & Appl. Chem., vol. 59, No. 2, 1987, pp. 257-268.
Grodberg et al., “ompT Encodes the Escherichia coli Outer Membrane Protease That CleavesT7 Rna Polymerase luring Purification”, Journal of Bacteriology, Mar_ 1988, vol. 170, No. 3, pp. 1245-1253.
Gustavsson et al., “Optimisation of surface expression using the Aida autotransporter”, Micobial Cell Factories, 2011, 10:72, 10 pgs.
I-Iantke, “Regulation of Ferric Iron Transport in Escherichia coli K12: Isolation of a Constitutive Mutant”, Mol Gen Genet (1981) 182: 288-292.
Jahns et al., “Relevant uses of surface proteins-display on self-organized biological structures”, Microbial Biotechnology (2012) 5(2), 188-202.
Jarmander et al., “A dual tag system for facilitated detection of surface expressed proteins in Escherichia coli”, Microbial Cell Factories, 2012, 11:118, 10 pgs.
Jesty et al, “The Activation of Bovine Coagulation Factor X1”, Methods in Enzymology, vol. 45, 1976, pgs. 95-107.
Jong et al., “A Structurally informed autotransporter platform for efficient heterologous protein secretion and display”, Microbial Cell Factories, 2012, 11: 85, 11 pgs.
Jong et al., “YidC is Involved in the Biogenesis of the Secreted Autotransporter Hemoglobin Protease”, the Journal Df Biological Chemisry, vol. 285, No_ 51, Dec. 2010, pp. 39682-39690.
Jose et al., “The Autodisplay Story, from Discovery to Biotechnical and Biomedical Applications”, Microbiology and Molecular Biology Reviews, Dec. 2007, vol. 71, No. 4, pp. 600-619.
Jose et al., “Autodisplay of Active Sorbitol Dehydrogenase (SDH) Yields a Whole Cell Biocatalyst for the Synthesis of Rare Surgars”, ChemBioChem, 2004, 5, pgs. 491-499.
Jose et al., “Cellular surface display of dimeric Adx and whole cell P450-mediated steroid synthesis on E coli”, Journal of Biotechnology, 95 (2002), pp. 257-268.
King et al., “An Optimized Microplate Assay System for Quantitative Evaluation of Plant Cell Wall-Degrading Enzyme Activity of Fungal Culture Extracts”, Biotechology and Bioengineering, vol. 102, No. 4, Mar. 2009, pp. 1033-1044.
Klauser et al., Extracellular transport of cholera toxin B subunit using Neisseria IgA protease β-domain: ,mnformation-dependent outer membrane translocation, the EMBO Journal, vol. 9, No. 6, 1990, pp. 1991-1999.
Klauser et al., “Selective extracellular release of cholera toxin B subunit by Escherichia coli: dissection of Neisseria Igaβ-mediated outer membrane transport”, the Embo Journal, vol. 11, no. 6, 1992, pp_ 2327-2335_.
Ko et al., “Functional Cell Surface Display and Controlled Secretion of Diverse Agarolytic Enzymes by Escherichia coli with a Novel Ligation-Independent Cloning Vector Based on the Autotransporter YfaL, ”Applied and Environmental Microbiology, vol. 78, No. 9, May 2012, p. 3051-3058.
Kojima et al., “Expression and surface display of Cellulomonas endoglucanas in the ethanologenice bacterium lymobacter palmae”, Appl Microbiol Biotechnol (2012) 96: pp. 1093-1104.
Kovach et al., “Four new derivatives of the broad-host-range cloning vector pBBR1MCS, carrying different antibiotic-resistance cassettes”, Gene, 166 (1995), 175-176.
Laemmli et al., “Cleavage of Structrural Proteins during the Assembly of the Head of Bacteriophage T4”, Nature, vol. 227, Aug. 1970, 680-685.
Leyton et al., “From self sufficiency to dependence: mechanisms and factors important for autotransporter biogenesis”, Nature Reviews|Microbiology, vol. 10, Mar. 2012, pp. 213-225.
Luckett et al., “A Novel Virulence Strategy for Pseudomonas aeruginosa Mediated by an Autotransporter with Arginine-Specific Aminopeptidase Activity”, PLOS Pathogens, Aug. 2012, vol. 8, Issue 8, 21 pgs.
Lum et al., “IcsA autotransporter passenger promotes increased fusion protein expression on the cell surface”, Microbial Cell Factories, 2012, 11:20, 10 pgs.
Mangel et al., “Omptin: An Escherichia coli Outer Membrane Proteinase That Activates Plasminogen”, Methods in Enzymology, vol. 244, 27, 1994, pp. 384-399.
Maurer et al., “Autodisplay: One-Component System for Efficient Surface Display and Release of Soluble Recombinant Proteins from Escherichia coli”, Journal of Bacteriology, Feb. 1997, vol. 179, No. 3, pp. 794-804.
Nicolay et al., “Characterization of Esterase a, a Pseudomonas stutzeri A15 Autotransporter”, Applied and Environmental Microbiology, 2012, vol. 78, No. 8, pp. 2533-2542.
Nicolay et al., “Probing the applicability of autotransporter based surface display with the EstA autotransporter of seudomonas stutzeri A15” , Microbial Cell Factories 11:158, 2012; 11 pgs.
Ramesh et al., “Single-cell Characterization of Autotransporter-mediated Escherichia coli Surface Display of Disulfide Bond-containing Proteins”, The Journal of Biological Chemistry, vol. 287, No. 46, Nov. 9, 2012, pp. 38580-38589.
Roberts, “The power of evolution: accessing the synthetic potential of 450s”, Chemistry & Biology, Oct. 1999, 6, pp. R269-R272.
Sarhan et al., “Cloning, protein expression and display of synthetic multi-epitope mycobacterial antigens on Salmonella typhi Ty21 a cell surface”, Indian Journal of Experimental Biology, vol. 49, Sep. 2011, pp. 645-653.
Schultheiss et al., “Functional esterase surface display by the autotransporter pathway in Escherichia coli”, Journal of Molecular Catalysis B: Enzymatic 18 (2002), pp. 89-97.
Sevastsyanovich et al., “A generalised module for the selective extracellular accumulation of recombinant proteins”, Microbial Cell Factories, 2012, 11: 69, 11 pgs.
Spohn et al., “B-cell epitopes of the Nef protein”, Research in Virology, vol. 143, 1992 pp. 70-81.
Van Gerven et al., “Surface display of the receptor-binding domain of the F17a-G fimbrial adhesin through the autotransporter AIDA-I leads to permeability of bacterial cells”, Microbiology (2009), 155, pp. 468-476.
Weiss et al., “Prevalence, Biogenesis, and Functionality of the Serine Protease Autotransporter EspP”, Toxins, 2013, 5, pp. 25-48.
Welch et al., “Design Parameters to Control Synthetic Gene Expression in Escherichia coli”, PloS One, Sep. 2009, vol. 4, issue 9, 10 pgs.

(56) References Cited

OTHER PUBLICATIONS

Wells et al., "Autotransporters of Escherichia Coli: a sequence-based characterization", Microbiology (2010), 156, pp. 2459-2469.
Wells et al., "EhaA is a novel autotransporter protein of enterohemorrhagic Escherichia coli O157:H7 that contributes to adhesion and biofilm formation", Environmental Microbiology, (2008), 10(3), pp. 589-604.
Xiao et al., "Microplate-Based Filter Paper Assay to Measure Total Cellulase Activity", Wiley Periodicals, Inc., Ehotechnol. Bioeng., 2004, pp. 832-837.
Xin et al, "Exploring the Versatility of the Autotmasporter BrkA for the Presentation of Enterovirus 71 Vaccine candidates at the Surface of Attenuated Bordetella pertussis", Procedia in Vaccinology, 2 (2010) pp. 66-72.
Written Opinion of the International Preliminary Examination Authority cited in PCT/EP2014/054383 dated Mar. 25, 2015, 7 pages.
Notification of Transmittal of the International Preliminary Report on Patentability cited in PCT/EP2014/054383 dated Jul. 2, 2015, 26 pgs.
Notification of Transmittal of the International Search Report and the Written Opinion of the International Searching Authority, or the Declaration cited in PCT/EP2014/054383 dated Aug. 4, 2014, 13 pgs.

* cited by examiner (B)

Figure 11
(A)
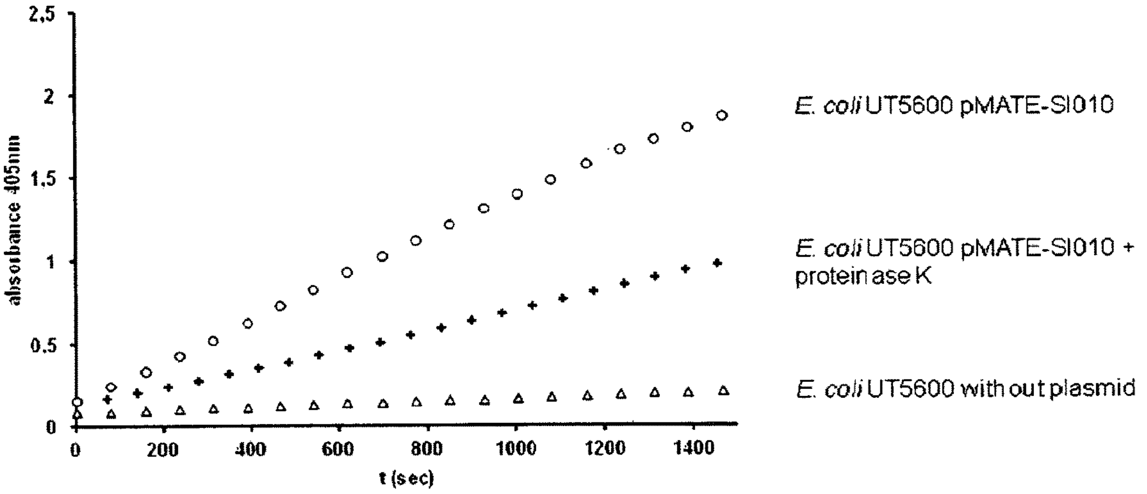
(B)
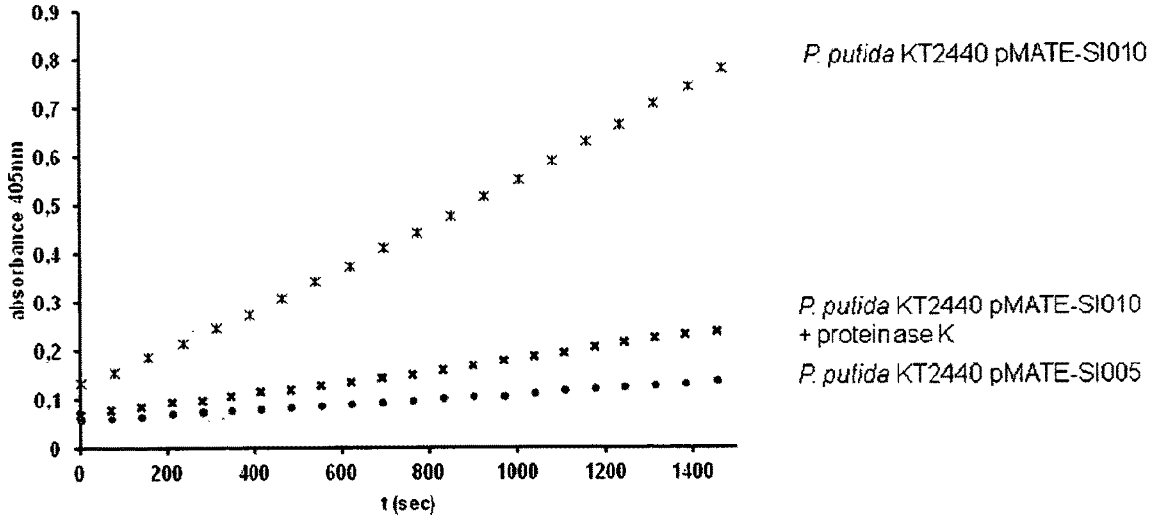

Figure 12
(A)
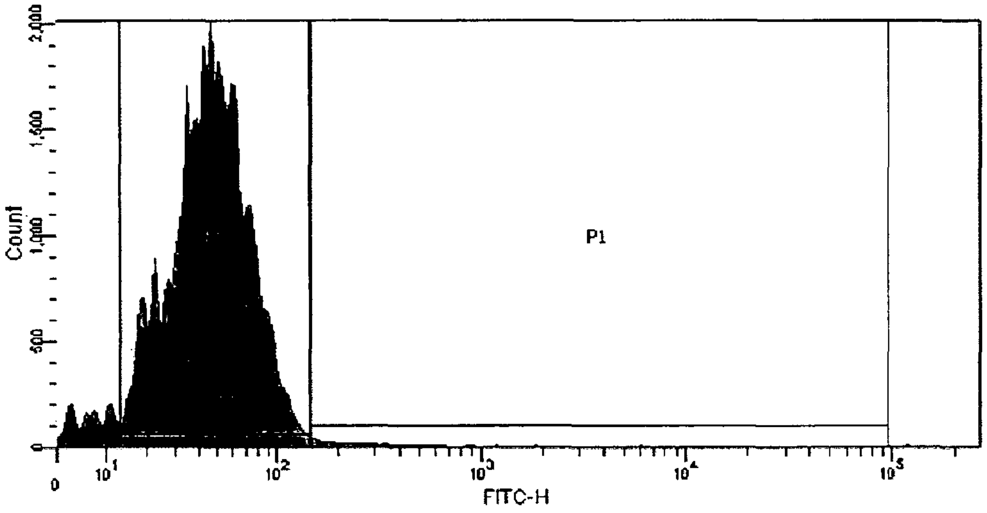
(B)
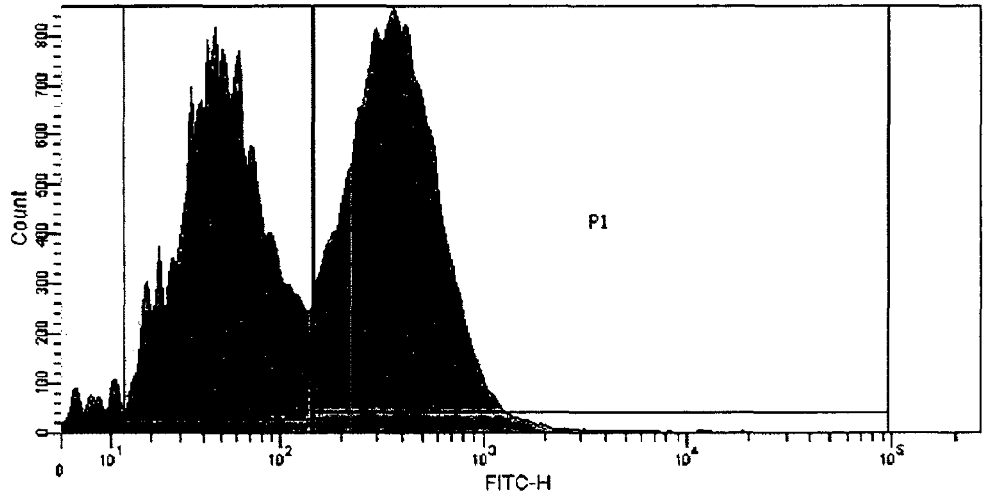

SDS-PAGE with Coomassie stain

SDS-PAGE with esterase activity stain

Figure 14A, B

(A)

SEQUENCE LISTING

```
<160> NUMBER OF SEQ ID NOS: 36

<210> SEQ ID NO 1
<211> LENGTH: 1467
<212> TYPE: DNA
<213> ORGANISM: Artificial Sequence
<220> FEATURE:
<223> OTHER INFORMATION: sequence encoding EhaA transmembrane linker and
      transporter domain,codon-optimized sequence derived from EhaA
      sequence of E. coli

<400> SEQUENCE: 1

ctgaccaaca atggcacgct gatgacgggt atgagcggtc aacaagcggg taacgttctg      60

gttgttaagg gcaattacca tggcaataac ggccagctgg tcatgaacac ggttctgaac     120

ggcgatgata gcgtgaccga caagctggtg gtcgagggcg acacctctgg tacgaccgca     180

gtgacggtga ataatgcagg cggtacgggt gccaaaaccc tgaacggtat tgagttgatc     240

cacgttgacg gtaagagcga gggcgagttt gtgcaggcag gccgcattgt tgctggcgct     300

tatgactata cgctggcccg tggtcagggc gcgaatagcg gtaactggta tctgaccagc     360

ggctccgact ccccggaact gcaaccggag cctgatccga tgccgaatcc ggagccaaac     420

ccgaacccgg aaccgaaccc aaatccgacc ccgactccgg gtccggactt gaacgttgat     480

aacgacctgc gtccggaggc cggttcgtac atcgcgaacc tggcagcggc caatacgatg     540

tttacgaccc gtctgcacga acgcctgggt aatacctact ataccgatat ggtcactggt     600

gaacagaaac aaaccaccat gtggatgcgc cacgagggtg gtcacaataa gtggcgcgac     660

ggtagcggcc agttgaaaac ccagagcaat cgctacgttc tgcaattggg cggtgatgtg     720
```

```
gcgcaatgga gccaaaacgg cagcgaccgt tggcatgtcg gtgtgatggc aggttacggc    780

aacagcgaca gcaagaccat ctccagccgt accggttacc gtgcgaaggc aagcgtcaac    840

ggttacagca ccggcctgta tgccacctgg tatgctgatg atgagagccg caacggtgct    900

tacttggaca gctgggcaca gtattcttgg ttcgataata cggtgaaagg cgacgacctg    960

cagagcgaaa gctacaaatc gaaaggtttc accgcgagcc tggaagccgg ctataagcac   1020

aaactggcgg aattcaatgg cagccagggt actcgtaacg aatggtacgt tcaaccgcag   1080

gcgcaagtca cttggatggg cgttaaggcg gataaacacc gtgagagcaa cggtacgttg   1140

gtgcatagca acggtgatgg taatgtccaa acccgtctgg gtgtgaaaac gtggctgaag   1200

tcccatcaca aaatggacga cggtaaatct cgtgaatttc agccgttcgt ggaagttaac   1260

tggctgcata atagcaagga tttcagcacg agcatggatg gtgtctccgt tacccaggac   1320

ggcgcacgta acattgcgga gatcaagacc ggcgtcgagg gtcagctgaa tgcgaatctg   1380

aatgtttggg gtaacgtggg tgttcaagta gcggaccgtg gttacaatga taccagcgcg   1440

atggtgggta ttaagtggca gttttaa                                       1467
```

<210> SEQ ID NO 2
<211> LENGTH: 488
<212> TYPE: PRT
<213> ORGANISM: Artificial Sequence
<220> FEATURE:
<223> OTHER INFORMATION: sequence of EhaA transmembrane linker and transporter domain derived from E. coli EhaA sequence

<400> SEQUENCE: 2

```
Leu Thr Asn Asn Gly Thr Leu Met Thr Gly Met Ser Gly Gln Gln Ala
1               5                   10                  15

Gly Asn Val Leu Val Val Lys Gly Asn Tyr His Gly Asn Asn Gly Gln
            20                  25                  30

Leu Val Met Asn Thr Val Leu Asn Gly Asp Asp Ser Val Thr Asp Lys
        35                  40                  45

Leu Val Val Glu Gly Asp Thr Ser Gly Thr Thr Ala Val Thr Val Asn
    50                  55                  60

Asn Ala Gly Gly Thr Gly Ala Lys Thr Leu Asn Gly Ile Glu Leu Ile
65                  70                  75                  80

His Val Asp Gly Lys Ser Glu Gly Glu Phe Val Gln Ala Gly Arg Ile
                85                  90                  95

Val Ala Gly Ala Tyr Asp Tyr Thr Leu Ala Arg Gly Gln Gly Ala Asn
            100                 105                 110

Ser Gly Asn Trp Tyr Leu Thr Ser Gly Ser Asp Ser Pro Glu Leu Gln
        115                 120                 125

Pro Glu Pro Asp Pro Met Pro Asn Pro Glu Pro Asn Pro Asn Pro Glu
    130                 135                 140

Pro Asn Pro Asn Pro Thr Pro Thr Pro Gly Pro Asp Leu Asn Val Asp
145                 150                 155                 160

Asn Asp Leu Arg Pro Glu Ala Gly Ser Tyr Ile Ala Asn Leu Ala Ala
                165                 170                 175

Ala Asn Thr Met Phe Thr Thr Arg Leu His Glu Arg Leu Gly Asn Thr
            180                 185                 190

Tyr Tyr Thr Asp Met Val Thr Gly Glu Gln Lys Gln Thr Thr Met Trp
        195                 200                 205

Met Arg His Glu Gly Gly His Asn Lys Trp Arg Asp Gly Ser Gly Gln
    210                 215                 220
```

-continued

```
Leu Lys Thr Gln Ser Asn Arg Tyr Val Leu Gln Leu Gly Gly Asp Val
225                 230                 235                 240

Ala Gln Trp Ser Gln Asn Gly Ser Asp Arg Trp His Val Gly Val Met
                245                 250                 255

Ala Gly Tyr Gly Asn Ser Asp Ser Lys Thr Ile Ser Ser Arg Thr Gly
            260                 265                 270

Tyr Arg Ala Lys Ala Ser Val Asn Gly Tyr Ser Thr Gly Leu Tyr Ala
        275                 280                 285

Thr Trp Tyr Ala Asp Asp Glu Ser Arg Asn Gly Ala Tyr Leu Asp Ser
    290                 295                 300

Trp Ala Gln Tyr Ser Trp Phe Asp Asn Thr Val Lys Gly Asp Asp Leu
305                 310                 315                 320

Gln Ser Glu Ser Tyr Lys Ser Lys Gly Phe Thr Ala Ser Leu Glu Ala
                325                 330                 335

Gly Tyr Lys His Lys Leu Ala Glu Phe Asn Gly Ser Gln Gly Thr Arg
            340                 345                 350

Asn Glu Trp Tyr Val Gln Pro Gln Ala Gln Val Thr Trp Met Gly Val
        355                 360                 365

Lys Ala Asp Lys His Arg Glu Ser Asn Gly Thr Leu Val His Ser Asn
    370                 375                 380

Gly Asp Gly Asn Val Gln Thr Arg Leu Gly Val Lys Thr Trp Leu Lys
385                 390                 395                 400

Ser His His Lys Met Asp Asp Gly Lys Ser Arg Glu Phe Gln Pro Phe
                405                 410                 415

Val Glu Val Asn Trp Leu His Asn Ser Lys Asp Phe Ser Thr Ser Met
            420                 425                 430

Asp Gly Val Ser Val Thr Gln Asp Gly Ala Arg Asn Ile Ala Glu Ile
        435                 440                 445

Lys Thr Gly Val Glu Gly Gln Leu Asn Ala Asn Leu Asn Val Trp Gly
    450                 455                 460

Asn Val Gly Val Gln Val Ala Asp Arg Gly Tyr Asn Asp Thr Ser Ala
465                 470                 475                 480

Met Val Gly Ile Lys Trp Gln Phe
                485
```

<210> SEQ ID NO 3
<211> LENGTH: 5262
<212> TYPE: DNA
<213> ORGANISM: Artificial Sequence
<220> FEATURE:
<223> OTHER INFORMATION: pMATE-MT004, for the surface display of 6xHis
      using the pMATE system

<400> SEQUENCE: 3

```
ctcatgacca aaatccctta acgtgagtta cgcgcgcgtc gttccactga gcgtcagacc     60

ccgtagaaaa gatcaaagga tcttcttgag atcctttttt tctgcgcgta atctgctgct    120

tgcaaacaaa aaaaccaccg ctaccagcgg tggtttgttt gccggatcaa gagctaccaa    180

ctctttttcc gaaggtaact ggcttcagca gagcgcagat accaaatact gttcttctag    240

tgtagccgta gttagcccac cacttcaaga actctgtagc accgcctaca tacctcgctc    300

tgctaatcct gttaccagtg gctgctgcca gtggcgataa gtcgtgtctt accgggttgg    360

actcaagacg atagttaccg gataaggcgc agcggtcggg ctgaacgggg ggttcgtgca    420

cacagcccag cttggagcga acgacctaca ccgaactgag atacctacag cgtgagctat    480

gagaaagcgc cacgcttccc gaagggagaa aggcggacag gtatccggta agcggcaggg    540
```

-continued

```
tcggaacagg agagcgcacg agggagcttc caggggggaaa cgcctggtat ctttatagtc    600
ctgtcgggtt tcgccacctc tgacttgagc gtcgattttt gtgatgctcg tcaggggggc    660
ggagcctatg gaaaaacgcc agcaacgcgg cctttttacg gttcctggcc ttttgctggc    720
cttttgctca catgttcttt cctgcgttat cccctgattc tgtggataac cgtattaccg    780
cctttgagtg agctgatacc gctcgccgca gccgaacgac cgagcgcagc gagtcagtga    840
gcgaggaagc ggaaggcgag agtagggaac tgccaggcat caaactaagc agaaggcccc    900
tgacggatgg cctttttgcg tttctacaaa ctctttctgt gttgtaaaac gacggccagt    960
cttaagctcg ggccccctgg gcggttctga taacgagtaa tcgttaatcc gcaaataacg   1020
taaaaacccg cttcggcggg tttttttatg gggggagttt agggaaagag catttgtcag   1080
aatatttaag ggcgcctgtc actttgcttg atatatgaga attatttaac cttataaatg   1140
agaaaaaagc aacgcacttt aaataagata cgttgctttt tcgattgatg aacacctata   1200
attaaactat tcatctatta tttatgattt tttgtatata caatatttct agtttgttaa   1260
agagaattaa gaaaataaat ctcgaaaata ataaagggaa aatcagtttt tgatatcaaa   1320
attatacatg tcaacgataa tacaaaatat aatacaaact ataagatgtt atcagtattt   1380
attatgcatt tagaataaat tttgtgtcgc ccttaattgt gagcggataa caattacgag   1440
cttcatgcac agtgaaatca tgaaaaattt atttgctttg tgagcggata acaattataa   1500
tatgtggaat tgtgagcgct cacaattcca caacggtttc cctctagaaa taattttgtt   1560
taacttttag gagttaaaac atatgatcaa actgaaattc ggcgtcttct tcaccgtact   1620
gctgtcctct gcttacgctc acggtactcc gcagaacatc acccaccacc atcaccatca   1680
tatcgaaggt cgtctcgagc atatgagatc tggtaccgct cgtcgtgcta ttgagggccg   1740
catcccggaa tactttaaac tgaccaacaa tggcacgctg atgacgggta tgagcggtca   1800
acaagcgggt aacgttctgg ttgttaaggg caattaccat ggcaataacg gccagctggt   1860
catgaacacg gttctgaacg gcgatgatag cgtgaccgac aagctggtgg tcgagggcga   1920
cacctctggt acgaccgcag tgacggtgaa taatgcaggc ggtacgggtg ccaaaaccct   1980
gaacggtatt gagttgatcc acgttgacgg taagagcgag ggcgagtttg tgcaggcagg   2040
ccgcattgtt gctggcgctt atgactatac gctggcccgt ggtcagggcg cgaatagcgg   2100
taactggtat ctgaccagcg gctccgactc cccggaactg caaccggagc ctgatccgat   2160
gccgaatccg gagccaaacc cgaacccgga accgaaccca aatccgaccc cgactccggg   2220
tccggacttg aacgttgata acgacctgcg tccggaggcc ggttcgtaca tcgcgaacct   2280
ggcagcggcc aatacgatgt ttacgacccg tctgcacgaa cgcctgggta atacctacta   2340
taccgatatg gtcactggtg aacagaaaca aaccaccatg tggatgcgcc acgagggtgg   2400
tcacaataag tggcgcgacg gtagcggcca gttgaaaacc cagagcaatc gctacgttct   2460
gcaattgggc ggtgatgtgg cgcaatggag ccaaaacggc agcgaccgtt ggcatgtcgg   2520
tgtgatggca ggttacggca acagcgacag caagaccatc tccagccgta ccggttaccg   2580
tgcgaaggca agcgtcaacg gttacagcac cggcctgtat gccacctggt atgctgatga   2640
tgagagccgc aacggtgctt acttggacag ctgggcacag tattcttggt tcgataatac   2700
ggtgaaaggc gacgacctgc agagcgaaag ctacaaatcg aaaggtttca ccgcgagcct   2760
ggaagccggc tataagcaca aactggcgga attcaatggc agccagggta ctcgtaacga   2820
atggtacgtt caaccgcagg cgcaagtcac ttggatgggc gttaaggcgg ataaacaccg   2880
```

```
tgagagcaac ggtacgttgg tgcatagcaa cggtgatggt aatgtccaaa cccgtctggg   2940
tgtgaaaacg tggctgaagt cccatcacaa aatggacgac ggtaaatctc gtgaatttca   3000
gccgttcgtg gaagttaact ggctgcataa tagcaaggat ttcagcacga gcatggatgg   3060
tgtctccgtt acccaggacg gcgcacgtaa cattgcggag atcaagaccg gcgtcgaggg   3120
tcagctgaat gcgaatctga atgtttgggg taacgtgggt gttcaagtag cggaccgtgg   3180
ttacaatgat accagcgcga tggtgggtat taagtggcag ttttaactcg agccccaagg   3240
gcgacacccc ctaattagcc cgggcgaaag gcccagtctt tcgactgagc ctttcgtttt   3300
atttgatgcc tggcagttcc ctactctcgc atggggagtc cccacactac catcggcgct   3360
acggcgtttc acttctgagt tcggcatggg gtcaggtggg accaccgcgc tactgccgcc   3420
aggcaaacaa ggggtgttat gagccatatt caggtataaa tgggctcgcg ataatgttca   3480
gaattggtta attggttgta acactgaccc ctatttgttt atttttctaa atacattcaa   3540
atatgtatcc gctcatgaga caataaccct gataaatgct tcaataatat tgaaaaagga   3600
agaatatgag ccatattcaa cgggaaacgt cgaggccgcg attaaattcc aacatggatg   3660
ctgatttata tgggtataaa tgggctcgcg ataatgtcgg gcaatcaggt gcgacaatct   3720
atcgcttgta tgggaagccc gatgcgccag agttgtttct gaaacatggc aaaggtagcg   3780
ttgccaatga tgttacagat gagatggtca gactaaactg gctgacggaa tttatgccac   3840
ttccgaccat caagcatttt atccgtactc ctgatgatgc atggttactc accactgcga   3900
tccccggaaa aacagcgttc caggtattag aagaatatcc tgattcaggt gaaaatattg   3960
ttgatgcgct ggcagtgttc ctgcgccggt tgcactcgat tcctgtttgt aattgtcctt   4020
ttaacagcga tcgcgtattt cgcctcgctc aggcgcaatc acgaatgaat aacggtttgg   4080
ttgatgcgag tgattttgat gacgagcgta atggctggcc tgttgaacaa gtctggaaag   4140
aaatgcataa acttttgcca ttctcaccgg attcagtcgt cactcatggt gatttctcac   4200
ttgataacct tatttttgac gaggggaaat taataggttg tattgatgtt ggacgagtcg   4260
gaatcgcaga ccgataccag gatcttgcca tcctatggaa ctgcctcggt gagttttctc   4320
cttcattaca gaaacggctt tttcaaaaat atggtattga taatcctgat atgaataaat   4380
tgcagtttca tttgatgctc gatgagtttt tctaagcggc gcgccatcga atctcgcgcc   4440
gatcaactgg gtgccagcgt ggtggtgtcg atggtagaac gaagcggcgt cgaagcctgt   4500
aaagcggcgg tgcacaatct tctcgcgcaa cgcgtcagtg ggctgatcat taactatccg   4560
ctggatgacc aggatgccat tgctgtggaa gctgcctgca ctaatgttcc ggcgttattt   4620
cttgatgtct ctgaccagac acccatcaac agtattattt tctcccatga ggacggtacg   4680
cgactgggcg tggagcatct ggtcgcattg ggtcaccagc aaatcgcgct gttagcgggc   4740
ccattaagtt ctgtctcggc gcgtctgcgt ctggctggct ggcataaata tctcactcgc   4800
aatcaaattc agccgatagc ggaacgggaa ggcgactgga gtgccatgtc cggttttcaa   4860
caaaccatgc aaatgctgaa tgagggcatc gttcccactg cgatgctggt tgccaacgat   4920
cagatggcgc tgggcgcaat gcgcgccatt accgagtccg ggctgcgcgt tggtgcggat   4980
atctcggtag tgggatacga cgataccgaa gatagctcat gttatatccc gccgttaacc   5040
accatcaaac aggattttcg cctgctgggg caaaccagcg tggaccgctt gctgcaactc   5100
tctcagggcc aggcggtgaa gggcaatcag ctgttgccag tctcactggt gaaaagaaaa   5160
accaccctgg cgcccaatac gcaaaccgcc tctccccgcg cgttggccga ttcattaatg   5220
cagctggcac gacaggtttc ccgactggaa agcgggcagt ga                      5262
```

-continued

<210> SEQ ID NO 4
<211> LENGTH: 547
<212> TYPE: PRT
<213> ORGANISM: Artificial Sequence
<220> FEATURE:
<223> OTHER INFORMATION: pMATE-MT004, for the surface display of 6xHis
using the pMATE system

<400> SEQUENCE: 4

```
Met Ile Lys Leu Lys Phe Gly Val Phe Phe Thr Val Leu Leu Ser Ser
1               5                   10                  15

Ala Tyr Ala His Gly Thr Pro Gln Asn Ile Thr His His His His His
            20                  25                  30

His Ile Glu Gly Arg Leu Glu His Met Arg Ser Gly Thr Ala Arg Arg
        35                  40                  45

Ala Ile Glu Gly Arg Ile Pro Glu Tyr Phe Lys Leu Thr Asn Asn Gly
    50                  55                  60

Thr Leu Met Thr Gly Met Ser Gly Gln Gln Ala Gly Asn Val Leu Val
65                  70                  75                  80

Val Lys Gly Asn Tyr His Gly Asn Asn Gly Gln Leu Val Met Asn Thr
                85                  90                  95

Val Leu Asn Gly Asp Asp Ser Val Thr Asp Lys Leu Val Val Glu Gly
            100                 105                 110

Asp Thr Ser Gly Thr Thr Ala Val Thr Val Asn Asn Ala Gly Gly Thr
        115                 120                 125

Gly Ala Lys Thr Leu Asn Gly Ile Glu Leu Ile His Val Asp Gly Lys
    130                 135                 140

Ser Glu Gly Glu Phe Val Gln Ala Gly Arg Ile Val Ala Gly Ala Tyr
145                 150                 155                 160

Asp Tyr Thr Leu Ala Arg Gly Gln Gly Ala Asn Ser Gly Asn Trp Tyr
                165                 170                 175

Leu Thr Ser Gly Ser Asp Ser Pro Glu Leu Gln Pro Glu Pro Asp Pro
            180                 185                 190

Met Pro Asn Pro Glu Pro Asn Pro Asn Pro Glu Pro Asn Pro Asn Pro
        195                 200                 205

Thr Pro Thr Pro Gly Pro Asp Leu Asn Val Asp Asn Asp Leu Arg Pro
    210                 215                 220

Glu Ala Gly Ser Tyr Ile Ala Asn Leu Ala Ala Ala Asn Thr Met Phe
225                 230                 235                 240

Thr Thr Arg Leu His Glu Arg Leu Gly Asn Thr Tyr Tyr Thr Asp Met
                245                 250                 255

Val Thr Gly Glu Gln Lys Gln Thr Thr Met Trp Met Arg His Glu Gly
            260                 265                 270

Gly His Asn Lys Trp Arg Asp Gly Ser Gly Gln Leu Lys Thr Gln Ser
        275                 280                 285

Asn Arg Tyr Val Leu Gln Leu Gly Gly Asp Val Ala Gln Trp Ser Gln
    290                 295                 300

Asn Gly Ser Asp Arg Trp His Val Gly Val Met Ala Gly Tyr Gly Asn
305                 310                 315                 320

Ser Asp Ser Lys Thr Ile Ser Ser Arg Thr Gly Tyr Arg Ala Lys Ala
                325                 330                 335

Ser Val Asn Gly Tyr Ser Thr Gly Leu Tyr Ala Thr Trp Tyr Ala Asp
            340                 345                 350

Asp Glu Ser Arg Asn Gly Ala Tyr Leu Asp Ser Trp Ala Gln Tyr Ser
```

```
        355                 360                 365

Trp Phe Asp Asn Thr Val Lys Gly Asp Asp Leu Gln Ser Glu Ser Tyr
    370                 375                 380

Lys Ser Lys Gly Phe Thr Ala Ser Leu Glu Ala Gly Tyr Lys His Lys
385                 390                 395                 400

Leu Ala Glu Phe Asn Gly Ser Gln Gly Thr Arg Asn Glu Trp Tyr Val
                405                 410                 415

Gln Pro Gln Ala Gln Val Thr Trp Met Gly Val Lys Ala Asp Lys His
            420                 425                 430

Arg Glu Ser Asn Gly Thr Leu Val His Ser Asn Gly Asp Gly Asn Val
        435                 440                 445

Gln Thr Arg Leu Gly Val Lys Thr Trp Leu Lys Ser His His Lys Met
    450                 455                 460

Asp Asp Gly Lys Ser Arg Glu Phe Gln Pro Phe Val Glu Val Asn Trp
465                 470                 475                 480

Leu His Asn Ser Lys Asp Phe Ser Thr Ser Met Asp Gly Val Ser Val
                485                 490                 495

Thr Gln Asp Gly Ala Arg Asn Ile Ala Glu Ile Lys Thr Gly Val Glu
            500                 505                 510

Gly Gln Leu Asn Ala Asn Leu Asn Val Trp Gly Asn Val Gly Val Gln
        515                 520                 525

Val Ala Asp Arg Gly Tyr Asn Asp Thr Ser Ala Met Val Gly Ile Lys
    530                 535                 540

Trp Gln Phe
545


<210> SEQ ID NO 5
<211> LENGTH: 6273
<212> TYPE: DNA
<213> ORGANISM: Artificial Sequence
<220> FEATURE:
<223> OTHER INFORMATION: pMATE-MT006, for the surface display of GFP
      using the pMATE system

<400> SEQUENCE: 5

ctcatgacca aaatccctta acgtgagtta cgcgcgcgtc gttccactga gcgtcagacc      60

ccgtagaaaa gatcaaagga tcttcttgag atcctttttt tctgcgcgta atctgctgct     120

tgcaaacaaa aaaaccaccg ctaccagcgg tggtttgttt gccggatcaa gagctaccaa     180

ctctttttcc gaaggtaact ggcttcagca gagcgcagat accaaatact gttcttctag     240

tgtagccgta gttagcccac cacttcaaga actctgtagc accgcctaca tacctcgctc     300

tgctaatcct gttaccagtg gctgctgcca gtggcgataa gtcgtgtctt accgggttgg     360

actcaagacg atagttaccg gataaggcgc agcggtcggg ctgaacgggg ggttcgtgca     420

cacagcccag cttggagcga acgacctaca ccgaactgag atacctacag cgtgagctat     480

gagaaagcgc cacgcttccc gaagggagaa aggcggacag gtatccggta agcggcaggg     540

tcggaacagg agagcgcacg agggagcttc caggggggaaa cgcctggtat ctttatagtc     600

ctgtcgggtt tcgccacctc tgacttgagc gtcgattttt gtgatgctcg tcaggggggc     660

ggagcctatg gaaaaacgcc agcaacgcgg cctttttacg gttcctggcc ttttgctggc     720

cttttgctca catgttcttt cctgcgttat cccctgattc tgtggataac cgtattaccg     780

cctttgagtg agctgatacc gctcgccgca gccgaacgac cgagcgcagc gagtcagtga     840

gcgaggaagc ggaaggcgag agtagggaac tgccaggcat caaactaagc agaaggcccc     900
```

-continued

```
tgacggatgg cctttttgcg tttctacaaa ctctttctgt gttgtaaaac gacggccagt    960
cttaagctcg ggcccctgg  gcggttctga taacgagtaa tcgttaatcc gcaaataacg   1020
taaaaacccg cttcggcggg tttttttatg gggggagttt agggaaagag catttgtcag   1080
aatatttaag ggcgcctgtc actttgcttg atatatgaga attatttaac cttataaatg   1140
agaaaaaagc aacgcacttt aaataagata cgttgctttt tcgattgatg aacacctata   1200
attaaactat tcatctatta tttatgattt tttgtatata caatatttct agtttgttaa   1260
agagaattaa gaaaataaat ctcgaaaata ataaagggaa aatcagtttt tgatatcaaa   1320
attatacatg tcaacgataa tacaaaatat aatacaaact ataagatgtt atcagtattt   1380
attatgcatt tagaataaat tttgtgtcgc ccttaattgt gagcggataa caattacgag   1440
cttcatgcac agtgaaatca tgaaaaattt atttgctttg tgagcggata acaattataa   1500
tatgtggaat tgtgagcgct cacaattcca caacggtttc cctctagaaa taattttgtt   1560
taacttttag gagttaaaac atatgatcaa actgaaattc ggcgtcttct tcaccgtact   1620
gctgtcctct gcttacgctc acggtactcc gcagaacatc acccaccacc atcaccatca   1680
tatcgaaggt cgtatgagta aaggagaaga acttttcact ggagttgtcc caattcttgt   1740
tgaattagat ggtgatgtta atgggcacaa attttctgtc agtggagagg gtgaaggtga   1800
tgcaacatac ggaaaactta cccttaaatt tatttgcact actggaaaac tacctgttcc   1860
atggccaaca cttgtcacta ctttcgcgta tggtcttcaa tgctttgcga gatacccaga   1920
tcatatgaaa cagcatgact ttttcaagag tgccatgccc gaaggttatg tacaggaaag   1980
aactatattt ttcaaagatg acgggaacta caagacacgt gctgaagtca agtttgaagg   2040
tgataccctt gttaatagaa tcgagttaaa aggtattgat tttaaagaag atggaaacat   2100
tcttggacac aaattggaat acaactataa ctcacacaat gtatacatca tggcagacaa   2160
acaaaagaat ggaatcaaag ttaacttcaa aattagacac aacattgaag atggaagcgt   2220
tcaactagca gaccattatc aacaaaatac tccaattggc gatggccctg tccttttacc   2280
agacaaccat tacctgtcca cacaatctgc cctttcgaaa gatcccaacg aaaagagaga   2340
ccacatggtc cttcttgagt ttgtaacagc tgctgggatt acacatggca tggatgaact   2400
atacaaaggc gctcgtcgtg ctattgaggg ccgcatcccg gaatacttta aactgaccaa   2460
caatggcacg ctgatgacgg gtatgagcgg tcaacaagcg ggtaacgttc tggttgttaa   2520
gggcaattac catggcaata acggccagct ggtcatgaac acggttctga acggcgatga   2580
tagcgtgacc gacaagctgg tggtcgaggg cgacacctct ggtacgaccg cagtgacggt   2640
gaataatgca ggcggtacgg gtgccaaaac cctgaacggt attgagttga tccacgttga   2700
cggtaagagc gagggcgagt ttgtgcaggc aggccgcatt gttgctggcg cttatgacta   2760
tacgctggcc cgtggtcagg gcgcgaatag cggtaactgg tatctgacca gcggctccga   2820
ctccccggaa ctgcaaccgg agcctgatcc gatgccgaat ccggagccaa acccgaaccc   2880
ggaaccgaac ccaaatccga ccccgactcc gggtccggac ttgaacgttg ataacgacct   2940
gcgtccggag gccggttcgt acatcgcgaa cctggcagcg gccaatacga tgtttacgac   3000
ccgtctgcac gaacgcctgg gtaataccta ctataccgat atggtcactg gtgaacagaa   3060
acaaaccacc atgtggatgc gccacgaggg tggtcacaat aagtggcgcg acggtagcgg   3120
ccagttgaaa acccagagca atcgctacgt tctgcaattg ggcggtgatg tggcgcaatg   3180
gagccaaaac ggcagcgacc gttggcatgt cggtgtgatg gcaggttacg gcaacagcga   3240
cagcaagacc atctccagcc gtaccggtta ccgtgcgaag gcaagcgtca acggttacag   3300
```

caccggcctg tatgccacct ggtatgctga tgatgagagc cgcaacggtg cttacttgga 3360
cagctgggca cagtattctt ggttcgataa tacggtgaaa ggcgacgacc tgcagagcga 3420
aagctacaaa tcgaaaggtt tcaccgcgag cctggaagcc ggctataagc acaaactggc 3480
ggaattcaat ggcagccagg gtactcgtaa cgaatggtac gttcaaccgc aggcgcaagt 3540
cacttggatg ggcgttaagg cggataaaca ccgtgagagc aacggtacgt tggtgcatag 3600
caacggtgat ggtaatgtcc aaacccgtct gggtgtgaaa acgtggctga agtcccatca 3660
caaaatggac gacggtaaat ctcgtgaatt tcagccgttc gtggaagtta actggctgca 3720
taatagcaag gatttcagca cgagcatgga tggtgtctcc gttacccagg acggcgcacg 3780
taacattgcg gagatcaaga ccggcgtcga gggtcagctg aatgcgaatc tgaatgtttg 3840
gggtaacgtg ggtgttcaag tagcggaccg tggttacaat gataccagcg cgatggtggg 3900
tattaagtgg cagttttaac tcgagcccca agggcgacac cccctaatta gcccgggcga 3960
aaggcccagt ctttcgactg agcctttcgt tttatttgat gcctggcagt tccctactct 4020
cgcatgggga gtccccacac taccatcggc gctacggcgt ttcacttctg agttcggcat 4080
ggggtcaggt gggaccaccg cgctactgcc gccaggcaaa caaggggtgt tatgagccat 4140
attcaggtat aaatgggctc gcgataatgt tcagaattgg ttaattggtt gtaacactga 4200
cccctatttg tttatttttc taaatacatt caaatatgta tccgctcatg agacaataac 4260
cctgataaat gcttcaataa tattgaaaaa ggaagaatat gagccatatt caacgggaaa 4320
cgtcgaggcc gcgattaaat tccaacatgg atgctgattt atatgggtat aaatgggctc 4380
gcgataatgt cgggcaatca ggtgcgacaa tctatcgctt gtatgggaag cccgatgcgc 4440
cagagttgtt tctgaaacat ggcaaaggta gcgttgccaa tgatgttaca gatgagatgg 4500
tcagactaaa ctggctgacg gaatttatgc cacttccgac catcaagcat tttatccgta 4560
ctcctgatga tgcatggtta ctcaccactg cgatccccgg aaaaacagcg ttccaggtat 4620
tagaagaata tcctgattca ggtgaaaata ttgttgatgc gctggcagtg ttcctgcgcc 4680
ggttgcactc gattcctgtt tgtaattgtc cttttaacag cgatcgcgta tttcgcctcg 4740
ctcaggcgca atcacgaatg aataacggtt tggttgatgc gagtgatttt gatgacgagc 4800
gtaatggctg gcctgttgaa caagtctgga aagaaatgca taaacttttg ccattctcac 4860
cggattcagt cgtcactcat ggtgatttct cacttgataa ccttattttt gacgagggga 4920
aattaatagg ttgtattgat gttggacgag tcggaatcgc agaccgatac caggatcttg 4980
ccatcctatg gaactgcctc ggtgagtttt ctccttcatt acagaaacgg ctttttcaaa 5040
aatatggtat tgataatcct gatatgaata aattgcagtt tcatttgatg ctcgatgagt 5100
ttttctaagc ggcgcgccat cgaatggcgc aaaacctttc gcggtatggc atgatagcgc 5160
ccggaagaga gtcaattcag ggtggtgaat atgaaaccag taacgttata cgatgtcgca 5220
gagtatgccg gtgtctctta tcagaccgtt tcccgcgtgg tgaaccaggc cagccacgtt 5280
tctgcgaaaa cgcgggaaaa agtggaagcg gcgatggcgg agctgaatta cattcccaac 5340
cgcgtggcac aacaactggc gggcaaacag tcgttgctga ttggcgttgc cacctccagt 5400
ctggccctgc acgcgccgtc gcaaattgtc gcggcgatta aatctcgcgc cgatcaactg 5460
ggtgccagcg tggtggtgtc gatggtagaa cgaagcggcg tcgaagcctg taaagcggcg 5520
gtgcacaatc ttctcgcgca acgcgtcagt gggctgatca ttaactatcc gctggatgac 5580
caggatgcca ttgctgtgga agctgcctgc actaatgttc cggcgttatt tcttgatgtc 5640

```
tctgaccaga cacccatcaa cagtattatt ttctcccatg aggacggtac gcgactgggc   5700

gtggagcatc tggtcgcatt gggtcaccag caaatcgcgc tgttagcggg cccattaagt   5760

tctgtctcgg cgcgtctgcg tctggctggc tggcataaat atctcactcg caatcaaatt   5820

cagccgatag cggaacggga aggcgactgg agtgccatgt ccggttttca acaaaccatg   5880

caaatgctga atgagggcat cgttcccact gcgatgctgg ttgccaacga tcagatggcg   5940

ctgggcgcaa tgcgcgccat taccgagtcc gggctgcgcg ttggtgcgga tatctcggta   6000

gtgggatacg acgataccga agatagctca tgttatatcc cgccgttaac caccatcaaa   6060

caggattttc gcctgctggg gcaaaccagc gtggaccgct tgctgcaact ctctcagggc   6120

caggcggtga agggcaatca gctgttgcca gtctcactgg tgaaaagaaa aaccaccctg   6180

gcgcccaata cgcaaaccgc ctctccccgc gcgttggccg attcattaat gcagctggca   6240

cgacaggttt cccgactgga aagcgggcag tga                                6273


<210> SEQ ID NO 6
<211> LENGTH: 778
<212> TYPE: PRT
<213> ORGANISM: Artificial Sequence
<220> FEATURE:
<223> OTHER INFORMATION: Polypeptide sequence of the autotransporter
      fusion protein encoded by pMATE-MT006, for the surface display of
      GFP using the pMATE system

<400> SEQUENCE: 6

Met Ile Lys Leu Lys Phe Gly Val Phe Phe Thr Val Leu Leu Ser Ser
1               5                   10                  15

Ala Tyr Ala His Gly Thr Pro Gln Asn Ile Thr His His His His His
            20                  25                  30

His Ile Glu Gly Arg Met Ser Lys Gly Glu Glu Leu Phe Thr Gly Val
        35                  40                  45

Val Pro Ile Leu Val Glu Leu Asp Gly Asp Val Asn Gly His Lys Phe
    50                  55                  60

Ser Val Ser Gly Glu Gly Glu Gly Asp Ala Thr Tyr Gly Lys Leu Thr
65                  70                  75                  80

Leu Lys Phe Ile Cys Thr Thr Gly Lys Leu Pro Val Pro Trp Pro Thr
                85                  90                  95

Leu Val Thr Thr Phe Ala Tyr Gly Leu Gln Cys Phe Ala Arg Tyr Pro
            100                 105                 110

Asp His Met Lys Gln His Asp Phe Phe Lys Ser Ala Met Pro Glu Gly
        115                 120                 125

Tyr Val Gln Glu Arg Thr Ile Phe Phe Lys Asp Asp Gly Asn Tyr Lys
    130                 135                 140

Thr Arg Ala Glu Val Lys Phe Glu Gly Asp Thr Leu Val Asn Arg Ile
145                 150                 155                 160

Glu Leu Lys Gly Ile Asp Phe Lys Glu Asp Gly Asn Ile Leu Gly His
                165                 170                 175

Lys Leu Glu Tyr Asn Tyr Asn Ser His Asn Val Tyr Ile Met Ala Asp
            180                 185                 190

Lys Gln Lys Asn Gly Ile Lys Val Asn Phe Lys Ile Arg His Asn Ile
        195                 200                 205

Glu Asp Gly Ser Val Gln Leu Ala Asp His Tyr Gln Gln Asn Thr Pro
    210                 215                 220

Ile Gly Asp Gly Pro Val Leu Leu Pro Asp Asn His Tyr Leu Ser Thr
225                 230                 235                 240
```

-continued

```
Gln Ser Ala Leu Ser Lys Asp Pro Asn Glu Lys Arg Asp His Met Val
                245                 250                 255

Leu Leu Glu Phe Val Thr Ala Ala Gly Ile Thr His Gly Met Asp Glu
            260                 265                 270

Leu Tyr Lys Gly Ala Arg Arg Ala Ile Glu Gly Arg Ile Pro Glu Tyr
        275                 280                 285

Phe Lys Leu Thr Asn Asn Gly Thr Leu Met Thr Gly Met Ser Gly Gln
    290                 295                 300

Gln Ala Gly Asn Val Leu Val Val Lys Gly Asn Tyr His Gly Asn Asn
305                 310                 315                 320

Gly Gln Leu Val Met Asn Thr Val Leu Asn Gly Asp Asp Ser Val Thr
                325                 330                 335

Asp Lys Leu Val Val Glu Gly Asp Thr Ser Gly Thr Thr Ala Val Thr
            340                 345                 350

Val Asn Asn Ala Gly Gly Thr Gly Ala Lys Thr Leu Asn Gly Ile Glu
        355                 360                 365

Leu Ile His Val Asp Gly Lys Ser Glu Gly Glu Phe Val Gln Ala Gly
    370                 375                 380

Arg Ile Val Ala Gly Ala Tyr Asp Tyr Thr Leu Ala Arg Gly Gln Gly
385                 390                 395                 400

Ala Asn Ser Gly Asn Trp Tyr Leu Thr Ser Gly Ser Asp Ser Pro Glu
                405                 410                 415

Leu Gln Pro Glu Pro Asp Pro Met Pro Asn Pro Glu Pro Asn Pro Asn
            420                 425                 430

Pro Glu Pro Asn Pro Asn Pro Thr Pro Thr Pro Gly Pro Asp Leu Asn
        435                 440                 445

Val Asp Asn Asp Leu Arg Pro Glu Ala Gly Ser Tyr Ile Ala Asn Leu
    450                 455                 460

Ala Ala Ala Asn Thr Met Phe Thr Thr Arg Leu His Glu Arg Leu Gly
465                 470                 475                 480

Asn Thr Tyr Tyr Thr Asp Met Val Thr Gly Glu Gln Lys Gln Thr Thr
                485                 490                 495

Met Trp Met Arg His Glu Gly Gly His Asn Lys Trp Arg Asp Gly Ser
            500                 505                 510

Gly Gln Leu Lys Thr Gln Ser Asn Arg Tyr Val Leu Gln Leu Gly Gly
        515                 520                 525

Asp Val Ala Gln Trp Ser Gln Asn Gly Ser Asp Arg Trp His Val Gly
    530                 535                 540

Val Met Ala Gly Tyr Gly Asn Ser Asp Ser Lys Thr Ile Ser Ser Arg
545                 550                 555                 560

Thr Gly Tyr Arg Ala Lys Ala Ser Val Asn Gly Tyr Ser Thr Gly Leu
                565                 570                 575

Tyr Ala Thr Trp Tyr Ala Asp Asp Glu Ser Arg Asn Gly Ala Tyr Leu
            580                 585                 590

Asp Ser Trp Ala Gln Tyr Ser Trp Phe Asp Asn Thr Val Lys Gly Asp
        595                 600                 605

Asp Leu Gln Ser Glu Ser Tyr Lys Ser Lys Gly Phe Thr Ala Ser Leu
    610                 615                 620

Glu Ala Gly Tyr Lys His Lys Leu Ala Glu Phe Asn Gly Ser Gln Gly
625                 630                 635                 640

Thr Arg Asn Glu Trp Tyr Val Gln Pro Gln Ala Gln Val Thr Trp Met
                645                 650                 655

Gly Val Lys Ala Asp Lys His Arg Glu Ser Asn Gly Thr Leu Val His
```

-continued

```
            660                 665                 670

Ser Asn Gly Asp Gly Asn Val Gln Thr Arg Leu Gly Val Lys Thr Trp
        675                 680                 685

Leu Lys Ser His His Lys Met Asp Asp Gly Lys Ser Arg Glu Phe Gln
    690                 695                 700

Pro Phe Val Glu Val Asn Trp Leu His Asn Ser Lys Asp Phe Ser Thr
705                 710                 715                 720

Ser Met Asp Gly Val Ser Val Thr Gln Asp Gly Ala Arg Asn Ile Ala
                725                 730                 735

Glu Ile Lys Thr Gly Val Glu Gly Gln Leu Asn Ala Asn Leu Asn Val
            740                 745                 750

Trp Gly Asn Val Gly Val Gln Val Ala Asp Arg Gly Tyr Asn Asp Thr
        755                 760                 765

Ser Ala Met Val Gly Ile Lys Trp Gln Phe
    770                 775


<210> SEQ ID NO 7
<211> LENGTH: 6434
<212> TYPE: DNA
<213> ORGANISM: Artificial Sequence
<220> FEATURE:
<223> OTHER INFORMATION: pMATE-SI005, for the surface display of 6xHis
      using the pMATE system in a broad range of bacterial hosts

<400> SEQUENCE: 7

ttaccaatta tgacaacttg acggctacat cattcacttt ttcttcacaa ccggcacgga     60

actcgctcgg gctggccccg gtgcattttt taaatacccg cgagaaatag agttgatcgt    120

caaaaccaac attgcgaccg acggtggcga taggcatccg ggtggtgctc aaaagcagct    180

tcgcctggct gatacgttgg tcctcgcgcc agcttaagac gctaatccct aactgctggc    240

ggaaaagatg tgacagacgc gacggcgaca agcaaacatg ctgtgcgacg ctggcgatat    300

caaaattgct gtctgccagg tgatcgctga tgtactgaca agcctcgcgt acccgattat    360

ccatcggtgg atggagcgac tcgttaatcg cttccatgcg ccgcagtaac aattgctcaa    420

gcagatttat cgccagcagc tccgaatagc gcccttcccc ttgcccggcg ttaatgattt    480

gcccaaacag gtcgctgaaa tgcggctggt gcgcttcatc cgggcgaaag aaccccgtat    540

tggcaaatat tgacggccag ttaagccatt catgccagta ggcgcgcgga cgaaagtaaa    600

cccactggtg ataccattcg cgagcctccg gatgacgacc gtagtgatga atctctcctg    660

gcgggaacag caaaatatca cccggtcggc aaacaaattc tcgtccctga tttttcacca    720

ccccctgacc gcgaatggtg agattgagaa tataaccttt cattcccagc ggtcggtcga    780

taaaaaaatc gagataaccg ttggcctcaa tcggcgttaa acccgccacc agatgggcat    840

taaacgagta tcccggcagc aggggatcat tttgcgcttc agccatactt ttcatactcc    900

cgccattcag agaagaaacc aattgtccat attgcatcag acattgccgt cactgcgtct    960

tttactggct cttctcgcta accaaaccgg taaccccgct tattaaaagc attctgtaac   1020

aaagcgggac caaagccatg acaaaaacgc gtaacaaaag tgtctataat cacggcagaa   1080

aagtccacat tgattatttg cacggcgtca cactttgcta tgccatagca tttttatcca   1140

taagattagc ggatcctacc tgacgctttt tatcgcaact ctctactgtt tctccatacc   1200

cgtttttttgg gctaacagga ggaattaacc atgatcaaac tgaaattcgg cgtcttcttc   1260

accgtactgc tgtcctctgc ttacgctcac ggtactccgc agaacatcac ccaccaccat   1320

caccatcata tcgaaggtcg tctcgagcat atgagatctg gtaccgctcg tcgtgctatt   1380
```

-continued

```
gagggccgca tcccggaata ctttaaactg accaacaatg gcacgctgat gacgggtatg   1440
agcggtcaac aagcgggtaa cgttctggtt gttaagggca attaccatgg caataacggc   1500
cagctggtca tgaacacggt tctgaacggc gatgatagcg tgaccgacaa gctggtggtc   1560
gagggcgaca cctctggtac gaccgcagtg acggtgaata atgcaggcgg tacgggtgcc   1620
aaaaccctga acggtattga gttgatccac gttgacggta agagcgaggg cgagtttgtg   1680
caggcaggcc gcattgttgc tggcgcttat gactatacgc tggcccgtgg tcagggcgcg   1740
aatagcggta actggtatct gaccagcggc tccgactccc cggaactgca accggagcct   1800
gatccgatgc cgaatccgga gccaaacccg aacccggaac cgaacccaaa tccgaccccg   1860
actccgggtc cggacttgaa cgttgataac gacctgcgtc cggaggccgg ttcgtacatc   1920
gcgaacctgg cagcggccaa tacgatgttt acgacccgtc tgcacgaacg cctgggtaat   1980
acctactata ccgatatggt cactggtgaa cagaaacaaa ccaccatgtg gatgcgccac   2040
gagggtggtc acaataagtg gcgcgacggt agcggccagt tgaaaaccca gagcaatcgc   2100
tacgttctgc aattgggcgg tgatgtggcg caatggagcc aaaacggcag cgaccgttgg   2160
catgtcggtg tgatggcagg ttacggcaac agcgacagca agaccatctc cagccgtacc   2220
ggttaccgtg cgaaggcaag cgtcaacggt tacagcaccg gcctgtatgc cacctggtat   2280
gctgatgatg agagccgcaa cggtgcttac ttggacagct gggcacagta ttcttggttc   2340
gataatacgg tgaaaggcga cgacctgcag agcgaaagct acaaatcgaa aggtttcacc   2400
gcgagcctgg aagccggcta taagcacaaa ctggcggaat tcaatggcag ccagggtact   2460
cgtaacgaat ggtacgttca accgcaggcg caagtcactt ggatgggcgt taaggcggat   2520
aaacaccgtg agagcaacgg tacgttggtg catagcaacg gtgatggtaa tgtccaaacc   2580
cgtctgggtg tgaaaacgtg gctgaagtcc catcacaaaa tggacgacgg taaatctcgt   2640
gaatttcagc cgttcgtgga agttaactgg ctgcataata gcaaggattt cagcacgagc   2700
atggatggtg tctccgttac ccaggacggc gcacgtaaca ttgcggagat caagaccggc   2760
gtcgagggtc agctgaatgc gaatctgaat gtttggggta acgtgggtgt tcaagtagcg   2820
gaccgtggtt acaatgatac cagcgcgatg gtgggtatta agtggcagtt ttaatgagtt   2880
taaacggtct ccagcttggc tgttttggcg gatgagagaa gattttcagc ctgatacaga   2940
ttaaatcaga acgcagaagc ggtctgataa aacagaattt gcctggcggc agtagcgcgg   3000
tggtcccacc tgaccccatg ccgaactcag aagtgaaacg ccgtagcgcc gatggtagtg   3060
tggggtctcc ccatgcgaga gtagggaact gccaggcatc aaataaaacg aaaggctcag   3120
tcgaaagact gggcgaggcg gctacagccg atagtctgga acagcgcact tacgggttgc   3180
tgcgcaaccc aagtgctacc ggcgcggcag cgtgacccgt gtcggcggct ccaacggctc   3240
gccatcgtcc agaaaacacg gctcatcggg catcggcagg cgctgctgcc cgcgccgttc   3300
ccattcctcc gtttcggtca aggctggcag gtctggttcc atgcccggaa tgccgggctg   3360
gctgggcggc tcctcgccgg ggccggtcgg tagttgctgc tcgcccggat acagggtcgg   3420
gatgcggcgc aggtcgccat gccccaacag cgattcgtcc tggtcgtcgt gatcaaccac   3480
cacggcggca ctgaacaccg acaggcgcaa ctggtcgcgg ggctggcccc acgccacgcg   3540
gtcattgacc acgtaggccg acacggtgcc ggggccgttg agcttcacga cggagatcca   3600
gcgctcggcc accaagtcct tgactgcgta ttggaccgtc cgcaaagaac gtccgatgag   3660
cttggaaagt gtcttctggc tgaccaccac ggcgttctgg tggcccatct gcgccacgag   3720
```

-continued

```
gtgatgcagc agcattgccg ccgtgggttt cctcgcaata agcccggccc acgcctcatg   3780
cgctttgcgt tccgtttgca cccagtgacc gggcttgttc ttggcttgaa tgccgatttc   3840
tctggactgc gtggccatgc ttatctccat gcggtagggt gccgcacggt tgcggcacca   3900
tgcgcaatca gctgcaactt ttcggcagcg cgacaacaat tatgcgttgc gtaaaagtgg   3960
cagtcaatta cagattttct ttaacctacg caatgagcta ttgcgggggg tgccgcaatg   4020
agctgttgcg taccccccctt ttttaagttg ttgattttta agtctttcgc atttcgccct   4080
atatctagtt ctttggtgcc caaagaaggg cacccctgcg gggttccccc acgccttcgg   4140
cgcggctccc cctccggcaa aaagtggccc ctccggggct tgttgatcga ctgcgcggcc   4200
ttcggccttg cccaaggtgg cgctgccccc ttggaacccc cgcactcgcc gccgtgaggc   4260
tcggggggca ggcgggcggg cttcgccttc gactgccccc actcgcatag gcttgggtcg   4320
ttccaggcgc gtcaaggcca agccgctgcg cggtcgctgc gcgagccttg acccgccttc   4380
cacttggtgt ccaaccggca agcgaagcgc gcaggccgca ggccggaggc ttttccccag   4440
agaaaattaa aaaaattgat ggggcaaggc cgcaggccgc gcagttggag ccggtgggta   4500
tgtggtcgaa ggctgggtag ccggtgggca atccctgtgg tcaagctcgt gggcaggcgc   4560
agcctgtcca tcagcttgtc cagcagggtt gtccacgggc cgagcgaagc gagccagccg   4620
gtggccgctc gcggccatcg tccacatatc cacgggctgg caagggagcg cagcgaccgc   4680
gcagggcgaa gcccggagag caagcccgta gggcgccgca gccgccgtag gcggtcacga   4740
ctttgcgaag caaagtctag tgagtatact caagcattga gtggcccgcc ggaggcaccg   4800
ccttgcgctg cccccgtcga gccggttgga caccaaaagg gaggggcagg ctgcgcgctt   4860
ggcgtaatca tggtcatagc tgtttcctgt gtgaaattgt tatccgctca caattccaca   4920
caacatacga gccggaagca taaagtgtaa agcctggggt gcctaatgag tgagctaact   4980
cacattaatt gcgttgcgct cactgcccgc tttccagtcg ggaaacctgt cgtgccagct   5040
gcattaatga atcggccaac gcgcggggag aggcggtttg cgtattgggc gcatgcataa   5100
aaactgttgt aattcattaa gcattctgcc gacatggaag ccatcacaaa cggcatgatg   5160
aacctgaatc gccagcggca tcagcacctt gtcgccttgc gtataatatt tgcccatggg   5220
ggtgggcgaa gaactccagc atgagatccc cgcgctggag gatcatccag ccggcgtccc   5280
ggaaaacgat tccgaagccc aacctttcat agaaggcggc ggtggaatcg aaatctcgtg   5340
atggcaggtt gggcgtcgct tggtcggtca tttcgaaccc cagagtcccg ctcagaagaa   5400
ctcgtcaaga aggcgataga aggcgatgcg ctgcgaatcg ggagcggcga taccgtaaag   5460
cacgaggaag cggtcagccc attcgccgcc aagctcttca gcaatatcac gggtagccaa   5520
cgctatgtcc tgatagcggt ccgccacacc cagccggcca cagtcgatga atccagaaaa   5580
gcggccattt tccaccatga tattcggcaa gcaggcatcg ccatgggtca cgacgagatc   5640
ctcgccgtcg ggcatgcgcg ccttgagcct ggcgaacagt tcggctggcg cgagcccctg   5700
atgctcttcg tccagatcat cctgatcgac aagaccggct tccatccgag tacgtgctcg   5760
ctcgatgcga tgtttcgctt ggtggtcgaa tgggcaggta gccggatcaa gcgtatgcag   5820
ccgccgcatt gcatcagcca tgatggatac tttctcggca ggagcaaggt gagatgacag   5880
gagatcctgc cccggcactt cgcccaatag cagccagtcc cttcccgctt cagtgacaac   5940
gtcgagcaca gctgcgcaag gaacgcccgt cgtggccagc cacgatagcc gcgctgcctc   6000
gtcctgcagt tcattcaggg caccggacag gtcggtcttg acaaaaagaa ccgggcgccc   6060
ctgcgctgac agccggaaca cggcggcatc agagcagccg attgtctgtt gtgcccagtc   6120
```

```
atagccgaat agcctctcca cccaagcggc cggagaacct gcgtgcaatc catcttgttc   6180

aatcatgcga aacgatcctc atcctgtctc ttgatcagat cttgatcccc tgcgccatca   6240

gatccttggc ggcaagaaag ccatccagtt tactttgcag ggcttcccaa ccttaccaga   6300

gggcgcccca gctggcaatt ccggttcgct tgctgtccat aaaaccgccc agtctagcta   6360

tcgccatgta agcccactgc aagctacctg ctttctcttt gcgcttgcgt ttcccttgt    6420

ccagatagcc cagt                                                     6434
```

<210> SEQ ID NO 8
<211> LENGTH: 547
<212> TYPE: PRT
<213> ORGANISM: Artificial Sequence
<220> FEATURE:
<223> OTHER INFORMATION: autotransporter fusion protein encoded by pMATE-SI005, for the surface display of 6xHis using the pMATE system in a broad range of bacterial hosts

<400> SEQUENCE: 8

```
Met Ile Lys Leu Lys Phe Gly Val Phe Phe Thr Val Leu Leu Ser Ser
1               5                   10                  15

Ala Tyr Ala His Gly Thr Pro Gln Asn Ile Thr His His His His His
            20                  25                  30

His Ile Glu Gly Arg Leu Glu His Met Arg Ser Gly Thr Ala Arg Arg
        35                  40                  45

Ala Ile Glu Gly Arg Ile Pro Glu Tyr Phe Lys Leu Thr Asn Asn Gly
    50                  55                  60

Thr Leu Met Thr Gly Met Ser Gly Gln Gln Ala Gly Asn Val Leu Val
65                  70                  75                  80

Val Lys Gly Asn Tyr His Gly Asn Asn Gly Gln Leu Val Met Asn Thr
                85                  90                  95

Val Leu Asn Gly Asp Asp Ser Val Thr Asp Lys Leu Val Val Glu Gly
            100                 105                 110

Asp Thr Ser Gly Thr Thr Ala Val Thr Val Asn Asn Ala Gly Gly Thr
        115                 120                 125

Gly Ala Lys Thr Leu Asn Gly Ile Glu Leu Ile His Val Asp Gly Lys
    130                 135                 140

Ser Glu Gly Glu Phe Val Gln Ala Gly Arg Ile Val Ala Gly Ala Tyr
145                 150                 155                 160

Asp Tyr Thr Leu Ala Arg Gly Gln Gly Ala Asn Ser Gly Asn Trp Tyr
                165                 170                 175

Leu Thr Ser Gly Ser Asp Ser Pro Glu Leu Gln Pro Glu Pro Asp Pro
            180                 185                 190

Met Pro Asn Pro Glu Pro Asn Pro Asn Pro Glu Pro Asn Pro Asn Pro
        195                 200                 205

Thr Pro Thr Pro Gly Pro Asp Leu Asn Val Asp Asn Asp Leu Arg Pro
    210                 215                 220

Glu Ala Gly Ser Tyr Ile Ala Asn Leu Ala Ala Ala Asn Thr Met Phe
225                 230                 235                 240

Thr Thr Arg Leu His Glu Arg Leu Gly Asn Thr Tyr Tyr Thr Asp Met
                245                 250                 255

Val Thr Gly Glu Gln Lys Gln Thr Thr Met Trp Met Arg His Glu Gly
            260                 265                 270

Gly His Asn Lys Trp Arg Asp Gly Ser Gly Gln Leu Lys Thr Gln Ser
        275                 280                 285
```

```
Asn Arg Tyr Val Leu Gln Leu Gly Gly Asp Val Ala Gln Trp Ser Gln
    290                 295                 300

Asn Gly Ser Asp Arg Trp His Val Gly Val Met Ala Gly Tyr Gly Asn
305                 310                 315                 320

Ser Asp Ser Lys Thr Ile Ser Ser Arg Thr Gly Tyr Arg Ala Lys Ala
                325                 330                 335

Ser Val Asn Gly Tyr Ser Thr Gly Leu Tyr Ala Thr Trp Tyr Ala Asp
            340                 345                 350

Asp Glu Ser Arg Asn Gly Ala Tyr Leu Asp Ser Trp Ala Gln Tyr Ser
        355                 360                 365

Trp Phe Asp Asn Thr Val Lys Gly Asp Asp Leu Gln Ser Glu Ser Tyr
    370                 375                 380

Lys Ser Lys Gly Phe Thr Ala Ser Leu Glu Ala Gly Tyr Lys His Lys
385                 390                 395                 400

Leu Ala Glu Phe Asn Gly Ser Gln Gly Thr Arg Asn Glu Trp Tyr Val
                405                 410                 415

Gln Pro Gln Ala Gln Val Thr Trp Met Gly Val Lys Ala Asp Lys His
            420                 425                 430

Arg Glu Ser Asn Gly Thr Leu Val His Ser Asn Gly Asp Gly Asn Val
        435                 440                 445

Gln Thr Arg Leu Gly Val Lys Thr Trp Leu Lys Ser His His Lys Met
    450                 455                 460

Asp Asp Gly Lys Ser Arg Glu Phe Gln Pro Phe Val Glu Val Asn Trp
465                 470                 475                 480

Leu His Asn Ser Lys Asp Phe Ser Thr Ser Met Asp Gly Val Ser Val
                485                 490                 495

Thr Gln Asp Gly Ala Arg Asn Ile Ala Glu Ile Lys Thr Gly Val Glu
            500                 505                 510

Gly Gln Leu Asn Ala Asn Leu Asn Val Trp Gly Asn Val Gly Val Gln
        515                 520                 525

Val Ala Asp Arg Gly Tyr Asn Asp Thr Ser Ala Met Val Gly Ile Lys
    530                 535                 540

Trp Gln Phe
545
```

<210> SEQ ID NO 9
<211> LENGTH: 7457
<212> TYPE: DNA
<213> ORGANISM: Artificial Sequence
<220> FEATURE:
<223> OTHER INFORMATION: pMATE-SI010, for the surface display of estA catalytic domain using the pMATE system in a broad range of bacterial hosts

<400> SEQUENCE: 9

```
ttaccaatta tgacaacttg acggctacat cattcacttt ttcttcacaa ccggcacgga     60

actcgctcgg gctggccccg gtgcattttt taaatacccg cgagaaatag agttgatcgt    120

caaaaccaac attgcgaccg acggtggcga taggcatccg ggtggtgctc aaaagcagct    180

tcgcctggct gatacgttgg tcctcgcgcc agcttaagac gctaatccct aactgctggc    240

ggaaaagatg tgacagacgc gacggcgaca agcaaacatg ctgtgcgacg ctggcgatat    300

caaaattgct gtctgccagg tgatcgctga tgtactgaca agcctcgcgt acccgattat    360

ccatcggtgg atggagcgac tcgttaatcg cttccatgcg ccgcagtaac aattgctcaa    420

gcagatttat cgccagcagc tccgaatagc gcccttcccc ttgcccggcg ttaatgattt    480
```

-continued

```
gcccaaacag gtcgctgaaa tgcggctggt gcgcttcatc cgggcgaaag aaccccgtat    540
tggcaaatat tgacggccag ttaagccatt catgccagta ggcgcgcgga cgaaagtaaa    600
cccactggtg ataccattcg cgagcctccg gatgacgacc gtagtgatga atctctcctg    660
gcgggaacag caaaatatca cccggtcggc aaacaaattc tcgtccctga tttttcacca    720
ccccctgacc gcgaatggtg agattgagaa tataaccttt cattcccagc ggtcggtcga    780
taaaaaaatc gagataaccg ttggcctcaa tcggcgttaa acccgccacc agatgggcat    840
taaacgagta tcccggcagc aggggatcat tttgcgcttc agccatactt ttcatactcc    900
cgccattcag agaagaaacc aattgtccat attgcatcag acattgccgt cactgcgtct    960
tttactggct cttctcgcta accaaaccgg taaccccgct tattaaaagc attctgtaac   1020
aaagcgggac caaagccatg acaaaaacgc gtaacaaaag tgtctataat cacggcagaa   1080
aagtccacat tgattatttg cacggcgtca cactttgcta tgccatagca tttttatcca   1140
taagattagc ggatcctacc tgacgctttt tatcgcaact ctctactgtt tctccatacc   1200
cgtttttttgg gctaacagga ggaattaacc atgatcaaac tgaaattcgg cgtcttcttc   1260
accgtactgc tgtcctctgc ttacgctcac ggtactccgc agaacatcac ccaccaccat   1320
caccatcata tcgaaggtcg tctcgagggc ggcggtgacg acaacgccgc gcccgccgcc   1380
ccgccggccg gcgtgcagaa gcagatcgtc tcgttcggcg acagcctgtc cgacgctggc   1440
acctattcgc cgcagatcct gctcggcttc ggcggcgggc gcttcaccac caatccgggc   1500
gaggtctgga cccagaaggt ggccgaatac ttcggcgaca cgctcaagcc cgcctacgaa   1560
ggcggcttcg ggtcccgct gcaggccacc ggcggcctgg gctacgccca gggcggctcg   1620
cgcgtgacgc tgcagccggg cctcggccac gccgacgcct cggtgccgaa cgccgacttc   1680
gcccaggcca ccaccacgcc gatcgccacc caggtgcagc agtacctgca ggcgcacggc   1740
agcttcaacg ccaaccagat cgtgctgatc aacggcggcg ccaacgacat cctgttccag   1800
gcgcaagtcg cggccgcggc cggcaatacc ccggccgccc aagtcgcggc cgcgcaggcg   1860
gtcggcctgg cggcccagca gttcggccag atcatcgcgc agatcgccaa cgccggcgcc   1920
agccacgtgt tcgtcgccaa catgcccgac atcggcacca cgccgctggc ggtggccggc   1980
ggcgccgcca cccaggccgc gctgacccag ctctcgggcc tgttcaacca gacgctgaac   2040
gccacgctcg ccgcgctgca ggtcgacacc agcaaggtca aggtgatgga cgtgtacacc   2100
tggcaggacg gcatcggcgc gaacttccag gccaacggct tcacggtcgg caataccggc   2160
acggcctgca acctgaccgc catggcggcg gccgccgcga aggccggggt ggccaatccg   2220
agcggcttcg cctcctcgct gttctgctcg ccgcagacct acacggtggc caacgccgac   2280
cagacctaca tgttcgccga cacggtgcac ccgaccacgc gcctgcatgc gctggtcgcg   2340
cagttcgtcg agcagcagat cgcggcggcc ggcgtcacca agggtaccgc tcgtcgtgct   2400
attgagggcc gcatcccgga atactttaaa ctgaccaaca atggcacgct gatgacgggt   2460
atgagcggtc aacaagcggg taacgttctg gttgttaagg gcaattacca tggcaataac   2520
ggccagctgg tcatgaacac ggttctgaac ggcgatgata gcgtgaccga caagctggtg   2580
gtcgagggcg acacctctgg tacgaccgca gtgacggtga ataatgcagg cggtacgggt   2640
gccaaaaccc tgaacggtat tgagttgatc cacgttgacg gtaagagcga gggcgagttt   2700
gtgcaggcag gccgcattgt tgctggcgct tatgactata cgctggcccg tggtcagggc   2760
gcgaatagcg gtaactggta tctgaccagc ggctccgact ccccggaact gcaaccggag   2820
cctgatccga tgccgaatcc ggagccaaac ccgaacccgg aaccgaaccc aaatccgacc   2880
```

-continued

```
ccgactccgg gtccggactt gaacgttgat aacgacctgc gtccggaggc cggttcgtac   2940
atcgcgaacc tggcagcggc caatacgatg tttacgaccc gtctgcacga acgcctgggt   3000
aatacctact ataccgatat ggtcactggt gaacagaaac aaaccaccat gtggatgcgc   3060
cacgagggtg gtcacaataa gtggcgcgac ggtagcggcc agttgaaaac ccagagcaat   3120
cgctacgttc tgcaattggg cggtgatgtg gcgcaatgga gccaaaacgg cagcgaccgt   3180
tggcatgtcg gtgtgatggc aggttacggc aacagcgaca gcaagaccat ctccagccgt   3240
accggttacc gtgcgaaggc aagcgtcaac ggttacagca ccggcctgta tgccacctgg   3300
tatgctgatg atgagagccg caacggtgct tacttggaca gctgggcaca gtattcttgg   3360
ttcgataata cggtgaaagg cgacgacctg cagagcgaaa gctacaaatc gaaaggtttc   3420
accgcgagcc tggaagccgg ctataagcac aaactggcgg aattcaatgg cagccagggt   3480
actcgtaacg aatggtacgt tcaaccgcag gcgcaagtca cttggatggg cgttaaggcg   3540
gataaacacc gtgagagcaa cggtacgttg gtgcatagca acggtgatgg taatgtccaa   3600
acccgtctgg gtgtgaaaac gtggctgaag tcccatcaca aaatggacga cggtaaatct   3660
cgtgaatttc agccgttcgt ggaagttaac tggctgcata atagcaagga tttcagcacg   3720
agcatggatg gtgtctccgt tacccaggac ggcgcacgta acattgcgga gatcaagacc   3780
ggcgtcgagg gtcagctgaa tgcgaatctg aatgtttggg gtaacgtggg tgttcaagta   3840
gcggaccgtg gttacaatga taccagcgcg atggtgggta ttaagtggca gttttaatga   3900
gtttaaacgg tctccagctt ggctgttttg gcggatgaga gaagattttc agcctgatac   3960
agattaaatc agaacgcaga agcggtctga taaaacagaa tttgcctggc ggcagtagcg   4020
cggtggtccc acctgacccc atgccgaact cagaagtgaa acgccgtagc gccgatggta   4080
gtgtggggtc tccccatgcg agagtaggga actgccaggc atcaaataaa acgaaaggct   4140
cagtcgaaag actgggcgag gcggctacag ccgatagtct ggaacagcgc acttacgggt   4200
tgctgcgcaa cccaagtgct accggcgcgg cagcgtgacc cgtgtcggcg gctccaacgg   4260
ctcgccatcg tccagaaaac acggctcatc gggcatcggc aggcgctgct gcccgcgccg   4320
ttcccattcc tccgtttcgg tcaaggctgg caggtctggt tccatgcccg gaatgccggg   4380
ctggctgggc ggctcctcgc cggggccggt cggtagttgc tgctcgcccg gatacagggt   4440
cgggatgcgg cgcaggtcgc catgccccaa cagcgattcg tcctggtcgt cgtgatcaac   4500
caccacggcg gcactgaaca ccgacaggcg caactggtcg cggggctggc cccacgccac   4560
gcggtcattg accacgtagg ccgacacggt gccggggccg ttgagcttca cgacggagat   4620
ccagcgctcg gccaccaagt ccttgactgc gtattggacc gtccgcaaag aacgtccgat   4680
gagcttggaa agtgtcttct ggctgaccac cacggcgttc tggtggccca tctgcgccac   4740
gaggtgatgc agcagcattg ccgccgtggg tttcctcgca ataagcccgg cccacgcctc   4800
atgcgctttg cgttccgttt gcacccagtg accgggcttg ttcttggctt gaatgccgat   4860
ttctctggac tgcgtggcca tgcttatctc catgcggtag ggtgccgcac ggttgcggca   4920
ccatgcgcaa tcagctgcaa cttttcggca gcgcgacaac aattatgcgt tgcgtaaaag   4980
tggcagtcaa ttacagattt tctttaacct acgcaatgag ctattgcggg gggtgccgca   5040
atgagctgtt gcgtaccccc ctttttttaag ttgttgattt ttaagtcttt cgcatttcgc   5100
cctatatcta gttctttggt gcccaaagaa gggcacccct gcggggttcc cccacgcctt   5160
cggcgcggct ccccctccgg caaaaagtgg cccctccggg gcttgttgat cgactgcgcg   5220
```

-continued

```
gccttcggcc ttgcccaagg tggcgctgcc cccttggaac ccccgcactc gccgccgtga   5280
ggctcggggg gcaggcgggc gggcttcgcc ttcgactgcc cccactcgca taggcttggg   5340
tcgttccagg cgcgtcaagg ccaagccgct gcgcggtcgc tgcgcgagcc ttgacccgcc   5400
ttccacttgg tgtccaaccg gcaagcgaag cgcgcaggcc gcaggccgga ggcttttccc   5460
cagagaaaat taaaaaaatt gatggggcaa ggccgcaggc cgcgcagttg gagccggtgg   5520
gtatgtggtc gaaggctggg tagccggtgg gcaatccctg tggtcaagct cgtgggcagg   5580
cgcagcctgt ccatcagctt gtccagcagg gttgtccacg ggccgagcga agcgagccag   5640
ccggtggccg ctcgcggcca tcgtccacat atccacgggc tggcaaggga gcgcagcgac   5700
cgcgcagggc gaagcccgga gagcaagccc gtagggcgcc gcagccgccg taggcggtca   5760
cgactttgcg aagcaaagtc tagtgagtat actcaagcat tgagtggccc gccggaggca   5820
ccgccttgcg ctgcccccgt cgagccggtt ggacaccaaa agggaggggc aggctgcgcg   5880
cttggcgtaa tcatggtcat agctgtttcc tgtgtgaaat tgttatccgc tcacaattcc   5940
acacaacata cgagccggaa gcataaagtg taaagcctgg ggtgcctaat gagtgagcta   6000
actcacatta attgcgttgc gctcactgcc cgctttccag tcgggaaacc tgtcgtgcca   6060
gctgcattaa tgaatcggcc aacgcgcggg gagaggcggt ttgcgtattg ggcgcatgca   6120
taaaaactgt tgtaattcat taagcattct gccgacatgg aagccatcac aaacggcatg   6180
atgaacctga atcgccagcg gcatcagcac cttgtcgcct tgcgtataat atttgcccat   6240
gggggtgggc gaagaactcc agcatgagat ccccgcgctg gaggatcatc cagccggcgt   6300
cccggaaaac gattccgaag cccaaccttt catagaaggc ggcggtggaa tcgaaatctc   6360
gtgatggcag gttgggcgtc gcttggtcgg tcatttcgaa ccccagagtc ccgctcagaa   6420
gaactcgtca agaaggcgat agaaggcgat gcgctgcgaa tcgggagcgg cgataccgta   6480
aagcacgagg aagcggtcag cccattcgcc gccaagctct tcagcaatat cacgggtagc   6540
caacgctatg tcctgatagc ggtccgccac acccagccgg ccacagtcga tgaatccaga   6600
aaagcggcca ttttccacca tgatattcgg caagcaggca tcgccatggg tcacgacgag   6660
atcctcgccg tcgggcatgc gcgccttgag cctggcgaac agttcggctg gcgcgagccc   6720
ctgatgctct tcgtccagat catcctgatc gacaagaccg gcttccatcc gagtacgtgc   6780
tcgctcgatg cgatgtttcg cttggtggtc gaatgggcag gtagccggat caagcgtatg   6840
cagccgccgc attgcatcag ccatgatgga tactttctcg gcaggagcaa ggtgagatga   6900
caggagatcc tgccccggca cttcgcccaa tagcagccag tcccttcccg cttcagtgac   6960
aacgtcgagc acagctgcgc aaggaacgcc cgtcgtggcc agccacgata gccgcgctgc   7020
ctcgtcctgc agttcattca gggcaccgga caggtcggtc ttgacaaaaa gaaccgggcg   7080
cccctgcgct gacagccgga acacggcggc atcagagcag ccgattgtct gttgtgccca   7140
gtcatagccg aatagcctct ccacccaagc ggccggagaa cctgcgtgca atccatcttg   7200
ttcaatcatg cgaaacgatc ctcatcctgt ctcttgatca gatcttgatc ccctgcgcca   7260
tcagatcctt ggcggcaaga aagccatcca gtttactttg cagggcttcc caaccttacc   7320
agagggcgcc ccagctggca attccggttc gcttgctgtc cataaaaccg cccagtctag   7380
ctatcgccat gtaagcccac tgcaagctac ctgctttctc tttgcgcttg cgttttccct   7440
tgtccagata gcccagt                                                  7457
```

<210> SEQ ID NO 10
<211> LENGTH: 888

```
<212> TYPE: PRT
<213> ORGANISM: Artificial Sequence
<220> FEATURE:
<223> OTHER INFORMATION: autotransporter fusion protein encoded by
      pMATE-SI010, for the surface display of B. gladioli EstA esterase
      domain using the pMATE system in a broad range of bacterial hosts

<400> SEQUENCE: 10

Met Ile Lys Leu Lys Phe Gly Val Phe Phe Thr Val Leu Leu Ser Ser
1               5                   10                  15

Ala Tyr Ala His Gly Thr Pro Gln Asn Ile Thr His His His His His
            20                  25                  30

His Ile Glu Gly Arg Leu Glu Gly Gly Gly Asp Asp Asn Ala Ala Pro
        35                  40                  45

Ala Ala Pro Pro Ala Gly Val Gln Lys Gln Ile Val Ser Phe Gly Asp
    50                  55                  60

Ser Leu Ser Asp Ala Gly Thr Tyr Ser Pro Gln Ile Leu Leu Gly Phe
65                  70                  75                  80

Gly Gly Gly Arg Phe Thr Thr Asn Pro Gly Glu Val Trp Thr Gln Lys
                85                  90                  95

Val Ala Glu Tyr Phe Gly Asp Thr Leu Lys Pro Ala Tyr Glu Gly Gly
            100                 105                 110

Phe Gly Val Pro Leu Gln Ala Thr Gly Gly Leu Gly Tyr Ala Gln Gly
        115                 120                 125

Gly Ser Arg Val Thr Leu Gln Pro Gly Leu Gly His Ala Asp Ala Ser
    130                 135                 140

Val Pro Asn Ala Asp Phe Ala Gln Ala Thr Thr Thr Pro Ile Ala Thr
145                 150                 155                 160

Gln Val Gln Gln Tyr Leu Gln Ala His Gly Ser Phe Asn Ala Asn Gln
                165                 170                 175

Ile Val Leu Ile Asn Gly Gly Ala Asn Asp Ile Leu Phe Gln Ala Gln
            180                 185                 190

Val Ala Ala Ala Ala Gly Asn Thr Pro Ala Ala Gln Val Ala Ala Ala
        195                 200                 205

Gln Ala Val Gly Leu Ala Ala Gln Gln Phe Gly Gln Ile Ile Ala Gln
    210                 215                 220

Ile Ala Asn Ala Gly Ala Ser His Val Phe Val Ala Asn Met Pro Asp
225                 230                 235                 240

Ile Gly Thr Thr Pro Leu Ala Val Ala Gly Gly Ala Ala Thr Gln Ala
                245                 250                 255

Ala Leu Thr Gln Leu Ser Gly Leu Phe Asn Gln Thr Leu Asn Ala Thr
            260                 265                 270

Leu Ala Ala Leu Gln Val Asp Thr Ser Lys Val Lys Val Met Asp Val
        275                 280                 285

Tyr Thr Trp Gln Asp Gly Ile Gly Ala Asn Phe Gln Ala Asn Gly Phe
    290                 295                 300

Thr Val Gly Asn Thr Gly Thr Ala Cys Asn Leu Thr Ala Met Ala Ala
305                 310                 315                 320

Ala Ala Ala Lys Ala Gly Val Ala Asn Pro Ser Gly Phe Ala Ser Ser
                325                 330                 335

Leu Phe Cys Ser Pro Gln Thr Tyr Thr Val Ala Asn Ala Asp Gln Thr
            340                 345                 350

Tyr Met Phe Ala Asp Thr Val His Pro Thr Thr Arg Leu His Ala Leu
        355                 360                 365

Val Ala Gln Phe Val Glu Gln Gln Ile Ala Ala Ala Gly Val Thr Lys
```

```
    370                 375                 380

Gly Thr Ala Arg Arg Ala Ile Glu Gly Arg Ile Pro Glu Tyr Phe Lys
385                 390                 395                 400

Leu Thr Asn Asn Gly Thr Leu Met Thr Gly Met Ser Gly Gln Gln Ala
                405                 410                 415

Gly Asn Val Leu Val Val Lys Gly Asn Tyr His Gly Asn Asn Gly Gln
            420                 425                 430

Leu Val Met Asn Thr Val Leu Asn Gly Asp Asp Ser Val Thr Asp Lys
        435                 440                 445

Leu Val Val Glu Gly Asp Thr Ser Gly Thr Thr Ala Val Thr Val Asn
    450                 455                 460

Asn Ala Gly Gly Thr Gly Ala Lys Thr Leu Asn Gly Ile Glu Leu Ile
465                 470                 475                 480

His Val Asp Gly Lys Ser Glu Gly Glu Phe Val Gln Ala Gly Arg Ile
                485                 490                 495

Val Ala Gly Ala Tyr Asp Tyr Thr Leu Ala Arg Gly Gln Gly Ala Asn
            500                 505                 510

Ser Gly Asn Trp Tyr Leu Thr Ser Gly Ser Asp Ser Pro Glu Leu Gln
        515                 520                 525

Pro Glu Pro Asp Pro Met Pro Asn Pro Glu Pro Asn Pro Asn Pro Glu
    530                 535                 540

Pro Asn Pro Asn Pro Thr Pro Thr Pro Gly Pro Asp Leu Asn Val Asp
545                 550                 555                 560

Asn Asp Leu Arg Pro Glu Ala Gly Ser Tyr Ile Ala Asn Leu Ala Ala
                565                 570                 575

Ala Asn Thr Met Phe Thr Thr Arg Leu His Glu Arg Leu Gly Asn Thr
            580                 585                 590

Tyr Tyr Thr Asp Met Val Thr Gly Glu Gln Lys Gln Thr Thr Met Trp
        595                 600                 605

Met Arg His Glu Gly Gly His Asn Lys Trp Arg Asp Gly Ser Gly Gln
    610                 615                 620

Leu Lys Thr Gln Ser Asn Arg Tyr Val Leu Gln Leu Gly Gly Asp Val
625                 630                 635                 640

Ala Gln Trp Ser Gln Asn Gly Ser Asp Arg Trp His Val Gly Val Met
                645                 650                 655

Ala Gly Tyr Gly Asn Ser Asp Ser Lys Thr Ile Ser Ser Arg Thr Gly
            660                 665                 670

Tyr Arg Ala Lys Ala Ser Val Asn Gly Tyr Ser Thr Gly Leu Tyr Ala
        675                 680                 685

Thr Trp Tyr Ala Asp Asp Glu Ser Arg Asn Gly Ala Tyr Leu Asp Ser
    690                 695                 700

Trp Ala Gln Tyr Ser Trp Phe Asp Asn Thr Val Lys Gly Asp Asp Leu
705                 710                 715                 720

Gln Ser Glu Ser Tyr Lys Ser Lys Gly Phe Thr Ala Ser Leu Glu Ala
                725                 730                 735

Gly Tyr Lys His Lys Leu Ala Glu Phe Asn Gly Ser Gln Gly Thr Arg
            740                 745                 750

Asn Glu Trp Tyr Val Gln Pro Gln Ala Gln Val Thr Trp Met Gly Val
        755                 760                 765

Lys Ala Asp Lys His Arg Glu Ser Asn Gly Thr Leu Val His Ser Asn
    770                 775                 780

Gly Asp Gly Asn Val Gln Thr Arg Leu Gly Val Lys Thr Trp Leu Lys
785                 790                 795                 800
```

```
Ser His His Lys Met Asp Asp Gly Lys Ser Arg Glu Phe Gln Pro Phe
                805                 810                 815

Val Glu Val Asn Trp Leu His Asn Ser Lys Asp Phe Ser Thr Ser Met
            820                 825                 830

Asp Gly Val Ser Val Thr Gln Asp Gly Ala Arg Asn Ile Ala Glu Ile
        835                 840                 845

Lys Thr Gly Val Glu Gly Gln Leu Asn Ala Asn Leu Asn Val Trp Gly
    850                 855                 860

Asn Val Gly Val Gln Val Ala Asp Arg Gly Tyr Asn Asp Thr Ser Ala
865                 870                 875                 880

Met Val Gly Ile Lys Trp Gln Phe
                885


<210> SEQ ID NO 11
<211> LENGTH: 8465
<212> TYPE: DNA
<213> ORGANISM: Artificial Sequence
<220> FEATURE:
<223> OTHER INFORMATION: pMATE-SI012, for the surface display of estA
      catalytic domain using the pMATE system in a broad range of
      bacterial hosts

<400> SEQUENCE: 11

tgcgcgcttg gcgtaatcat ggtcatagct gtttcctgtg tgaaattgtt atccgctcac     60

aattccacac aacatacgag ccggaagcat aaagtgtaaa gcctggggtg cctaatgagt    120

gagctaactc acattaattg cgttgcgctc actgcccgct ttccagtcgg gaaacctgtc    180

gtgccagctg cattaatgaa tcggccaacg cgcggggaga ggcggtttgc gtattgggcg    240

catgcataaa aactgttgta attcattaag cattctgccg acatggaagc catcacaaac    300

ggcatgatga acctgaatcg ccagcggcat cagcaccttg tcgccttgcg tataatattt    360

gcccatgggg gtgggcgaag aactccagca tgagatcccc gcgctggagg atcatccagc    420

cggcgtcccg gaaaacgatt ccgaagccca acctttcata gaaggcggcg gtggaatcga    480

aatctcgtga tggcaggttg ggcgtcgctt ggtcggtcat ttcgaacccc agagtcccgc    540

tcagaagaac tcgtcaagaa ggcgatagaa ggcgatgcgc tgcgaatcgg gagcggcgat    600

accgtaaagc acgaggaagc ggtcagccca ttcgccgcca agctcttcag caatatcacg    660

ggtagccaac gctatgtcct gatagcggtc cgccacaccc agccggccac agtcgatgaa    720

tccagaaaag cggccatttt ccaccatgat attcggcaag caggcatcgc catgggtcac    780

gacgagatcc tcgccgtcgg gcatgcgcgc cttgagcctg gcgaacagtt cggctggcgc    840

gagcccctga tgctcttcgt ccagatcatc ctgatcgaca agaccggctt ccatccgagt    900

acgtgctcgc tcgatgcgat gtttcgcttg gtggtcgaat gggcaggtag ccggatcaag    960

cgtatgcagc cgccgcattg catcagccat gatggatact ttctcggcag gagcaaggtg   1020

agatgacagg agatcctgcc ccggcacttc gcccaatagc agccagtccc ttcccgcttc   1080

agtgacaacg tcgagcacag ctgcgcaagg aacgcccgtc gtggccagcc acgatagccg   1140

cgctgcctcg tcctgcagtt cattcagggc accggacagg tcggtcttga caaaaagaac   1200

cgggcgcccc tgcgctgaca gccggaacac ggcggcatca gagcagccga ttgtctgttg   1260

tgcccagtca tagccgaata gcctctccac ccaagcggcc ggagaacctg cgtgcaatcc   1320

atcttgttca atcatgcgaa acgatcctca tcctgtctct tgatcagatc ttgatcccct   1380

gcgccatcag atccttggcg gcaagaaagc catccagttt actttgcagg gcttcccaac   1440
```

-continued

```
cttaccagag ggcgccccag ctggcaattc cggttcgctt gctgtccata aaaccgccca   1500
gtctagctat cgccatgtaa gcccactgca agctacctgc tttctctttg cgcttgcgtt   1560
ttcccttgtc cagatagccc agtagctgac attcatccca ggtggcactt ttcggggaaa   1620
tgtgcgcgcc cgcgttcctg ctggcgctgg gcctgtttct ggcgctggac ttcccgctgt   1680
tccgtcagca gcttttcgcc cacggccttg atgatcgcgg cggccttggc ctgcatatcc   1740
cgattcaacg gccccagggc gtccagaacg ggcttcaggc gctcccgaag gtctcgggcc   1800
gtctcttggg cttgatcggc cttcttgcgc atctcacgcg ctcctgcggc ggcctgtagg   1860
gcaggctcat accccctgccg aaccgctttt gtcagccggt cggccacggc ttccggcgtc   1920
tcaacgcgct ttgagattcc cagcttttcg gccaatccct gcggtgcata ggcgcgtggc   1980
tcgaccgctt gcgggctgat ggtgacgtgg cccactggtg gccgctccag ggcctcgtag   2040
aacgcctgaa tgcgcgtgtg acgtgccttg ctgccctcga tgccccgttg cagccctaga   2100
tcggccacag cggccgcaaa cgtggtctgg tcgcgggtca tctgcgcttt gttgccgatg   2160
aactccttgg ccgacagcct gccgtcctgc gtcagcggca ccacgaacgc ggtcatgtgc   2220
gggctggttt cgtcacggtg gatgctggcc gtcacgatgc gatccgcccc gtacttgtcc   2280
gccagccact tgtgcgcctt ctcgaagaac gccgcctgct gttcttggct ggccgacttc   2340
caccattccg ggctggccgt catgacgtac tcgaccgcca acacagcgtc cttgcgccgc   2400
ttctctggca gcaactcgcg cagtcggccc atcgcttcat cggtgctgct ggccgcccag   2460
tgctcgttct ctggcgtcct gctggcgtca gcgttgggcg tctcgcgctc gcggtaggcg   2520
tgcttgagac tggccgccac gttgcccatt ttcgccagct tcttgcatcg catgatcgcg   2580
tatgccgcca tgcctgcccc tcccttttgg tgtccaaccg gctcgacggg ggcagcgcaa   2640
ggcggtgcct ccggcgggcc actcaatgct tgagtatact cactagactt tgcttcgcaa   2700
agtcgtgacc gcctacggcg gctgcggcgc cctacgggct tgctctccgg gcttcgccct   2760
gcgcggtcgc tgcgctccct tgccagcccg tggatatgtg gacgatggcc gcgagcggcc   2820
accggctggc tcgcttcgct cggcccgtgg acaaccctgc tggacaagct gatggacagg   2880
ctgcgcctgc ccacgagctt gaccacaggg attgcccacc ggctacccag ccttcgacca   2940
catacccacc ggctccaact gcgcggcctg cggccttgcc ccatcaattt ttttaatttt   3000
ctctggggaa aagcctccgg cctgcggcct gcgcgcttcg cttgccggtt ggacaccaag   3060
tggaaggcgg gtcaaggctc gcgcagcgac cgcgcagcgg cttggccttg acgcgcctgg   3120
aacgacccaa gcctatgcga gtgggggcag tcgaaggcga agcccgcccg cctgcccccc   3180
gagcctcacg gcggcgagtg cgggggttcc aagggggcag cgccaccttg ggcaaggccg   3240
aaggccgcgc agtcgatcaa caagccccgg aggggccact ttttgccgga gggggagccg   3300
cgccgaaggc gtgggggaac cccgcagggg tgcccttctt tgggcaccaa agaactagat   3360
atagggcgaa atgcgaaaga cttaaaaatc aacaacttaa aaaagggggg tacgcaacag   3420
ctcattgcgg caccccccgc aatagctcat tgcgtaggtt aaagaaaatc tgtaattgac   3480
tgccactttt acgcaacgca taattgttgt cgcgctgccg aaaagttgca gctgattgcg   3540
catggtgccg caaccgtgcg gcaccctacc gcatggagat aagcatggcc acgcagtcca   3600
gagaaatcgg cattcaagcc aagaacaagc ccggtcactg ggtgcaaacg gaacgcaaag   3660
cgcatgaggc gtgggccggg cttattgcga ggaaacccac ggcggcaatg ctgctgcatc   3720
acctcgtggc gcagatgggc caccagaacg ccgtggtggt cagccagaag acactttcca   3780
agctcatcgg acgttctttg cggacggtcc aatacgcagt caaggacttg gtggccgagc   3840
```

-continued gctggatctc cgtcgtgaag ctcaacggcc ccggcaccgt gtcggcctac gtggtcaatg 3900
accgcgtggc gtggggccag ccccgcgacc agttgcgcct gtcggtgttc agtgccgccg 3960
tggtggttga tcacgacgac caggacgaat cgctgttggg gcatggcgac ctgcgccgca 4020
tcccgaccct gtatccgggc gagcagcaac taccgaccgg ccccggcgag gagccgccca 4080
gccagcccgg cattccgggc atggaaccag acctgccagc cttgaccgaa acggaggaat 4140
gggaacggcg cgggcagcag cgcctgccga tgcccgatga gccgtgtttt ctggacgatg 4200
gcgagccgtt ggagccgccg acacgggtca cgctgccgcg ccggtagcac ttgggttgcg 4260
cagcaacccg taagtgcgct gttccagact atcggctgta gccgcctcgt taccaattat 4320
gacaacttga cggctacatc attcactttt tcttcacaac cggcacggaa ctcgctcggg 4380
ctggccccgg tgcatttttt aaatacccgc gagaaataga gttgatcgtc aaaaccaaca 4440
ttgcgaccga cggtggcgat aggcatccgg gtggtgctca aaagcagctt cgcctggctg 4500
atacgttggt cctcgcgcca gcttaagacg ctaatcccta actgctggcg gaaaagatgt 4560
gacagacgcg acggcgacaa gcaaacatgc tgtgcgacgc tggcgatatc aaaattgctg 4620
tctgccaggt gatcgctgat gtactgacaa gcctcgcgta cccgattatc catcggtgga 4680
tggagcgact cgttaatcgc ttccatgcgc cgcagtaaca attgctcaag cagatttatc 4740
gccagcagct ccgaatagcg cccttcccct tgcccggcgt taatgatttg cccaaacagg 4800
tcgctgaaat gcggctggtg cgcttcatcc gggcgaaaga accccgtatt ggcaaatatt 4860
gacggccagt taagccattc atgccagtag gcgcgcggac gaaagtaaac ccactggtga 4920
taccattcgc gagcctccgg atgacgaccg tagtgatgaa tctctcctgg cgggaacagc 4980
aaaatatcac ccggtcggca aacaaattct cgtccctgat ttttcaccac cccctgaccg 5040
cgaatggtga gattgagaat ataacctttc attcccagcg gtcggtcgat aaaaaaatcg 5100
agataaccgt tggcctcaat cggcgttaaa cccgccacca gatgggcatt aaacgagtat 5160
cccggcagca ggggatcatt ttgcgcttca gccatacttt tcatactccc gccattcaga 5220
gaagaaacca attgtccata ttgcatcaga cattgccgtc actgcgtctt ttactggctc 5280
ttctcgctaa ccaaaccggt aaccccgctt attaaaagca ttctgtaaca aagcgggacc 5340
aaagccatga caaaaacgcg taacaaaagt gtctataatc acggcagaaa agtccacatt 5400
gattatttgc acggcgtcac actttgctat gccatagcat ttttatccat aagattagcg 5460
gatcctacct gacgcttttt atcgcaactc tctactgttt ctccataccc gtttttttggg 5520
ctaacaggag gaattaacca tgatcaaact gaaattcggc gtcttcttca ccgtactgct 5580
gtcctctgct tacgctcacg gtactccgca gaacatcacc caccaccatc accatcatat 5640
cgaaggtcgt ctcgagggcg gcggtgacga caacgccgcg cccgccgccc cgccggccgg 5700
cgtgcagaag cagatcgtct cgttcggcga cagcctgtcc gacgctggca cctattcgcc 5760
gcagatcctg ctcggcttcg gcggcgggcg cttcaccacc aatccgggcg aggtctggac 5820
ccagaaggtg gccgaatact tcggcgacac gctcaagccc gcctacgaag gcggcttcgg 5880
ggtcccgctg caggccaccg gcggcctggg ctacgcccag ggcggctcgc gcgtgacgct 5940
gcagccgggc ctcggccacg ccgacgcctc ggtgccgaac gccgacttcg cccaggccac 6000
caccacgccg atcgccaccc aggtgcagca gtacctgcag gcgcacggca gcttcaacgc 6060
caaccagatc gtgctgatca acggcggcgc caacgacatc ctgttccagg cgcaagtcgc 6120
ggccgcggcc ggcaataccc cggccgccca agtcgcggcc gcgcaggcgg tcggcctggc 6180

-continued

```
ggcccagcag ttcggccaga tcatcgcgca gatcgccaac gccggcgcca gccacgtgtt   6240
cgtcgccaac atgcccgaca tcggcaccac gccgctggcg gtggccggcg gcgccgccac   6300
ccaggccgcg ctgacccagc tctcgggcct gttcaaccag acgctgaacg ccacgctcgc   6360
cgcgctgcag gtcgacacca gcaaggtcaa ggtgatggac gtgtacacct ggcaggacgg   6420
catcggcgcg aacttccagg ccaacggctt cacggtcggc aataccggca cggcctgcaa   6480
cctgaccgcc atggcggcgg ccgccgcgaa ggccggggtg gccaatccga gcggcttcgc   6540
ctcctcgctg ttctgctcgc cgcagaccta cacggtggcc aacgccgacc agacctacat   6600
gttcgccgac acggtgcacc cgaccacgcg cctgcatgcg ctggtcgcgc agttcgtcga   6660
gcagcagatc gcggcggccg gcgtcaccaa gggtaccgct cgtcgtgcta ttgagggccg   6720
catcccggaa tactttaaac tgaccaacaa tggcacgctg atgacgggta tgagcggtca   6780
acaagcgggt aacgttctgg ttgttaaggg caattaccat ggcaataacg gccagctggt   6840
catgaacacg gttctgaacg gcgatgatag cgtgaccgac aagctggtgg tcgagggcga   6900
cacctctggt acgaccgcag tgacggtgaa taatgcaggc ggtacgggtg ccaaaaccct   6960
gaacggtatt gagttgatcc acgttgacgg taagagcgag ggcgagtttg tgcaggcagg   7020
ccgcattgtt gctggcgctt atgactatac gctggcccgt ggtcagggcg cgaatagcgg   7080
taactggtat ctgaccagcg gctccgactc cccggaactg caaccggagc ctgatccgat   7140
gccgaatccg gagccaaacc cgaacccgga accgaaccca aatccgaccc cgactccggg   7200
tccggacttg aacgttgata acgacctgcg tccggaggcc ggttcgtaca tcgcgaacct   7260
ggcagcggcc aatacgatgt ttacgacccg tctgcacgaa cgcctgggta atacctacta   7320
taccgatatg gtcactggtg aacagaaaca aaccaccatg tggatgcgcc acgagggtgg   7380
tcacaataag tggcgcgacg gtagcggcca gttgaaaacc cagagcaatc gctacgttct   7440
gcaattgggc ggtgatgtgg cgcaatggag ccaaaacggc agcgaccgtt ggcatgtcgg   7500
tgtgatggca ggttacggca acagcgacag caagaccatc tccagccgta ccggttaccg   7560
tgcgaaggca agcgtcaacg gttacagcac cggcctgtat gccacctggt atgctgatga   7620
tgagagccgc aacggtgctt acttggacag ctgggcacag tattcttggt tcgataatac   7680
ggtgaaaggc gacgacctgc agagcgaaag ctacaaatcg aaaggtttca ccgcgagcct   7740
ggaagccggc tataagcaca aactggcgga attcaatggc agccagggta ctcgtaacga   7800
atggtacgtt caaccgcagg cgcaagtcac ttggatgggc gttaaggcgg ataaacaccg   7860
tgagagcaac ggtacgttgg tgcatagcaa cggtgatggt aatgtccaaa cccgtctggg   7920
tgtgaaaacg tggctgaagt cccatcacaa aatggacgac ggtaaatctc gtgaatttca   7980
gccgttcgtg gaagttaact ggctgcataa tagcaaggat ttcagcacga gcatggatgg   8040
tgtctccgtt acccaggacg gcgcacgtaa cattgcggag atcaagaccg gcgtcgaggg   8100
tcagctgaat gcgaatctga atgtttgggg taacgtgggt gttcaagtag cggaccgtgg   8160
ttacaatgat accagcgcga tggtgggtat taagtggcag ttttaatgag tttaaacggt   8220
ctccagcttg gctgttttgg cggatgagag aagattttca gcctgataca gattaaatca   8280
gaacgcagaa gcggtctgat aaaacagaat ttgcctggcg gcagtagcgc ggtggtccca   8340
cctgacccca tgccgaactc agaagtgaaa cgccgtagcg ccgatggtag tgtggggtct   8400
ccccatgcga gagtagggaa ctgccaggca tcaaataaaa cgaaaggctc agtcgaaaga   8460
ctggg                                                                8465
```

-continued

<210> SEQ ID NO 12
<211> LENGTH: 888
<212> TYPE: PRT
<213> ORGANISM: Artificial Sequence
<220> FEATURE:
<223> OTHER INFORMATION: autotransporter fusion protein encoded by pMATE-SI012, for the surface display of B. gladioli EstA esterase domain using the pMATE system in a broad range of bacterial hosts

<400> SEQUENCE: 12

```
Met Ile Lys Leu Lys Phe Gly Val Phe Phe Thr Val Leu Leu Ser Ser
1               5                   10                  15

Ala Tyr Ala His Gly Thr Pro Gln Asn Ile Thr His His His His His
            20                  25                  30

His Ile Glu Gly Arg Leu Glu Gly Gly Gly Asp Asp Asn Ala Ala Pro
        35                  40                  45

Ala Ala Pro Pro Ala Gly Val Gln Lys Gln Ile Val Ser Phe Gly Asp
    50                  55                  60

Ser Leu Ser Asp Ala Gly Thr Tyr Ser Pro Gln Ile Leu Leu Gly Phe
65                  70                  75                  80

Gly Gly Gly Arg Phe Thr Thr Asn Pro Gly Glu Val Trp Thr Gln Lys
                85                  90                  95

Val Ala Glu Tyr Phe Gly Asp Thr Leu Lys Pro Ala Tyr Glu Gly Gly
            100                 105                 110

Phe Gly Val Pro Leu Gln Ala Thr Gly Gly Leu Gly Tyr Ala Gln Gly
        115                 120                 125

Gly Ser Arg Val Thr Leu Gln Pro Gly Leu Gly His Ala Asp Ala Ser
    130                 135                 140

Val Pro Asn Ala Asp Phe Ala Gln Ala Thr Thr Thr Pro Ile Ala Thr
145                 150                 155                 160

Gln Val Gln Gln Tyr Leu Gln Ala His Gly Ser Phe Asn Ala Asn Gln
                165                 170                 175

Ile Val Leu Ile Asn Gly Gly Ala Asn Asp Ile Leu Phe Gln Ala Gln
            180                 185                 190

Val Ala Ala Ala Ala Gly Asn Thr Pro Ala Ala Gln Val Ala Ala Ala
        195                 200                 205

Gln Ala Val Gly Leu Ala Ala Gln Gln Phe Gly Gln Ile Ile Ala Gln
    210                 215                 220

Ile Ala Asn Ala Gly Ala Ser His Val Phe Val Ala Asn Met Pro Asp
225                 230                 235                 240

Ile Gly Thr Thr Pro Leu Ala Val Ala Gly Gly Ala Ala Thr Gln Ala
                245                 250                 255

Ala Leu Thr Gln Leu Ser Gly Leu Phe Asn Gln Thr Leu Asn Ala Thr
            260                 265                 270

Leu Ala Ala Leu Gln Val Asp Thr Ser Lys Val Lys Val Met Asp Val
        275                 280                 285

Tyr Thr Trp Gln Asp Gly Ile Gly Ala Asn Phe Gln Ala Asn Gly Phe
    290                 295                 300

Thr Val Gly Asn Thr Gly Thr Ala Cys Asn Leu Thr Ala Met Ala Ala
305                 310                 315                 320

Ala Ala Ala Lys Ala Gly Val Ala Asn Pro Ser Gly Phe Ala Ser Ser
                325                 330                 335

Leu Phe Cys Ser Pro Gln Thr Tyr Thr Val Ala Asn Ala Asp Gln Thr
            340                 345                 350

Tyr Met Phe Ala Asp Thr Val His Pro Thr Thr Arg Leu His Ala Leu
        355                 360                 365
```

-continued

```
Val Ala Gln Phe Val Glu Gln Gln Ile Ala Ala Ala Gly Val Thr Lys
    370                 375                 380

Gly Thr Ala Arg Arg Ala Ile Glu Gly Arg Ile Pro Glu Tyr Phe Lys
385                 390                 395                 400

Leu Thr Asn Asn Gly Thr Leu Met Thr Gly Met Ser Gly Gln Gln Ala
                405                 410                 415

Gly Asn Val Leu Val Val Lys Gly Asn Tyr His Gly Asn Asn Gly Gln
            420                 425                 430

Leu Val Met Asn Thr Val Leu Asn Gly Asp Asp Ser Val Thr Asp Lys
        435                 440                 445

Leu Val Val Glu Gly Asp Thr Ser Gly Thr Thr Ala Val Thr Val Asn
    450                 455                 460

Asn Ala Gly Gly Thr Gly Ala Lys Thr Leu Asn Gly Ile Glu Leu Ile
465                 470                 475                 480

His Val Asp Gly Lys Ser Glu Gly Glu Phe Val Gln Ala Gly Arg Ile
                485                 490                 495

Val Ala Gly Ala Tyr Asp Tyr Thr Leu Ala Arg Gly Gln Gly Ala Asn
            500                 505                 510

Ser Gly Asn Trp Tyr Leu Thr Ser Gly Ser Asp Ser Pro Glu Leu Gln
        515                 520                 525

Pro Glu Pro Asp Pro Met Pro Asn Pro Glu Pro Asn Pro Asn Pro Glu
    530                 535                 540

Pro Asn Pro Asn Pro Thr Pro Thr Pro Gly Pro Asp Leu Asn Val Asp
545                 550                 555                 560

Asn Asp Leu Arg Pro Glu Ala Gly Ser Tyr Ile Ala Asn Leu Ala Ala
                565                 570                 575

Ala Asn Thr Met Phe Thr Thr Arg Leu His Glu Arg Leu Gly Asn Thr
            580                 585                 590

Tyr Tyr Thr Asp Met Val Thr Gly Glu Gln Lys Gln Thr Thr Met Trp
        595                 600                 605

Met Arg His Glu Gly Gly His Asn Lys Trp Arg Asp Gly Ser Gly Gln
    610                 615                 620

Leu Lys Thr Gln Ser Asn Arg Tyr Val Leu Gln Leu Gly Gly Asp Val
625                 630                 635                 640

Ala Gln Trp Ser Gln Asn Gly Ser Asp Arg Trp His Val Gly Val Met
                645                 650                 655

Ala Gly Tyr Gly Asn Ser Asp Ser Lys Thr Ile Ser Ser Arg Thr Gly
            660                 665                 670

Tyr Arg Ala Lys Ala Ser Val Asn Gly Tyr Ser Thr Gly Leu Tyr Ala
        675                 680                 685

Thr Trp Tyr Ala Asp Asp Glu Ser Arg Asn Gly Ala Tyr Leu Asp Ser
    690                 695                 700

Trp Ala Gln Tyr Ser Trp Phe Asp Asn Thr Val Lys Gly Asp Asp Leu
705                 710                 715                 720

Gln Ser Glu Ser Tyr Lys Ser Lys Gly Phe Thr Ala Ser Leu Glu Ala
                725                 730                 735

Gly Tyr Lys His Lys Leu Ala Glu Phe Asn Gly Ser Gln Gly Thr Arg
            740                 745                 750

Asn Glu Trp Tyr Val Gln Pro Gln Ala Gln Val Thr Trp Met Gly Val
        755                 760                 765

Lys Ala Asp Lys His Arg Glu Ser Asn Gly Thr Leu Val His Ser Asn
    770                 775                 780
```

```
Gly Asp Gly Asn Val Gln Thr Arg Leu Gly Val Lys Thr Trp Leu Lys
785                 790                 795                 800

Ser His His Lys Met Asp Asp Gly Lys Ser Arg Glu Phe Gln Pro Phe
                805                 810                 815

Val Glu Val Asn Trp Leu His Asn Ser Lys Asp Phe Ser Thr Ser Met
            820                 825                 830

Asp Gly Val Ser Val Thr Gln Asp Gly Ala Arg Asn Ile Ala Glu Ile
        835                 840                 845

Lys Thr Gly Val Glu Gly Gln Leu Asn Ala Asn Leu Asn Val Trp Gly
    850                 855                 860

Asn Val Gly Val Gln Val Ala Asp Arg Gly Tyr Asn Asp Thr Ser Ala
865                 870                 875                 880

Met Val Gly Ile Lys Trp Gln Phe
                885


<210> SEQ ID NO 13
<211> LENGTH: 6252
<212> TYPE: DNA
<213> ORGANISM: Artificial Sequence
<220> FEATURE:
<223> OTHER INFORMATION: pMATE-SI015, for the surface display of
      6xHis-mCherry using the pMATE system

<400> SEQUENCE: 13

ctcatgacca aaatccctta acgtgagtta cgcgcgcgtc gttccactga gcgtcagacc     60

ccgtagaaaa gatcaaagga tcttcttgag atcctttttt tctgcgcgta atctgctgct    120

tgcaaacaaa aaaaccaccg ctaccagcgg tggtttgttt gccggatcaa gagctaccaa    180

ctctttttcc gaaggtaact ggcttcagca gagcgcagat accaaatact gttcttctag    240

tgtagccgta gttagcccac cacttcaaga actctgtagc accgcctaca tacctcgctc    300

tgctaatcct gttaccagtg gctgctgcca gtggcgataa gtcgtgtctt accgggttgg    360

actcaagacg atagttaccg gataaggcgc agcggtcggg ctgaacgggg ggttcgtgca    420

cacagcccag cttggagcga acgacctaca ccgaactgag atacctacag cgtgagctat    480

gagaaagcgc cacgcttccc gaagggagaa aggcggacag gtatccggta agcggcaggg    540

tcggaacagg agagcgcacg agggagcttc caggggggaaa cgcctggtat ctttatagtc    600

ctgtcgggtt tcgccacctc tgacttgagc gtcgattttt gtgatgctcg tcaggggggc    660

ggagcctatg gaaaaacgcc agcaacgcgg cctttttacg gttcctggcc ttttgctggc    720

cttttgctca catgttcttt cctgcgttat cccctgattc tgtggataac cgtattaccg    780

cctttgagtg agctgatacc gctcgccgca gccgaacgac cgagcgcagc gagtcagtga    840

gcgaggaagc ggaaggcgag agtagggaac tgccaggcat caaactaagc agaaggcccc    900

tgacggatgg cctttttgcg tttctacaaa ctctttctgt gttgtaaaac gacggccagt    960

cttaagctcg ggccccctgg gcggttctga taacgagtaa tcgttaatcc gcaaataacg   1020

taaaaacccg cttcggcggg tttttttatg gggggagttt agggaaagag catttgtcag   1080

aatatttaag ggcgcctgtc actttgcttg atatatgaga attatttaac cttataaatg   1140

agaaaaaagc aacgcacttt aaataagata cgttgctttt tcgattgatg aacacctata   1200

attaaactat tcatctatta tttatgattt tttgtatata caatatttct agtttgttaa   1260

agagaattaa gaaaataaat ctcgaaaata ataaagggaa aatcagtttt tgatatcaaa   1320

attatacatg tcaacgataa tacaaaatat aatacaaact ataagatgtt atcagtattt   1380

attatgcatt tagaataaat tttgtgtcgc ccttaattgt gagcggataa caattacgag   1440
```

-continued

```
cttcatgcac agtgaaatca tgaaaaattt atttgctttg tgagcggata acaattataa   1500
tatgtggaat tgtgagcgct cacaattcca caacggtttc cctctagaaa taattttgtt   1560
taacttttag gagttaaaac atatgatcaa actgaaattc ggcgtcttct tcaccgtact   1620
gctgtcctct gcttacgctc acggtactcc gcagaacatc acccaccacc atcaccatca   1680
tatggtgagc aagggcgagg aggataacat ggccatcatc aaggagttca tgcgcttcaa   1740
ggtgcacatg gagggctccg tgaacggcca cgagttcgag atcgagggcg agggcgaggg   1800
ccgcccctac gagggcaccc agaccgccaa gctgaaggtg accaagggtg gccccctgcc   1860
cttcgcctgg gacatcctgt cccctcagtt catgtacggc tccaaggcct acgtgaagca   1920
ccccgccgac atccccgact acttgaagct gtccttcccc gagggcttca agtgggagcg   1980
cgtgatgaac ttcgaggacg gcggcgtggt gaccgtgacc caggactcct ccctgcagga   2040
cggcgagttc atctacaagg tgaagctgcg cggcaccaac ttcccctccg acggccccgt   2100
aatgcagaag aagaccatgg gctgggaggc ctcctccgag cggatgtacc ccgaggacgg   2160
cgccctgaag ggcgagatca agcagaggct gaagctgaag gacggcggcc actacgacgc   2220
tgaggtcaag accacctaca aggccaagaa gcccgtgcag ctgcccggcg cctacaacgt   2280
caacatcaag ttggacatca cctcccacaa cgaggactac accatcgtgg aacagtacga   2340
acgcgccgag ggccgccact ccaccggcgg catggacgag ctgtacaagg ctcgtcgtgc   2400
tattgagggc cgcatcccgg aatactttaa actgaccaac aatggcacgc tgatgacggg   2460
tatgagcggt caacaagcgg gtaacgttct ggttgttaag ggcaattacc atggcaataa   2520
cggccagctg gtcatgaaca cggttctgaa cggcgatgat agcgtgaccg acaagctggt   2580
ggtcgagggc gacacctctg gtacgaccgc agtgacggtg aataatgcag gcggtacggg   2640
tgccaaaacc ctgaacggta ttgagttgat ccacgttgac ggtaagagcg agggcgagtt   2700
tgtgcaggca ggccgcattg ttgctggcgc ttatgactat acgctggccc gtggtcaggg   2760
cgcgaatagc ggtaactggt atctgaccag cggctccgac tccccggaac tgcaaccgga   2820
gcctgatccg atgccgaatc cggagccaaa cccgaacccg gaaccgaacc caaatccgac   2880
cccgactccg ggtccggact tgaacgttga taacgacctg cgtccggagg ccggttcgta   2940
catcgcgaac ctggcagcgg ccaatacgat gtttacgacc cgtctgcacg aacgcctggg   3000
taatacctac tataccgata tggtcactgg tgaacagaaa caaaccacca tgtggatgcg   3060
ccacgagggt ggtcacaata agtggcgcga cggtagcggc cagttgaaaa cccagagcaa   3120
tcgctacgtt ctgcaattgg gcggtgatgt ggcgcaatgg agccaaaacg gcagcgaccg   3180
ttggcatgtc ggtgtgatgg caggttacgg caacagcgac agcaagacca tctccagccg   3240
taccggttac cgtgcgaagg caagcgtcaa cggttacagc accggcctgt atgccacctg   3300
gtatgctgat gatgagagcc gcaacggtgc ttacttggac agctgggcac agtattcttg   3360
gttcgataat acggtgaaag gcgacgacct gcagagcgaa agctacaaat cgaaaggttt   3420
caccgcgagc ctggaagccg gctataagca caaactggcg gaattcaatg gcagccaggg   3480
tactcgtaac gaatggtacg ttcaaccgca ggcgcaagtc acttggatgg gcgttaaggc   3540
ggataaacac cgtgagagca acggtacgtt ggtgcatagc aacggtgatg gtaatgtcca   3600
aacccgtctg ggtgtgaaaa cgtggctgaa gtcccatcac aaaatggacg acggtaaatc   3660
tcgtgaattt cagccgttcg tggaagttaa ctggctgcat aatagcaagg atttcagcac   3720
gagcatggat ggtgtctccg ttacccagga cggcgcacgt aacattgcgg agatcaagac   3780
```

-continued

```
cggcgtcgag ggtcagctga atgcgaatct gaatgtttgg ggtaacgtgg gtgttcaagt   3840
agcggaccgt ggttacaatg ataccagcgc gatggtgggt attaagtggc agttttaact   3900
cgagccccaa gggcgacacc ccctaattag cccgggcgaa aggcccagtc tttcgactga   3960
gcctttcgtt ttatttgatg cctggcagtt ccctactctc gcatggggag tccccacact   4020
accatcggcg ctacggcgtt tcacttctga gttcggcatg gggtcaggtg ggaccaccgc   4080
gctactgccg ccaggcaaac aaggggtgtt atgagccata ttcaggtata aatgggctcg   4140
cgataatgtt cagaattggt taattggttg taacactgac ccctatttgt ttatttttct   4200
aaatacattc aaatatgtat ccgctcatga gacaataacc ctgataaatg cttcaataat   4260
attgaaaaag gaagaatatg agccatattc aacgggaaac gtcgaggccg cgattaaatt   4320
ccaacatgga tgctgattta tatgggtata aatgggctcg cgataatgtc gggcaatcag   4380
gtgcgacaat ctatcgcttg tatgggaagc ccgatgcgcc agagttgttt ctgaaacatg   4440
gcaaaggtag cgttgccaat gatgttacag atgagatggt cagactaaac tggctgacgg   4500
aatttatgcc acttccgacc atcaagcatt ttatccgtac tcctgatgat gcatggttac   4560
tcaccactgc gatccccgga aaaacagcgt tccaggtatt agaagaatat cctgattcag   4620
gtgaaaatat tgttgatgcg ctggcagtgt tcctgcgccg gttgcactcg attcctgttt   4680
gtaattgtcc ttttaacagc gatcgcgtat ttcgcctcgc tcaggcgcaa tcacgaatga   4740
ataacggttt ggttgatgcg agtgattttg atgacgagcg taatggctgg cctgttgaac   4800
aagtctggaa agaaatgcat aaacttttgc cattctcacc ggattcagtc gtcactcatg   4860
gtgatttctc acttgataac cttatttttg acgaggggaa attaataggt tgtattgatg   4920
ttggacgagt cggaatcgca gaccgatacc aggatcttgc catcctatgg aactgcctcg   4980
gtgagttttc tccttcatta cagaaacggc tttttcaaaa atatggtatt gataatcctg   5040
atatgaataa attgcagttt catttgatgc tcgatgagtt tttctaagcg gcgcgccatc   5100
gaatggcgca aaacctttcg cggtatggca tgatagcgcc cggaagagag tcaattcagg   5160
gtggtgaata tgaaaccagt aacgttatac gatgtcgcag agtatgccgg tgtctcttat   5220
cagaccgttt cccgcgtggt gaaccaggcc agccacgttt ctgcgaaaac gcgggaaaaa   5280
gtggaagcgg cgatggcgga gctgaattac attcccaacc gcgtggcaca acaactggcg   5340
ggcaaacagt cgttgctgat tggcgttgcc acctccagtc tggccctgca cgcgccgtcg   5400
caaattgtcg cggcgattaa atctcgcgcc gatcaactgg gtgccagcgt ggtggtgtcg   5460
atggtagaac gaagcggcgt cgaagcctgt aaagcggcgg tgcacaatct tctcgcgcaa   5520
cgcgtcagtg ggctgatcat taactatccg ctggatgacc aggatgccat tgctgtggaa   5580
gctgcctgca ctaatgttcc ggcgttattt cttgatgtct ctgaccagac acccatcaac   5640
agtattattt tctcccatga ggacggtacg cgactgggcg tggagcatct ggtcgcattg   5700
ggtcaccagc aaatcgcgct gttagcgggc ccattaagtt ctgtctcggc gcgtctgcgt   5760
ctggctggct ggcataaata tctcactcgc aatcaaattc agccgatagc ggaacgggaa   5820
ggcgactgga gtgccatgtc cggttttcaa caaaccatgc aaatgctgaa tgagggcatc   5880
gttcccactg cgatgctggt tgccaacgat cagatggcgc tgggcgcaat gcgcgccatt   5940
accgagtccg ggctgcgcgt tggtgcggat atctcggtag tgggatacga cgataccgaa   6000
gatagctcat gttatatccc gccgttaacc accatcaaac aggattttcg cctgctgggg   6060
caaaccagcg tggaccgctt gctgcaactc tctcagggcc aggcggtgaa gggcaatcag   6120
ctgttgccag tctcactggt gaaaagaaaa accaccctgg cgcccaatac gcaaaccgcc   6180
```

tctccccgcg cgttggccga ttcattaatg cagctggcac gacaggtttc ccgactggaa 6240
agcgggcagt ga 6252

<210> SEQ ID NO 14
<211> LENGTH: 771
<212> TYPE: PRT
<213> ORGANISM: Artificial Sequence
<220> FEATURE:
<223> OTHER INFORMATION: autotransporter fusion protein encoded by pMATE-SI015, for the surface display of 6xHis-mCherry using the pMATE system

<400> SEQUENCE: 14

Met Ile Lys Leu Lys Phe Gly Val Phe Phe Thr Val Leu Leu Ser Ser
1 5 10 15

Ala Tyr Ala His Gly Thr Pro Gln Asn Ile Thr His His His His His
20 25 30

His Met Val Ser Lys Gly Glu Glu Asp Asn Met Ala Ile Ile Lys Glu
35 40 45

Phe Met Arg Phe Lys Val His Met Glu Gly Ser Val Asn Gly His Glu
50 55 60

Phe Glu Ile Glu Gly Glu Gly Glu Gly Arg Pro Tyr Glu Gly Thr Gln
65 70 75 80

Thr Ala Lys Leu Lys Val Thr Lys Gly Gly Pro Leu Pro Phe Ala Trp
85 90 95

Asp Ile Leu Ser Pro Gln Phe Met Tyr Gly Ser Lys Ala Tyr Val Lys
100 105 110

His Pro Ala Asp Ile Pro Asp Tyr Leu Lys Leu Ser Phe Pro Glu Gly
115 120 125

Phe Lys Trp Glu Arg Val Met Asn Phe Glu Asp Gly Gly Val Val Thr
130 135 140

Val Thr Gln Asp Ser Ser Leu Gln Asp Gly Glu Phe Ile Tyr Lys Val
145 150 155 160

Lys Leu Arg Gly Thr Asn Phe Pro Ser Asp Gly Pro Val Met Gln Lys
165 170 175

Lys Thr Met Gly Trp Glu Ala Ser Ser Glu Arg Met Tyr Pro Glu Asp
180 185 190

Gly Ala Leu Lys Gly Glu Ile Lys Gln Arg Leu Lys Leu Lys Asp Gly
195 200 205

Gly His Tyr Asp Ala Glu Val Lys Thr Thr Tyr Lys Ala Lys Lys Pro
210 215 220

Val Gln Leu Pro Gly Ala Tyr Asn Val Asn Ile Lys Leu Asp Ile Thr
225 230 235 240

Ser His Asn Glu Asp Tyr Thr Ile Val Glu Gln Tyr Glu Arg Ala Glu
245 250 255

Gly Arg His Ser Thr Gly Gly Met Asp Glu Leu Tyr Lys Ala Arg Arg
260 265 270

Ala Ile Glu Gly Arg Ile Pro Glu Tyr Phe Lys Leu Thr Asn Asn Gly
275 280 285

Thr Leu Met Thr Gly Met Ser Gly Gln Gln Ala Gly Asn Val Leu Val
290 295 300

Val Lys Gly Asn Tyr His Gly Asn Asn Gly Gln Leu Val Met Asn Thr
305 310 315 320

Val Leu Asn Gly Asp Asp Ser Val Thr Asp Lys Leu Val Val Glu Gly
325 330 335

-continued

Asp Thr Ser Gly Thr Thr Ala Val Thr Val Asn Asn Ala Gly Gly Thr
340 345 350

Gly Ala Lys Thr Leu Asn Gly Ile Glu Leu Ile His Val Asp Gly Lys
355 360 365

Ser Glu Gly Glu Phe Val Gln Ala Gly Arg Ile Val Ala Gly Ala Tyr
370 375 380

Asp Tyr Thr Leu Ala Arg Gly Gln Gly Ala Asn Ser Gly Asn Trp Tyr
385 390 395 400

Leu Thr Ser Gly Ser Asp Ser Pro Glu Leu Gln Pro Glu Pro Asp Pro
405 410 415

Met Pro Asn Pro Glu Pro Asn Pro Asn Pro Glu Pro Asn Pro Asn Pro
420 425 430

Thr Pro Thr Pro Gly Pro Asp Leu Asn Val Asp Asn Asp Leu Arg Pro
435 440 445

Glu Ala Gly Ser Tyr Ile Ala Asn Leu Ala Ala Ala Asn Thr Met Phe
450 455 460

Thr Thr Arg Leu His Glu Arg Leu Gly Asn Thr Tyr Tyr Thr Asp Met
465 470 475 480

Val Thr Gly Glu Gln Lys Gln Thr Thr Met Trp Met Arg His Glu Gly
485 490 495

Gly His Asn Lys Trp Arg Asp Gly Ser Gly Gln Leu Lys Thr Gln Ser
500 505 510

Asn Arg Tyr Val Leu Gln Leu Gly Gly Asp Val Ala Gln Trp Ser Gln
515 520 525

Asn Gly Ser Asp Arg Trp His Val Gly Val Met Ala Gly Tyr Gly Asn
530 535 540

Ser Asp Ser Lys Thr Ile Ser Ser Arg Thr Gly Tyr Arg Ala Lys Ala
545 550 555 560

Ser Val Asn Gly Tyr Ser Thr Gly Leu Tyr Ala Thr Trp Tyr Ala Asp
565 570 575

Asp Glu Ser Arg Asn Gly Ala Tyr Leu Asp Ser Trp Ala Gln Tyr Ser
580 585 590

Trp Phe Asp Asn Thr Val Lys Gly Asp Asp Leu Gln Ser Glu Ser Tyr
595 600 605

Lys Ser Lys Gly Phe Thr Ala Ser Leu Glu Ala Gly Tyr Lys His Lys
610 615 620

Leu Ala Glu Phe Asn Gly Ser Gln Gly Thr Arg Asn Glu Trp Tyr Val
625 630 635 640

Gln Pro Gln Ala Gln Val Thr Trp Met Gly Val Lys Ala Asp Lys His
645 650 655

Arg Glu Ser Asn Gly Thr Leu Val His Ser Asn Gly Asp Gly Asn Val
660 665 670

Gln Thr Arg Leu Gly Val Lys Thr Trp Leu Lys Ser His His Lys Met
675 680 685

Asp Asp Gly Lys Ser Arg Glu Phe Gln Pro Phe Val Glu Val Asn Trp
690 695 700

Leu His Asn Ser Lys Asp Phe Ser Thr Ser Met Asp Gly Val Ser Val
705 710 715 720

Thr Gln Asp Gly Ala Arg Asn Ile Ala Glu Ile Lys Thr Gly Val Glu
725 730 735

Gly Gln Leu Asn Ala Asn Leu Asn Val Trp Gly Asn Val Gly Val Gln
740 745 750

Val Ala Asp Arg Gly Tyr Asn Asp Thr Ser Ala Met Val Gly Ile Lys
755 760 765

Trp Gln Phe
770

<210> SEQ ID NO 15
<211> LENGTH: 1349
<212> TYPE: PRT
<213> ORGANISM: Escherichia coli
<220> FEATURE:
<221> NAME/KEY: MISC_FEATURE
<223> OTHER INFORMATION: EhaA protein, accession number YP_003498036, genbank identifier GI:291281218

<400> SEQUENCE: 15

Met Ala Phe Asn Ala Leu Leu Phe Met Gln Ser Trp Phe Tyr Leu Asp
1 5 10 15

Val Leu Leu Glu Ile Val Met Asn Lys Ile Tyr Arg Leu Lys Trp Asn
20 25 30

Arg Ser Arg Asn Cys Trp Ser Val Cys Ser Glu Leu Gly Ser Arg Val
35 40 45

Lys Gly Lys Lys Ser Arg Ala Val Leu Ile Ser Ala Ile Ser Leu Tyr
50 55 60

Ser Ser Leu Val Phe Ala Asp Asp Val Ile Val Asn Gln Asp Lys Thr
65 70 75 80

Ile Asp Phe Gly Lys Glu Asn Gln Ser Ile Asp Tyr Arg Ile Thr Val
85 90 95

Thr Asp Asn Ala Asn Leu Val Ile Asn Ala Thr Asp Thr Ser Arg Pro
100 105 110

Arg Leu Thr Leu Ala Ser Gly Gly Gly Leu Asp Ile Thr Gly Gly Lys
115 120 125

Val Thr Ile Asn Gly Pro Leu Asn Phe Leu Leu Lys Gly Thr Gly Phe
130 135 140

Leu Asn Val Ser Asn Ala Gly Ser Glu Leu Tyr Ala Asp Asp Leu Tyr
145 150 155 160

Glu Ser Asn Ser Gly Met Arg His Asp Arg Gly Tyr Phe Asn Val Ser
165 170 175

Asn Gly Gly Lys Ile His Val Lys Gly Thr Ser Arg Leu Thr Tyr Leu
180 185 190

Gln Gly Asn Val Ser Gly Glu Gly Ser Gln Val Asn Ser Glu Thr Phe
195 200 205

Phe Met Gly Val Tyr Gly Ser Tyr Gly Gly Asn Gln Tyr Leu Ser Val
210 215 220

Asn Asn Gly Gly Glu Val Asn Ala Arg Lys Gln Ile Ser Leu Gly Tyr
225 230 235 240

Tyr Asp Gln Val Ser Asp Thr Thr Leu Ala Val Ser Glu Gly Gly Lys
245 250 255

Ile Ser Ala Pro Thr Ile Ser Leu Ser Thr Asn Ser Glu Leu Ala Leu
260 265 270

Gly Ala Gln Glu Gly Ser Ala Ala Lys Ala Ala Gly Ile Ile Asp Ala
275 280 285

Glu Lys Ile Glu Phe Val Trp Ala Lys Thr Ser Glu Lys Lys Ile Thr
290 295 300

Leu Asn His Thr Asp Lys Asp Ala Thr Ile Ser Ala Asp Ile Val Ser
305 310 315 320

Gly Ser Glu Gly Leu Gly Tyr Ile Asn Ala Leu Asn Gly Thr Thr Tyr

-continued

```
                325                 330                 335

Leu Thr Gly Asp Asn Ser Ala Phe Ser Gly Lys Val Lys Ile Glu Gln
            340                 345                 350

Asn Gly Ala Leu Gly Ile Thr Gln Asn Ile Gly Thr Ala Glu Ile Asn
        355                 360                 365

Asn Arg Gly Lys Leu His Leu Lys Ala Asp Asp Ser Met Thr Phe Ala
    370                 375                 380

Asn Lys Ile Ser Gly Asn Gly Thr Ile Ser Ile Asp Ser Gly Thr Val
385                 390                 395                 400

Glu Leu Thr Gly Asn Asn Tyr Ala Phe Ser Gly Tyr Ile Asp Val Ala
                405                 410                 415

Ser Gly Ala Val Ala Val Ile Ser Glu Asp Lys Asn Ile Gly Arg Ala
            420                 425                 430

Glu Leu Asp Val Asp Gly Lys Leu Gln Ile Asn Ala Asn Lys Asp Trp
        435                 440                 445

Val Phe Asp Asn Asp Leu Glu Gly Arg Gly Ile Val Glu Ile Asn Met
    450                 455                 460

Gly Asn His Glu Phe Ser Phe Asp Glu Phe Ala Tyr Thr Asp Trp Phe
465                 470                 475                 480

Gln Gly Ser Leu Ala Phe Gln Asn Thr Thr Phe Asn Leu Glu Lys Asn
                485                 490                 495

Ala Glu Phe Leu Gln Lys Gly Gly Ile Thr Ala Gly Gln Gly Ser Leu
            500                 505                 510

Val Thr Val Gly Lys Gly Ala His Ser Ile Ser Thr Leu Gly Phe Ser
        515                 520                 525

Gly Gly Thr Val Asp Phe Gly Ala Leu Thr Ala Gly Ala Gln Met Thr
    530                 535                 540

Glu Gly Thr Val Asn Val Ser Lys Thr Leu Asp Leu Arg Gly Glu Gly
545                 550                 555                 560

Val Ile Gln Val Ser Asp Ser Asp Val Val Arg Ser Val Ser Arg Asp
                565                 570                 575

Ile Asp Ser Ala Leu Ser Leu Thr Glu Val Asp Asp Gly Asn Ser Thr
            580                 585                 590

Ile Lys Leu Val Asp Ala Gln Gly Ala Glu Val Leu Gly Asp Ala Gly
        595                 600                 605

Asn Leu Gln Leu Gln Asp Lys Asn Gly Gln Ile Leu Ser Ser Ser Ala
    610                 615                 620

Gln Arg Asp Ile Gln Gln Asn Gly Gln Lys Ala Ala Val Gly Thr Tyr
625                 630                 635                 640

Asp Tyr Arg Leu Thr Ser Gly Val Asn Asn Asp Gly Leu Tyr Ile Gly
                645                 650                 655

Tyr Gly Leu Thr Gln Leu Asp Leu His Ala Thr Asp Ser Asp Ala Leu
            660                 665                 670

Val Leu Ser Ser Asn Gly Lys Ser Glu Asn Ala Ala Asp Leu Ser Ala
        675                 680                 685

Lys Ile Thr Gly Ser Gly Asp Leu Ala Phe Ser Ser Gln Lys Gly Gln
    690                 695                 700

Thr Val Ser Leu Ser Asn Lys Asp Asn Asp Tyr Thr Gly Val Thr Asp
705                 710                 715                 720

Leu Arg Ser Gly Thr Leu Leu Leu Asn Asn Asp Asn Val Leu Gly Asn
                725                 730                 735

Thr His Glu Leu Arg Leu Ala Ala Glu Thr Glu Leu Asp Met Asn Gly
            740                 745                 750
```

-continued

His Ser Gln Thr Val Gly Thr Leu Asn Gly Ser Ala Asp Ser Leu Leu
755 760 765

Ser Leu Asn Gly Gly Ser Leu Thr Val Thr Asn Gly Gly Thr Ser Thr
770 775 780

Gly Ser Leu Thr Gly Ser Gly Glu Leu Asn Ile Gln Gly Gly Thr Leu
785 790 795 800

Asp Ile Ala Gly Asp Asn Ser Asn Leu Thr Ala Asn Val Asn Ile Ala
805 810 815

Asn Ser Ala Asn Val Leu Val Ser His Ala Gln Gly Leu Gly Ser Ala
820 825 830

Asn Val Glu Asn Asn Gly Thr Leu Ala Leu Asn Asn Ser Ala Glu Lys
835 840 845

Arg Ala Ala Ala Ser Val Asn Tyr Ala Leu Gly Gly Asn Leu Thr Asn
850 855 860

Asn Gly Thr Leu Met Thr Gly Met Ser Gly Gln Gln Ala Gly Asn Val
865 870 875 880

Leu Val Val Lys Gly Asn Tyr His Gly Asn Asn Gly Gln Leu Val Met
885 890 895

Asn Thr Val Leu Asn Gly Asp Asp Ser Val Thr Asp Lys Leu Val Val
900 905 910

Glu Gly Asp Thr Ser Gly Thr Thr Ala Val Thr Val Asn Asn Ala Gly
915 920 925

Gly Thr Gly Ala Lys Thr Leu Asn Gly Ile Glu Leu Ile His Val Asp
930 935 940

Gly Lys Ser Glu Gly Glu Phe Val Gln Ala Gly Arg Ile Val Ala Gly
945 950 955 960

Ala Tyr Asp Tyr Thr Leu Ala Arg Gly Gln Gly Ala Asn Ser Gly Asn
965 970 975

Trp Tyr Leu Thr Ser Gly Ser Asp Ser Pro Glu Leu Gln Pro Glu Pro
980 985 990

Asp Pro Met Pro Asn Pro Glu Pro Asn Pro Asn Pro Glu Pro Asn Pro
995 1000 1005

Asn Pro Thr Pro Thr Pro Gly Pro Asp Leu Asn Val Asp Asn Asp
1010 1015 1020

Leu Arg Pro Glu Ala Gly Ser Tyr Ile Ala Asn Leu Ala Ala Ala
1025 1030 1035

Asn Thr Met Phe Thr Thr Arg Leu His Glu Arg Leu Gly Asn Thr
1040 1045 1050

Tyr Tyr Thr Asp Met Val Thr Gly Glu Gln Lys Gln Thr Thr Met
1055 1060 1065

Trp Met Arg His Glu Gly Gly His Asn Lys Trp Arg Asp Gly Ser
1070 1075 1080

Gly Gln Leu Lys Thr Gln Ser Asn Arg Tyr Val Leu Gln Leu Gly
1085 1090 1095

Gly Asp Val Ala Gln Trp Ser Gln Asn Gly Ser Asp Arg Trp His
1100 1105 1110

Val Gly Val Met Ala Gly Tyr Gly Asn Ser Asp Ser Lys Thr Ile
1115 1120 1125

Ser Ser Arg Thr Gly Tyr Arg Ala Lys Ala Ser Val Asn Gly Tyr
1130 1135 1140

Ser Thr Gly Leu Tyr Ala Thr Trp Tyr Ala Asp Asp Glu Ser Arg
1145 1150 1155

```
Asn Gly  Ala Tyr Leu Asp Ser  Trp Ala Gln Tyr Ser  Trp Phe Asp
    1160                 1165                 1170

Asn Thr  Val Lys Gly Asp Asp  Leu Gln Ser Glu Ser  Tyr Lys Ser
    1175                 1180                 1185

Lys Gly  Phe Thr Ala Ser Leu  Glu Ala Gly Tyr Lys  His Lys Leu
    1190                 1195                 1200

Ala Glu  Phe Asn Gly Ser Gln  Gly Thr Arg Asn Glu  Trp Tyr Val
    1205                 1210                 1215

Gln Pro  Gln Ala Gln Val Thr  Trp Met Gly Val Lys  Ala Asp Lys
    1220                 1225                 1230

His Arg  Glu Ser Asn Gly Thr  Leu Val His Ser Asn  Gly Asp Gly
    1235                 1240                 1245

Asn Val  Gln Thr Arg Leu Gly  Val Lys Thr Trp Leu  Lys Ser His
    1250                 1255                 1260

His Lys  Met Asp Asp Gly Lys  Ser Arg Glu Phe Gln  Pro Phe Val
    1265                 1270                 1275

Glu Val  Asn Trp Leu His Asn  Ser Lys Asp Phe Ser  Thr Ser Met
    1280                 1285                 1290

Asp Gly  Val Ser Val Thr Gln  Asp Gly Ala Arg Asn  Ile Ala Glu
    1295                 1300                 1305

Ile Lys  Thr Gly Val Glu Gly  Gln Leu Asn Ala Asn  Leu Asn Val
    1310                 1315                 1320

Trp Gly  Asn Val Gly Val Gln  Val Ala Asp Arg Gly  Tyr Asn Asp
    1325                 1330                 1335

Thr Ser  Ala Met Val Gly Ile  Lys Trp Gln Phe
    1340                 1345
```

<210> SEQ ID NO 16
<211> LENGTH: 612
<212> TYPE: DNA
<213> ORGANISM: Artificial Sequence
<220> FEATURE:
<223> OTHER INFORMATION: sequence encoding EhaA transmembrane linker, codon-optimized sequence derived from EhaA sequence of E. coli

<400> SEQUENCE: 16

```
ctgaccaaca atggcacgct gatgacgggt atgagcggtc aacaagcggg taacgttctg      60

gttgttaagg gcaattacca tggcaataac ggccagctgg tcatgaacac ggttctgaac     120

ggcgatgata gcgtgaccga caagctggtg gtcgagggcg acacctctgg tacgaccgca     180

gtgacggtga ataatgcagg cggtacgggt gccaaaaccc tgaacggtat tgagttgatc     240

cacgttgacg gtaagagcga gggcgagttt gtgcaggcag gccgcattgt tgctggcgct     300

tatgactata cgctggcccg tggtcagggc gcgaatagcg gtaactggta tctgaccagc     360

ggctccgact ccccggaact gcaaccggag cctgatccga tgccgaatcc ggagccaaac     420

ccgaacccgg aaccgaaccc aaatccgacc ccgactccgg gtccggactt gaacgttgat     480

aacgacctgc gtccggaggc cggttcgtac atcgcgaacc tggcagcggc caatacgatg     540

tttacgaccc gtctgcacga acgcctgggt aatacctact ataccgatat ggtcactggt     600

gaacagaaac aa                                                         612
```

<210> SEQ ID NO 17
<211> LENGTH: 204
<212> TYPE: PRT
<213> ORGANISM: Artificial Sequence
<220> FEATURE:
<223> OTHER INFORMATION: EhaA transmembrane linker sequence, derived from EhaA sequence obtained from E.coli

<400> SEQUENCE: 17

Leu Thr Asn Asn Gly Thr Leu Met Thr Gly Met Ser Gly Gln Gln Ala
1               5                   10                  15

Gly Asn Val Leu Val Val Lys Gly Asn Tyr His Gly Asn Asn Gly Gln
            20                  25                  30

Leu Val Met Asn Thr Val Leu Asn Gly Asp Asp Ser Val Thr Asp Lys
        35                  40                  45

Leu Val Val Glu Gly Asp Thr Ser Gly Thr Thr Ala Val Thr Val Asn
    50                  55                  60

Asn Ala Gly Gly Thr Gly Ala Lys Thr Leu Asn Gly Ile Glu Leu Ile
65                  70                  75                  80

His Val Asp Gly Lys Ser Glu Gly Glu Phe Val Gln Ala Gly Arg Ile
                85                  90                  95

Val Ala Gly Ala Tyr Asp Tyr Thr Leu Ala Arg Gly Gln Gly Ala Asn
            100                 105                 110

Ser Gly Asn Trp Tyr Leu Thr Ser Gly Ser Asp Ser Pro Glu Leu Gln
        115                 120                 125

Pro Glu Pro Asp Pro Met Pro Asn Pro Glu Pro Asn Pro Asn Pro Glu
    130                 135                 140

Pro Asn Pro Asn Pro Thr Pro Thr Pro Gly Pro Asp Leu Asn Val Asp
145                 150                 155                 160

Asn Asp Leu Arg Pro Glu Ala Gly Ser Tyr Ile Ala Asn Leu Ala Ala
                165                 170                 175

Ala Asn Thr Met Phe Thr Thr Arg Leu His Glu Arg Leu Gly Asn Thr
            180                 185                 190

Tyr Tyr Thr Asp Met Val Thr Gly Glu Gln Lys Gln
        195                 200

<210> SEQ ID NO 18
<211> LENGTH: 855
<212> TYPE: DNA
<213> ORGANISM: Artificial Sequence
<220> FEATURE:
<223> OTHER INFORMATION: sequence encoding EhaA transporter domain,
      codon-optimized sequence derived from EhaA sequence of E. coli

<400> SEQUENCE: 18
accaccatgt ggatgcgcca cgagggtggt cacaataagt ggcgcgacgg tagcggccag      60
ttgaaaaccc agagcaatcg ctacgttctg caattgggcg gtgatgtggc gcaatggagc     120
caaaacggca gcgaccgttg gcatgtcggt gtgatggcag gttacggcaa cagcgacagc     180
aagaccatct ccagccgtac cggttaccgt gcgaaggcaa gcgtcaacgg ttacagcacc     240
ggcctgtatg ccacctggta tgctgatgat gagagccgca acggtgctta cttggacagc     300
tgggcacagt attcttggtt cgataatacg gtgaaaggcg acgacctgca gagcgaaagc     360
tacaaatcga aaggtttcac cgcgagcctg gaagccggct ataagcacaa actggcggaa     420
ttcaatggca gccagggtac tcgtaacgaa tggtacgttc aaccgcaggc gcaagtcact     480
tggatgggcg ttaaggcgga taaacaccgt gagagcaacg gtacgttggt gcatagcaac     540
ggtgatggta atgtccaaac ccgtctgggt gtgaaaacgt ggctgaagtc ccatcacaaa     600
atggacgacg gtaaatctcg tgaatttcag ccgttcgtgg aagttaactg gctgcataat     660
agcaaggatt tcagcacgag catggatggt gtctccgtta cccaggacgg cgcacgtaac     720
attgcggaga tcaagaccgg cgtcgagggt cagctgaatg cgaatctgaa tgtttggggt     780
aacgtgggtg ttcaagtagc ggaccgtggt tacaatgata ccagcgcgat ggtgggtatt 840
aagtggcagt tttaa 855

<210> SEQ ID NO 19
<211> LENGTH: 284
<212> TYPE: PRT
<213> ORGANISM: Artificial Sequence
<220> FEATURE:
<223> OTHER INFORMATION: EhaA transporter domain derived from EhaA sequence of E.coli

<400> SEQUENCE: 19

Thr Thr Met Trp Met Arg His Glu Gly Gly His Asn Lys Trp Arg Asp
1 5 10 15

Gly Ser Gly Gln Leu Lys Thr Gln Ser Asn Arg Tyr Val Leu Gln Leu
20 25 30

Gly Gly Asp Val Ala Gln Trp Ser Gln Asn Gly Ser Asp Arg Trp His
35 40 45

Val Gly Val Met Ala Gly Tyr Gly Asn Ser Asp Ser Lys Thr Ile Ser
50 55 60

Ser Arg Thr Gly Tyr Arg Ala Lys Ala Ser Val Asn Gly Tyr Ser Thr
65 70 75 80

Gly Leu Tyr Ala Thr Trp Tyr Ala Asp Asp Glu Ser Arg Asn Gly Ala
85 90 95

Tyr Leu Asp Ser Trp Ala Gln Tyr Ser Trp Phe Asp Asn Thr Val Lys
100 105 110

Gly Asp Asp Leu Gln Ser Glu Ser Tyr Lys Ser Lys Gly Phe Thr Ala
115 120 125

Ser Leu Glu Ala Gly Tyr Lys His Lys Leu Ala Glu Phe Asn Gly Ser
130 135 140

Gln Gly Thr Arg Asn Glu Trp Tyr Val Gln Pro Gln Ala Gln Val Thr
145 150 155 160

Trp Met Gly Val Lys Ala Asp Lys His Arg Glu Ser Asn Gly Thr Leu
165 170 175

Val His Ser Asn Gly Asp Gly Asn Val Gln Thr Arg Leu Gly Val Lys
180 185 190

Thr Trp Leu Lys Ser His His Lys Met Asp Asp Gly Lys Ser Arg Glu
195 200 205

Phe Gln Pro Phe Val Glu Val Asn Trp Leu His Asn Ser Lys Asp Phe
210 215 220

Ser Thr Ser Met Asp Gly Val Ser Val Thr Gln Asp Gly Ala Arg Asn
225 230 235 240

Ile Ala Glu Ile Lys Thr Gly Val Glu Gly Gln Leu Asn Ala Asn Leu
245 250 255

Asn Val Trp Gly Asn Val Gly Val Gln Val Ala Asp Arg Gly Tyr Asn
260 265 270

Asp Thr Ser Ala Met Val Gly Ile Lys Trp Gln Phe
275 280

<210> SEQ ID NO 20
<211> LENGTH: 4002
<212> TYPE: DNA
<213> ORGANISM: Artificial Sequence
<220> FEATURE:
<223> OTHER INFORMATION: Nucleotide sequence of the autotransporter fusion gene encoded by pMATE-exoglucanase, for the surface display of an exoglucanase using the pMATE system

<400> SEQUENCE: 20
atgatcaaac tgaaattcgg cgtcttcttc accgtactgc tgtcctctgc ttacgctcac 60
ggtactccgc agaacatcac ccaccaccat caccatcata tcgaaggtcg tctcgagctg 120
gaagataaaa gcagcaaact gccggattac aaaaacgatc tgctgtatga acgtaccttt 180
gatgaaggtc tgtgttttcc gtggcatacc tgtgaagata gcggtggtaa atgtgatttt 240
gccgttgttg atgttccggg tgaaccgggt aataaagcat ttcgtctgac cgttattgat 300
aaaggccaga ataaatggtc agtgcagatg cgtcatcgtg gtattaccct ggaacagggt 360
catacctata ccgttcgttt taccatttgg agcgataaaa gctgtcgtgt gtatgcaaaa 420
attggtcaga tgggcgaacc gtataccgaa tattggaata ataactggaa cccgtttaat 480
ctgacccctg gtcagaaact gaccgttgaa cagaatttta ccatgaacta tccgaccgat 540
gatacctgcg aattcacctt tcatctgggt ggtgaactgg cagcaggcac cccgtattat 600
gtttatctgg atgatgttag cctgtacgat ccgcgttttg ttaaaccggt tgaatatgtt 660
ctgccgcagc cggatgttcg tgttaatcag gttggttatc tgccgtttgc caaaaaatac 720
gcaaccgttg ttagcagcag caccagtccg ctgaaatggc agctgctgaa tagcgcaaat 780
caggtggttc tggaaggcaa taccattccg aaaggtctgg ataaagatag ccaggattat 840
gtgcattgga tcgatttcag caactttaaa accgaaggca aaggctacta ctttaaactg 900
ccgaccgtta atagcgatac caattatagc catccgtttg atattagcgc agatatctat 960
agcaaaatga aatttgatgc cctggccttc ttttatcata aacgtagcgg tattccgatc 1020
gaaatgccgt atgcaggcgg tgaacagtgg acccgtccgg caggtcatat tggtattgaa 1080
ccgaataaag gtgataccaa tgttccgacc tggcctcagg atgatgaata tgcaggtcgt 1140
ccgcagaaat attacaccaa agatgttacc ggtggttggt atgatgccgg tgatcatggc 1200
aaatatgttg tgaatggtgg tattgcagtt tggaccctga tgaacatgta tgagcgtgcc 1260
aaaattcgcg gtattgccaa tcagggtgca tataaagatg gtggcatgaa tattccggaa 1320
cgcaataatg gttatccgga cattctggat gaagcacgtt gggaaattga atttttcaaa 1380
aaaatgcagg ttaccgaaaa agaagatccg agcattgcag gtatggtgca tcataaaatt 1440
catgattttc gttggaccgc actgggtatg ctgccgcatg aagatccgca gcctcgttat 1500
ctgcgtccgg ttagcaccgc agcaaccctg aattttgcag ccaccctggc acagagcgca 1560
cgtctgtgga aagattatga tccgaccttt gcagcagatt gtctggaaaa agcagaaatt 1620
gcatggcagg cagcactgaa acatccggat atttatgcag aatatacacc gggtagtggt 1680
ggtccgggtg gcggtccgta taatgatgat tatgttggtg atgagtttta ttgggcagcc 1740
tgtgaactgt atgttaccac cggcaaagat gagtataaaa actatctgat gaactcaccg 1800
cactacctgg aaatgcctgc aaaaatgggt gaaaatggtg gtgcaaatgg tgaagataat 1860
ggtctgtggg gttgttttac ctggggtaca acccagggtc tgggcaccat tacactggca 1920
ctggtggaaa atggtctgcc tgcaaccgat attcagaaag cacgtaataa cattgcaaaa 1980
gcagccgatc gttggctgga aaatattgaa gaacagggtt atcgtctgcc gattaaacag 2040
gccgaagatg aacgtggtgg ctatccgtgg ggtagcaata gctttattct gaatcagatg 2100
atcgtgatgg gctatgccta tgattttacc ggcaatagca aatatctgga cggtatgcag 2160
gatggtatga gctatctgct gggtcgcaat ggtctggatc agagctatgt gaccggttat 2220
ggtgaacgtc cgctgcagaa tccgcatgat cgcttttgga caccgcagac cagcaaaaaa 2280

```
ttccctgcac cgcctccggg tattattgcg ggtggtccga atagccgttt tgaagatcct   2340

accattaccg cagcagtgaa aaaagatacc cctcctcaga aatgctatat cgatcatacc   2400

gatagctggt ccaccaatga aattaccgtt aattggaatg caccgtttgc atgggttacc   2460

gcgtacctgg atgaaattga tctgattggt accgctcgtc gtgctattga gggccgcatc   2520

ccggaatact ttaaactgac caacaatggc acgctgatga cgggtatgag cggtcaacaa   2580

gcgggtaacg ttctggttgt taagggcaat taccatggca ataacggcca gctggtcatg   2640

aacacggttc tgaacggcga tgatagcgtg accgacaagc tggtggtcga gggcgacacc   2700

tctggtacga ccgcagtgac ggtgaataat gcaggcggta cgggtgccaa aaccctgaac   2760

ggtattgagt tgatccacgt tgacggtaag agcgagggcg agtttgtgca ggcaggccgc   2820

attgttgctg gcgcttatga ctatacgctg gcccgtggtc agggcgcgaa tagcggtaac   2880

tggtatctga ccagcggctc cgactccccg gaactgcaac cggagcctga tccgatgccg   2940

aatccggagc caaacccgaa cccggaaccg aacccaaatc cgaccccgac tccgggtccg   3000

gacttgaacg ttgataacga cctgcgtccg gaggccggtt cgtacatcgc gaacctggca   3060

gcggccaata cgatgtttac gacccgtctg cacgaacgcc tgggtaatac ctactatacc   3120

gatatggtca ctggtgaaca gaaacaaacc accatgtgga tgcgccacga gggtggtcac   3180

aataagtggc gcgacggtag cggccagttg aaaacccaga gcaatcgcta cgttctgcaa   3240

ttgggcggtg atgtggcgca atggagccaa aacggcagcg accgttggca tgtcggtgtg   3300

atggcaggtt acggcaacag cgacagcaag accatctcca gccgtaccgg ttaccgtgcg   3360

aaggcaagcg tcaacggtta cagcaccggc ctgtatgcca cctggtatgc tgatgatgag   3420

agccgcaacg gtgcttactt ggacagctgg gcacagtatt cttggttcga taatacggtg   3480

aaaggcgacg acctgcagag cgaaagctac aaatcgaaag gtttcaccgc gagcctggaa   3540

gccggctata agcacaaact ggcggaattc aatggcagcc agggtactcg taacgaatgg   3600

tacgttcaac cgcaggcgca agtcacttgg atgggcgtta aggcggataa acaccgtgag   3660

agcaacggta cgttggtgca tagcaacggt gatggtaatg tccaaacccg tctgggtgtg   3720

aaaacgtggc tgaagtccca tcacaaaatg gacgacggta aatctcgtga atttcagccg   3780

ttcgtggaag ttaactggct gcataatagc aaggatttca gcacgagcat ggatggtgtc   3840

tccgttaccc aggacggcgc acgtaacatt gcggagatca agaccggcgt cgagggtcag   3900

ctgaatgcga atctgaatgt ttggggtaac gtgggtgttc aagtagcgga ccgtggttac   3960

aatgatacca gcgcgatggt gggtattaag tggcagtttt aa                     4002
```

<210> SEQ ID NO 21
<211> LENGTH: 1333
<212> TYPE: PRT
<213> ORGANISM: Artificial Sequence
<220> FEATURE:
<223> OTHER INFORMATION: Polypeptide sequence of the autotransporter fusion protein encoded by pMATE-exoglucanase, for the surface display of an exoglucanase using the pMATE system

<400> SEQUENCE: 21

```
Met Ile Lys Leu Lys Phe Gly Val Phe Phe Thr Val Leu Leu Ser Ser
1               5                   10                  15

Ala Tyr Ala His Gly Thr Pro Gln Asn Ile Thr His His His His His
            20                  25                  30

His Ile Glu Gly Arg Leu Glu Leu Glu Asp Lys Ser Ser Lys Leu Pro
        35                  40                  45
```

-continued

```
Asp Tyr Lys Asn Asp Leu Leu Tyr Glu Arg Thr Phe Asp Glu Gly Leu
    50                  55                  60

Cys Phe Pro Trp His Thr Cys Glu Asp Ser Gly Gly Lys Cys Asp Phe
65                  70                  75                  80

Ala Val Val Asp Val Pro Gly Glu Pro Gly Asn Lys Ala Phe Arg Leu
                85                  90                  95

Thr Val Ile Asp Lys Gly Gln Asn Lys Trp Ser Val Gln Met Arg His
            100                 105                 110

Arg Gly Ile Thr Leu Glu Gln Gly His Thr Tyr Thr Val Arg Phe Thr
        115                 120                 125

Ile Trp Ser Asp Lys Ser Cys Arg Val Tyr Ala Lys Ile Gly Gln Met
    130                 135                 140

Gly Glu Pro Tyr Thr Glu Tyr Trp Asn Asn Asn Trp Asn Pro Phe Asn
145                 150                 155                 160

Leu Thr Pro Gly Gln Lys Leu Thr Val Glu Gln Asn Phe Thr Met Asn
                165                 170                 175

Tyr Pro Thr Asp Asp Thr Cys Glu Phe Thr Phe His Leu Gly Gly Glu
            180                 185                 190

Leu Ala Ala Gly Thr Pro Tyr Tyr Val Tyr Leu Asp Asp Val Ser Leu
        195                 200                 205

Tyr Asp Pro Arg Phe Val Lys Pro Val Glu Tyr Val Leu Pro Gln Pro
    210                 215                 220

Asp Val Arg Val Asn Gln Val Gly Tyr Leu Pro Phe Ala Lys Lys Tyr
225                 230                 235                 240

Ala Thr Val Val Ser Ser Ser Thr Ser Pro Leu Lys Trp Gln Leu Leu
                245                 250                 255

Asn Ser Ala Asn Gln Val Val Leu Glu Gly Asn Thr Ile Pro Lys Gly
            260                 265                 270

Leu Asp Lys Asp Ser Gln Asp Tyr Val His Trp Ile Asp Phe Ser Asn
        275                 280                 285

Phe Lys Thr Glu Gly Lys Gly Tyr Tyr Phe Lys Leu Pro Thr Val Asn
    290                 295                 300

Ser Asp Thr Asn Tyr Ser His Pro Phe Asp Ile Ser Ala Asp Ile Tyr
305                 310                 315                 320

Ser Lys Met Lys Phe Asp Ala Leu Ala Phe Phe Tyr His Lys Arg Ser
                325                 330                 335

Gly Ile Pro Ile Glu Met Pro Tyr Ala Gly Gly Glu Gln Trp Thr Arg
            340                 345                 350

Pro Ala Gly His Ile Gly Ile Glu Pro Asn Lys Gly Asp Thr Asn Val
        355                 360                 365

Pro Thr Trp Pro Gln Asp Asp Glu Tyr Ala Gly Arg Pro Gln Lys Tyr
    370                 375                 380

Tyr Thr Lys Asp Val Thr Gly Gly Trp Tyr Asp Ala Gly Asp His Gly
385                 390                 395                 400

Lys Tyr Val Val Asn Gly Gly Ile Ala Val Trp Thr Leu Met Asn Met
                405                 410                 415

Tyr Glu Arg Ala Lys Ile Arg Gly Ile Ala Asn Gln Gly Ala Tyr Lys
            420                 425                 430

Asp Gly Gly Met Asn Ile Pro Glu Arg Asn Asn Gly Tyr Pro Asp Ile
        435                 440                 445

Leu Asp Glu Ala Arg Trp Glu Ile Glu Phe Phe Lys Lys Met Gln Val
    450                 455                 460

Thr Glu Lys Glu Asp Pro Ser Ile Ala Gly Met Val His His Lys Ile
```

-continued

```
465                 470                 475                 480

His Asp Phe Arg Trp Thr Ala Leu Gly Met Leu Pro His Glu Asp Pro
                485                 490                 495

Gln Pro Arg Tyr Leu Arg Pro Val Ser Thr Ala Ala Thr Leu Asn Phe
            500                 505                 510

Ala Ala Thr Leu Ala Gln Ser Ala Arg Leu Trp Lys Asp Tyr Asp Pro
        515                 520                 525

Thr Phe Ala Ala Asp Cys Leu Glu Lys Ala Glu Ile Ala Trp Gln Ala
    530                 535                 540

Ala Leu Lys His Pro Asp Ile Tyr Ala Glu Tyr Thr Pro Gly Ser Gly
545                 550                 555                 560

Gly Pro Gly Gly Gly Pro Tyr Asn Asp Asp Tyr Val Gly Asp Glu Phe
                565                 570                 575

Tyr Trp Ala Ala Cys Glu Leu Tyr Val Thr Thr Gly Lys Asp Glu Tyr
            580                 585                 590

Lys Asn Tyr Leu Met Asn Ser Pro His Tyr Leu Glu Met Pro Ala Lys
        595                 600                 605

Met Gly Glu Asn Gly Gly Ala Asn Gly Glu Asp Asn Gly Leu Trp Gly
    610                 615                 620

Cys Phe Thr Trp Gly Thr Thr Gln Gly Leu Gly Thr Ile Thr Leu Ala
625                 630                 635                 640

Leu Val Glu Asn Gly Leu Pro Ala Thr Asp Ile Gln Lys Ala Arg Asn
                645                 650                 655

Asn Ile Ala Lys Ala Ala Asp Arg Trp Leu Glu Asn Ile Glu Glu Gln
            660                 665                 670

Gly Tyr Arg Leu Pro Ile Lys Gln Ala Glu Asp Glu Arg Gly Gly Tyr
        675                 680                 685

Pro Trp Gly Ser Asn Ser Phe Ile Leu Asn Gln Met Ile Val Met Gly
    690                 695                 700

Tyr Ala Tyr Asp Phe Thr Gly Asn Ser Lys Tyr Leu Asp Gly Met Gln
705                 710                 715                 720

Asp Gly Met Ser Tyr Leu Leu Gly Arg Asn Gly Leu Asp Gln Ser Tyr
                725                 730                 735

Val Thr Gly Tyr Gly Glu Arg Pro Leu Gln Asn Pro His Asp Arg Phe
            740                 745                 750

Trp Thr Pro Gln Thr Ser Lys Lys Phe Pro Ala Pro Pro Pro Gly Ile
        755                 760                 765

Ile Ala Gly Gly Pro Asn Ser Arg Phe Glu Asp Pro Thr Ile Thr Ala
    770                 775                 780

Ala Val Lys Lys Asp Thr Pro Pro Gln Lys Cys Tyr Ile Asp His Thr
785                 790                 795                 800

Asp Ser Trp Ser Thr Asn Glu Ile Thr Val Asn Trp Asn Ala Pro Phe
                805                 810                 815

Ala Trp Val Thr Ala Tyr Leu Asp Glu Ile Asp Leu Ile Gly Thr Ala
            820                 825                 830

Arg Arg Ala Ile Glu Gly Arg Ile Pro Glu Tyr Phe Lys Leu Thr Asn
        835                 840                 845

Asn Gly Thr Leu Met Thr Gly Met Ser Gly Gln Gln Ala Gly Asn Val
    850                 855                 860

Leu Val Val Lys Gly Asn Tyr His Gly Asn Asn Gly Gln Leu Val Met
865                 870                 875                 880

Asn Thr Val Leu Asn Gly Asp Asp Ser Val Thr Asp Lys Leu Val Val
                885                 890                 895
```

-continued

```
Glu Gly Asp Thr Ser Gly Thr Thr Ala Val Thr Val Asn Asn Ala Gly
            900                 905                 910

Gly Thr Gly Ala Lys Thr Leu Asn Gly Ile Glu Leu Ile His Val Asp
        915                 920                 925

Gly Lys Ser Glu Gly Glu Phe Val Gln Ala Gly Arg Ile Val Ala Gly
    930                 935                 940

Ala Tyr Asp Tyr Thr Leu Ala Arg Gly Gln Gly Ala Asn Ser Gly Asn
945                 950                 955                 960

Trp Tyr Leu Thr Ser Gly Ser Asp Ser Pro Glu Leu Gln Pro Glu Pro
                965                 970                 975

Asp Pro Met Pro Asn Pro Glu Pro Asn Pro Asn Pro Glu Pro Asn Pro
            980                 985                 990

Asn Pro Thr Pro Thr Pro Gly Pro  Asp Leu Asn Val Asp  Asn Asp Leu
        995                 1000                1005

Arg Pro  Glu Ala Gly Ser Tyr  Ile Ala Asn Leu Ala  Ala Ala Asn
    1010                1015                1020

Thr Met  Phe Thr Thr Arg Leu  His Glu Arg Leu Gly  Asn Thr Tyr
    1025                1030                1035

Tyr Thr  Asp Met Val Thr Gly  Glu Gln Lys Gln Thr  Thr Met Trp
    1040                1045                1050

Met Arg  His Glu Gly Gly His  Asn Lys Trp Arg Asp  Gly Ser Gly
    1055                1060                1065

Gln Leu  Lys Thr Gln Ser Asn  Arg Tyr Val Leu Gln  Leu Gly Gly
    1070                1075                1080

Asp Val  Ala Gln Trp Ser Gln  Asn Gly Ser Asp Arg  Trp His Val
    1085                1090                1095

Gly Val  Met Ala Gly Tyr Gly  Asn Ser Asp Ser Lys  Thr Ile Ser
    1100                1105                1110

Ser Arg  Thr Gly Tyr Arg Ala  Lys Ala Ser Val Asn  Gly Tyr Ser
    1115                1120                1125

Thr Gly  Leu Tyr Ala Thr Trp  Tyr Ala Asp Asp Glu  Ser Arg Asn
    1130                1135                1140

Gly Ala  Tyr Leu Asp Ser Trp  Ala Gln Tyr Ser Trp  Phe Asp Asn
    1145                1150                1155

Thr Val  Lys Gly Asp Asp Leu  Gln Ser Glu Ser Tyr  Lys Ser Lys
    1160                1165                1170

Gly Phe  Thr Ala Ser Leu Glu  Ala Gly Tyr Lys His  Lys Leu Ala
    1175                1180                1185

Glu Phe  Asn Gly Ser Gln Gly  Thr Arg Asn Glu Trp  Tyr Val Gln
    1190                1195                1200

Pro Gln  Ala Gln Val Thr Trp  Met Gly Val Lys Ala  Asp Lys His
    1205                1210                1215

Arg Glu  Ser Asn Gly Thr Leu  Val His Ser Asn Gly  Asp Gly Asn
    1220                1225                1230

Val Gln  Thr Arg Leu Gly Val  Lys Thr Trp Leu Lys  Ser His His
    1235                1240                1245

Lys Met  Asp Asp Gly Lys Ser  Arg Glu Phe Gln Pro  Phe Val Glu
    1250                1255                1260

Val Asn  Trp Leu His Asn Ser  Lys Asp Phe Ser Thr  Ser Met Asp
    1265                1270                1275

Gly Val  Ser Val Thr Gln Asp  Gly Ala Arg Asn Ile  Ala Glu Ile
    1280                1285                1290
```

-continued

```
Lys Thr  Gly Val Glu Gly Gln  Leu Asn Ala Asn Leu  Asn Val Trp
    1295                 1300                 1305

Gly Asn  Val Gly Val Gln Val  Ala Asp Arg Gly Tyr  Asn Asp Thr
    1310                 1315                 1320

Ser Ala  Met Val Gly Ile Lys  Trp Gln Phe
    1325                 1330


<210> SEQ ID NO 22
<211> LENGTH: 3042
<212> TYPE: DNA
<213> ORGANISM: Artificial Sequence
<220> FEATURE:
<223> OTHER INFORMATION: Nucleotide sequence of the autotransporter
      fusion gene encoded by pMATE-endoglucanase, for the surface
      display of an endoglucanase using the pMATE system

<400> SEQUENCE: 22

atgatcaaac tgaaattcgg cgtcttcttc accgtactgc tgtcctctgc ttacgctcac     60

ggtactccgc agaacatcac ccaccaccat caccatcata tcgaaggtcg tctcgaggca    120

ggcaccaaaa caccggttgc aaaaaatggt cagctgagta ttaaaggcac ccagctggtt    180

aatcgtgatg gtaaagcagt gcagctgaaa ggtattagca gccatggtct gcagtggtat    240

ggtgaatttg ttaataaaga cagcctgaaa tggctgcgtg atgattgggg tattaccgtt    300

tttcgtgcag caatgtatac cgcagatggt ggctatattg ataatccgag cgttaaaaac    360

aaagtgaaag aagcagttga agcagccaaa gaactgggca tttatgtgat tattgattgg    420

cacattctga acgatggtaa tccgaatcag aacaaagaaa aagcgaaaga atttttcaaa    480

gaaatgagca gcctgtatgg caataccccg aatgtgattt atgaaattgc caatgaaccg    540

aatggtgatg tgaattggaa acgcgatatc aaaccgtatg ccgaagaagt gattagcgtt    600

attcgtaaaa atgacccgga caacattatt atcgttggca ccggcacctg gtcacaggat    660

gttaatgatg cagcagatga tcaactgaaa gatgccaatg ttatgtatgc cctgcatttt    720

tatgcaggca cccatggtca gtttctgcgt gataaagcaa attatgcact gagcaaaggt    780

gcaccggttt ttgttaccga atggggcacc agtgatgcaa gcggtaatgg tggtgttttt    840

ctggatcaga gccgtgaatg gctgaattat ctggatagca aaaccattag ctgggtgaac    900

tggaatctga gcgataaaca agaaagcagc agcgcactga aaccgggtgc aagcaaaaca    960

ggtggttggc gtctgagtga tctgagcgca agcggcacct ttgttcgtga aaatattctg   1020

ggtacaaaag atagcaccaa agacattccg gaaacaccgg caaaagataa accgacccaa   1080

gaaaatggta ttagcgttca gtatcgtgcc ggtgatggta gcatgaatag caatcagatt   1140

cgtccgcagc tgcagatcaa aaacaatggt aataccaccg tggatctgaa agacgttacc   1200

gcacgttatt ggtataacgc caaaaacaaa ggccagaatg tggattgtga ttatgcacag   1260

ctgggttgtg gtaatatgac ccataaattt gtgacactgc acaaaccgaa acagggtgca   1320

gatacctatc tggaactggg tttcaaaaat ggcaccctgg caccgggtgc ctcaaccggt   1380

aatattcagc tgcgtctgca taacgatgat tggagcaatt atgcccagag cggtgattat   1440

agctttttca aaagcaacac ctttaaaacc accaaaaaaa tcaccctgta tgaccagggt   1500

aaactgattt ggggcaccga accgaacggt accgctcgtc gtgctattga gggccgcatc   1560

ccggaatact ttaaactgac caacaatggc acgctgatga cgggtatgag cggtcaacaa   1620

gcgggtaacg ttctggttgt taagggcaat taccatggca ataacggcca gctggtcatg   1680

aacacggttc tgaacggcga tgatagcgtg accgacaagc tggtggtcga gggcgacacc   1740
```

-continued

```
tctggtacga ccgcagtgac ggtgaataat gcaggcggta cgggtgccaa aaccctgaac   1800

ggtattgagt tgatccacgt tgacggtaag agcgagggcg agtttgtgca ggcaggccgc   1860

attgttgctg gcgcttatga ctatacgctg gcccgtggtc agggcgcgaa tagcggtaac   1920

tggtatctga ccagcggctc cgactccccg gaactgcaac cggagcctga tccgatgccg   1980

aatccggagc caaacccgaa cccggaaccg aacccaaatc cgaccccgac tccgggtccg   2040

gacttgaacg ttgataacga cctgcgtccg gaggccggtt cgtacatcgc gaacctggca   2100

gcggccaata cgatgtttac gacccgtctg cacgaacgcc tgggtaatac ctactatacc   2160

gatatggtca ctggtgaaca gaaacaaacc accatgtgga tgcgccacga gggtggtcac   2220

aataagtggc gcgacggtag cggccagttg aaaacccaga gcaatcgcta cgttctgcaa   2280

ttgggcggtg atgtggcgca atggagccaa aacggcagcg accgttggca tgtcggtgtg   2340

atggcaggtt acggcaacag cgacagcaag accatctcca gccgtaccgg ttaccgtgcg   2400

aaggcaagcg tcaacggtta cagcaccggc ctgtatgcca cctggtatgc tgatgatgag   2460

agccgcaacg gtgcttactt ggacagctgg gcacagtatt cttggttcga taatacggtg   2520

aaaggcgacg acctgcagag cgaaagctac aaatcgaaag gtttcaccgc gagcctggaa   2580

gccggctata agcacaaact ggcggaattc aatggcagcc agggtactcg taacgaatgg   2640

tacgttcaac cgcaggcgca agtcacttgg atgggcgtta aggcggataa acaccgtgag   2700

agcaacggta cgttggtgca tagcaacggt gatggtaatg tccaaacccg tctgggtgtg   2760

aaaacgtggc tgaagtccca tcacaaaatg gacgacggta aatctcgtga atttcagccg   2820

ttcgtggaag ttaactggct gcataatagc aaggatttca gcacgagcat ggatggtgtc   2880

tccgttaccc aggacggcgc acgtaacatt gcggagatca agaccggcgt cgagggtcag   2940

ctgaatgcga atctgaatgt ttggggtaac gtgggtgttc aagtagcgga ccgtggttac   3000

aatgatacca gcgcgatggt gggtattaag tggcagtttt aa                      3042
```

<210> SEQ ID NO 23
<211> LENGTH: 1013
<212> TYPE: PRT
<213> ORGANISM: Artificial Sequence
<220> FEATURE:
<223> OTHER INFORMATION: Polypeptide sequence of the autotransporter fusion protein encoded by pMATE-endoglucanase, for the surface display of an endoglucanase using the pMATE system

<400> SEQUENCE: 23

```
Met Ile Lys Leu Lys Phe Gly Val Phe Phe Thr Val Leu Leu Ser Ser
1               5                   10                  15

Ala Tyr Ala His Gly Thr Pro Gln Asn Ile Thr His His His His His
            20                  25                  30

His Ile Glu Gly Arg Leu Glu Ala Gly Thr Lys Thr Pro Val Ala Lys
        35                  40                  45

Asn Gly Gln Leu Ser Ile Lys Gly Thr Gln Leu Val Asn Arg Asp Gly
    50                  55                  60

Lys Ala Val Gln Leu Lys Gly Ile Ser Ser His Gly Leu Gln Trp Tyr
65                  70                  75                  80

Gly Glu Phe Val Asn Lys Asp Ser Leu Lys Trp Leu Arg Asp Asp Trp
                85                  90                  95

Gly Ile Thr Val Phe Arg Ala Ala Met Tyr Thr Ala Asp Gly Gly Tyr
            100                 105                 110

Ile Asp Asn Pro Ser Val Lys Asn Lys Val Lys Glu Ala Val Glu Ala
        115                 120                 125
```

-continued

```
Ala Lys Glu Leu Gly Ile Tyr Val Ile Ile Asp Trp His Ile Leu Asn
    130                 135                 140

Asp Gly Asn Pro Asn Gln Asn Lys Glu Lys Ala Lys Glu Phe Phe Lys
145                 150                 155                 160

Glu Met Ser Ser Leu Tyr Gly Asn Thr Pro Asn Val Ile Tyr Glu Ile
                165                 170                 175

Ala Asn Glu Pro Asn Gly Asp Val Asn Trp Lys Arg Asp Ile Lys Pro
            180                 185                 190

Tyr Ala Glu Glu Val Ile Ser Val Ile Arg Lys Asn Asp Pro Asp Asn
        195                 200                 205

Ile Ile Ile Val Gly Thr Gly Thr Trp Ser Gln Asp Val Asn Asp Ala
    210                 215                 220

Ala Asp Asp Gln Leu Lys Asp Ala Asn Val Met Tyr Ala Leu His Phe
225                 230                 235                 240

Tyr Ala Gly Thr His Gly Gln Phe Leu Arg Asp Lys Ala Asn Tyr Ala
                245                 250                 255

Leu Ser Lys Gly Ala Pro Val Phe Val Thr Glu Trp Gly Thr Ser Asp
            260                 265                 270

Ala Ser Gly Asn Gly Gly Val Phe Leu Asp Gln Ser Arg Glu Trp Leu
        275                 280                 285

Asn Tyr Leu Asp Ser Lys Thr Ile Ser Trp Val Asn Trp Asn Leu Ser
    290                 295                 300

Asp Lys Gln Glu Ser Ser Ser Ala Leu Lys Pro Gly Ala Ser Lys Thr
305                 310                 315                 320

Gly Gly Trp Arg Leu Ser Asp Leu Ser Ala Ser Gly Thr Phe Val Arg
                325                 330                 335

Glu Asn Ile Leu Gly Thr Lys Asp Ser Thr Lys Asp Ile Pro Glu Thr
            340                 345                 350

Pro Ala Lys Asp Lys Pro Thr Gln Glu Asn Gly Ile Ser Val Gln Tyr
        355                 360                 365

Arg Ala Gly Asp Gly Ser Met Asn Ser Asn Gln Ile Arg Pro Gln Leu
    370                 375                 380

Gln Ile Lys Asn Asn Gly Asn Thr Thr Val Asp Leu Lys Asp Val Thr
385                 390                 395                 400

Ala Arg Tyr Trp Tyr Asn Ala Lys Asn Lys Gly Gln Asn Val Asp Cys
                405                 410                 415

Asp Tyr Ala Gln Leu Gly Cys Gly Asn Met Thr His Lys Phe Val Thr
            420                 425                 430

Leu His Lys Pro Lys Gln Gly Ala Asp Thr Tyr Leu Glu Leu Gly Phe
        435                 440                 445

Lys Asn Gly Thr Leu Ala Pro Gly Ala Ser Thr Gly Asn Ile Gln Leu
    450                 455                 460

Arg Leu His Asn Asp Asp Trp Ser Asn Tyr Ala Gln Ser Gly Asp Tyr
465                 470                 475                 480

Ser Phe Phe Lys Ser Asn Thr Phe Lys Thr Thr Lys Lys Ile Thr Leu
                485                 490                 495

Tyr Asp Gln Gly Lys Leu Ile Trp Gly Thr Glu Pro Asn Gly Thr Ala
            500                 505                 510

Arg Arg Ala Ile Glu Gly Arg Ile Pro Glu Tyr Phe Lys Leu Thr Asn
        515                 520                 525

Asn Gly Thr Leu Met Thr Gly Met Ser Gly Gln Gln Ala Gly Asn Val
    530                 535                 540
```

```
Leu Val Val Lys Gly Asn Tyr His Gly Asn Asn Gly Gln Leu Val Met
545                 550                 555                 560

Asn Thr Val Leu Asn Gly Asp Asp Ser Val Thr Asp Lys Leu Val Val
                565                 570                 575

Glu Gly Asp Thr Ser Gly Thr Thr Ala Val Thr Val Asn Asn Ala Gly
            580                 585                 590

Gly Thr Gly Ala Lys Thr Leu Asn Gly Ile Glu Leu Ile His Val Asp
        595                 600                 605

Gly Lys Ser Glu Gly Glu Phe Val Gln Ala Gly Arg Ile Val Ala Gly
    610                 615                 620

Ala Tyr Asp Tyr Thr Leu Ala Arg Gly Gln Gly Ala Asn Ser Gly Asn
625                 630                 635                 640

Trp Tyr Leu Thr Ser Gly Ser Asp Ser Pro Glu Leu Gln Pro Glu Pro
                645                 650                 655

Asp Pro Met Pro Asn Pro Glu Pro Asn Pro Asn Pro Glu Pro Asn Pro
            660                 665                 670

Asn Pro Thr Pro Thr Pro Gly Pro Asp Leu Asn Val Asp Asn Asp Leu
        675                 680                 685

Arg Pro Glu Ala Gly Ser Tyr Ile Ala Asn Leu Ala Ala Ala Asn Thr
    690                 695                 700

Met Phe Thr Thr Arg Leu His Glu Arg Leu Gly Asn Thr Tyr Tyr Thr
705                 710                 715                 720

Asp Met Val Thr Gly Glu Gln Lys Gln Thr Thr Met Trp Met Arg His
                725                 730                 735

Glu Gly Gly His Asn Lys Trp Arg Asp Gly Ser Gly Gln Leu Lys Thr
            740                 745                 750

Gln Ser Asn Arg Tyr Val Leu Gln Leu Gly Gly Asp Val Ala Gln Trp
        755                 760                 765

Ser Gln Asn Gly Ser Asp Arg Trp His Val Gly Val Met Ala Gly Tyr
    770                 775                 780

Gly Asn Ser Asp Ser Lys Thr Ile Ser Ser Arg Thr Gly Tyr Arg Ala
785                 790                 795                 800

Lys Ala Ser Val Asn Gly Tyr Ser Thr Gly Leu Tyr Ala Thr Trp Tyr
                805                 810                 815

Ala Asp Asp Glu Ser Arg Asn Gly Ala Tyr Leu Asp Ser Trp Ala Gln
            820                 825                 830

Tyr Ser Trp Phe Asp Asn Thr Val Lys Gly Asp Asp Leu Gln Ser Glu
        835                 840                 845

Ser Tyr Lys Ser Lys Gly Phe Thr Ala Ser Leu Glu Ala Gly Tyr Lys
    850                 855                 860

His Lys Leu Ala Glu Phe Asn Gly Ser Gln Gly Thr Arg Asn Glu Trp
865                 870                 875                 880

Tyr Val Gln Pro Gln Ala Gln Val Thr Trp Met Gly Val Lys Ala Asp
                885                 890                 895

Lys His Arg Glu Ser Asn Gly Thr Leu Val His Ser Asn Gly Asp Gly
            900                 905                 910

Asn Val Gln Thr Arg Leu Gly Val Lys Thr Trp Leu Lys Ser His His
        915                 920                 925

Lys Met Asp Asp Gly Lys Ser Arg Glu Phe Gln Pro Phe Val Glu Val
    930                 935                 940

Asn Trp Leu His Asn Ser Lys Asp Phe Ser Thr Ser Met Asp Gly Val
945                 950                 955                 960

Ser Val Thr Gln Asp Gly Ala Arg Asn Ile Ala Glu Ile Lys Thr Gly
```

-continued

```
                965                 970                 975

Val Glu Gly Gln Leu Asn Ala Asn Leu Asn Val Trp Gly Asn Val Gly
            980                 985                 990

Val Gln Val Ala Asp Arg Gly Tyr  Asn Asp Thr Ser Ala  Met Val Gly
        995                 1000                1005

Ile Lys  Trp Gln Phe
    1010
```

<210> SEQ ID NO 24
<211> LENGTH: 2973
<212> TYPE: DNA
<213> ORGANISM: Artificial Sequence
<220> FEATURE:
<223> OTHER INFORMATION: Nucleotide sequence of the autotransporter fusion gene encoded by pMATE-beta-glucosidase, for the surface display of a beta-glucosidase using the pMATE system

<400> SEQUENCE: 24

```
atgatcaaac tgaaattcgg cgtcttcttc accgtactgc tgtcctctgc ttacgctcac     60

ggtactccgc agaacatcac ccaccaccat caccatcata tcgaaggtcg tctcgagagc    120

aaaattacct tcccgaaaga ttttatctgg ggtagcgcaa ccgcagcata tcagattgaa    180

ggtgcatata atgaagatgg caaaggcgaa agcatttggg atcgttttag ccatacaccg    240

ggtaatattg cagatggtca taccggtgat gttgcctgtg atcattatca tcgttatgaa    300

gaggatatca aaatcatgaa agagatcggc atcaaaagct atcgctttag cattagctgg    360

cctcgtattt ttccggaagg caccggtaaa ctgaatcaga aaggtctgga tttctataaa    420

cgtctgacca atctgctgct ggaaaatggt attatgcctg caattaccct gtatcattgg    480

gatctgccgc agaaactgca ggataaaggt ggttggaaaa atcgtgatac caccgattat    540

ttcaccgaat atagcgaggt gatctttaaa aacctgggtg atattgtgcc gatctggttt    600

acccataatg aaccgggtgt tgttagcctg ctgggtcatt ttctgggtat tcatgcaccg    660

ggtattaaag atctgcgtac cagcctggaa gttagccata acctgctgct gagccatggt    720

aaagcagtta aactgtttcg cgagatgaat attgatgccc agattggtat tgcactgaac    780

ctgagctatc attatccggc aagcgaaaaa gcagaagata ttgaagcagc agaactgagc    840

tttagcctgg caggtcgttg gtatctggat ccggttctga aaggtcgtta tccggaaaat    900

gcactgaaac tgtacaaaaa aaaaggcatc gaactgtcgt tcccggaaga tgatctgaaa    960

ctgattagcc agccgattga ttttatcgcc tttaacaatt atagcagcga gttcatcaaa   1020

tatgatccga gcagcgaaag cggttttagt ccggcaaata gcattctgga aaaattcgag   1080

aaaaccgata tgggctggat tatctatccg gaaggtctgt atgatctgct gatgctgctg   1140

gatcgtgatt atggcaaacc gaatattgtg attagcgaaa atggtgcagc cttcaaagat   1200

gaaattggta gcaatggcaa aatcgaggat accaaacgta tccagtatct gaaagattat   1260

ctgacccagg cacatcgtgc aattcaggat ggtgttaatc tgaaagcata ttatctgtgg   1320

tccctgctgg ataattttga atgggcatat ggttacaaca aacgctttgg tattgtgcac   1380

gtgaattttg ataccctgga acgcaaaatc aaagatagcg gctattggta taaagaggtg   1440

atcaaaaaca acggctttgg taccgctcgt cgtgctattg agggccgcat cccggaatac   1500

tttaaactga ccaacaatgg cacgctgatg acgggtatga gcggtcaaca agcgggtaac   1560

gttctggttg ttaagggcaa ttaccatggc aataacggcc agctggtcat gaacacggtt   1620

ctgaacggcg atgatagcgt gaccgacaag ctggtggtcg agggcgacac ctctggtacg   1680
```

```
accgcagtga cggtgaataa tgcaggcggt acgggtgcca aaaccctgaa cggtattgag   1740

ttgatccacg ttgacggtaa gagcgagggc gagtttgtgc aggcaggccg cattgttgct   1800

ggcgcttatg actatacgct ggcccgtggt cagggcgcga atagcggtaa ctggtatctg   1860

accagcggct ccgactcccc ggaactgcaa ccggagcctg atccgatgcc gaatccggag   1920

ccaaacccga acccggaacc gaacccaaat ccgaccccga ctccgggtcc ggacttgaac   1980

gttgataacg acctgcgtcc ggaggccggt tcgtacatcg cgaacctggc agcggccaat   2040

acgatgttta cgacccgtct gcacgaacgc ctgggtaata cctactatac cgatatggtc   2100

actggtgaac agaaacaaac caccatgtgg atgcgccacg agggtggtca caataagtgg   2160

cgcgacggta gcggccagtt gaaaacccag agcaatcgct acgttctgca attgggcggt   2220

gatgtggcgc aatggagcca aaacggcagc gaccgttggc atgtcggtgt gatggcaggt   2280

tacggcaaca gcgacagcaa gaccatctcc agccgtaccg gttaccgtgc gaaggcaagc   2340

gtcaacggtt acagcaccgg cctgtatgcc acctggtatg ctgatgatga gagccgcaac   2400

ggtgcttact tggacagctg ggcacagtat tcttggttcg ataatacggt gaaaggcgac   2460

gacctgcaga gcgaaagcta caaatcgaaa ggtttcaccg cgagcctgga agccggctat   2520

aagcacaaac tggcggaatt caatggcagc cagggtactc gtaacgaatg gtacgttcaa   2580

ccgcaggcgc aagtcacttg gatgggcgtt aaggcggata aacaccgtga gagcaacggt   2640

acgttggtgc atagcaacgg tgatggtaat gtccaaaccc gtctgggtgt gaaaacgtgg   2700

ctgaagtccc atcacaaaat ggacgacggt aaatctcgtg aatttcagcc gttcgtggaa   2760

gttaactggc tgcataatag caaggatttc agcacgagca tggatggtgt ctccgttacc   2820

caggacggcg cacgtaacat tgcggagatc aagaccggcg tcgagggtca gctgaatgcg   2880

aatctgaatg tttggggtaa cgtgggtgtt caagtagcgg accgtggtta caatgatacc   2940

agcgcgatgg tgggtattaa gtggcagttt taa                                2973
```

```
<210> SEQ ID NO 25
<211> LENGTH: 990
<212> TYPE: PRT
<213> ORGANISM: Artificial Sequence
<220> FEATURE:
<223> OTHER INFORMATION: Polypeptide sequence of the autotransporter
      fusion protein encoded by pMATE-beta-glucosidase, for the surface
      display of a beta-glucosidase using the pMATE system

<400> SEQUENCE: 25

Met Ile Lys Leu Lys Phe Gly Val Phe Phe Thr Val Leu Leu Ser Ser
1               5                   10                  15

Ala Tyr Ala His Gly Thr Pro Gln Asn Ile Thr His His His His His
            20                  25                  30

His Ile Glu Gly Arg Leu Glu Ser Lys Ile Thr Phe Pro Lys Asp Phe
        35                  40                  45

Ile Trp Gly Ser Ala Thr Ala Ala Tyr Gln Ile Glu Gly Ala Tyr Asn
    50                  55                  60

Glu Asp Gly Lys Gly Glu Ser Ile Trp Asp Arg Phe Ser His Thr Pro
65                  70                  75                  80

Gly Asn Ile Ala Asp Gly His Thr Gly Asp Val Ala Cys Asp His Tyr
                85                  90                  95

His Arg Tyr Glu Glu Asp Ile Lys Ile Met Lys Glu Ile Gly Ile Lys
            100                 105                 110

Ser Tyr Arg Phe Ser Ile Ser Trp Pro Arg Ile Phe Pro Glu Gly Thr
        115                 120                 125
```

-continued

```
Gly Lys Leu Asn Gln Lys Gly Leu Asp Phe Tyr Lys Arg Leu Thr Asn
    130                 135                 140

Leu Leu Leu Glu Asn Gly Ile Met Pro Ala Ile Thr Leu Tyr His Trp
145                 150                 155                 160

Asp Leu Pro Gln Lys Leu Gln Asp Lys Gly Gly Trp Lys Asn Arg Asp
                165                 170                 175

Thr Thr Asp Tyr Phe Thr Glu Tyr Ser Glu Val Ile Phe Lys Asn Leu
            180                 185                 190

Gly Asp Ile Val Pro Ile Trp Phe Thr His Asn Glu Pro Gly Val Val
        195                 200                 205

Ser Leu Leu Gly His Phe Leu Gly Ile His Ala Pro Gly Ile Lys Asp
    210                 215                 220

Leu Arg Thr Ser Leu Glu Val Ser His Asn Leu Leu Leu Ser His Gly
225                 230                 235                 240

Lys Ala Val Lys Leu Phe Arg Glu Met Asn Ile Asp Ala Gln Ile Gly
                245                 250                 255

Ile Ala Leu Asn Leu Ser Tyr His Tyr Pro Ala Ser Glu Lys Ala Glu
            260                 265                 270

Asp Ile Glu Ala Ala Glu Leu Ser Phe Ser Leu Ala Gly Arg Trp Tyr
        275                 280                 285

Leu Asp Pro Val Leu Lys Gly Arg Tyr Pro Glu Asn Ala Leu Lys Leu
    290                 295                 300

Tyr Lys Lys Lys Gly Ile Glu Leu Ser Phe Pro Glu Asp Asp Leu Lys
305                 310                 315                 320

Leu Ile Ser Gln Pro Ile Asp Phe Ile Ala Phe Asn Asn Tyr Ser Ser
                325                 330                 335

Glu Phe Ile Lys Tyr Asp Pro Ser Ser Glu Ser Gly Phe Ser Pro Ala
            340                 345                 350

Asn Ser Ile Leu Glu Lys Phe Glu Lys Thr Asp Met Gly Trp Ile Ile
        355                 360                 365

Tyr Pro Glu Gly Leu Tyr Asp Leu Leu Met Leu Leu Asp Arg Asp Tyr
    370                 375                 380

Gly Lys Pro Asn Ile Val Ile Ser Glu Asn Gly Ala Ala Phe Lys Asp
385                 390                 395                 400

Glu Ile Gly Ser Asn Gly Lys Ile Glu Asp Thr Lys Arg Ile Gln Tyr
                405                 410                 415

Leu Lys Asp Tyr Leu Thr Gln Ala His Arg Ala Ile Gln Asp Gly Val
            420                 425                 430

Asn Leu Lys Ala Tyr Tyr Leu Trp Ser Leu Leu Asp Asn Phe Glu Trp
        435                 440                 445

Ala Tyr Gly Tyr Asn Lys Arg Phe Gly Ile Val His Val Asn Phe Asp
    450                 455                 460

Thr Leu Glu Arg Lys Ile Lys Asp Ser Gly Tyr Trp Tyr Lys Glu Val
465                 470                 475                 480

Ile Lys Asn Asn Gly Phe Gly Thr Ala Arg Arg Ala Ile Glu Gly Arg
                485                 490                 495

Ile Pro Glu Tyr Phe Lys Leu Thr Asn Asn Gly Thr Leu Met Thr Gly
            500                 505                 510

Met Ser Gly Gln Gln Ala Gly Asn Val Leu Val Val Lys Gly Asn Tyr
        515                 520                 525

His Gly Asn Asn Gly Gln Leu Val Met Asn Thr Val Leu Asn Gly Asp
    530                 535                 540
```

-continued

```
Asp Ser Val Thr Asp Lys Leu Val Val Glu Gly Asp Thr Ser Gly Thr
545                 550                 555                 560

Thr Ala Val Thr Val Asn Asn Ala Gly Gly Thr Gly Ala Lys Thr Leu
                565                 570                 575

Asn Gly Ile Glu Leu Ile His Val Asp Gly Lys Ser Glu Gly Glu Phe
            580                 585                 590

Val Gln Ala Gly Arg Ile Val Ala Gly Ala Tyr Asp Tyr Thr Leu Ala
        595                 600                 605

Arg Gly Gln Gly Ala Asn Ser Gly Asn Trp Tyr Leu Thr Ser Gly Ser
    610                 615                 620

Asp Ser Pro Glu Leu Gln Pro Glu Pro Asp Pro Met Pro Asn Pro Glu
625                 630                 635                 640

Pro Asn Pro Asn Pro Glu Pro Asn Pro Asn Pro Thr Pro Thr Pro Gly
                645                 650                 655

Pro Asp Leu Asn Val Asp Asn Asp Leu Arg Pro Glu Ala Gly Ser Tyr
            660                 665                 670

Ile Ala Asn Leu Ala Ala Ala Asn Thr Met Phe Thr Thr Arg Leu His
        675                 680                 685

Glu Arg Leu Gly Asn Thr Tyr Tyr Thr Asp Met Val Thr Gly Glu Gln
    690                 695                 700

Lys Gln Thr Thr Met Trp Met Arg His Glu Gly Gly His Asn Lys Trp
705                 710                 715                 720

Arg Asp Gly Ser Gly Gln Leu Lys Thr Gln Ser Asn Arg Tyr Val Leu
                725                 730                 735

Gln Leu Gly Gly Asp Val Ala Gln Trp Ser Gln Asn Gly Ser Asp Arg
            740                 745                 750

Trp His Val Gly Val Met Ala Gly Tyr Gly Asn Ser Asp Ser Lys Thr
        755                 760                 765

Ile Ser Ser Arg Thr Gly Tyr Arg Ala Lys Ala Ser Val Asn Gly Tyr
    770                 775                 780

Ser Thr Gly Leu Tyr Ala Thr Trp Tyr Ala Asp Asp Glu Ser Arg Asn
785                 790                 795                 800

Gly Ala Tyr Leu Asp Ser Trp Ala Gln Tyr Ser Trp Phe Asp Asn Thr
                805                 810                 815

Val Lys Gly Asp Asp Leu Gln Ser Glu Ser Tyr Lys Ser Lys Gly Phe
            820                 825                 830

Thr Ala Ser Leu Glu Ala Gly Tyr Lys His Lys Leu Ala Glu Phe Asn
        835                 840                 845

Gly Ser Gln Gly Thr Arg Asn Glu Trp Tyr Val Gln Pro Gln Ala Gln
    850                 855                 860

Val Thr Trp Met Gly Val Lys Ala Asp Lys His Arg Glu Ser Asn Gly
865                 870                 875                 880

Thr Leu Val His Ser Asn Gly Asp Gly Asn Val Gln Thr Arg Leu Gly
                885                 890                 895

Val Lys Thr Trp Leu Lys Ser His His Lys Met Asp Asp Gly Lys Ser
            900                 905                 910

Arg Glu Phe Gln Pro Phe Val Glu Val Asn Trp Leu His Asn Ser Lys
        915                 920                 925

Asp Phe Ser Thr Ser Met Asp Gly Val Ser Val Thr Gln Asp Gly Ala
    930                 935                 940

Arg Asn Ile Ala Glu Ile Lys Thr Gly Val Glu Gly Gln Leu Asn Ala
945                 950                 955                 960

Asn Leu Asn Val Trp Gly Asn Val Gly Val Gln Val Ala Asp Arg Gly
```

965 970 975

Tyr Asn Asp Thr Ser Ala Met Val Gly Ile Lys Trp Gln Phe
980 985 990

<210> SEQ ID NO 26
<211> LENGTH: 1344
<212> TYPE: DNA
<213> ORGANISM: Escherichia coli
<220> FEATURE:
<221> NAME/KEY: misc_feature
<223> OTHER INFORMATION: AIDA-I

<400> SEQUENCE: 26
cttaatccta caaaagaaag tgcaggtaat actcttaccg tgtcaaatta tactgggaca 60
ccgggaagtg ttatttctct tggtggtgtg cttgaaggag ataattcact tacggaccgt 120
ctggtggtga aaggtaatac ctctggtcaa agtgacatcg tttacgtcaa tgaagatggc 180
agtggtggtc agacgagaga tggtattaat attatttctg tagagggaaa ttctgatgca 240
gaattctctc tgaagaaccg cgtagttgcc ggagcttatg attacacact gcagaaagga 300
aacgagagtg ggacagataa taagggatgg tatttaacca gtcatcttcc cacatctgat 360
acccggcaat acagaccgga gaacggaagt tatgctacca atatgacact ggctaactca 420
ctgttcctca tggatttgaa tgagcgtaag caattcaggg ccatgagtga taatacacag 480
cctgagtctg catccgtgtg gatgaggatc actggaggaa gaagctctgg taagcttaat 540
gacgggcaaa ataaaacaac aaccaatcag tttatcaatc agctcggggg ggatatttat 600
aaattccatg ctgaacaact gggtgatttt accttaggga ttatgggagg atacgcgaat 660
gcaaaaggta aaacgataaa ttacacgagc aacaaagctg ccagaaacac actggatggt 720
tattctgtcg ggtatacggg tacgtggtat cagaatgggg aaaatgcaac agggctcttt 780
gctgaaactt ggatgcaata taactggttt aatgcatcag tgaaaggtga cggactggaa 840
gaagaaaaat ataatctgaa tggtttaacc gcttctgcag gtgggggata taacctgaat 900
gtgcacacat ggacatcacc tgaaggaata acaggtgaat tctggttgca gcctcatttg 960
caggctgtct ggatgggggt tacaccggat acacatcagg aggataacgg aacggtggtg 1020
cagggagcag ggaaaaataa tattcagaca aaagcaggta ttcgtgcatc ctggaaggtg 1080
aaaagcaccc tggataagga taccgggcgg gagttcagtc cgtatataga ggcaaactgg 1140
atccataaca ctcatgaatt tggtgttaaa atgagtgatg acagccagtt gttgtcaggt 1200
agccgaaatc agggagagat aaagacaggt attgaagggg tgattactca aaacttgtca 1260
gtgaatggcg gagtcgcata tcaggcagga ggtcacggga gcaatgccat ctccggagca 1320
ctggggataa aatacagctt ctga 1344

<210> SEQ ID NO 27
<211> LENGTH: 447
<212> TYPE: PRT
<213> ORGANISM: Escherichia coli
<220> FEATURE:
<221> NAME/KEY: MISC_FEATURE
<223> OTHER INFORMATION: AIDA-I

<400> SEQUENCE: 27

Leu Asn Pro Thr Lys Glu Ser Ala Gly Asn Thr Leu Thr Val Ser Asn
1 5 10 15

Tyr Thr Gly Thr Pro Gly Ser Val Ile Ser Leu Gly Gly Val Leu Glu
20 25 30

```
Gly Asp Asn Ser Leu Thr Asp Arg Leu Val Val Lys Gly Asn Thr Ser
        35                  40                  45

Gly Gln Ser Asp Ile Val Tyr Val Asn Glu Asp Gly Ser Gly Gly Gln
    50                  55                  60

Thr Arg Asp Gly Ile Asn Ile Ile Ser Val Glu Gly Asn Ser Asp Ala
65                  70                  75                  80

Glu Phe Ser Leu Lys Asn Arg Val Val Ala Gly Ala Tyr Asp Tyr Thr
                85                  90                  95

Leu Gln Lys Gly Asn Glu Ser Gly Thr Asp Asn Lys Gly Trp Tyr Leu
            100                 105                 110

Thr Ser His Leu Pro Thr Ser Asp Thr Arg Gln Tyr Arg Pro Glu Asn
        115                 120                 125

Gly Ser Tyr Ala Thr Asn Met Thr Leu Ala Asn Ser Leu Phe Leu Met
    130                 135                 140

Asp Leu Asn Glu Arg Lys Gln Phe Arg Ala Met Ser Asp Asn Thr Gln
145                 150                 155                 160

Pro Glu Ser Ala Ser Val Trp Met Arg Ile Thr Gly Gly Arg Ser Ser
                165                 170                 175

Gly Lys Leu Asn Asp Gly Gln Asn Lys Thr Thr Thr Asn Gln Phe Ile
            180                 185                 190

Asn Gln Leu Gly Gly Asp Ile Tyr Lys Phe His Ala Glu Gln Leu Gly
        195                 200                 205

Asp Phe Thr Leu Gly Ile Met Gly Gly Tyr Ala Asn Ala Lys Gly Lys
    210                 215                 220

Thr Ile Asn Tyr Thr Ser Asn Lys Ala Ala Arg Asn Thr Leu Asp Gly
225                 230                 235                 240

Tyr Ser Val Gly Val Tyr Gly Thr Trp Tyr Gln Asn Gly Glu Asn Ala
                245                 250                 255

Thr Gly Leu Phe Ala Glu Thr Trp Met Gln Tyr Asn Trp Phe Asn Ala
            260                 265                 270

Ser Val Lys Gly Asp Gly Leu Glu Glu Glu Lys Tyr Asn Leu Asn Gly
        275                 280                 285

Leu Thr Ala Ser Ala Gly Gly Gly Tyr Asn Leu Asn Val His Thr Trp
    290                 295                 300

Thr Ser Pro Glu Gly Ile Thr Gly Glu Phe Trp Leu Gln Pro His Leu
305                 310                 315                 320

Gln Ala Val Trp Met Gly Val Thr Pro Asp Thr His Gln Glu Asp Asn
                325                 330                 335

Gly Thr Val Val Gln Gly Ala Gly Lys Asn Asn Ile Gln Thr Lys Ala
            340                 345                 350

Gly Ile Arg Ala Ser Trp Lys Val Lys Ser Thr Leu Asp Lys Asp Thr
        355                 360                 365

Gly Arg Glu Phe Ser Pro Tyr Ile Glu Ala Asn Trp Ile His Asn Thr
    370                 375                 380

His Glu Phe Gly Val Lys Met Ser Asp Asp Ser Gln Leu Leu Ser Gly
385                 390                 395                 400

Ser Arg Asn Gln Gly Glu Ile Lys Thr Gly Ile Glu Gly Val Ile Thr
                405                 410                 415

Gln Asn Leu Ser Val Asn Gly Gly Val Ala Tyr Gln Ala Gly Gly His
            420                 425                 430

Gly Ser Asn Ala Ile Ser Gly Ala Leu Gly Ile Lys Tyr Ser Phe
        435                 440                 445
```

<210> SEQ ID NO 28
<211> LENGTH: 31
<212> TYPE: DNA
<213> ORGANISM: Artificial Sequence
<220> FEATURE:
<223> OTHER INFORMATION: MT15

<400> SEQUENCE: 28
gctcgtcgtg ctattgaggg ccgcatcccg g 31

<210> SEQ ID NO 29
<211> LENGTH: 33
<212> TYPE: DNA
<213> ORGANISM: Artificial Sequence
<220> FEATURE:
<223> OTHER INFORMATION: MT16

<400> SEQUENCE: 29
acgaccttcg atatgatggt gatggtggtg ggt 33

<210> SEQ ID NO 30
<211> LENGTH: 39
<212> TYPE: DNA
<213> ORGANISM: Artificial Sequence
<220> FEATURE:
<223> OTHER INFORMATION: MT17

<400> SEQUENCE: 30
catatcgaag gtcgtatgag taaaggagaa gaacttttc 39

<210> SEQ ID NO 31
<211> LENGTH: 39
<212> TYPE: DNA
<213> ORGANISM: Artificial Sequence
<220> FEATURE:
<223> OTHER INFORMATION: MT18

<400> SEQUENCE: 31
aatagcacga cgagcgcctt tgtatagttc atccatgcc 39

<210> SEQ ID NO 32
<211> LENGTH: 29
<212> TYPE: DNA
<213> ORGANISM: Artificial Sequence
<220> FEATURE:
<223> OTHER INFORMATION: SI020

<400> SEQUENCE: 32
gctcgtcgtg ctattgaggg ccgcatccc 29

<210> SEQ ID NO 33
<211> LENGTH: 30
<212> TYPE: DNA
<213> ORGANISM: Artificial Sequence
<220> FEATURE:
<223> OTHER INFORMATION: PQ019

<400> SEQUENCE: 33
atgatggtga tggtggtggg tgatgttctg 30

<210> SEQ ID NO 34
<211> LENGTH: 44
<212> TYPE: DNA
<213> ORGANISM: Artificial Sequence
<220> FEATURE:
<223> OTHER INFORMATION: SI021

-continued

<400> SEQUENCE: 34
aatagcacga cgagccttgt acagctcgtc catgccgccg gtgg 44

<210> SEQ ID NO 35
<211> LENGTH: 45
<212> TYPE: DNA
<213> ORGANISM: Artificial Sequence
<220> FEATURE:
<223> OTHER INFORMATION: PQ024

<400> SEQUENCE: 35
caccatcacc atcatatggt gagcaagggc gaggaggata acatg 45

<210> SEQ ID NO 36
<211> LENGTH: 1467
<212> TYPE: DNA
<213> ORGANISM: Escherichia coli
<220> FEATURE:
<221> NAME/KEY: misc_feature
<223> OTHER INFORMATION: EhaA original

<400> SEQUENCE: 36
ctgaccaaca acggtacgct gatgaccgga atgtcaggac agcaagctgg caatgtgtta 60
gtggtgaagg ggaactacca cggtaataac ggtcaactag taatgaatac ggtactgaat 120
ggcgatgact cagtaaccga taaattggtt gtcgagggcg atactagcgg cacgactgcc 180
gttacggtga ataacgctgg cggtacaggt gcgaaaaccc ttaacggtat cgaacttatc 240
catgtagacg gtaagtctga gggcgaattt gttcaggctg ggcgtatcgt tgcgggggcg 300
tatgactaca ctctcgcgcg tggacaaggg gcaaatagtg gtaactggta tctgaccagc 360
ggcagtgatt ctcctgaact gcagccggag ccagacccga tgccgaatcc agagccaaac 420
ccgaatccag agccgaaccc taacccgaca cctacgccgg gtccggatct gaatgtggat 480
aatgacctgc gaccggaggc gggtagctac attgcgaacc ttgcagcagc gaataccatg 540
ttcaccacgc gtctgcatga gcgtctgggt aatacgtact ataccgacat ggtgacgggt 600
gagcagaaac aaaccactat gtggatgcgc catgaaggtg gtcataataa atggcgtgat 660
ggcagcggcc agctgaaaac ccaaagcaat cgctatgttc tgcaactggg aggcgatgtc 720
gcgcagtgga gccaaaacgg cagcgaccgc tggcatgttg gggtcatggc gggatatggc 780
aacagcgaca gcaaaaccat ttcctcgcga accggttatc gtgcaaaagc gagtgtgaac 840
ggatatagca caggcctcta tgccacctgg tatgccgatg acgagtcgcg taatggcgcg 900
tatctcgaca gttgggcgca gtacagctgg tttgataaca cagtgaaagg ggatgactta 960
caaagtgaat cctataaatc aaaaggattt accgcttcac tggaagctgg atacaaacac 1020
aaattagctg aatttaatgg cagccaggga acgcgtaatg aatggtatgt tcagccgcaa 1080
gcacaggtta cctggatggg agtcaaagcc gataagcacc gcgaaagcaa cggaaccctc 1140
gttcatagca acggtgatgg caatgttcaa acccgacttg gcgtaaaaac ctggctgaag 1200
agccaccata aaatggatga cggtaaatcc cgcgagttcc agccgtttgt agaagtgaac 1260
tggctacata acagtaagga tttcagcacc agtatggatg gcgtgtctgt cactcaggat 1320
ggagcccgaa atattgctga gataaaaacc ggggtggaag gacagctaaa tgccaacctg 1380
aatgtctggg ggaatgtggg cgttcaggtt gccgataggg gatataatga cacctctgca 1440
atggttggca ttaagtggca attctga 1467

SURFACE DISPLAY OF FUNCTIONAL PROTEINS IN A BROAD RANGE OF GRAM NEGATIVE BACTERIA

CROSS REFERENCE TO RELATED APPLICATION

This application is a 35 U.S.C. 371 National Phase Entry Application from PCT/EP2014/054383, filed Mar. 6, 2014, which claims the benefit of European Patent Application No. 13159041.6 filed on Mar. 13, 2013, the disclosures of which are incorporated herein in their entirety by reference.

The present invention relates to a method for the surface display of a recombinant polypeptide on the surface of a host cell, said method comprising the steps: (a) providing a host cell transformed with a nucleic acid fusion operatively linked with an expression control sequence, said nucleic acid fusion comprising: (i) a portion encoding a signal peptide, (ii) a portion encoding the recombinant polypeptide to be displayed, (iii) a portion encoding a transmembrane linker, and (iv) a portion encoding the transporter domain of an EhaA protein, and (b) culturing the host cell under conditions wherein the nucleic acid fusion is expressed and the expression product comprising the recombinant polypeptide is displayed on the surface of the host cell.

Expression in bacteria is the method of choice for the commercial production of pharmaceutical and industrial proteins. *E. coli* is a versatile lab organism for the expression of recombinant proteins, their investigation and in some issues for even their production in preparative scales. For such purposes, a wide variety of vectors e.g. plasmids, suitable mutants and protocols are available. For being used in industrial applications or crude biotechnological production processes *E. coli* has several disadvantages. It usually does not grow to high cell densities in fermentation processes and needs high concentrations of glucose to gain growth energy. Being a natural gut inhabitant, it is not used to crude environments as water or soil, rather sensible to harsh treatments and is not resistant to organic solvents. Therefore, the aim of the present invention is to combine the advantages of surface display of recombinant proteins with the activa of host organisms different from *E. coli*, e.g. the natural soil bacterium *Pseudomonas* (putida), resistant to a variety of organic solvents, organisms that exploit other sources than glucose to gain growth energy e.g. *Rhodobacter* (light) or *Cupriavidus necator* (oxyhydrogen) and organisms that are—in contrast to *E. coli*—suitable for the efficient production of ethanol or other biofuels like *Zymomonas*. For this purpose an optimized second generation surface display system was developed, the MATE (maximized autotransporter expression) system, shown to be superior in *E. coli* and proven to be a versatile tool for the surface display of recombinant proteins in a wide variety of gram negative bacteria different from *E. coli.*

Autotransporter proteins are known to facilitate secretion either through release by *E. coli* proteases or through self-proteolysis after translocation. The perspectives for commercial protein secretion with the various autotransporter families were reviewed by Jong et al., (2010). Because the passenger remains attached to the cell, autotransporter secretion systems require endoproteolytic cleavage. The natural *E. coli* outer membrane protease OmpT is known to cleave in the linker region of some autotransporters. The display of the cholera toxin B subunit (CtxB) with AIDAI autotransporter in OmpT positive strains led to the release of the passenger into the growth medium (Maurer 1997, Jose 2002). The release of the passenger naturally lowers the amount of recombinant protein at the surface, reducing the efficiency of whole cell biocatalysis or screening. For this reason, Autodisplay in *E. coli* has typically been carried out in OmpT negative strains such as UT5600 or BI21.

Several autotransporters have passengers that naturally undergo self-proteolysis, releasing themselves into the growth medium after translocation across the outer membrane. By replacing the natural passenger with the target protein, this system has recently been utilised for secretion of a recombinant passenger (Sevastsyanovich et al. 2012).

Among other systems for the secretion of proteins in Gram-negative bacteria, the autotransporter pathway represents a solution of impressing simplicity. It is possible to transport a protein, regardless whether it is recombinant or the natural passenger, to the actual outer membrane, as long as its coding region lies between a typical signal peptide and a C-terminal domain called β-barrel. Based on these findings the autodisplay system has been developed by the use of the natural *E. coli* autotransporter protein AIDA-I (the adhesin involved in diffuse adherence) in a homologous *E. coli* host background (Jose et al. 2007). With the aid of a typical signal peptide, the precursor is transported across the inner membrane. Arrived in the periplasm, the C terminal part of the precursor forms a porin-like structure, a so-called β-barrel, within the outer membrane and through this pore the N terminally attached passenger (the actual protease) is translocated to the cell surface. To obtain full surface exposure of the passenger, a linker peptide is required in between the β-barrel and the passenger.

EhaA is an autotransporter protein derived from *E. coli* strain O157:H7. It has been demonstrated that EhaA is located at the cell surface and resulted in the formation of large cell aggregates, promoted significant biofilm formation and mediated adhesion to primary epithelial cell of the bovine terminal rectum (Wells et al., 2008).

EhaA has an identity to AIDA-I on the nucleic acid level of about 43% only. On level of the amino acid sequence, the identity is only about 34%.

Up to now, EhaA has not been expressed in a heterologous cell. In the present invention, it is has been surprisingly found that the transporter domain of EhaA can be successfully used for surface-display of a recombinant passenger proteins in a host cell heterologous to *E. coli*. Examples of such heterologous cells are *Pseudomonas* spp., *Rhodobacter* spp., *Zymomonas* spp. and *Cupriavidus* spp. Surprisingly, the cells expressing a construct of the present invention on the cell surface do not form aggregates or a biofilm. Aggregation or biofilm formation would make such cells unsuitable for biotechnological applications (for example, suspension culture).

By the heterologous expression, autodisplay of recombinant passenger proteins on a bacterial cell surface can be employed in species being more suitable in biotechnological applications than *E. coli*. Such cells include *Pseudomonas* spp., *Rhodobacter* spp., *Zymomonas* spp. and *Cupriavidus* spp., but are not limited thereto.

In the present invention, it has surprisingly found that the MATE system described herein results in a higher activity of the passenger displayed on a host cell than the AIDA-I system described in the prior art. For example, an EstA catalytic domain demonstrates an improved activity of conversion of p-nitrophenyl acetate compared with expression by the AIDA-I system (Example 6, FIG. 8). Furthermore, by the MATE system, the EstA catalytic domain can be functionally expressed on the surface of heterologous species such as *Salmonella enterica, Pseudomonas putida* or *Zymomonas mobilis* (Examples 7 to 9).

Example 10 describes the functional surface display of an active heterologous endoglucanase obtained from *Bacillus subtilis* on the ethanologenic bacteria *Zymobacter palmae* and *Zymomonas mobilis* using the MATE system of the present invention.

Example 11 describes the functional display of heterologeous bacterial cellulases obtained from different species (an endoglucanase obtained from *Bacillus subtilis*, an exoglucanase obtained from *Clostridium thermocellum* and a β-glucosidase obtained from *Clostridium thermocellum*) on the surface of *Pseudomonas putida* with the pMATE system of the present invention. Furthermore, it could be demonstrated that these three enzymes obtained from different species expressed on the cell surface together were able to degrade cellulose or a lignocellulosic substrate into reducing sugars (in particular glucose, cellubiose and cellulose-polysaccharide chains of variable length).

A first aspect of the present invention relates to a method for displaying a recombinant polypeptide on the surface of a host cell, said method comprising the steps:
(a) providing a host cell transformed with a nucleic acid fusion operatively linked with an expression control sequence, said nucleic acid fusion comprising:
  (i) a portion encoding a signal peptide,
  (ii) a portion encoding the recombinant polypeptide to be displayed,
  (iii) a portion encoding a transmembrane linker, and
  (iv) a portion encoding the transporter domain of an EhaA protein, and
(b) culturing the host cell under conditions wherein the nucleic acid fusion is expressed and the expression product comprising the recombinant polypeptide is displayed on the surface of the host cell.

The expression system as described herein employing the EhaA autotransporter domain is also termed MATE (maximized autotransporter expression) system of pMATE system. Plasmids (in particular expression plasmids comprising the nucleic acid fusion as described herein) to be used in the MATE system are also termed by the prefix "pMATE".

The expression product defined in step (b) is also termed herein as "polypeptide fusion".

By the method of the present invention, a functional recombinant polypeptide can be displayed. The recombinant polypeptide to be displayed may also be termed "passenger", "passenger polypeptide" or "passenger protein".

Step (a) of the methods of the present invention refers to the provision of a host cell. The host cell used in the method of the present invention is preferably a bacterium, more preferably a Gram-negative bacterium.

The Gram-negative bacterium can be selected from *E. coli, Salmonella* spp., *Zymomonas* spp., *Zymobacter* spp., *Pseudomonas* spp., *Cupriavidus* spp. (formerly known as *Ralstonia* spp.), *Rhodobacter* spp., *Acinetobacter* spp., *Gluconobacter* spp., *Gluconacetobacter* spp., *Acidomonas* spp., *Acetobacter* spp., *Paracoccous* spp., *Rhizobium* spp., *Xanthomonas* spp.

The Gram-negative bacterium is preferably not *E. coli*. In this case, the host cell is heterologous to the transporter domain of the EhaA protein. The Gram-negative bacterium is preferably selected from *Salmonella* spp., *Zymomonas* spp., *Zymobacter* spp., *Pseudomonas* spp., *Cupriavidus* spp., *Rhodobacter* spp., *Acinetobacter* spp., *Gluconobacter* spp., *Gluconacetobacter* spp., *Acidomonas* spp., *Acetobacter* spp., *Paracoccous* spp., *Rhizobium* spp., and *Xanthomonas* spp.

Another preferred selection of the Gram-negative bacterium is the selection from *Zymomonas* spp., *Zymobacter* spp., *Pseudomonas* spp., *Cupriavidus* spp., *Rhodobacter* spp., *Acinetobacter* spp., *Gluconobacter* spp., *Gluconacetobacter* spp., *Acidomonas* spp., *Acetobacter* spp., *Paracoccous* spp., *Rhizobium* spp., and *Xanthomonas* spp.

Another preferred selection of the Gram-negative bacterium is the selection from *Pseudomonas* spp., *Rhodobacter* spp., *Zymomonas* spp. and *Cupriavidus* spp.

A preferred *Salmonella* species is *Salmonella enterica*. A preferred *Zymomonas* species is *Zymomonas mobilis*. More preferred is *Zymomonas mobilis* strain DSM 3580. A preferred *Zymobacter* species is *Zymobacter palmae*. A preferred *Pseudomonas* species is *Pseudomonas putida* or *Pseudomonas fluorescens*. A preferred *Cupriavidus* species is *Cupriavidus necator* or *Cupriavidus metallidurans*. A preferred *Rhodobacter* species is *Rhodobacter capsulatus*. A preferred *Acinetobacter* species is *Acinetobacter baylyi* ADP1. A preferred *Gluconobacter* species is *Gluconobacter oxydans*. A preferred *Acetobacter* species is *Acetobacter xylinum*. A preferred *Paracoccous* species is *Paracoccous denitrificans*. A preferred *Rhizobium* species is *Rhizobium meliloti*. A preferred *Xanthomonas* species is *Xanthomonas campestris*.

The Gram-negative bacterium can be selected from *Salmonella enterica, Zymomonas mobilis Zymobacter palmae, Pseudomonas putida, Pseudomonas fluorescens, Cupriavidus necator, Cupriavidus metallidurans, Rhodobacter capsulatus, Acinetobacter baylyi* ADP1, *Gluconobacter oxydans, Gluconacetobacter* spp., *Acidomonas* spp., *Acetobacter xylinum, Paracoccous denitrificans, Rhizobium meliloti*, and *Xanthomonas campestris*.

The gram-negative bacterium can be an ethanologenic bacterium, for example *Zymomonas mobilis, Zymobacter palmae, P. putida* or *Klebsiella* spp.

According to the present invention, a host cell, particularly a host bacterium is provided which is transformed with a nucleic acid fusion operatively linked with an expression control sequence, i.e. a promoter, and optionally further sequences required for gene expression in the respective host cell. The skilled person knows suitable promoters and expression control sequences, in particular for expression in the host cell species as described herein. The promoter or/and the expression control sequence may be homologous or heterologous to the host cell. Preferably, the nucleic acid fusion is located on a recombinant vector, e.g. a plasmid vector.

By the method of the present invention, a combination of enzymes can be expressed. The host cell may be transformed with at least one nucleic acid fusion, for instance two, three, four, five or even more nucleic acid fusions. If two or more nucleic acid fusions are transformed into a host cell, the nucleic acid fusions preferably encode different recombinant polypeptides as described herein. If a host cell transformed with several nucleic acid fusions is used, these nucleic acid fusions may be located on a single vector or on a plurality of vectors.

At least one host cell as described herein, for instance two, three, four, five, six or even more host cells as described herein may be provided in the methods of the present invention. Each of these host cells is transformed with one nucleic acid fusion or at least one nucleic acid fusion, as described herein. Preferably, the nucleic acid fusions transformed in the at least one host cell encode different recombinant polypeptides as described herein.

The different recombinant polypeptides which may be provided in one or at least one host cell may form a functional unit, for instance the subunits of a functional unit, such as the subunits of an enzyme or the subunits or/and components of an enzyme complex.

An example for expression of at least one recombinant passenger is an endoglucanase (EC 3.2.1.4), an exoglucanase (EC 3.2.1.91) or/and a β-glucosidase (EC 3.2.1.21), and any combination thereof, expressed by the method of the present invention, as described herein.

The nucleic acid fusion comprises (i) a portion encoding a signal peptide, preferably a portion coding for a Gram-negative signal peptide allowing for transport into the periplasm through the inner cell membrane. The signal peptide may be a signal peptide homologous to the host cell. The signal peptide may also be a signal peptide heterologous to the host cell. An example of a suitable signal peptide is the CtxB signal peptide. The signal peptide can be cleaved off during maturation of the polypeptide fusion.

Further, the nucleic acid fusion comprises (ii) a portion encoding the recombinant polypeptide to be displayed. Any recombinant polypeptide can be displayed. The Examples of the present invention cover a broad range of recombinant polypeptides including GFP, RFP, an esterase EstA, an endoglucanase, an exoglucanase, a β-glucosidase and a polypeptide as short as $His_6$ (HHHHHH) displayed by the nucleic acid fusion of the present invention on the surface of a host cell.

In particular, the passenger is an enzyme, for example an enzyme selected from endoglucanases (EC 3.2.1.4), exoglucanases (EC 3.2.1.91), β-glucosidases (EC 3.2.1.21). ligninases, lignin peroxidases (EC 1.11.1.14), lipases (EC 3.1.1.3), esterases (EC 3.1.1.1), peroxidases (1.11.1.16), laccases (1.10.3.2), cellobiose dehydrogenases (EC 1.1.99.18), hexose-isomerases, pentose-isomerases, cytochrome P450 enzymes, formiat dehydrogenases (EC 1.2.1.2), cytochrome P450 reductase (EC 1.6.2.4), NADH oxidases (EC 1.6.3.x), dehydrogenases, prenyltransferases, xylanases (EC 3.2.1.8), proteases, transfructosidases, transglucosidases amylases (EC 3.2.1.1, EC 3.2.1.2, EC 3.2.1.3, EC 3.2.1.68), aldolases (EC 4.1.2.13), pectinases (EC 3.2.1.15), glucose oxidases (EC 1.1.3.4), hexose oxidases (EC 1.1.3.5), lactose oxidases (EC 1.1.3.x), sorbitol/xylitol oxidases (EC 1.1.3.41), D-gluconolactone oxidases (EC 1.1.3.x), pyranose oxidases (EC 1.1.3.10), isoamyl alcohol oxidases (EC 1.1.3.x), long-chain alcohol oxidases (EC 1.1.3.20), vanillyl-alcohol oxidases (EC 1.1.3.38), aryl-alcohol oxidases (EC 1.1.37), D-amino acid oxidases (EC 1.4.3.1, EC 1.4.3.3, EC 1.4.3.19), L-amino acid oxidases (EC 1.4.3.2, EC 1.4.3.1.1, EC 1.4.3.14, EC 1.4.3.16), monoamine oxidases (EC 1.4.3.4), fructosyl amine oxidases (EC 1.5.4.x), sulfhydril oxidases (EC 1.8.3.2), aromatic hydrocarbon dioxygenases (EC 1.14.12.x), and dehalogenases.

The dehalogenases include haloalkane dehalogenases, halocarboxylic acid dehalogenases, halohydrin dehalogenases, chloroacrylic acid dehalogenases, hexachlorocyclohexane dechlorinases, and atrazine chlorohydrolases, but are not limited thereto.

In a preferred embodiment an endoglucanase (EC 3.2.1.4), an exoglucanase (EC 3.2.1.91) or/and a β-glucosidase (EC 3.2.1.21), or any combination thereof, is expressed by the method of the present invention. If a combination of two or three of these enzymes is expressed, these enzymes can be co-expressed in a common cell, or each enzyme can be expressed in a separate cell. A combination of an endoglucanase (EC 3.2.1.4), an exoglucanase (EC 3.2.1.91) or/and a β-glucosidase (EC 3.2.1.21), expressed by the method of the present invention can by used in cellulose or/and lignocellulose degradation.

A preferred exoglucanase of the present invention can be obtained from *Clostridium thermocellum.*

Another preferred exoglucanase comprises amino acid positions 38-831 of SEQ ID NO:21, or a sequence being at least 70%, at least 80%, at least 90%, at least 95%, at least 98%, or at least 99% identical to positions 38-831 of SEQ ID NO:21.

A preferred exoglucanase of the present invention is encoded by SEQ ID NO:20, in particular by positions 112-2493 of SEQ ID NO:20, or by a sequence being at least 70%, at least 80%, at least 90%, at least 95%, at least 98%, or at least 99% identical to positions 112-2493 of SEQ ID NO:20.

A preferred endoglucanase of the present invention can be obtained from *Bacillus subtilis.*

A preferred endoglucanase of the present invention comprises amino acid positions 38-511 of SEQ ID NO:23, or a sequence being at least 70%, at least 80%, at least 90%, at least 95%, at least 98%, or at least 99% identical to positions 38-511 of SEQ ID NO:23.

A preferred endoglucanase of the present invention is encoded by SEQ ID NO:22, in particular by positions 112-1533 of SEQ ID NO:22, or by a sequence being at least 70%, at least 80%, at least 90%, at least 95%, at least 98%, or at least 99% identical to positions 112-1533 of SEQ ID NO:22.

A preferred β-glucosidase of the present invention can be obtained from *Clostridium thermocellum.*

A preferred β-glucosidase of the present invention comprises amino acid positions 38-488 of SEQ ID NO:25, or a sequence being at least 70%, at least 80%, at least 90%, at least 95%, at least 98%, or at least 99% identical to positions 38-488 of SEQ ID NO:25.

A preferred β-glucosidase of the present invention is encoded by SEQ ID NO:24, in particular by positions 112-1464 of SEQ ID NO:24, or by a sequence being at least 70%, at least 80%, at least 90%, at least 95%, at least 98%, or at least 99% identical to positions 112-1464 of SEQ ID NO:24.

In another preferred embodiment, the passenger is an esterase. Esterases represent a group of hydrolases that have a wide substrate tolerance and are able to catalyze a broad spectrum of reactions even in organic solvents. Moreover, esterases show high regio- and/or enantioselectivity. They are not restricted to dissolving an ester bond, but can also catalyze its formation and usually do not require any cofactors. Therefore, esterases in general are attractive tools for industrial applications such as chiral synthesis of pharmaceuticals or agrochemicals. Therefore lipolytic enzymes like esterases are attractive biotechnological tools. Another branch of lypolytic enzymes, named lipases (triacylglycerol acylhydrolases EC 3.1.1.3), which catalyze the hydrolysis of triglycerides in aqueous media, liberating free fatty acids and glycerol, or the reverse reaction in organic solvents as well, have gained particular interest, since they simultaneously show in addition to high enantio- and/or regio-selectivity an increased catalytic activity and thermostability in organic solvents. Contrary to esterases, which preferentially break ester bonds of short chain fatty acids, lipases are able to catalyze the hydrolysis of water-insoluble long-chain acylglycerols. So far, lipases have been established in numerous industries, such as the food industry, paper manufacturing, pharmaceutical processing, and detergents industry, reflecting their great importance.

Furthermore, the nucleic acid fusion comprises (iii) a portion encoding a transmembrane linker which is required for the presentation of the passenger polypeptide (ii) on the outer surface of the outer membrane of the host cell. A transmembrane linker domain may be used which is homologous with regard to the autotransporter, i.e. the transmembrane linker domain is encoded by a nucleic acid portion directly 5' to the autotransporter domain in the EhaA protein. Also a transmembrane linker domain may be used which is heterologous with regard to the autotransporter. The length of the transmembrane linker is preferably 30-160 amino acids. The transmembrane linker is preferably a transmembrane linker obtained from an EhaA protein as described herein.

Further, the nucleic acid fusion comprises (iv) a transporter domain of an EhaA protein. In the present invention, autodisplay by the transporter domain of an EhaA protein is the recombinant surface display of proteins or polypeptides by means of the autotransporter in any Gram-negative bacterium. The transporter domain of the EhaA protein according to the invention is preferably capable of forming a β-barrel structure.

The transporter domain of EhaA as described herein include variants which can e.g. be obtained by altering the amino acid sequence in the loop structures of the β-barrel not participating in the transmembrane portions. Optionally, the nucleic acid portions coding for the surface loops can be deleted completely. Also within the amphipathic β-sheet conserved amino exchanges, i.e. the exchange of an hydrophilic by another hydrophilic amino acid or/and the exchange of a hydrophobic by another hydrophobic amino acid may take place. Preferably, a variant has a sequence identity of at least 70%, at least 90%, at least 95% or at least 98% on the amino acid level to the respective native sequence of the autotransporter domain, in particular in the range of the β-sheets.

The EhaA protein of the present invention and a nucleic acid encoding therefor can be obtained from *E. coli*. The amino acid sequence of the *E. coli* EhaA protein is in particular described by YP_003498036 (for example, Version YP_003498036.1, genbank identifier GI:291281218). This amino acid sequence is described by SEQ ID NO:15. As can be seen from FIG. 25, the identity of EhaA and AIDA-I is about 43% on the nucleic acid level and about 34% on the amino acid.

The transmembrane linker (ii) is in particular encoded by a sequence comprising a sequence selected from the group consisting of:

(a) a nucleotide sequence comprising SEQ ID NO:16,
(b) a nucleotide sequence encoding SEQ ID NO:17,
(c) nucleotide sequences comprising a sequence being at least 70%, at least 80%, at least 90%, at least 95%, at least 98%, or at least 99% identical to SEQ ID NO:16 or/and a nucleotide sequence encoding SEQ ID NO:17, and
(d) nucleotide sequences which encodes the polypeptides encoded by (a), (b) or/and (c) within the scope of the degeneracy of the genetic code.

The transmembrane linker (ii) in particular comprises a sequence selected from the group consisting of:

(a) an amino acid sequence comprising SEQ ID NO:17, and
(b) sequences which are at least 70%, at least 80%, at least 90%, at least 95%, at least 98%, or at least 99% identical to the sequences of (a).

The transporter domain of the EhaA protein (iii) is in particular encoded by a sequence comprising a sequence selected from the group consisting of:

(a) a nucleotide sequence comprising SEQ ID NO:18,
(b) a nucleotide sequence encoding SEQ ID NO:19,
(c) nucleotide sequences comprising a sequence being at least 70%, at least 80%, at least 90%, at least 95%, at least 98%, or at least 99% identical to SEQ ID NO:18 or/and a nucleotide sequence encoding SEQ ID NO:19, and
(d) nucleotide sequences which encodes the polypeptides encoded by (a), (b) or/and (c) within the scope of the degeneracy of the genetic code.

The transporter domain of the EhaA protein (iii) in particular comprises a sequence selected from the group consisting of:

(a) an amino acid sequence comprising SEQ ID NO:19, and
(b) sequences which are at least 70%, at least 80%, at least 90%, at least 95%, at least 98%, or at least 99% identical to the sequences of (a).

The transmembrane linker (ii) and the transporter domain of the EhaA protein (iii) are in particular encoded by a sequence comprising a sequence selected from the group consisting of:

(a) a nucleotide sequence comprising SEQ ID NO:1,
(b) a nucleotide sequence encoding SEQ ID NO:2,
(c) nucleotide sequences comprising a sequence being at least 70%, at least 80%, at least 90%, at least 95%, at least 98%, or at least 99% identical to SEQ ID NO:1 or/and a nucleotide sequence encoding SEQ ID NO:2, and
(d) nucleotide sequences which encodes the polypeptides encoded by (a), (b) or/and (c) within the scope of the degeneracy of the genetic code.

The transmembrane linker (ii) and the transporter domain of the EhaA protein (iii) in particular comprises a sequence selected from the group consisting of:

(a) an amino acid sequence comprising SEQ ID NO:2, and
(b) sequences which are at least 70%, at least 80%, at least 90%, at least 95%, at least 98%, or at least 99% identical to the sequences of (a).

A sequence encoding the transmembrane linker or/and the transporter domain can be obtained from *E. coli* EhaA sequences.

Figure 25:
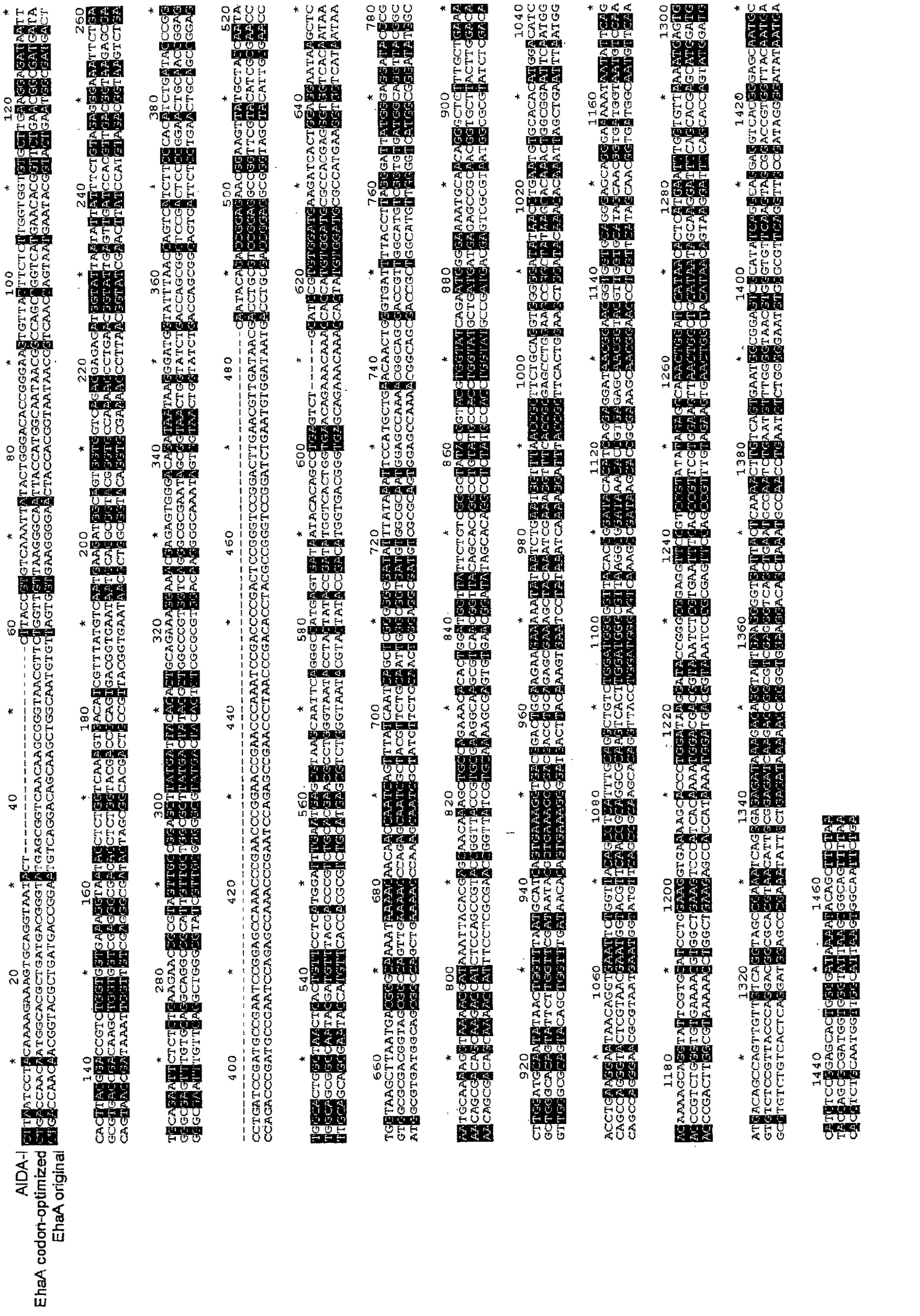
Figure 25:
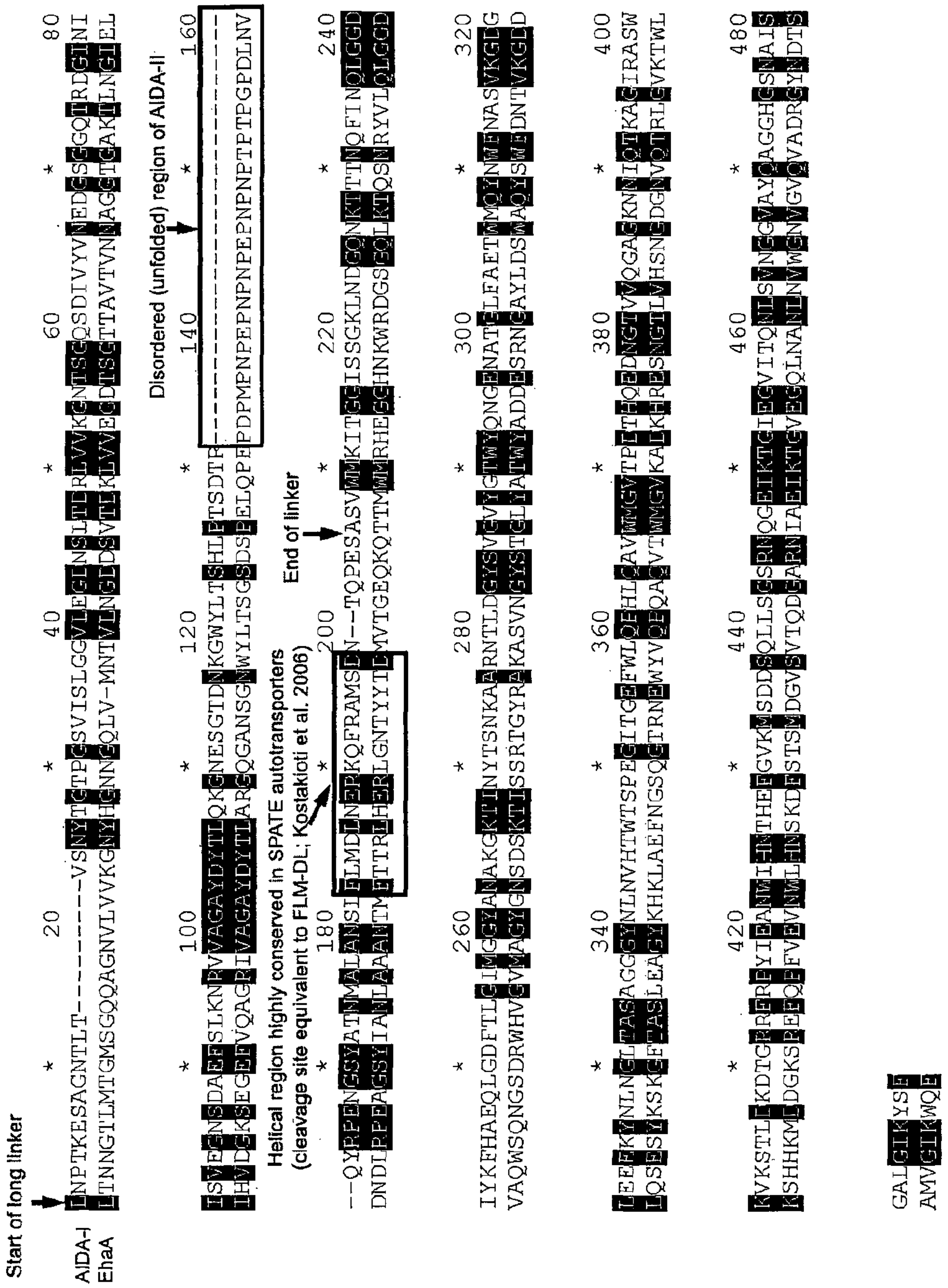

The sequence of the nucleic acid fusion can have a codon usage adapted to the host cell. In particular, the codon usage of the transmembrane linker sequence, the EhaA transporter domain or/and the passenger can be adapted to the host cell. More particular, the codon usage of the transmembrane linker sequence or/and the EhaA transporter domain can be adapted to the host cell. This is can improve expression if the EhaA transporter domain is heterologous to the host cell. Optimisation of codon usage does usually not affect the amino acid sequence. The EhaA nucleic acid sequence being codon-optimized can have an identity of about 80% identity with the natural EhaA sequence (FIG. 25).

Examples of codon-optimized nucleotide sequences are described in SEQ ID NO:1, 16 and 18.

Step (b) of the method of the present invention refers to culturing the host cell under conditions wherein the nucleic acid fusion is expressed and the expression product comprising the recombinant polypeptide is displayed on the surface of the host cell. The person skilled in the art knows suitable culture conditions, in particular for the host cell species as described herein. The method according to the invention allows for an efficient expression of passenger proteins on the surface of host cells, particularly *E. coli* or other Gram-negative bacterial cells up to 100 000 or more molecules per cell by using a liquid medium of the following composition: 5 g/l to 20 g/l, preferably about 10 g/l trypton, 2 g/l to 10 g/l, preferably about 5 g/l yeast extract, 5 g/l to 20 g/l, in particular about 10 g/l NaCl and the remaining part water. The medium should possibly contain as little as possible divalent cations, thus preferably Aqua bidest or highly purified water, e.g. Millipore water is used. The liquid medium may contain in addition preferably EDTA in a concentration of 2 μM to 20 μM, in particular 10 μM. Moreover, it contains preferably reducing reagents, such as 2-mercaptoethanol or dithiotreitol or dithioerythritol in a preferred concentration of 2 mM to 20 mM. The reducing reagents favour a non-folded structure of the polypeptide during transport. The liquid medium can further contain additional C-sources, preferably glucose, e.g. in an amount of up to 10 g/l, in order to favour secretion i.e. transfer of the passenger to the surrounding medium. For surface display preferably no additional C-source is added. Preferred culture conditions for Gram-negative cells, such as *E. coli, Z. mobilis, P. putida* and *S. enterica*, are described in the Examples.

If the host cell is a Gram-negative bacterium, the polypeptide synthesized in the cytoplasma can be translocated from the cytoplasm into the periplasmic space by crossing the inner membrane. This can be effected by the signal peptide. During maturation, the signal peptide can be cleaved off. The polypepide fusion to be displayed on the surface of a host cell can therefore comprise an amino acid sequence encoded by nucleic acid components (ii) to (iv), as described herein.

The components (i) to (iv) are fused in frame. The components (i) to (iv) in the nucleic acid fusion of the present invention are preferably oriented from 5' to 3'. In the expression product obtained in step (b), the amino acid sequences encoded by nucleic acid sequences (i) to (iv) are preferably arranged N terminal to C terminal.

The nucleic acid fusion can further comprise at least one nucleic acid sequence encoding an affinity tag. The nucleic acid sequence encoding the affinity tag can flank the portion (ii) encoding the recombinant polypeptide to be displayed. In this embodiment, the nucleic acid sequence encoding the affinity tag can be separated from portion (ii) by a sequence encoding at least one protease recognition sequence. The at least one protease recognition sequence can be a first protease recognition sequence. The at least one protease recognition sequence can be any protease recognition sequence as described herein. Preferably, the at least one protease recognition sequence is independently selected from factor Xa cleavage site, OmpT cleavage site, and TEV protease cleavage site.

The affinity tag can independently be selected from $His_6$ and epitopes. In particular, the epitope is recognised by a specific antibody, for example a monoclonal antibody. An example of a suitable epitope is the amino acid sequence PEYFK which is recognized by antibody Dü 142 (Spohn et al, 1992).

Furthermore, the nucleic acid fusion can comprise a nucleotide sequence encoding at least one protease recognition sequence, said nucleotide sequence being located between portions (ii) and portion (iii). The at least one protease recognition sequence can be a second protease recognition sequence. The at least one protease recognition sequence can be any protease recognition sequence as described herein. Preferably, the at least one protease recognition sequence is independently selected from factor Xa cleavage site, OmpT cleavage site, and TEV protease cleavage site.

The protease recognition sequence, as used herein, may be a recognition site for an intrinsic protease, i.e. a protease naturally occurring in the host cell, or an externally added protease. For example, the externally added protease may be an IgA protease (cf. EP-A-0 254 090), thrombin or factor X (factor Xa). The intrinsic protease may be e.g. selected from OmpT, OmpK or protease X. The protease may also be TEV.

In the method of the present invention, the portion (ii) encoding the recombinant polypeptide to be displayed can be flanked by at least one sequence comprising a multiple cloning site. The multiple cloning site is suitable for introduction of any further nucleic acid sequence, or for replacement of the portion (ii) encoding the passenger by a nucleotide sequence encoding another passenger.

Preferably, the portion (ii) is flanked by two sequences comprising a multiple cloning site. The first of these sequences is located 5' of portion (ii). The second of these sequences is located 3' of portion (ii).

The method of the present invention may comprise preparing a membrane preparation from the cell obtained in step (b). The membrane preparation may comprise membrane particles. The membrane particles may be membrane vesicles. Preferred membrane particles are outer membrane particles. In particular the method of the present invention may comprise preparing outer membrane particles of cells displaying a recombinant polypeptide on the surface, e.g. of Gram-negative bacterial cells. The person skilled in the art knows suitable conditions (e.g. Hantke, 1981, Schultheiss et al., 2002). Typical conditions for preparing membrane particles are employed in the examples of the present invention. Outer membrane particles from a host cell as described herein may be performed by a method comprising the steps:

(a) treating the host cell with a hydrolase (such as lysozyme) and optionally with a DNAse. This enzymatic treatment may be performed at room temperature. The hydrolase hydrolyses the cell wall within the periplasmic space. The cell wall comprises peptidoglycans to be hydrolyzed.
(b) optionally solubilizing the preparation of (a) with a tenside, such as Triton X-100, or/and with sarcosine, followed by optional centrifugation of cell debris. The thus obtained preparation of outer membrane particles may be centrifuged, washed and resuspended.

The diameter of the membrane particles may be in the range of 1 nm to 1000 nm, in the range of 50 nm to 500 nm, in the range of 75 to 200 nm, or in the range of 90 to 120 nm. At least 80%, at least 90%, at least 95%, or at least 98% of the membrane particles may have a diameter in a range selected from the ranges described herein.

In a host cell being a Gram-negative bacterium, after translocation, the recombinant passenger remains attached to the surface of the outer membrane by the β-barrel, which is serving as an anchor within the outer membrane. Due to the controlled integration of the β-barrel within the outer membrane, the C terminal part of the β-barrel is directed to the inner side of the outer membrane, whereas the N-terminal part of the linker, to which the recombinant passenger protein is covalently bound, is directed to the outer surface of the outer membrane, i.e. the environment. The recombinant passenger protein has an oriented location after transport, namely it is directed to the cellular surface. The recombinant passenger protein has the identical orientation as the lipopolysaccharide (LPS) layer which may be present in the outer membrane.

Membrane particles of the present invention prepared from the host cell of the present invention comprise the recombinant peptide at the surface directed to the environment. In contrast to the inner membrane which is a unit membrane, the outer membrane of Gram-negative bacteria, in particular *E. coli*, is asymmetric. The outer membrane may comprise an inner layer comprising phospholipids and an outer layer comprising LPS. LPS is hydrophilic and may contain several negative charges. By using outer membrane particles with anchored passenger proteins by a β-barrel for the coating of carriers, the outer side of the outer membrane, in particular the LPS side will be directed to the surface distal to the carrier. As a consequence the recombinant protein or a domain thereof, which are integrated in the outer membrane by autodisplay, will be directed to the surface distal to the carrier as well. The core part of the membrane particles may stabilize the interaction of the outer membrane layer obtained by applying outer membrane particles to the carrier by hydrophobic interactions and may contain lipoproteins or peptidoglycans.

The skilled person knows suitable methods to determine the degree of identity of nucleic acid sequences and amino acid sequences. Known algorithms, such as BLAST (for nucleic acids) or PBLAST (for amino acid sequences) may be used. A nucleic acid or polypeptide comprising sequences having at least 70%, at least 80%, at least 90%, at least 95%, at least 98%, or at least 99% identity to a given sequence includes fragments of the given nucleic acid or polypeptide.

The polypeptide of the present invention to be displayed on the surface of the cell may be a multimeric polypeptide. The multimeric recombinant polypeptide may be a homodimer, i.e. a polypeptide consisting of two identical subunits or a homomultimer, i.e. a polypeptide consisting of three or more identical subunits. On the other hand, the multimeric recombinant polypeptide may be a heterodimer, i.e. a polypeptide consisting of two different subunits or a heteromultimer consisting of three or more subunits wherein at least two of these subunits are different. For example, the multimeric polypeptide is comprised of a plurality of subunits which form a "single" multimeric polypeptide or a complex of a plurality of functionally associated polypeptides which may in turn be monomeric and/or multimeric polypeptides. It should be noted that at least one subunit of the multimeric recombinant protein may contain at least one prosthetic group as described herein. Further, is should be noted that the nucleic acid fusion may encode a plurality of polypeptide subunits as a polypeptide fusion which when presented on the cell surface forms a functional multimeric polypeptide.

Homodimers or homomultimers may be formed by a spontaneous association of several identical polypeptide subunits displayed on the host cell membrane. Heterodimers or heteromultimers may be formed by a spontaneous association of several different polypeptide subunits displayed on the host cell membrane.

On the other hand, a multimeric recombinant polypeptide may be formed by an association of at least one polypeptide subunit displayed on the host cell membrane, as described herein, and at least one soluble polypeptide subunit added to the host cell membrane. The added subunit may be identical to the displayed subunit or be different therefrom.

Another aspect of the present invention is a recombinant vector comprising the nucleic acid fusion as described herein, operatively linked to an expression control sequence. In particular, the recombinant vector comprises:

(i) a portion encoding a signal peptide,
(ii) a portion encoding a multiple cloning site,
(iii) a portion encoding a transmembrane linker, and
(iv) a portion encoding the transporter domain of an EhaA protein.

In this embodiment, the signal peptide is a signal peptide as described herein.

The multiple cloning site is a multiple cloning site as described herein. The multiple cloning site is in particular suitable for integration of a nucleic acid sequence encoding a recombinant polypeptide in frame with portions (i), (ii) and (iv). The transmembrane linker is a transmembrane linker as described herein. The transporter domain of the EhaA protein is a transporter domain of the EhaA protein as described herein. In this embodiment, the nucleic acid sequences (i) to (iv) are in particular arranged from 5' to 3'.

Another aspect of the present invention is a recombinant host cell comprising the recombinant vector as described herein.

Yet another aspect of the present invention is a method of displaying a recombinant polypeptide on the surface, said method comprising the steps (a) providing a recombinant vector comprising a multiple cloning site (ii), as described herein,
(b) inserting a sequence encoding the recombinant polypeptide to be displayed into the multiple cloning site (ii), and
(c) performing the method of displaying a recombinant polypeptide on the surface of a host cell, as described herein.

Yet another aspect of the present invention is a method for producing a host cell capable of displaying a recombinant polypeptide on the surface, said method comprising the steps (a) providing a recombinant vector comprising a multiple cloning site (ii), as described herein,
(b) inserting a sequence encoding the recombinant polypeptide to be displayed into the multiple cloning site (ii), and
(c) performing the method of displaying a recombinant polypeptide on the surface of a host cell, as described herein.

Yet another aspect of the present invention is a host cell capable of displaying the recombinant polypeptide on the surface. The host cell may be any host cell as described herein. The polypeptide fusion displayed on the cell surface comprises:

(I) a portion comprising the recombinant polypeptide to be displayed,
(II) a portion comprising a transmembrane linker, and
(III) a portion comprising the transporter domain of an EhaA protein.

The portion (I) is also termed "passenger", as described herein.

The displayed polypeptide is in particular a functional polypeptide, as described herein.

The portions (I) to (III) of the recombinant polypeptide (polypeptide fusion) displayed by the host cell of the present invention are encoded in particular by the components (ii), (iii), and (iv) of the nucleic acid fusion, as described herein.

Yet another aspect of the present invention is a membrane preparation comprising a recombinant polypeptide. The membrane preparation of the present invention may comprise membrane particles, as described herein.

The membrane preparation may be obtained from a host cell as described herein. The recombinant polypeptide of the may be any recombinant polypeptide as described herein.

Yet another aspect of the present invention is the use of a membrane preparation comprising a recombinant polypeptide in the manufacture of a carrier comprising a recombinant polypeptide.

The membrane preparation of the present invention may be employed for coating a carrier. The carrier may comprise a membrane preparation of the present invention, as described herein.

The carrier may comprise a hydrophobic surface. The hydrophobic surface may have a contact angle of more than 90°. A increasing surface angle of more than 30° indicates a gradually increasing hydrophobicity of a surface. In the present context, a hydrophobic surface may have a contact angle of at least 40°. The surface preferably has a hydrophobicity described by a contact angle of at least 40°, at least 50°, at least 60°, at least 65°, at least 70°.

Contact angles are preferably determined by the sessile drop method. The sessile drop method is a standard method for determining contact angles. Measurements may be performed with a contact angle goniometer. Preferred contact angles of the hydrophobic surface are in a range of 40° to 100°, 50° to 90°, or 60° to 80°.

The surface of the carrier may be a metal surface. A suitable metal surface has a contact angle e.g. in the range of 50° to 80°. A suitable metal may be selected from gold, silver, titanium, aluminium and alloys such as brass. A preferred surface is a gold surface. The gold surface may be employed as it is. An untreated gold surface has a hydrophobicity suitable for the carrier as described herein. A treatment of the gold surface with thiolated hydrocarbons or hydrocarbons with functional groups such as carboxylic acids or hydroxyl groups is not required.

Another preferred surface of the carrier comprises a polymer, for instance a surface usually employed in disposable materials for use in biochemical or/and medical science. The polymer may be an artificial polymer. Examples of artificial polymers include a polymer selected from polystyrenes, polypropylenes, and polycarbonates. The polystyrene may be produced from [2,2]paracyclophane monomers. Polystyrene surfaces may be treated with oxygene plasma introducing OH or/and methylene groups in order to modify the hydrophobicity. Examples of such modified surfaces include Maxi-sorp, Medi-sorp, Multi-sorp, and Poly-sorp surfaces. Another suitable polystyrene surface is Parylene N produced from [2,2]paracyclophane monomers. Yet another suitable surface is Parylene A [Poly(monoamino-p-xylene)]. Especially suitable are surfaces comprising a polymer having a hydrophobicity described by a contact angle of at least 50°. Suitable surfaces are selected from polystyrene, Parylene A, Parylene N, Maxi-sorp, Medi-sorp, Multi-sorp, and Poly-sorp. Preferred surfaces are selected from polystyrene, Parylene A, Parylene N, Maxi-sorp, Medi-sorp, and Poly-sorp.

The surface may comprise a natural polymer. Suitable natural polymers include polybutyrate and cellulose and derivatives thereof. A further surface is provided by latex particles, in particular latex beads.

Yet another surface is provided by C18-modified particles, in particular C18-modified monolithic silica particles. C18 refers to an alkyl group comprising 18 carbon atoms. C18-modified particles are known in the art.

Yet another suitable surface is a glass surface.

The surface may be modified is order to adjust the hydrophobicity. Modification may be performed by chemical treatment (i.e. by oxygen plasma), physical treatment (e.g. by laser irradiation or/and radioactive irradiation), or by mechanical treatment.

The method according to the invention and the host cells according to the invention can be used for a variety of different applications, e.g. as whole cell biofactories or membrane preparation biofactories for chemical synthesis procedures, e.g. for the synthesis of organic substances selected from enzyme substrates, drugs, hormones, starting materials and intermediates for syntheses procedures and chiral substances (cf. Roberts, Chemistry and Biology 6 (1999), R269-R272).

In particular, the method according to the invention and the host cells according to the invention, as described herein, can be used in the chemical synthesis, for example in enzymatically catalyzed enantioselective or/and regioselective steps.

Yet another aspect of the present invention is the surface display of cellulose degrading enzymes (cellulases) on an ethanologenic bacterium, such as a cell selected from *Z. mobilis, Z. palmae, P. putida*, and *Klebsiella* spp. by the method of the present invention. An ethanologenic bacterium, such as a cell selected from *Z. mobilis, Z. palmae, P. putida*, and *Klebsiella* spp. can provide a whole-cell catalytic system which is able to breakdown cellulose and ferment the formed monomeric sugars to ethanol in a single step.

*Klebsiella* spp. is in particular *Klebsiella oxytoca.*

An ethanologenic bacterium, as used herein, is a bactium capable of producing ethanol. Examples of ethanologenic bacteria include, but are not limited to *Z. mobilis Z. palmae, P. putida*, and *Klebsiella* spp, in particular *Klebsiella oxytoca.*

Surface display of a cellulose degrading enzyme (cellulase) on a *Z. mobilis* cell is preferred. Surface display of a cellulose degrading enzyme (cellulase) on a *Z. palmae* cell is also preferred. Surface display of a cellulose degrading enzyme (cellulase) on a *P. putida* cell is also preferred.

A further aspect of the present invention refers to a method of production of ethanol, said method comprising the steps:

(a) expressing at least one cellulose degrading enzyme on the surface of an ethanologenic bacterium, such as a cell selected from *Z. mobilis, Z. palmae, P. putida* and *Klebsiella* spp., by the method of displaying a recombinant polypeptide on the cell surface, as described herein, (b) contacting the cell of (a) with a cellulose containing substrate under suitable conditions wherein the at least one cellulose degrading enzyme expressed on the surface of an ethanologenic bacterium, such as a cell selected from *Z. mobilis, Z. palmae, P. putida* and *Klebsiella* spp., is capable of degrading cellulose into ethanol, and (c) obtaining the ethanol.

The skilled person knows suitable condition of (b) and (c).

In the method of production of ethanol, a preferred cell is a *Z. mobilis* cell. In the method of production of ethanol, another preferred cell is a *Z. palmae* cell. In the method of production of ethanol, yet another preferred cell is a *P. putida* cell. In the method of production of ethanol, yet another preferred cell is a *Klebsiella* spp. cell.

Yet another aspect of the present invention refers to a method of degrading cellulose or/and lignocellulose, said method comprising the steps:

(a) expressing at least one of an endoglucanase (EC 3.2.1.4), an exoglucanase (EC 3.2.1.91), an a 3-glucosidase (EC 3.2.1.21), by the method of the present invention of displaying a recombinant polypeptide on the surface of a cell, (b) contacting the cell of (a) with a cellulose or/and lignocellulose containing substrate under suitable conditions where the at least one enzyme expressed on the surface of the cell is capable of degrading the cellulose or/and lignocellulose, and (c) optionally obtaining at least one degradation product of the cellulose or/and lignocellulose.

In degradation of cellulose or/and lignocellulose, an endocellulase can cleave the beta-1,4-glycosidic bond, in particular in amorphous regions of the cellulose or/and lignocellulose, thereby generating cellulose polysaccharide chains of variable lengths. The cellulose polysaccharide chains include free terminal residues. An exoglucanase can cleave off cellobiose units from the terminal residues of the cellulose polysaccharides. Cellobiose can be converted into glucose by a β-glucosidase.

By the method method of degrading cellulose or/and lignocellulose, the cellulose or/and lignocellulose can be degraded into reducing sugers, in particular into glucose, cellubiose or/and cellulose-polysaccharide chains of variable lengths). It is preferred that the cellulose or/and lignocellulose is degraded into glucose.

The cell can be any cell as described herein. The cell can be selected from *Z. mobilis, Z. palmae* and *Pseudomonas* putida. In particular, the cell is a *Pseudomonas* spp. cell, more particular a *Pseudomonas putida* cell, most particular *Pseudomonas putida* KT2440.

In step (a), it is preferred to express a combination of an endoglucanase (EC 3.2.1.4), an exoglucanase (EC 3.2.1.91), or/and a β-glucosidase (EC 3.2.1.21). More preferred is a combination of an endoglucanase (EC 3.2.1.4), an exoglucanase (EC 3.2.1.91), and a β-glucosidase (EC 3.2.1.21).

The at least one of the enzymes of step (a) a can be expressed on a common cell, or each enzyme to be expressed can be expressed on a separate cell.

A preferred exoglucanase of the present invention can be obtained from *Clostridium thermocellum.*

A preferred exoglucanase of the present invention comprises amino acid positions 38-831 of SEQ ID NO:21, or a sequence being at least 70%, at least 80%, at least 90%, at least 95%, at least 98%, or at least 99% identical to positions 38-831 of SEQ ID NO:21.

A preferred exoglucanase of the present invention is encoded by SEQ ID NO:20, in particular by positions 112-2493 of SEQ ID NO:20, or by a sequence being at least 70%, at least 80%, at least 90%, at least 95%, at least 98%, or at least 99% identical to positions 112-2493 of SEQ ID NO:20.

A preferred endoglucanase of the present invention can be obtained from *Bacillus subtilis.*

A preferred endoglucanase of the present invention comprises amino acid positions 38-511 of SEQ ID NO:23, or a sequence being at least 70%, at least 80%, at least 90%, at least 95%, at least 98%, or at least 99% identical to positions 38-511 of SEQ ID NO:23.

A preferred endoglucanase of the present invention is encoded by SEQ ID NO:22, in particular by positions 112-1533 of SEQ ID NO:22, or by a sequence being at least 70%, at least 80%, at least 90%, at least 95%, at least 98%, or at least 99% identical to positions 112-1533 of SEQ ID NO:22.

A preferred β-glucosidase of the present invention can be obtained from *Clostridium thermocellum.*

A preferred β-glucosidase of the present invention comprises amino acid positions 38-488 of SEQ ID NO:25, or a sequence being at least 70%, at least 80%, at least 90%, at least 95%, at least 98%, or at least 99% identical to positions 38-488 of SEQ ID NO:25.

A preferred β-glucosidase of the present invention is encoded by SEQ ID NO:24, in particular by positions 112-1464 of SEQ ID NO:24, or by a sequence being at least 70%, at least 80%, at least 90%, at least 95%, at least 98%, or at least 99% identical to positions 112-1464 of SEQ ID NO:24.

The skilled person knows suitable condition of (b) and (c). Step (b) can be performed at a pH in the range of about 3 to about 7, about 4 to about 6.5, about 5 to about 6.5, or about 5.5 to about 6.5, or at a pH of about 6. A preferred pH is about 6.

Step (b) can be performed at a temperature in the range of about 45° C. to about 65° C., or about 50° C. to about 60° C., or at a temperature of about 55° C. A temperature of about 55° C. is preferred.

In step (b), a buffer can be used in a concentration of about 0.5 M to about 1.5 M, about 0.75 M to about 1.25 M, about 0.9 M to about 1.1 M, or about 1 M. A preferred buffer concentration is 1 M. Any suitable buffer can be used, for example citrate buffer (such as sodium citrate buffer).

Preferred conditions for step (b) include 1 M citrate buffer at a pH of about 6, and 55° C., or 1 M sodium citrate buffer at a pH of about 6, and 55° C.

SEQ ID NOs: 3, 5, 7, 9, 11, 13, 20, 22 and 24 describe specific examples of nucleic acid fusions of the present invention. SEQ ID NOs: 4, 6, 8, 10, 12, 14, 21, 23 and 25 describe polypeptides encoded by SEQ ID NOs: 3, 5, 7, 9, 11 13, 20, 22 and 24, respectively.

SEQ ID NO:3:

Nucleotide Sequence pMATE-MT004, for the Surface Display of 6×His using the MATE System Annotation of SEQ ID NO:3

| feature | position |
|---|---|
| pUC ori | 2-805 bp |
| T5 promoter | 1455-1502 bp |
| CtxB SP sequence | 1583-1663 bp |
| 6xHis | 1664-1681 bp |
| fXa cleavage site | 1682-1693 bp |
| MCS | 1694-1717 bp |
| OmpT cleavage site | 1718-1729 bp |
| fXa cleavage site (2.nd) | 1730-1741 bp |
| PEYFK epitope | 1745-1759 bp |
| MATE linker and β-barrel | 1760-3226 bp |
| KanR (kanamycine resistance cassette) | 3606-4415 bp |
| LacI repressor gene | 4431-5262 bp |

SEQ ID NO:4

Polypeptide Sequence of Autotransporter Fusion Protein Encoded by pMATE-MT004, for the Surface Display of 6×His using the MATE System Annotation of SEQ ID NO:4

| feature | position |
|---|---|
| CtxB SP | 1-27 aa |
| 6xHis | 28-33 aa |
| fXa cleavage site | 34-37 aa |
| MCS | 38-45 aa |
| OmpT cleavage site | 46-49 aa |
| fXa cleavage site (2.nd) | 50-53 aa |
| PEYFK epitope | 55-59 aa |
| MATE linker and β-barrel | 60-547 aa |

SEQ ID NO:5:

Nucleotide Sequence of pMATE-MT006, for the Surface Display of GFP using the MATE System Annotation of SEQ ID NO:5

| feature | position |
|---|---|
| pUC ori | 2-805 bp |
| T5 promoter | 1455-1502 bp |
| CtxB SP sequence | 1583-1663 bp |
| 6xHis | 1664-1681 bp |
| fXa cleavage site | 1682-1693 bp |
| GFPmut2 | 1694-2410 bp |
| OmpT cleavage site | 2411-2422 bp |
| fXa cleavage site (2.nd) | 2423-2434 bp |
| PEYFK epitope | 2438-2452 bp |
| MATE linker and β-barrel | 2453-3919 bp |
| KanR (kanamycine resistance cassette) | 4299-5108 bp |
| LacI repressor gene | 5191-6252 bp |

SEQ ID NO:6 Polypeptide Sequence of the Autotransporter Fusion Protein Encoded by pMATE-MT006, for the Surface Display of GFP using the MATE System Annotation of SEQ ID NO:6

| feature | position |
|---|---|
| CtxB SP | 1-27 aa |
| 6xHis | 28-33 aa |
| fXa cleavage site | 34-37 aa |
| GFPmut2 | 38-276 aa |
| OmpT cleavage site | 277-280 aa |
| fXa cleavage site (2.nd) | 281-284 aa |
| PEYFK epitope | 286-290 aa |
| MATE linker and β-barrel | 291-778 aa |

SEQ ID NO:7

Nucleotide Sequence of pMATE-SI005, for the Surface Display of 6×His using the MATE System in a Broad Range of Bacterial Hosts Annotation of SEQ ID NO:7

| feature | position |
|---|---|
| AraC | 1-895 bp |
| araBAD promoter | 916-1188 bp |
| CtxB SP sequence | 1231-1311 bp |
| 6xHis | 1312-1329 bp |
| fXa cleavage site | 1330-1341 bp |
| MCS | 1342-1365 bp |
| OmpT cleavage site | 1366-1377 bp |
| fXa cleavage site (2.nd) | 1378-1389 bp |
| PEYFK epitope | 1393-1407 bp |
| MATE linker and β-barrel | 1408-2874 bp |
| pBBR1 rep gene (broad host rep) | 3196-3858 bp |
| Kanamycine resistance cassette | 5392-6186 bp |

SEQ ID NO:8

Polypeptide Sequence of the Autotransporter Fusion Protein Encoded by pMATE-SI005, for the Surface Display of 6×His using the MATE System in a Broad Range of Bacterial Hosts Annotation of SEQ ID NO:8

| feature | position |
|---|---|
| CtxB SP | 1-27 aa |
| 6xHis | 28-33 aa |
| fXa cleavage site | 34-37 aa |
| MCS | 38-45 aa |
| OmpT cleavage site | 46-49 aa |
| fXa cleavage site (2.nd) | 50-53 aa |
| PEYFK epitope | 55-59 aa |
| MATE linker and β-barrel | 60-547 aa |

-continued

SEQ ID NO:9

Nucleotide Sequence of pMATE-SI010, for the Surface Display of estA Catalytic Domain using the MATE System in a Broad Range of Bacterial Hosts Annotation of SEQ ID NO:9

| feature | position |
|---|---|
| AraC | 1-895 bp |
| araBAD promoter | 916-1188 bp |
| CtxB SP sequence | 1231-1311 bp |
| 6xHis | 1312-1329 bp |
| fXa cleavage site | 1330-1341 bp |
| estA catalytic domain | 1342-2388 bp |
| OmpT cleavage site | 2389-2400 bp |
| fXa cleavage site (2.nd) | 2401-2412 bp |
| PEYFK epitope | 2416-2430 bp |
| MATE linker and β-barrel | 2431-3897 bp |
| pBBR1 rep gene (broad host rep) | 4219-4881 bp |
| Kanamycine resistance cassette | 6415-7209 bp |

SEQ ID NO:10

Polypeptide Sequence of the Autotransporter Fusion Protein Encoded by pMATE-SI010, for the Surface Display of *B. gladioli* EstA Esterase Domain using the MATE System in a Broad Range of Bacterial Hosts Annotation of SEQ ID NO:10

| feature | position |
|---|---|
| CtxB SP | 1-27 aa |
| 6xHis | 28-33 aa |
| fXa cleavage site | 34-37 aa |
| EstA catalytic domain | 38-386 aa |
| OmpT cleavage site | 387-390 aa |
| fXa cleavage site (2.nd) | 391-394 aa |
| PEYFK epitope | 396-400 aa |
| MATE linker and β-barrel | 401-888 aa |

SEQ ID NO:11

Nucleotide Sequence of pMATE-SI012, for the Surface Display of estA Catalytic Domain using the MATE System in a Broad Range of Bacterial Hosts Annotation of SEQ ID NO:11

| feature | position |
|---|---|
| Kanamycine resistance cassette | 541-1335 bp |
| Mob gene | 1593-2592 bp |
| pBBR1 rep gene (broad host rep) | 3585-4247 bp |
| AraC | 4310-5204 bp |
| araBAD promoter | 5225-5497 bp |
| CtxB SP sequence | 5540-5620 bp |
| 6xHis | 5621-5638 bp |
| fXa cleavage site | 5639-5650 bp |
| estA catalytic domain | 5651-6697 bp |
| OmpT cleavage site | 6698-6709 bp |
| fXa cleavage site (2.nd) | 6710-6721 bp |
| PEYFK epitope | 6725-6739 bp |
| MATE linker and β-barrel | 6740-8206 bp |

SEQ ID NO:12

Polypeptide Sequence of the Autotransporter Fusion Protein Encoded by pMATE-SI012, for the Surface Display of

*B. gladioli* EstA Esterase Domain using the MATE System in a Broad Range of Bacterial Hosts Annotation of SEQ ID NO:12

| feature | position |
|---|---|
| CtxB SP | 1-27 aa |
| 6xHis | 28-33 aa |
| fXa cleavage site | 34-37 aa |
| EstA catalytic domain | 38-386 aa |
| OmpT cleavage site | 387-390 aa |
| fXa cleavage site (2.nd) | 391-394 aa |
| PEYFK epitope | 396-400 aa |
| MATE linker and β-barrel | 401-888 aa |

SEQ ID NO:13

Nucleotide Sequence of pMATE-SI015, for the Surface Display of 6×His-mCherry using the MATE System Annotation of SEQ ID NO:13

| feature | position |
|---|---|
| pUC ori | 2-805 bp |
| T5 promoter | 1455-1502 bp |
| CtxB SP sequence | 1583-1663 bp |
| 6xHis | 1664-1681 bp |
| mCherry | 1682-2389 bp |
| OmpT cleavage site | 2390-2401 bp |
| fXa cleavage site | 2402-2413 bp |
| PEYFK epitope | 2417-2431 bp |
| MATE linker and β-barrel | 2432-3898 bp |
| KanR (kanamycine resistance cassette) | 4278-5087 bp |
| LacI repressor gene | 5170-6252 bp |

SEQ ID NO:14

Polypeptide Sequence of the Autotransporter Fusion Protein Encoded by pMATE-51015, for the Surface Display of 6×His-mCherry using the MATE System Annotation of SEQ ID NO:14

| feature | position |
|---|---|
| CtxB SP | 1-27 aa |
| 6xHis | 28-33 aa |
| mCherry | 34-269 aa |
| OmpT cleavage site | 270-273 aa |
| fXa cleavage site (2.nd) | 274-277 aa |
| PEYFK epitope | 279-283 aa |
| MATE linker and β-barrel | 284-771 aa |

SEQ ID NO:20

Nucleotide Sequence of the Autotransporter Fusion Gene Encoded by pMATE-exoglucanase, for the Surface Display of an Exoglucanase using the pMATE System (length 4002 bp)

Annotation of SEQ ID NO:20

| Feature | position |
|---|---|
| CtxB SP sequence | 1-81 bp |
| 6xHis | 82-99 bp |
| fXa cleavage site | 100-111 bp |
| exoglucanase | 112-2493 bp |
| OmpT cleavage site | 2494-2505 bp |
| fXa cleavage site (2.nd) | 2506-2517 bp |
| PEYFK epitope | 2521-2535 bp |
| MATE linker and β-barrel | 2536-4002 bp |

SEQ ID NO:21

Polypeptide Sequence of the Autotransporter Fusion Protein Encoded by pMATE-exoglucanase, for the Surface Display of an Exoglucanase using the pMATE System (length 1333 aa)

Annotation of SEQ ID NO:21

| Feature | position |
|---|---|
| CtxB SP | 1-27 aa |
| 6xHis | 28-33 aa |
| fXa cleavage site | 34-37 aa |
| exoglucanase | 38-831 aa |
| OmpT cleavage site | 832-835 aa |
| fXa cleavage site (2.nd) | 836-839 aa |
| PEYFK epitope | 841-845 aa |
| MATE linker and β-barrel | 846-1333 aa |

SEQ ID NO:22

Nucleotide Sequence of the Autotransporter Fusion Gene Encoded by pMATE-endoglucanase, for the Surface Display of an Endoglucanase using the pMATE System (length 3042 bp)

Annotation of SEQ ID NO:22

| Feature | position |
|---|---|
| CtxB SP sequence | 1-81 bp |
| 6xHis | 82-99 bp |
| fXa cleavage site | 100-111 bp |
| endoglucanase | 112-1533 bp |
| OmpT cleavage site | 1534-1545 bp |
| fXa cleavage site (2.nd) | 1546-1557 bp |
| PEYFK epitope | 1561-1575 bp |
| MATE linker and β-barrel | 1576-3042 bp |

SEQ ID NO:23

Polypeptide Sequence of the Autotransporter Fusion Protein Encoded by pMATE-endoglucanase, for the Surface Display of an Endoglucanase using the pMATE System (length 1013 aa)

Annotation of SEQ ID NO:23

| Feature | position |
|---|---|
| CtxB SP | 1-27 aa |
| 6xHis | 28-33 aa |
| fXa cleavage site | 34-37 aa |
| endoglucanase | 38-511 aa |
| OmpT cleavage site | 512-515 aa |
| fXa cleavage site (2.nd) | 516-519 aa |
| PEYFK epitope | 521-525 aa |
| MATE linker and β-barrel | 562-1013 aa |

SEQ ID NO:24

Nucleotide Sequence of the Autotransporter Fusion Gene Encoded by pMATE-f3-glucosidase, for the Surface Display of a β-glucosidase using the pMATE System (length 2973 bp)

Annotation of SEQ ID NO:24

| Feature | position |
|---|---|
| CtxB SP sequence | 1-81 bp |
| 6xHis | 82-99 bp |
| fXa cleavage site | 100-111 bp |
| β-glucosidase | 112-1464 bp |
| OmpT cleavage site | 1465-1476 bp |

-continued

| Feature | position |
|---|---|
| fXa cleavage site (2.nd) | 1477-1488 bp |
| PEYFK epitope | 1492-1506 bp |
| MATE linker and β-barrel | 1507-2973 bp |

SEQ ID NO:25

Polypeptide Sequence of the Autotransporter Fusion Protein Encoded by pMATE-f3-glucosidase, for the Surface Display of a β-glucosidase using the pMATE System (length 990 aa).

Annotation of SEQ ID NO:25

| Feature | position |
|---|---|
| CtxB SP | 1-27 aa |
| 6xHis | 28-33 aa |
| fXa cleavage site | 34-37 aa |
| β-glucosidase | 38-488 aa |
| OmpT cleavage site | 489-492 aa |
| fXa cleavage site (2.nd) | 493-496 aa |
| PEYFK epitope | 498-502 aa |
| MATE linker and β-barrel | 503-990 aa |

Further, the present invention shall be further illustrated by the following figures and examples:

FIG. 1: Use of the MATE system for the transport of 6×His to the outer membrane. *E. coli* BL21 cells were grown in LB medium to $OD_{600}$ of 0.5. Protein expression was induced by the addition of 1 mM IPTG, and the cells were harvested after 1 hour. Outer membrane proteins were isolated according to the modified method of Hantke et al. (1981). (A) SDS-PAGE of outer membrane proteins. (B) Western blot with antibody against 6×His. M=PageRuler prestained protein marker, 1=cells with negative control plasmid, expressing an unrelated peptide with AIDA-I (pST005), 2=cells with empty vector (pJExpress401), 3=cells with pMATE-MT004 without the addition of IPTG, 4=cells with pMATE-MT004 with 1 mM IPTG for the induction of protein expression. The arrow indicates the band associated with the MATE fusion protein. Equal amounts of protein were loaded in the gels used for Coomassie staining and Western blots.

Figure 2:
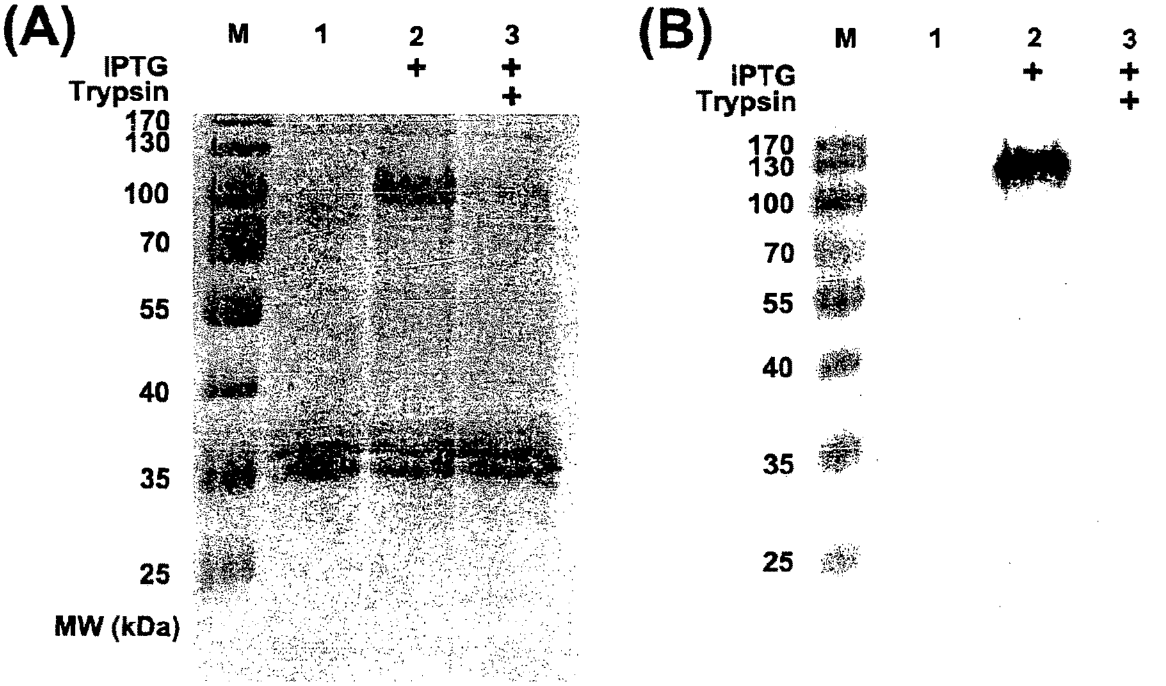

FIG. 2: Protease accessibility assay to confirm the surface display of GFP in *E. coli* with the MATE system. *E. coli* UT5600 cells containing pMATE-MT006 were harvested after the induction of protein expression with IPTG, and outer membrane proteins were isolated according to the modified method of Hantke (1981). (A) SDS-PAGE with Coomassie stain. (B) Western blot with polyclonal rabbit anti-GFP. M=PageRuler prestained protein marker, 1=cells without induction of protein expression (no IPTG), 2=cells with induction of protein expression, 3=cells with induction of protein expression and trypsin treatment. Samples were diluted 1:20 in loading buffer for Western blotting.

Figure 3:
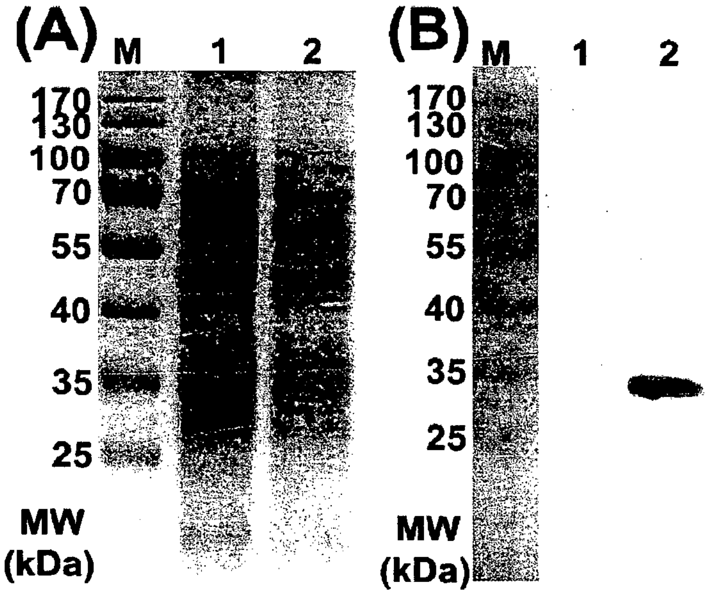

FIG. 3: Secretion of GFP into the cell growth media using the MATE system, based on the cleavage by the *E. coli* protease OmpT. *E. coli* cells containing pMATE-MT006 were grown in LB medium until $OD_{600}$ 0.5, and then expression of the fusion protein was induced with IPTG. After 1.5 h the cells were removed from the growth media by centrifugation followed by filtration. The proteins in the media were then concentrated by TCA precipitation and analysed with 12.5% SDS-PAGE. (A) SDS-PAGE with Coomassie stain showing all proteins released into the growth media. (B) Western blot to detect GFP released into the growth media c). M=PageRuler prestained protein marker, 1=*E. coli* UT5600 (OmpT negative strain), 2=*E. coli* UT2300 (OmpT positive parent strain). Equal amounts of protein were loaded for SDS-PAGE and Western blot.

Figure 4:
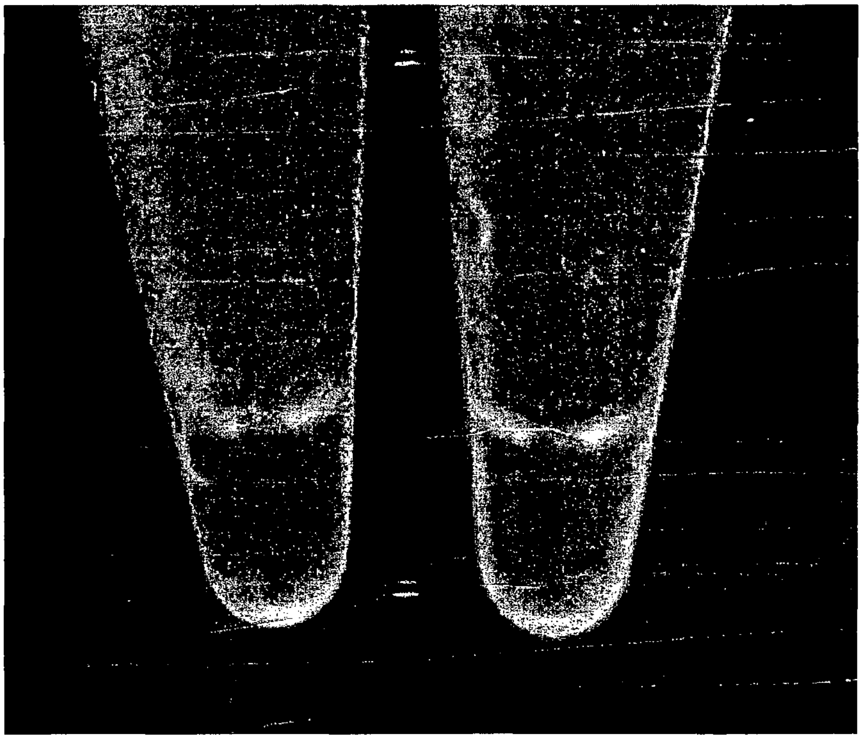

FIG. 4: Sample of mCherry and its negative control harvested from the supernatant of OmpT-positive and OmpT-negative *E. coli* strains. The RFP mCherry was secreted into the cell growth media using the pMATE-System, based on the cleavage by the *E. coli* protease OmpT. The OmpT-positive *E. coli* strain UT3200 and its derivate OmpT-negative strain *E. coli* UT5600 harbouring pMATE-SI015 were grown in LB medium until $OD_{600}$ 0.5, and then expression of the fusion protein was induced with 1 mM IPTG for 24 h. Cells were removed from the growth media by centrifugation. The supernatant of both strains was loaded on a Ni-NTA column for purification of 6×His mCherry.

Figure 5:
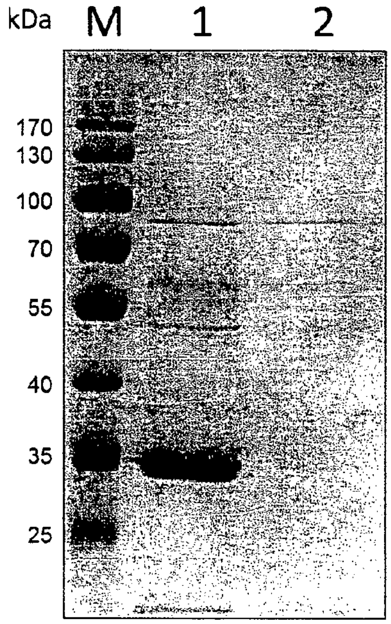

FIG. 5: SDS-PAGE with Coomassie stain of putative secreted affinity purified 6×His mCherry from OmpT-positive *E. coli* UT2300 and its derivate OmpT-negative strain *E. coli* UT5600 each harbouring the pMATE-SI015 plasmid. *E. coli* cells containing pMATE-SI015 were grown in LB media until $OD_{600}$ 0.5, and then expression of the fusion protein was induced with 1 mM IPTG. After 24 h the cells were removed from the growth media by centrifugation. The supernatant of both strains was loaded on a Ni-NTA column. 6×His proteins were eluted with 500 mM imidazole. After protein concentration, the eluate was loaded on a 10% polyacrylamide gel and subsequently stained with Coomassie. M=PageRuler prestained protein marker, 1=*E. coli* UT2300 harbouring pMATE-SI015 (OmpT positive parent strain), 2=*E. coli* UT5600 harbouring pMATE-SI015 (OmpT negative strain).

Figure 6:
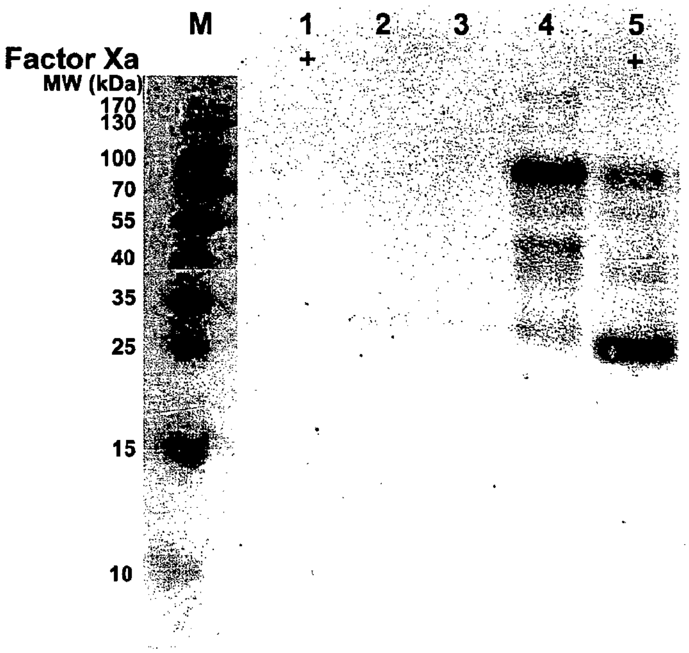

FIG. 6: Western blot showing the release of surface-displayed GFP into the supernatant by Factor Xa protease. Protein expression in *E. coli* UT5600 cells containing pMATE-MT006 was induced with 1 mM IPTG. Cells were washed and incubated for 16 h in buffer containing Factor Xa. Proteins were concentrated from the supernatant, separated by 12.5% SDS-PAGE. Western blotting was conducted with a polyclonal 1° against GFP as described in the materials and methods. M=PageRuler prestained protein marker, 1=Factor Xa protease alone 2=supernatant from cells without induction of protein expression (no IPTG), 3=supernatant from cells without induction of protein expression (no IPTG)+Factor Xa protease, 4=supernatant from cells with induction of protein expression, 5=supernatant from cells with induction of protein expression+Factor Xa protease.

Figure 7:
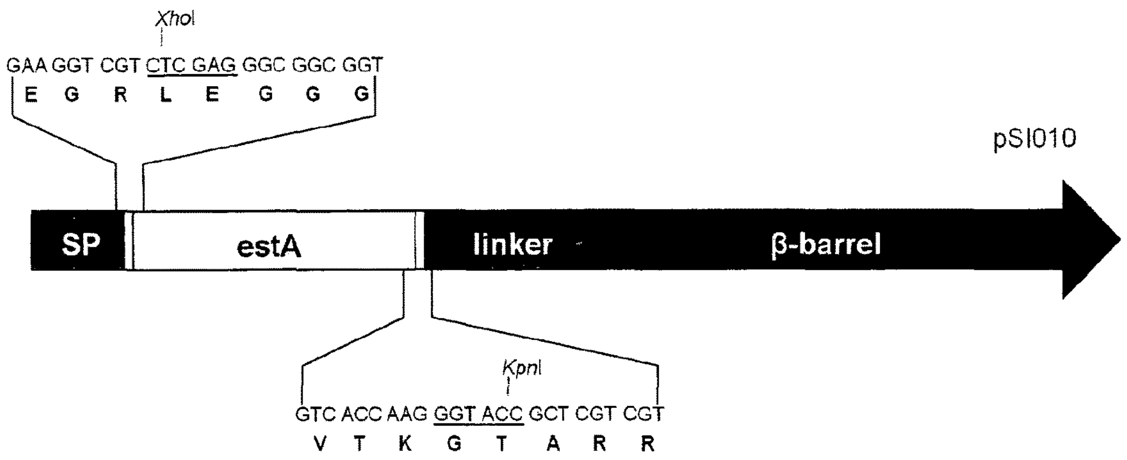

FIG. 7: Structure of the EstA-autotransporter fusion protein. Illustration of the parts from the fusion protein necessary for the surface display of the *B. gladioli* estA catalytic domain using the MATE system. SP=signal peptide. Restriction sites used for cloning are underlined.

Figure 8:
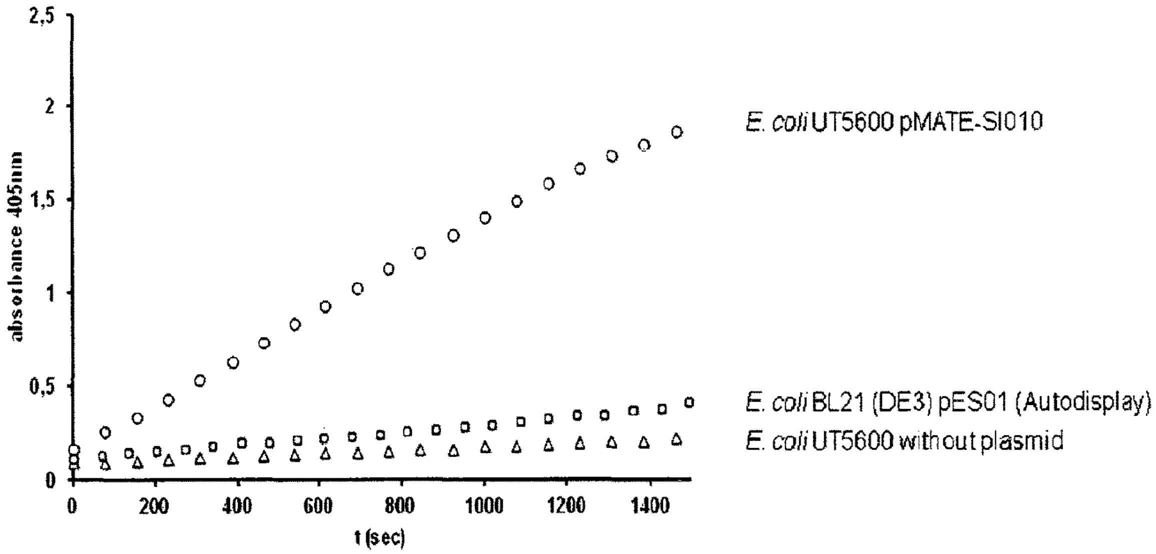

FIG. 8: Photometric esterase activity assay, based on the release of p-nitrophenol from pnitrophenyl acetate by *E. coli* whole cells. Cells contained either a MATE expression plasmid (pMATE-SI010) or an Autodisplay expression plasmid (pES01) for the surface expression of the estA esterase as an autotransporter passenger.$OD_{600}$ of cells in the assay was adjusted to 0.2.

Figure 9:
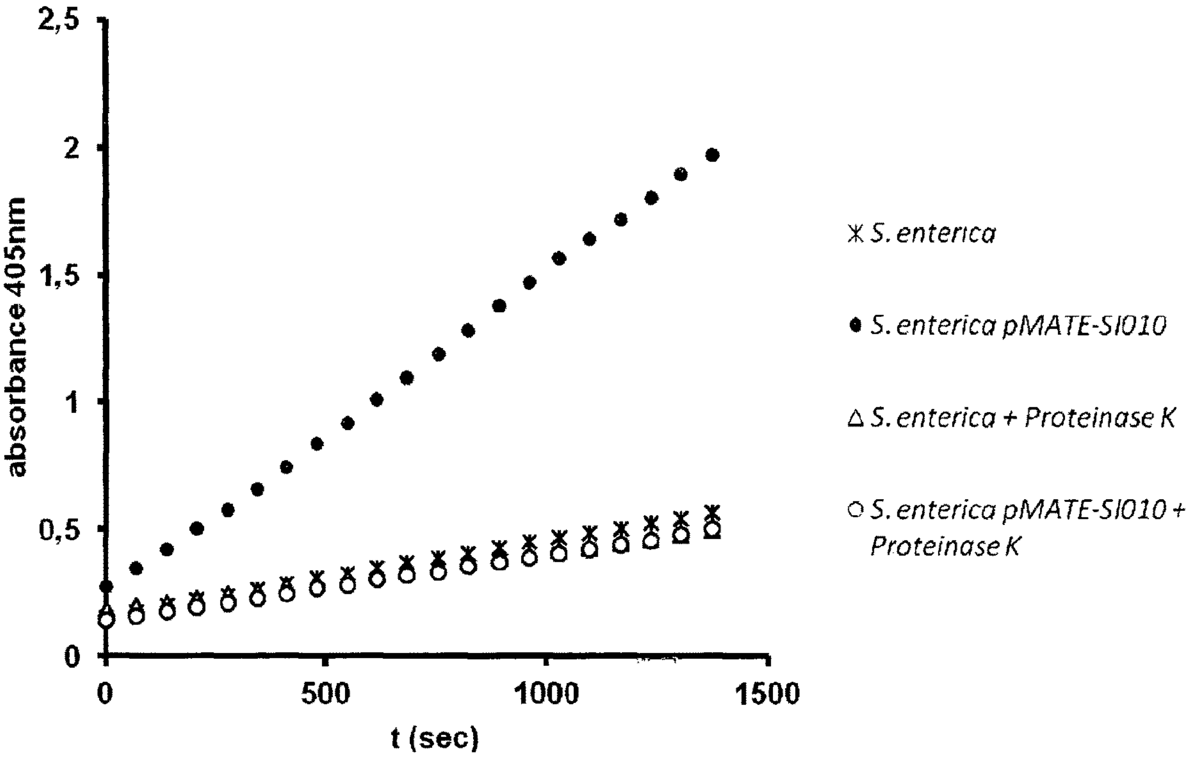

FIG. 9: Photometric activity assay after protease digestion. Release of pnitrophenol from pnitrophenyl acetate by either proteinase K treated or untreated whole cells of *S. enterica* and *S. enterica* pMATE-SI010 after 2 h of induction with 0.5% L-arabinose at 30° C. Final $OD_{600}$ in assay was adjusted to 0.2.

Figure 10:
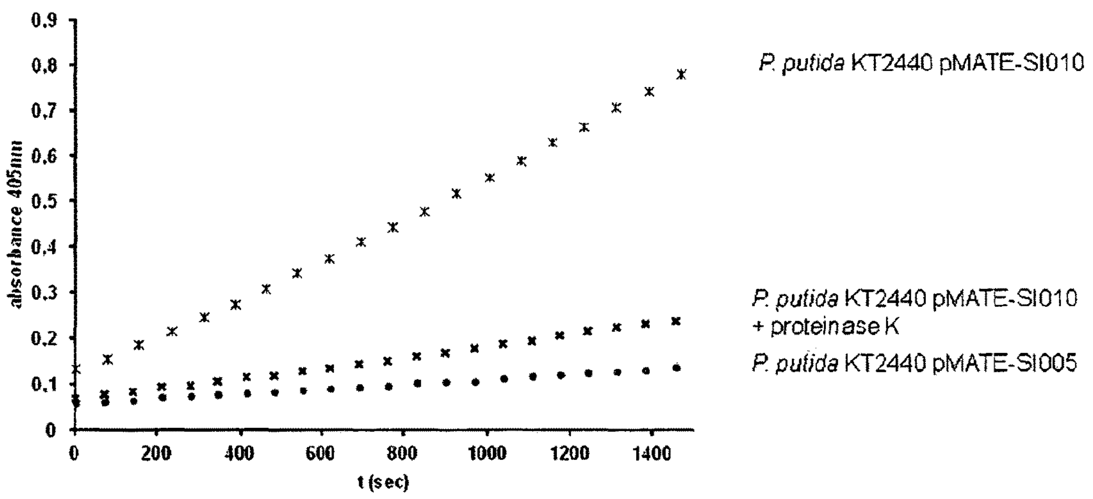

FIG. 10: Photometric esterase activity assay of whole cells, based on the hydrolysis of pnitrophenyl acetate. Protein expression was induced for 2 h with 0.5% L-arabinose at 30° C. Final $OD_{600}$ in assay was adjusted to 0.2.

FIG. 11: Photometric esterase activity assay of whole cells based on the hydrolysis of pnitrophenyl acetate. Protein expression was induced by 2 h with 0.5% L-arabinose at 30° C. (A) *E. coli* UT5600 or (B) *P. putida* KT2440.

FIG. 12: Flow cytometry analysis of cells displaying the EstA catalytic domain on the surface. After cleavage of the signal peptide, the Nterminal region of the EstA fusion protein is expected to contain a 6×His affinity tag. Cells of *P. putida* KT2440 were analysed after incubation of the samples with two antibodies, a primary monoclonal anti-6× His antibody and a secondary fluorescein-labelled detection antibody. (A) *P. putida* KT2440 cells without plasmid (negative control) and (B) *P. putida* KT2440 pMATE-SI010 cells displaying EstA catalytic domain on the surface.

Figure 13:
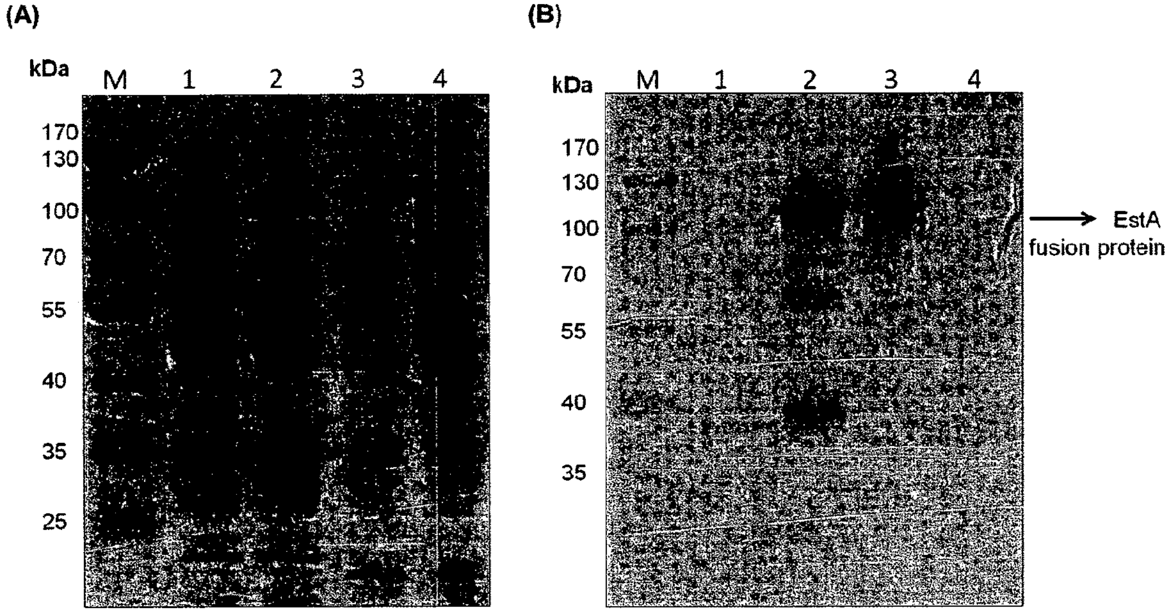

FIG. 13: Protein content and esterase activity of whole cells expressing EstA using the MATE system in *E. coli* and *P. putida*. Cells were grown until $OD_{600}$ 0.6, and gene expression induced by 0.5% (w/v) L-arabinose for 2 h at 30° C. (200 rpm). Cell suspensions were adjusted to an OD of 1 and after harvest. Proteins from whole cells were boiled in SDS-PAGE sample buffer for 30 minutes. The amount of protein loaded on each lane was normalised based on the optical density of the cell solution. (A) SDS-PAGE followed by Coomassie stain for total protein (B) SDS-PAGE followed by renaturation of the enzymes, and ingel stain for esterase activity (B) Designations: M: PageRuler prestained protein marker, 1: control, *E. coli* UT5600 without plasmid, 2: *E. coli* UT5600 pMATE-SI010 (EstA as passenger), 3: *P. putida* KT2440 pMATE-SI010 (EstA as passenger), 4: control, *P. putida* KT2440 pMATE-SI005 (6×His as passenger).

Figure 14:
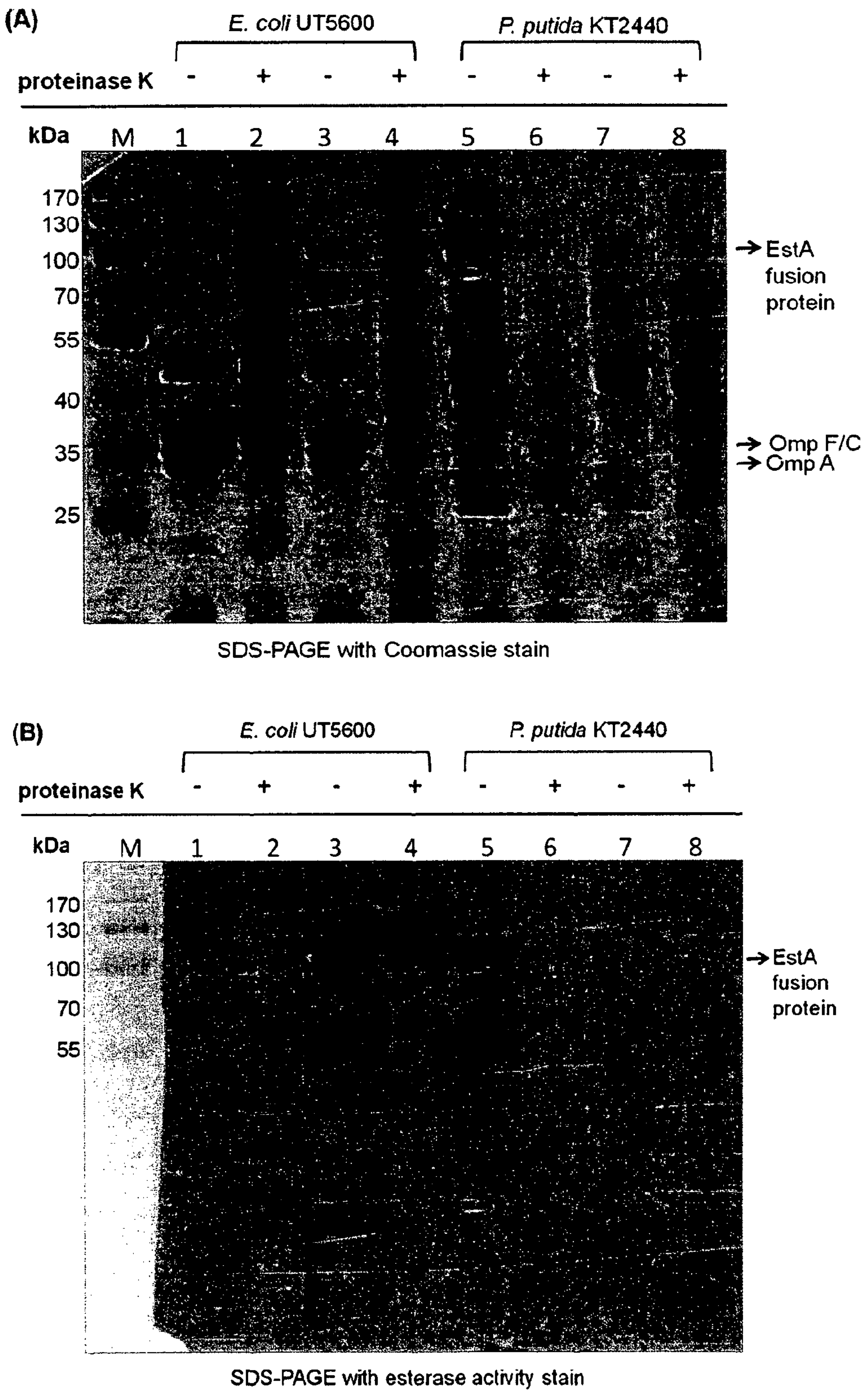

FIG. 14: Protein content and esterase activity of outer membranes after the expression of EstA using the MATE system in *E. coli* and *P. putida*. SDS-PAGE (10% w/v) analysis of outer membrane preparations and outer membrane preparations from whole cells after treatment with proteinase KK. Outer membrane proteins were isolated from *E. coli* UT5600 and *P. putida*

KT2440 strains. Cells were grown until $OD_{600}$ 0.6, and protein expression induced by 0.5% (w/v) Larabinose for 2 h at 30° C. (200 rpm). Cells were either used directly for preparations of outer membranes or with a prior incubation step with proteinase K and subsequent outer membrane preparation. (A)

Coomassie stain and (B) esterase activity stain after renaturation of enzymes. M: PageRuler prestained protein marker, 1: control, *E. coli* UT5600 without plasmid, 2: control, proteinase K treated *E. coli* UT5600 without plasmid, 3: *E. coli* UT5600 pMATE-SI010 (EstA as passenger), 4: proteinase K treated *E. coli* UT5600 pMATE-SI010, 5: *P. putida* KT2440 pMATE-SI010, 6: proteinase K treated *P. putida* KT2440, 7: control, *P. putida* KT2440 pMATE-SI005 (6×His as passenger), 8: control, proteinase KK treated *P. putida* KT2440 pMATE-SI005.

Figure 15:
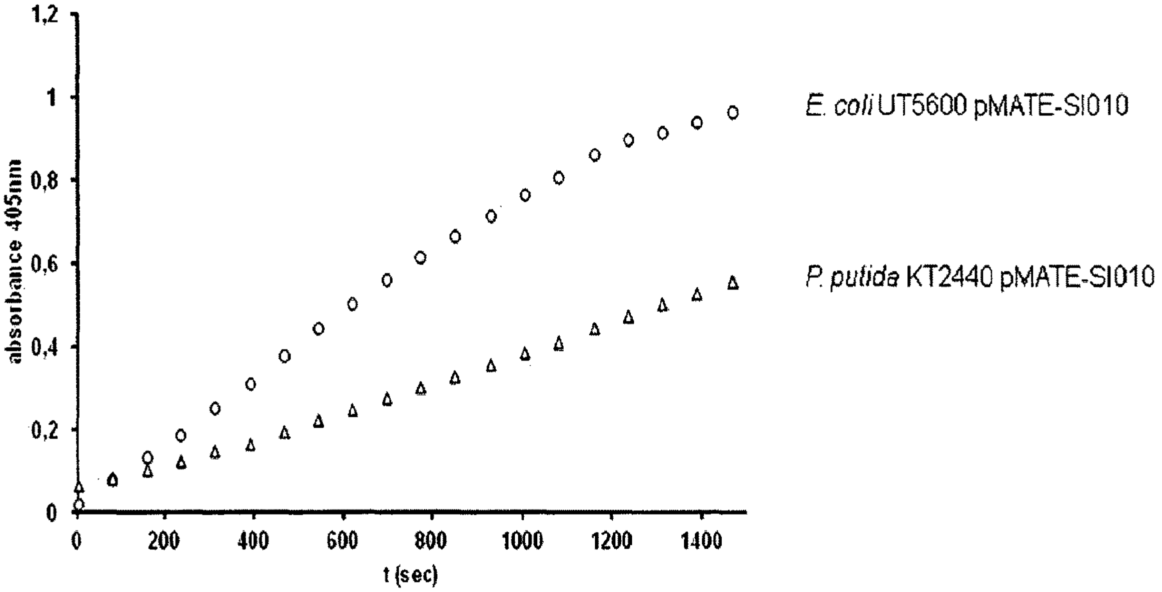

FIG. 15: Comparison of surface displayed esterase activity in *E. coli* and *P. putida* using the MATE system after correcting for intracellular activity. Data was reanalysed from FIG. 11. The activity from strains treated with proteinase K was subtracted from the overall activity seen in the whole cell assay.

Figure 16:
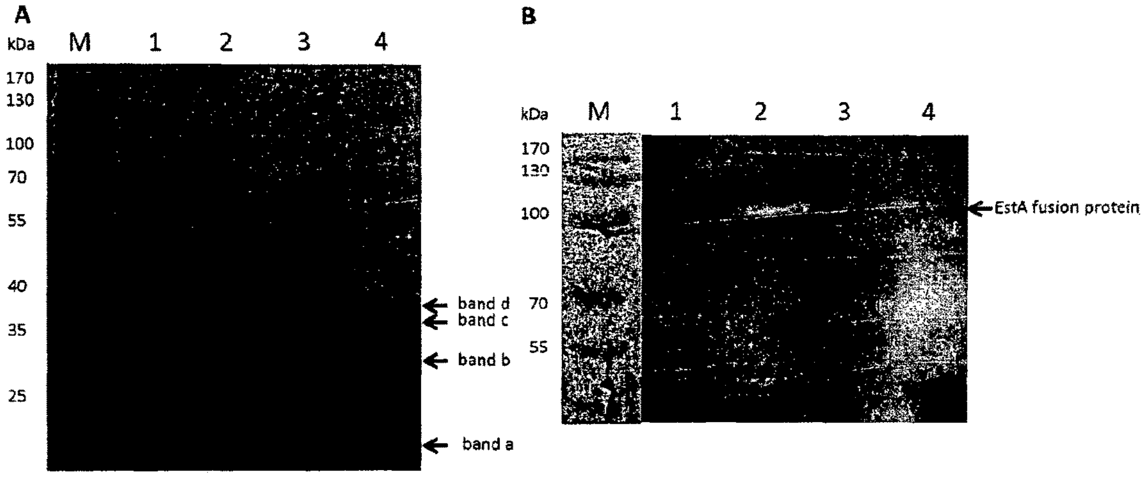

FIG. 16: SDS-PAGE (A) and Western Blot (B) analyses of *Z. mobilis* outer membrane preparations. *Z. mobilis* cells were cultivated in ZM Medium at 30° C., 60 rpm until $OD_{575}$ reached 0.6. Protein expression was, when needed, induced by addition of L-arabinose to a final concentration of 0.2% and incubation for further 2 h. Cells were then harvested and either used directly for preparations of outer membranes or incubated with 2.5% trypsin in 0.2 mol/L Tris-HCl pH 8.0 for 1 h at 37° C., 200 rpm prior to outer membrane protein isolation. Proteins were then separated by SDS-PAGE and (A) Coomassie stained or (B) transferred to a nitrocellulose membrane stained with anti-6×His primary antibodies. M: PageRuler prestained protein marker, 1: *Z. mobilis* without plasmid, induced, 2: *Z. mobilis* with plasmid, induced, 3: *Z. mobilis* with plasmid, not induced, 4: *Z. mobilis* with plasmid, induced and treated with Trypsin prior to outer membrane protein isolation.

Figure 17:
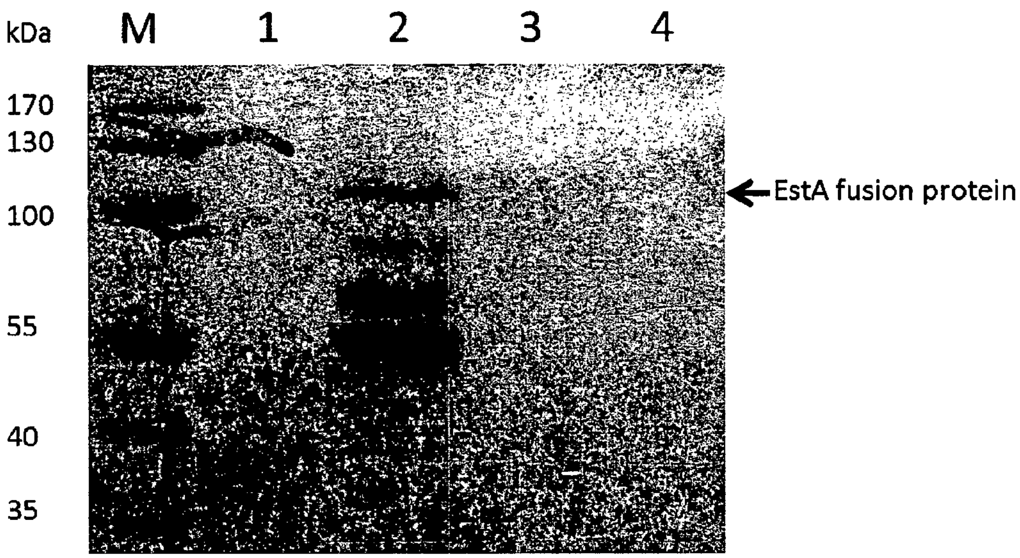

FIG. 17: Esterase acitivity staining of *Z. mobilis* outer membrane preparations. *Z. mobilis* cells were cultivated in ZM Medium at 30° C., 60 rpm until $OD_{578}$ reached 0.6. Protein expression was, when needed, induced by addition of L-arabinose to a final concentration of 0.2% and incubation for further 2 h. Cells were then harvested and either used directly for preparations of outer membranes or incubated with 2.5% trypsin in 0.2 mol/L Tris-HCl pH 8.0 for 1 h at 37° C., 200 rpm prior to outer membrane protein isolation. Proteins were then separated by SDS-PAGE and esterase activity stained. M: PageRuler prestained protein marker, 1: *Z. mobilis* without plasmid, induced, 2: *Z. mobilis* with plasmid, induced, 3: *Z. mobilis* with plasmid, not induced, 4: *Z. mobilis* with plasmid, induced and treated with Trypsin prior to outer membrane protein isolation.

Figure 18:
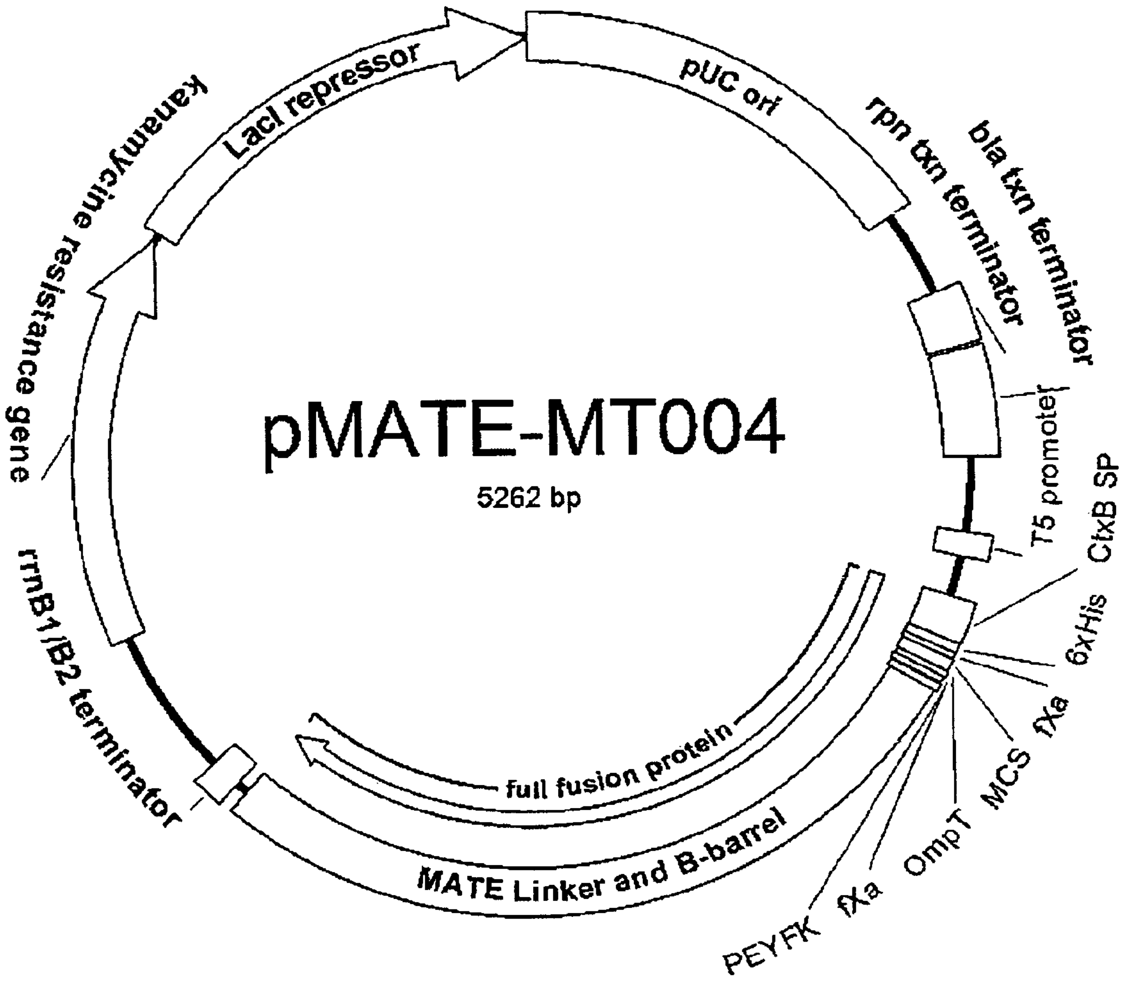

FIG. 18: Plasmid map of pMATE-MT004.

Figure 19:
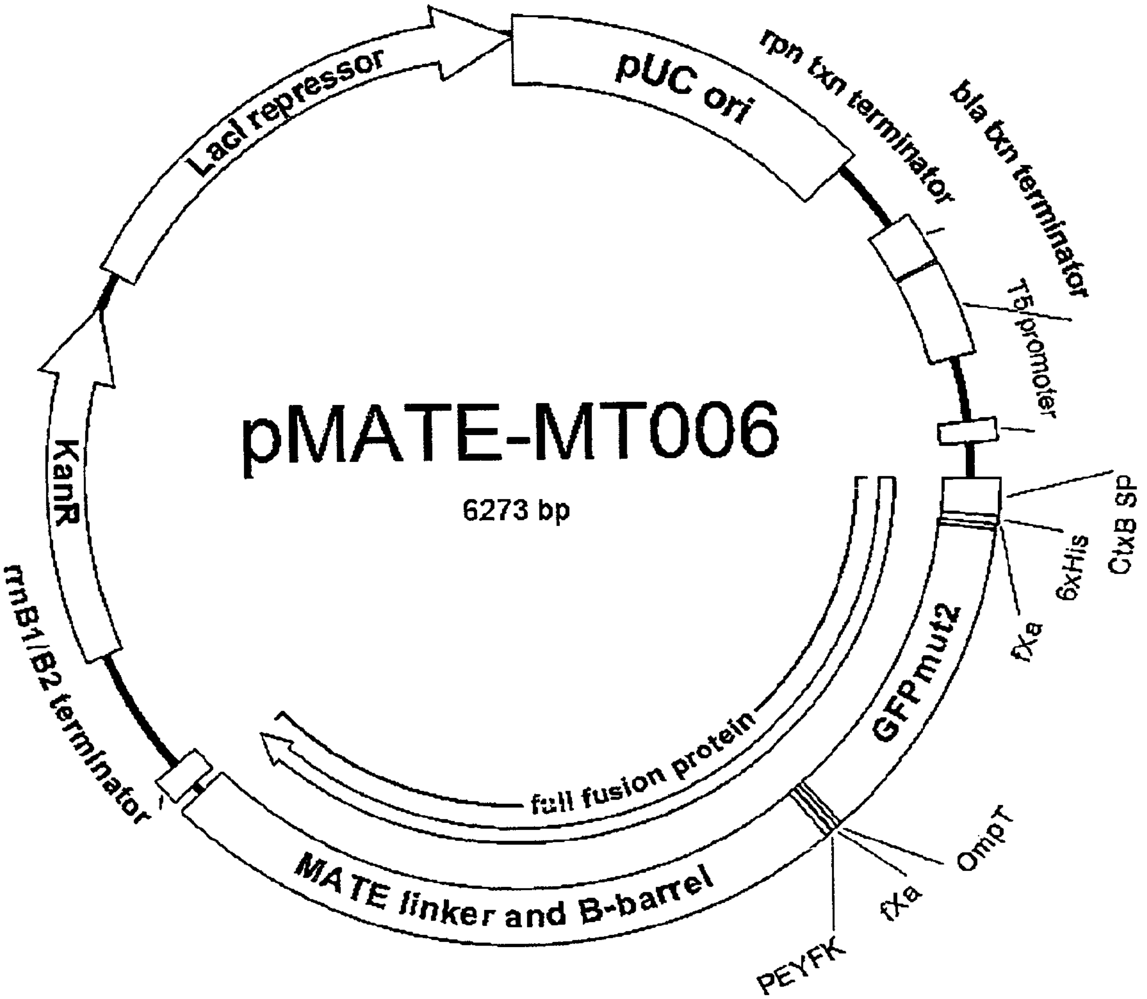

FIG. 19: Plasmid map of pMATE-MT006.

Figure 20:
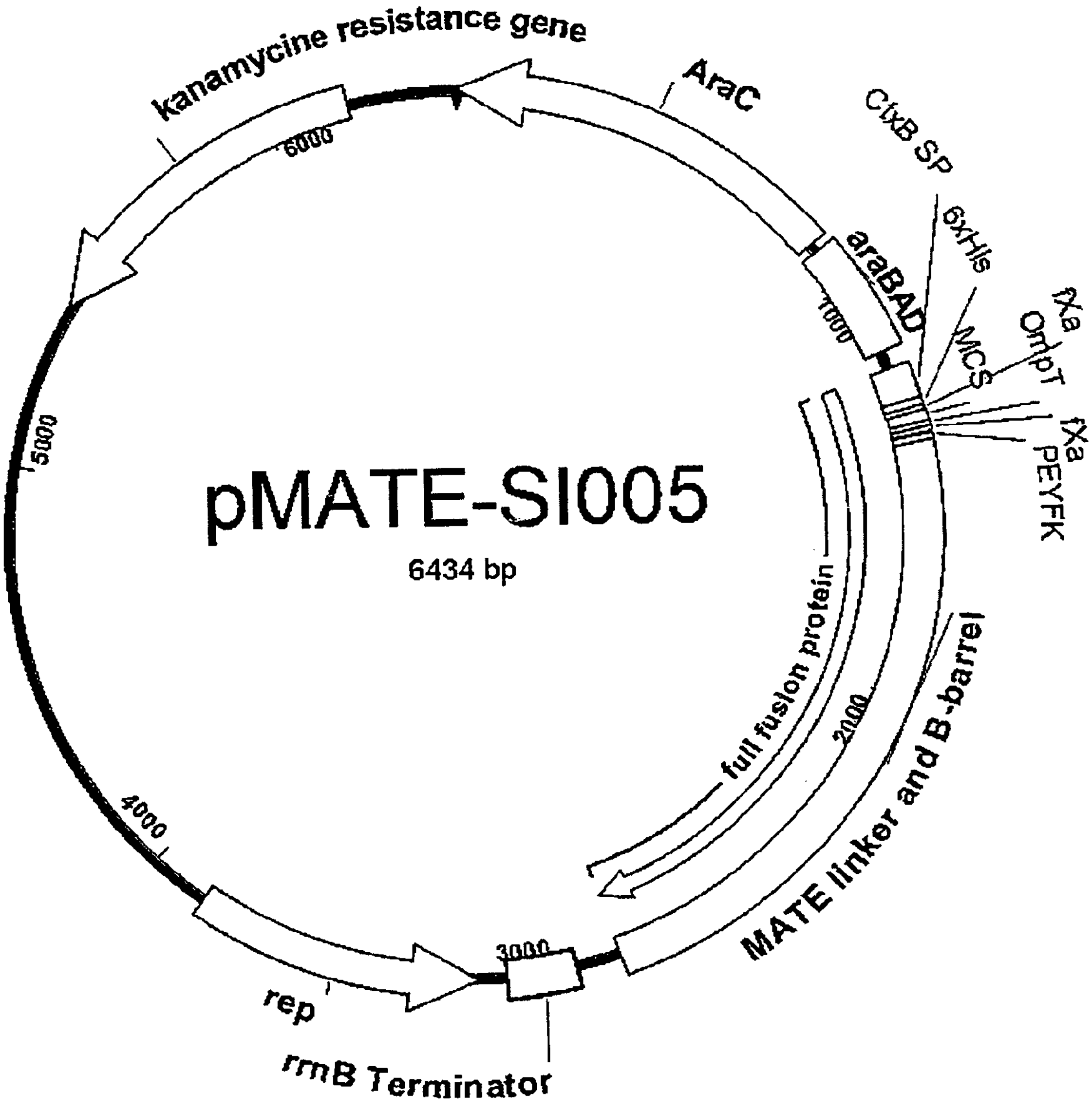

FIG. 20: Plasmid map of pMATE-SI005.

Figure 21:
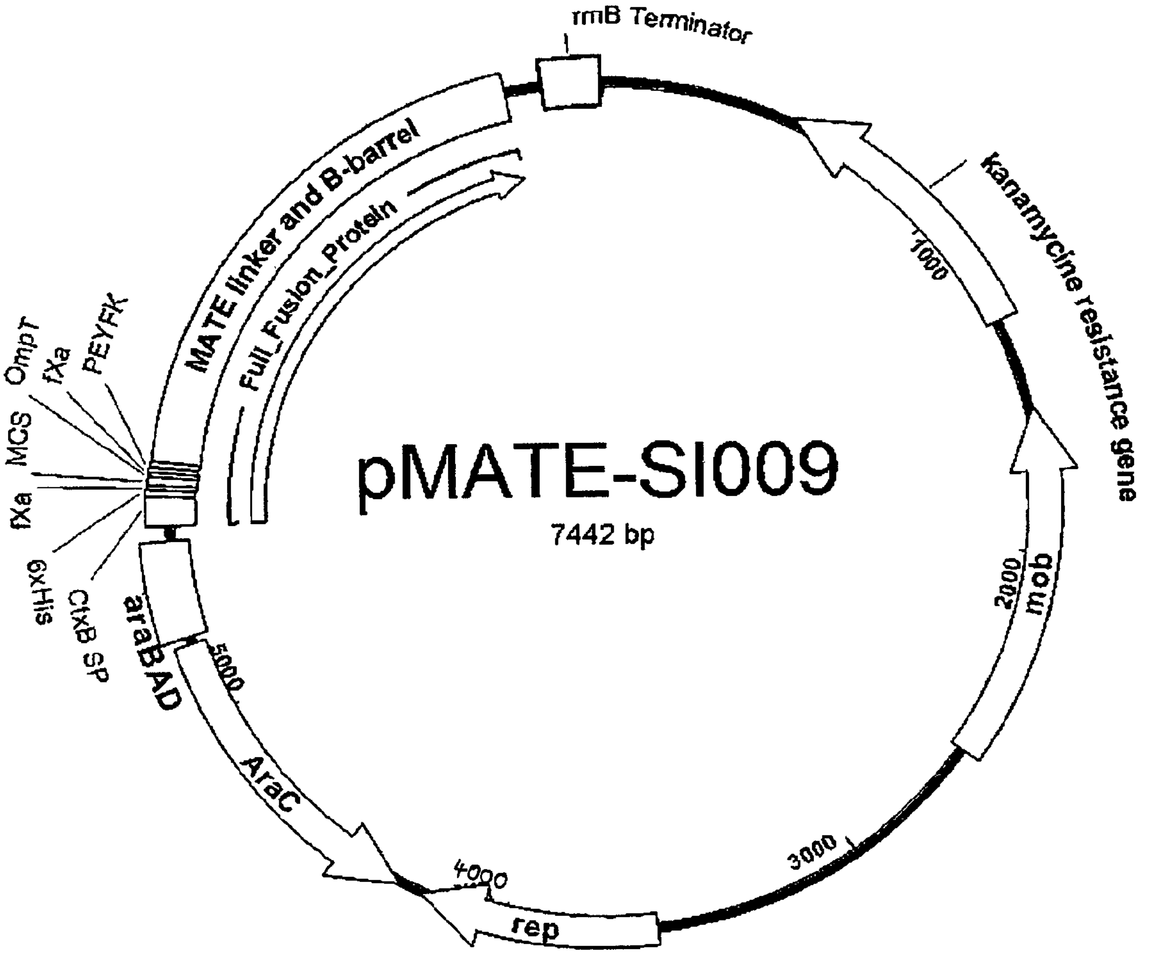

FIG. 21: Plasmid map of pMATE-SI009.

Figure 22:
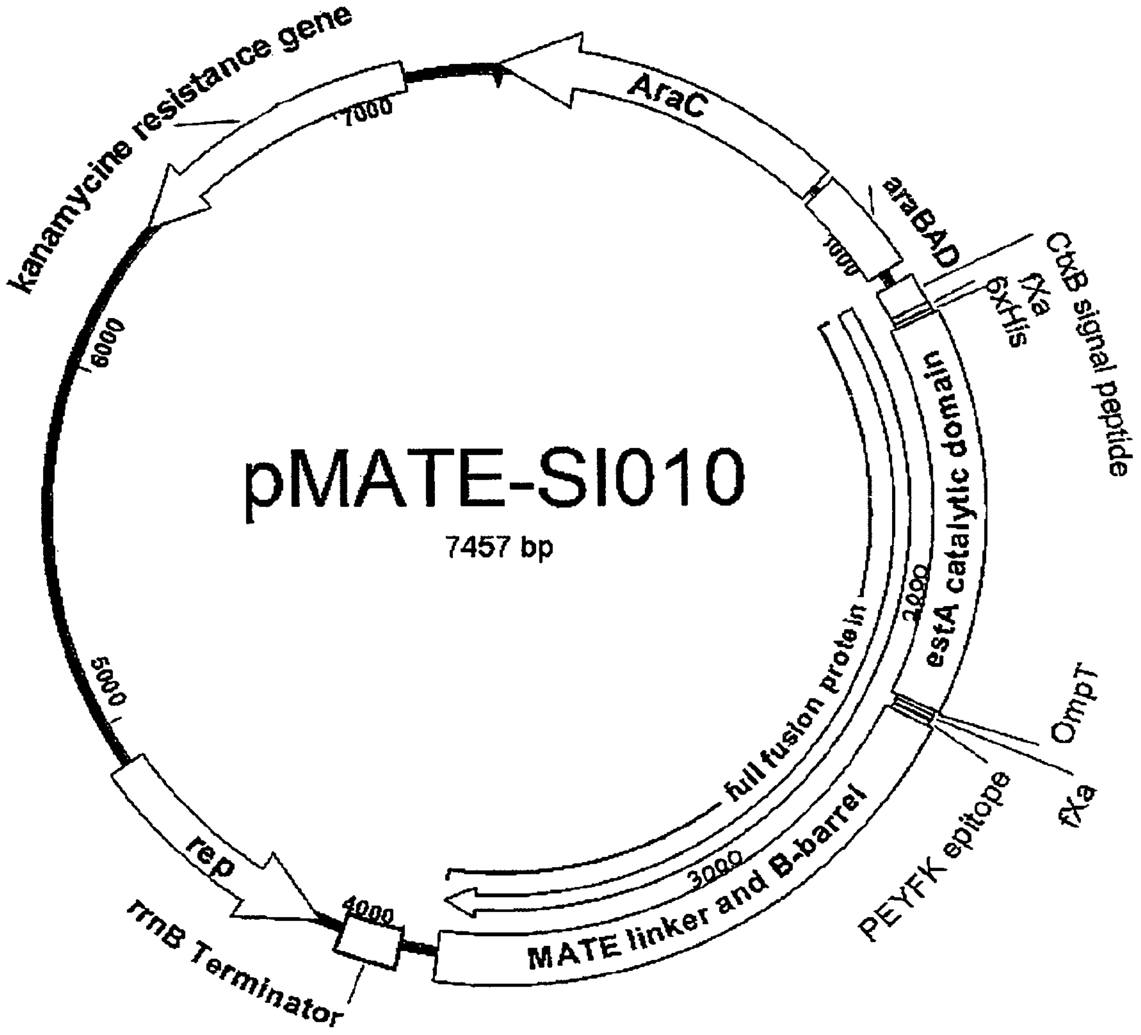

FIG. 22: Plasmid map of pMATE-SI010.

Figure 23:
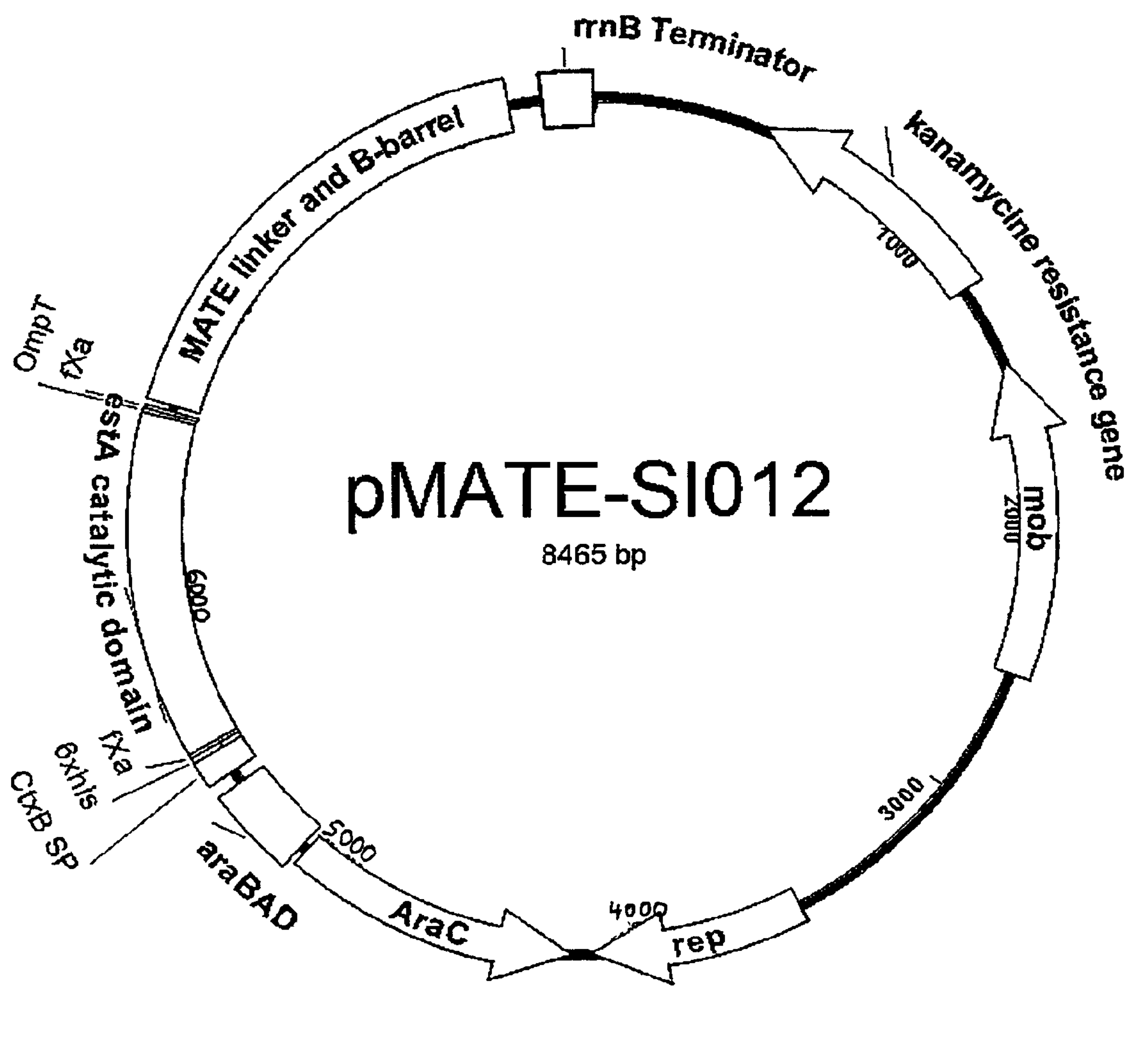

FIG. 23: Plasmid map of pMATE-SI012.

Figure 24:
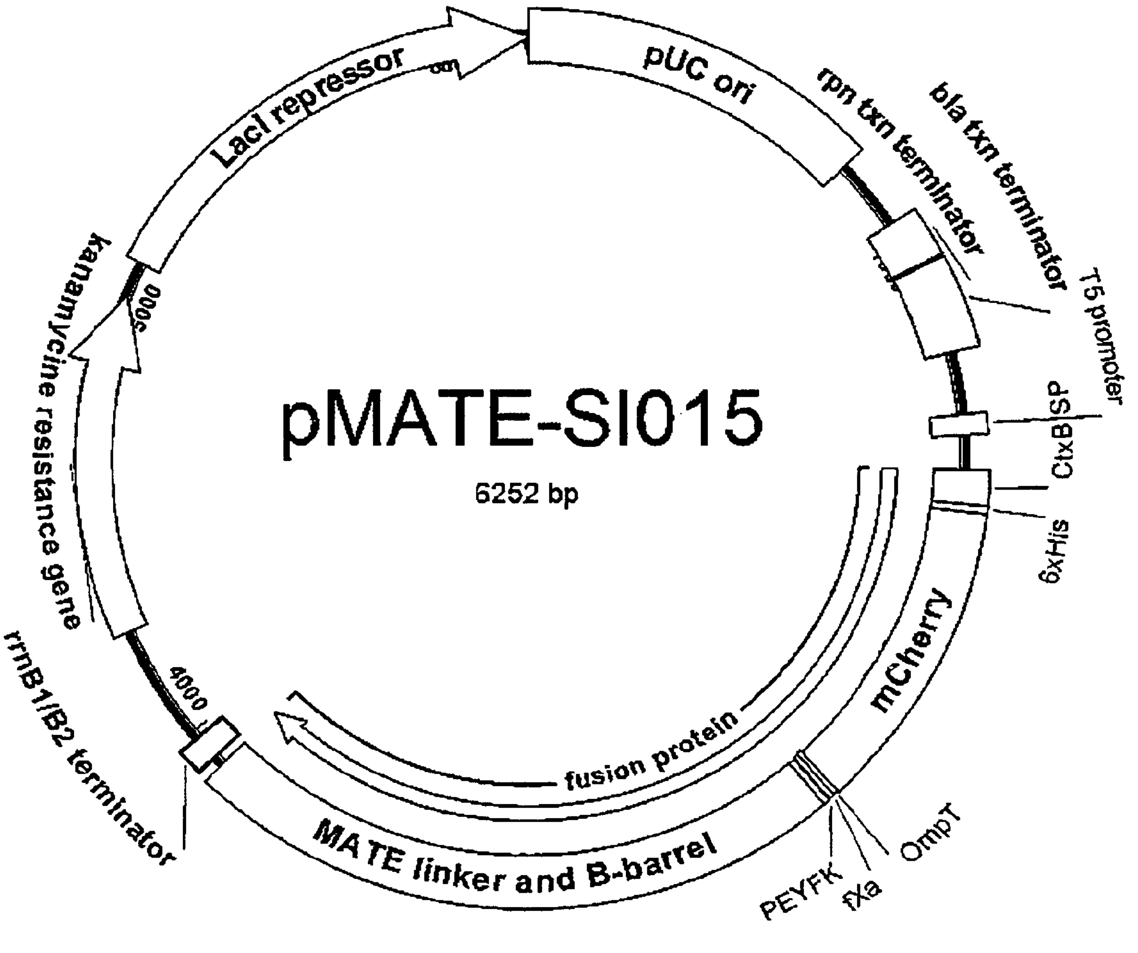

FIG. 24: Plasmid map of pMATE-SI015.

FIG. 25: Alignment of EhaA (natural sequence and codon-optimized sequence) and AIDA-I.

Figure 26:
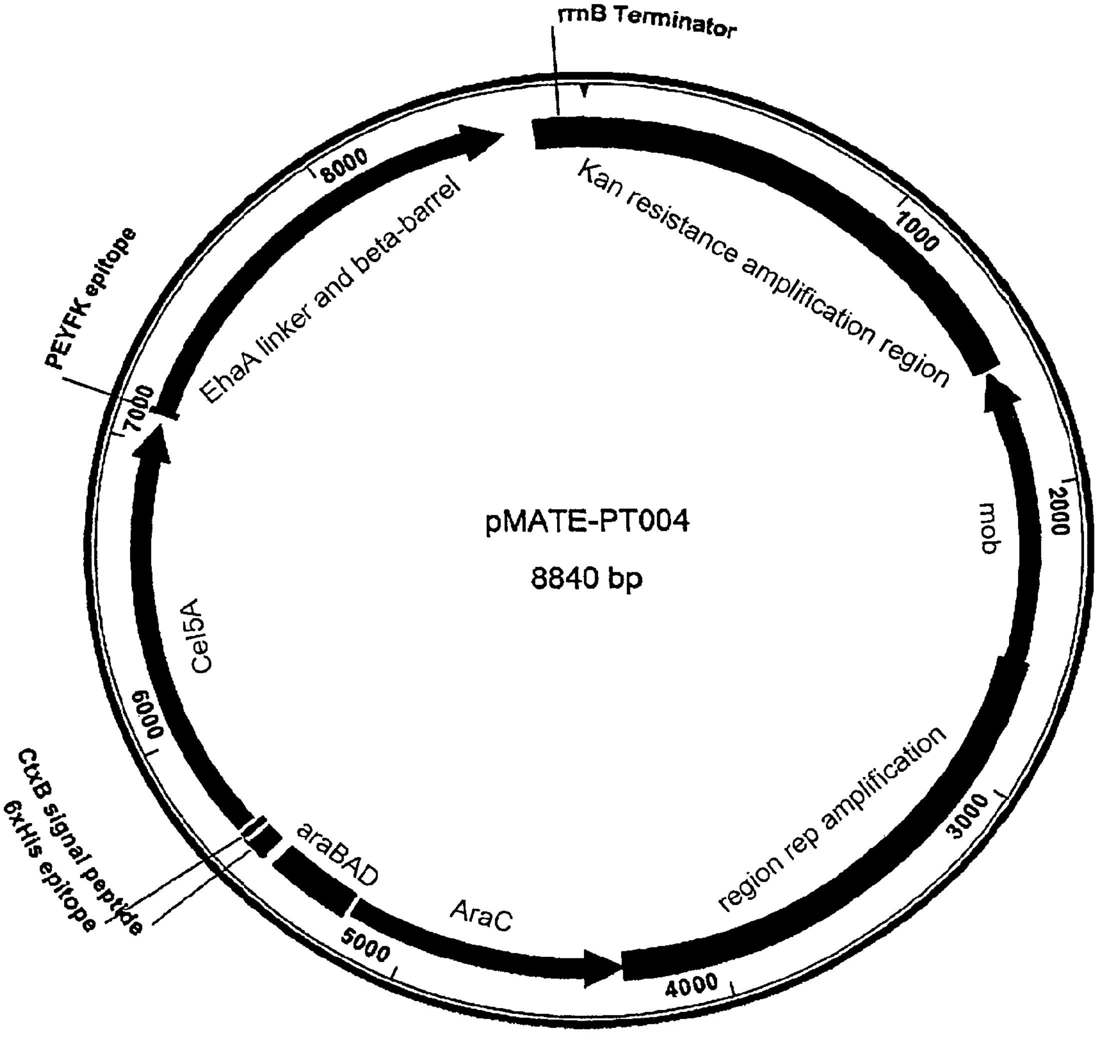

FIG. 26: Plasmid map of pMATE-PT004.

Figure 27:
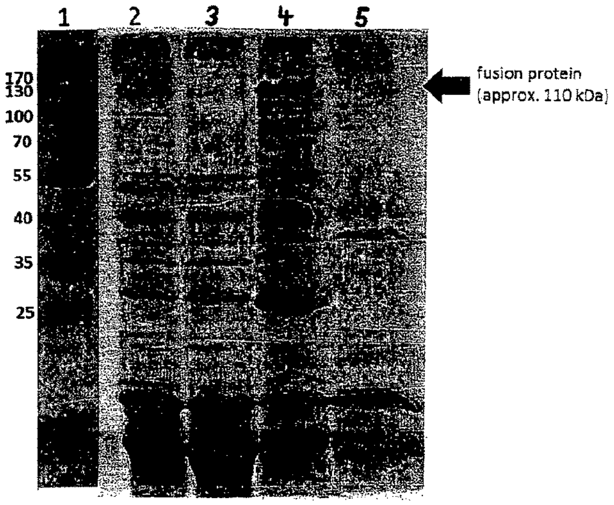

FIG. 27: SDS-PAGE of outer membrane isolates of *Z. palmae* cells. Cells were cultivated as described previously and, when necessary, induced at $OD_{578}$=0.5 for one hour with 0.2% arabinose. Outer membrane fraction was isolated, separated in a 12.5% polyacrylamide gel and stained with Coomassie Brilliant Blue. 1: Prestained protein ladder, molecular weight in kDa is indicated on the left. 2: *Z. palmae* wildtype cells, induced. 3: *Z. palmae* pMATE-PT004 cells, not induced. 4: *Z. palmae* pMATE-PT004 cells, induced. 5: *Z. palmae* pMATE-PT004 cells, induced and digested with trypsin.

Figure 28:
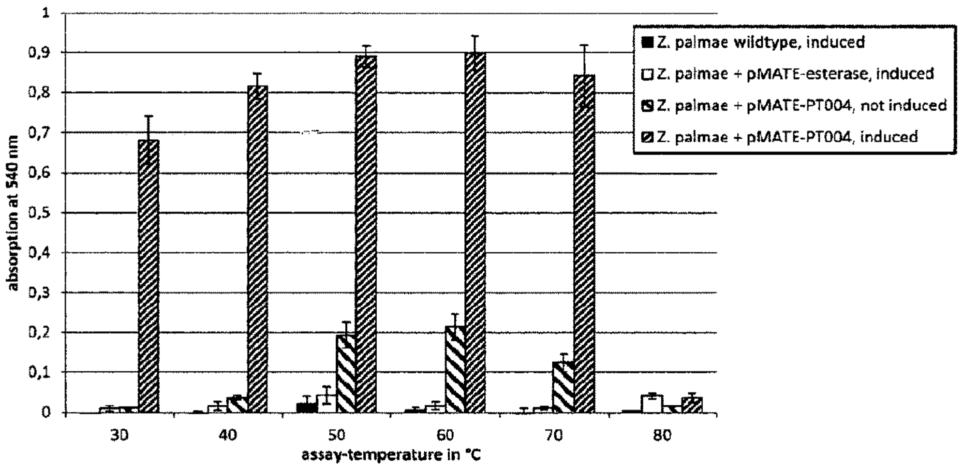

FIG. 28: Photometric CMC hydrolysis activity of *Z. palmae* whole cells based on the detection of reduced sugar formation via DNS assay. Cells were cultivated as described above and, when necessary, induced at $OD_{578}$=0.5 for one hour with 0.2% arabinose, adjusted to $OD_{578}$=25 and incubated with 1% CMC in sodium-citrate buffer, pH 6.0, for ten minutes. Cells were then removed and the supernatant applied to a DNS assay. Absorption values of blank samples (buffer and substrate) were substracted from the absorption values of cell samples.

Figure 29:
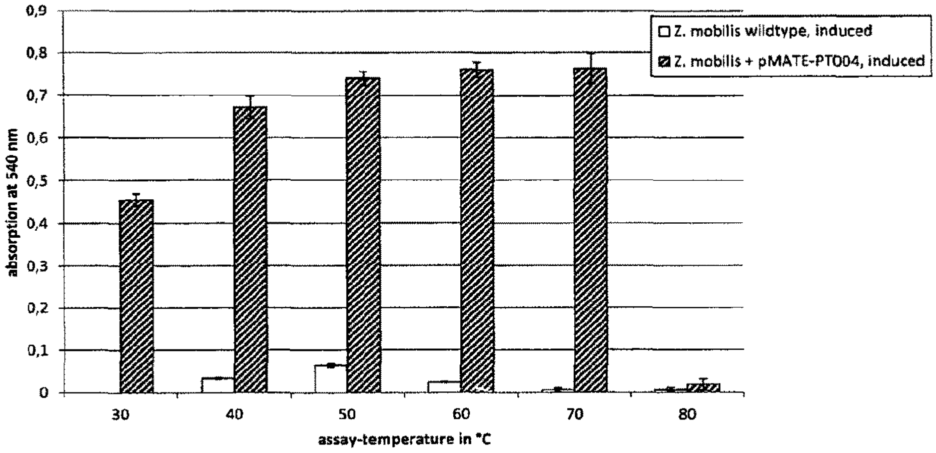

FIG. 29: Photometric CMC hydrolysis activity of *Z. mobilis* whole cells based on the detection of reduced sugar formation via DNS assay. Cells were cultivated as described above and, when necessary, induced at $OD_{578}$=0.5 for one hour with 0.2% arabinose, adjusted to $OD_{578}$=25 and incubated with 1% CMC in sodium-citrate buffer, pH 6.0, for ten minutes. Cells were then removed and the supernatant applied to a DNS assay. Absorption values of blank samples (buffer and substrate) were substracted from the absorption values of cell samples.

Figure 30:
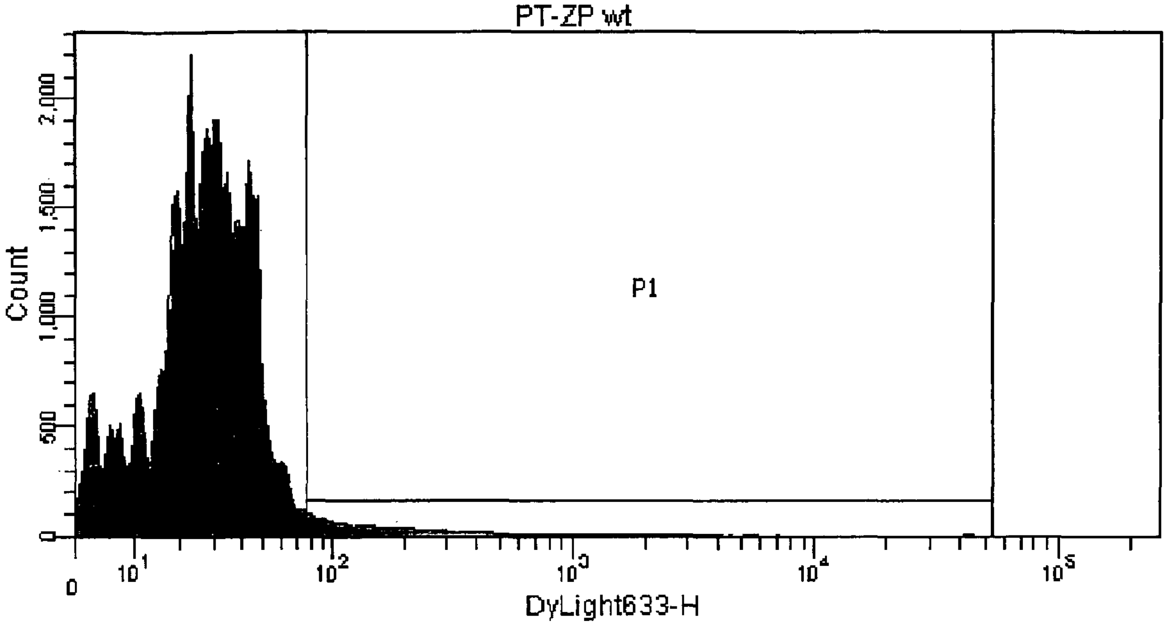

FIG. 30: FACS-histogram of *Z. palmae* wildtype cells, treated with anti-6×His 1° antibody and Dylight-633 conjugated 2° antibody; event count approx. 50,000.

Figure 31:
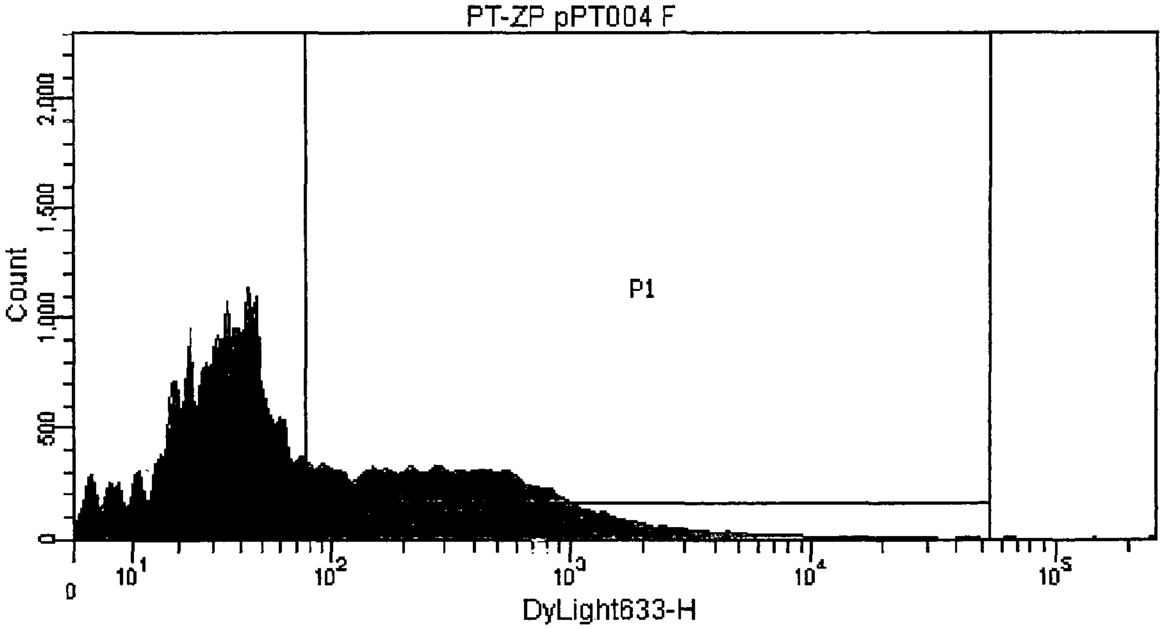

FIG. 31: FACS-histogram of induced *Z. palmae* pMATE-PT004 cells, treated with anti-6×His 1° antibody and Dylight-633 conjugated 2° antibody; event count approx. 50,000.

Figure 32:
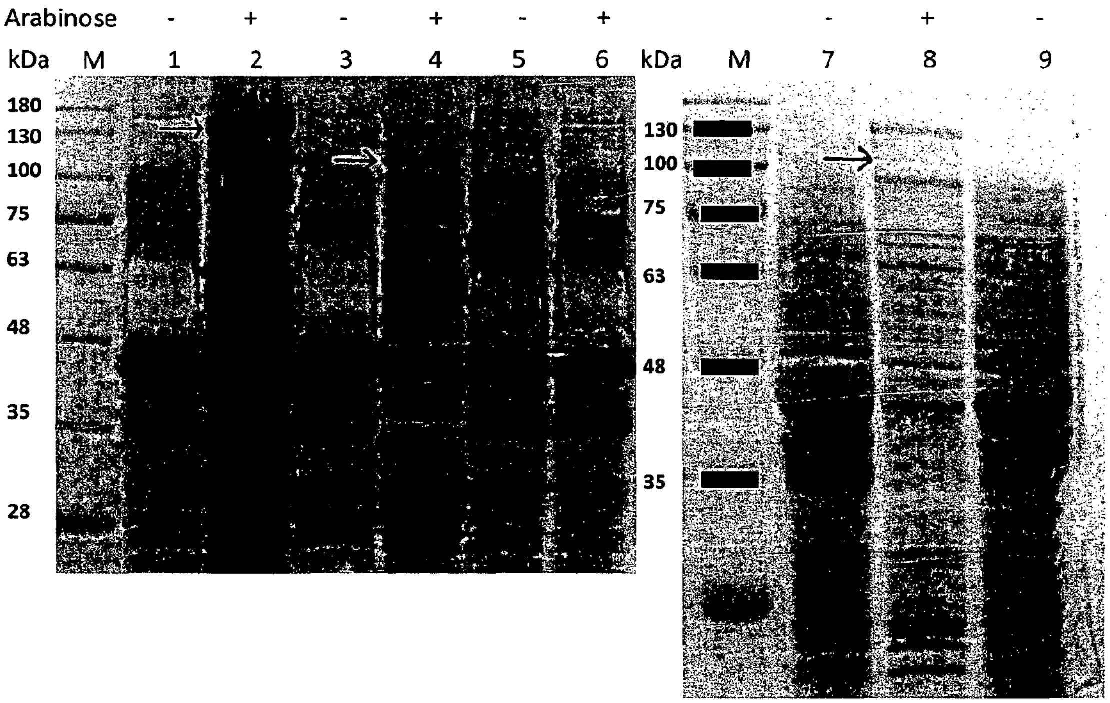

FIG. 32: Use of the pMATE system for the transport of cellulases to the outer membrane of *P. putida*. Cells were grown at 30° C. in LB medium to $OD_{578}$ of 0.5. Protein expression was induced by the addition of 0.2% (w/v) L-arabinose for 4 h at 30° C. Cells were harvested and the outer membrane proteins were isolated according to the modified method of Hantke et al. (1981). SDS PAGE of outer membrane proteins was stained with Coomassie. M: prestained protein marker, 1: *P. putida* KT2440 pMATE-exoglucanase without L-arabinose, 2: *P. putida* KT2440 pMATE-exoglucanase with L-arabinose, 3: *P. putida* KT2440 pMATE-endoglucanase without L-arabinose, 4: *P. putida* KT2440 pMATE-endoglucanase with L-arabinose, 5+9: *P. putida* KT2440 without plasmid, non-induced, 6: *P. putida* KT2440 without plasmid, induced, 7: *P. putida* KT2440 pMATE-3-glucosidase without L-arabinose, 8: *P. putida*

KT2440 pMATE-β-glucosidase with L-arabinose. The arrow indicates the band associated with the pMATE fusion protein.

Figure 33:
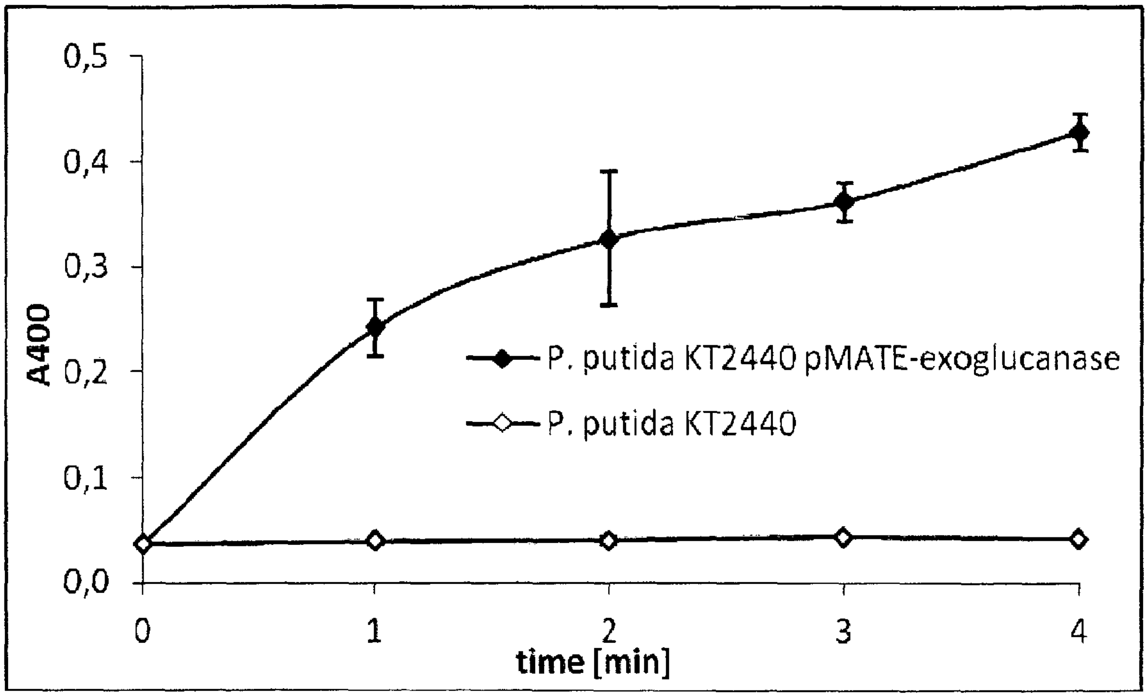

FIG. 33: Photometric exoglucanase activity assay of whole cells based on the hydrolysis of p-nitrophenyl-β-D-cellobioside. Protein expression was induced for 4 h with 0.2% L-arabinose at 30° C. Final $OD_{578}$ of cells was adjusted to 0.5.

Figure 34:
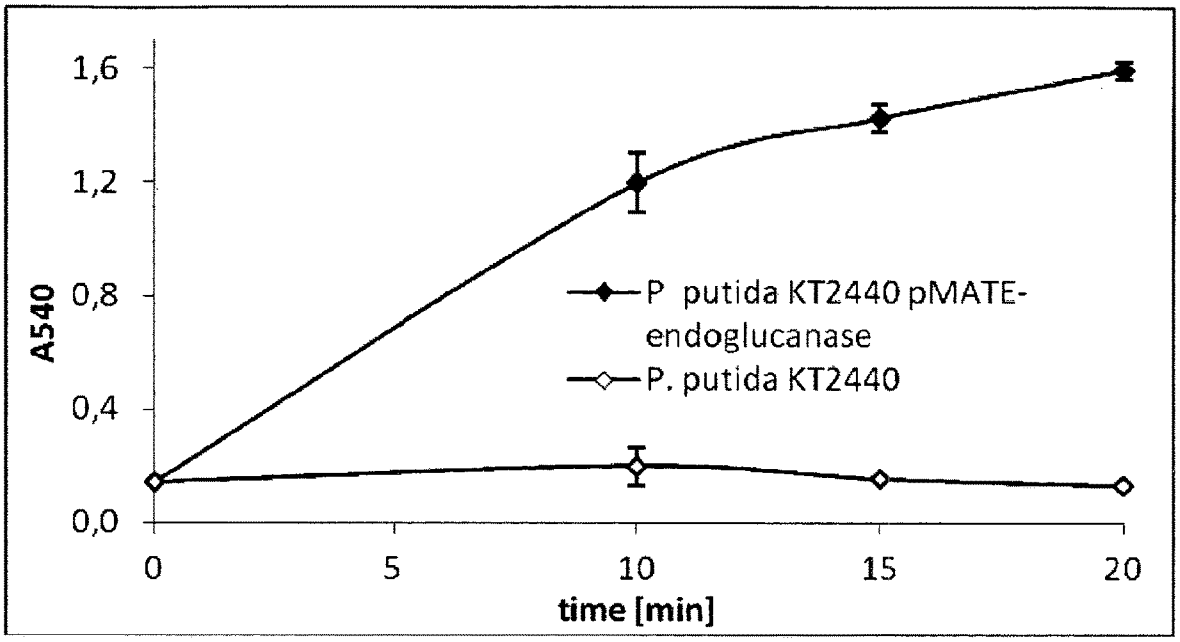

FIG. 34: Photometric endoglucanase activity assay of whole cells based on the detection of reducing sugars released from carboxymethylcellulose via DNS assay. Protein expression was induced for 4 h with 0.2% L-arabinose at 30° C. Final $OD_{578}$ of cells was adjusted to 20.

Figure 35:
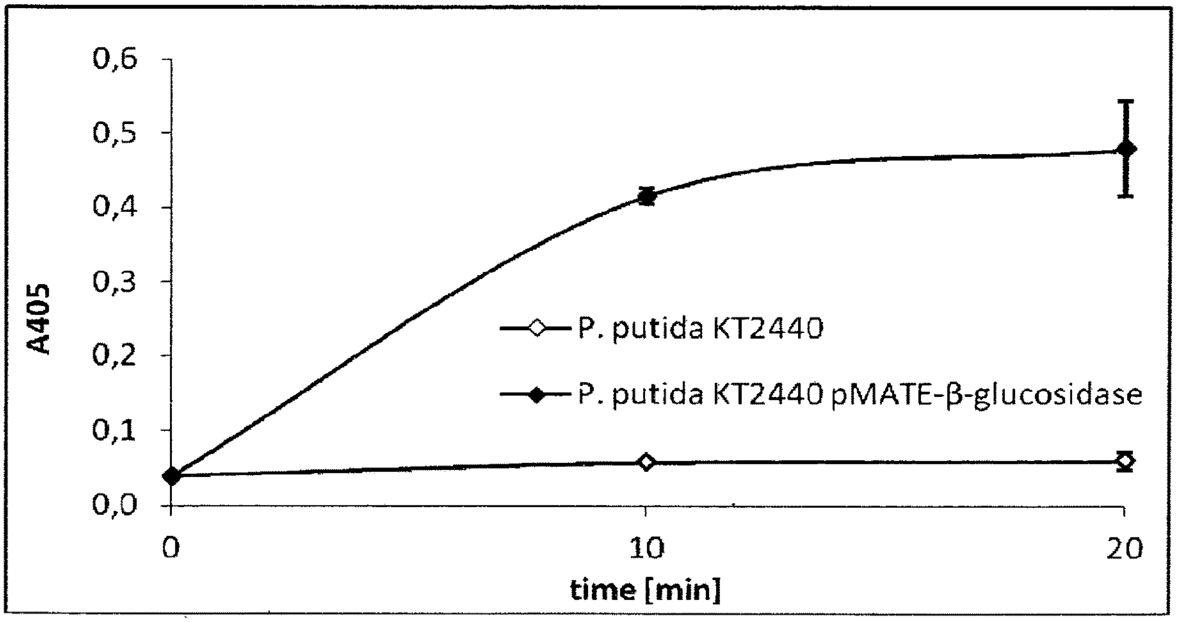

FIG. 35: Photometric β-glucosidase activity assay of whole cells based on the hydrolysis of p-nitrophenyl-β-D-glucopyranoside. Protein expression was induced for 4 h with 0.2% L-arabinose at 30° C. Final $OD_{578}$ of cells was adjusted to 20.

Figure 36:
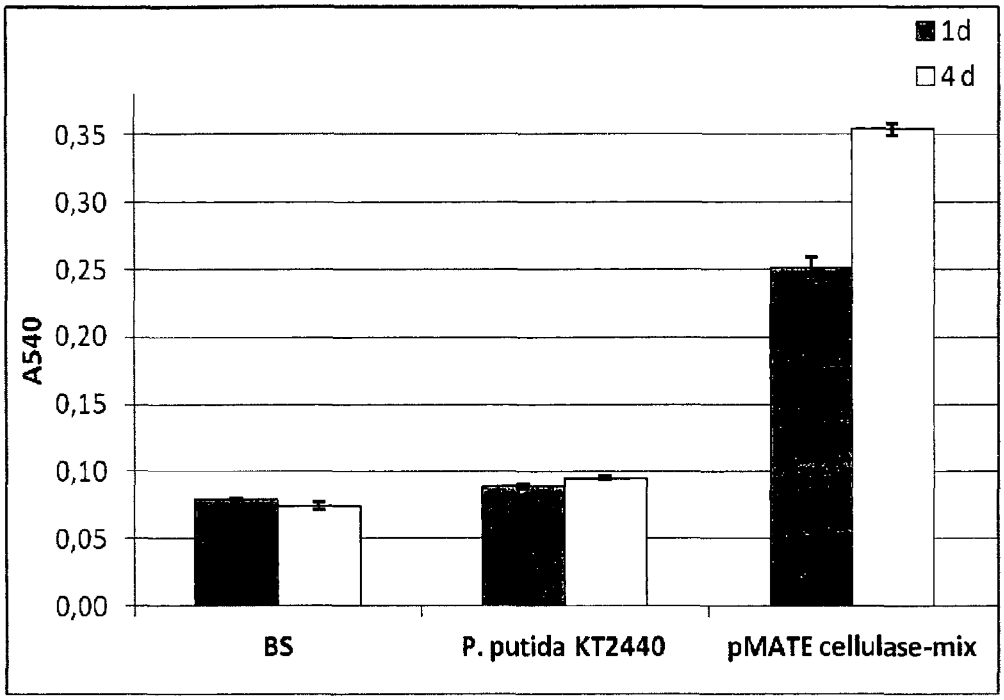

FIG. 36: Total pMATE-cellulase activity using the FPA at 55° C. Reducing sugars released from filter paper was detected via DNS assay. BS: Blank substrate (filter paper in buffer); pMATE-cellulase-mix: exoglucanase, endoglucanase and β-glucosidase expressing cells were mixed in equal parts. Protein expression was induced for 4 h with 0.2% L-arabinose at 30° C. Final $OD_{578}$ of total cells was adjusted to 50.

Figure 37:
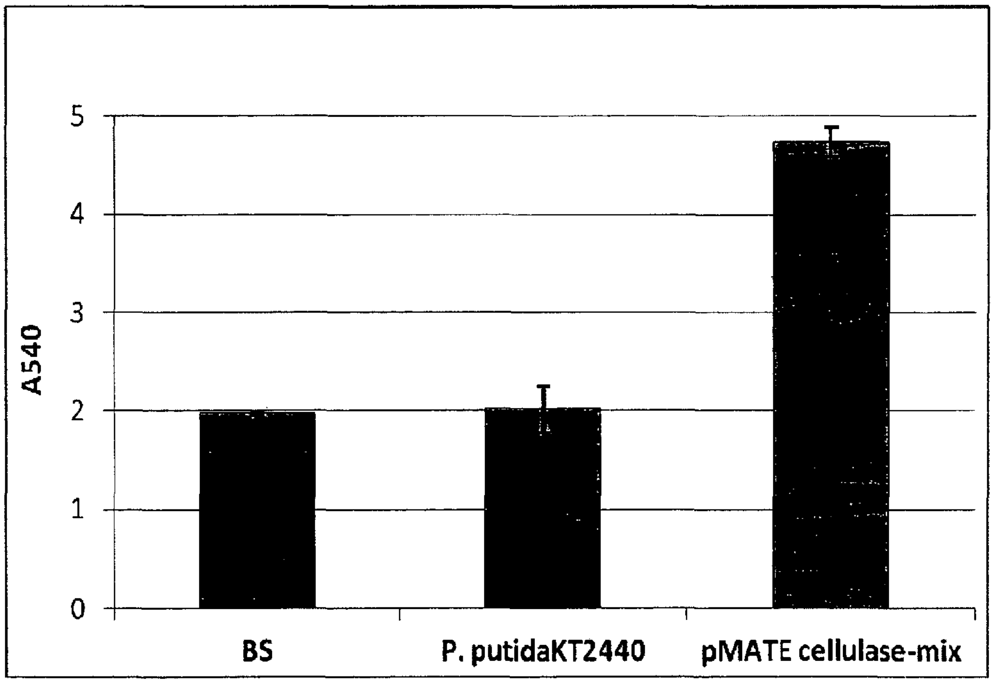

FIG. 37: EFB hydrolysis by pMATE-cellulases at 55° C. for 4 d. Reducing sugars released from 2.5% (dry weight) was detected via DNS assay. BS: Blank substrate (EFB in buffer); pMATE-cellulase-mix: exoglucanase, endoglucanase and β-glucosidase expressing cells were mixed in equal parts. Protein expression was induced for 4 h with 0.2% L-arabinose at 30° C. Final $OD_{578}$ of total cells was adjusted to 20.

Figure 38:
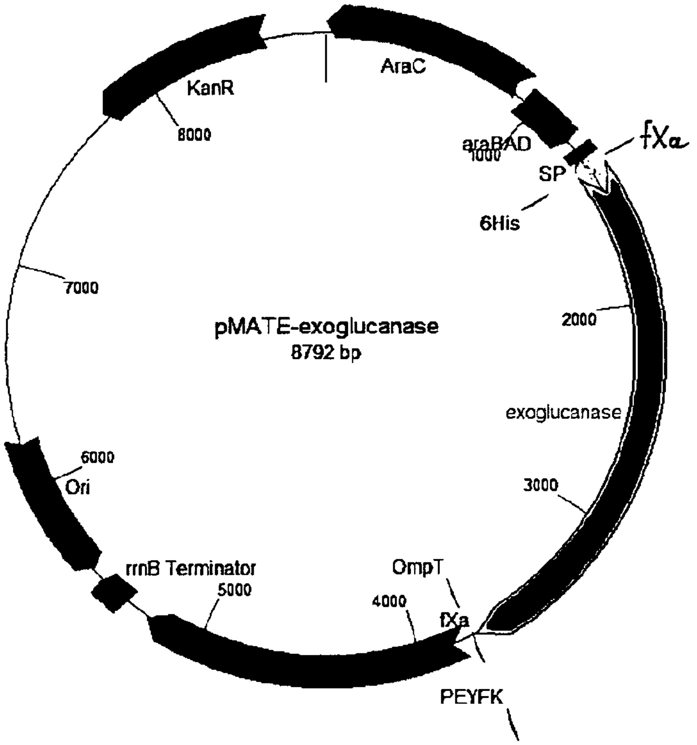

FIG. 38: Plasmid map of pMATE-exoglucanase. Annotation of the pMATE-exoglucanase plasmid:

| Feature | position |
|---|---|
| AraC | 4-902 bp |
| araBAD promoter | 912-1184 bp |
| CtxB SP sequence | 1227-1307 bp |
| 6xHis | 1308-1325 bp |
| fXa cleavage site | 1326-1337 bp |
| exoglucanase | 1338-3719 bp |
| OmpT cleavage site | 3720-3731 bp |
| fXa cleavage site (2.nd) | 3732-3743 bp |
| PEYFK epitope | 3747-3761 bp |
| MATE linker and β-barrel | 3762-5228 bp |
| pBBR1 rep gene (broad host rep) | 5550-6212 bp |
| KanR (kanamycine resistence cassette) | 7746-8540 bp |

Figure 39:
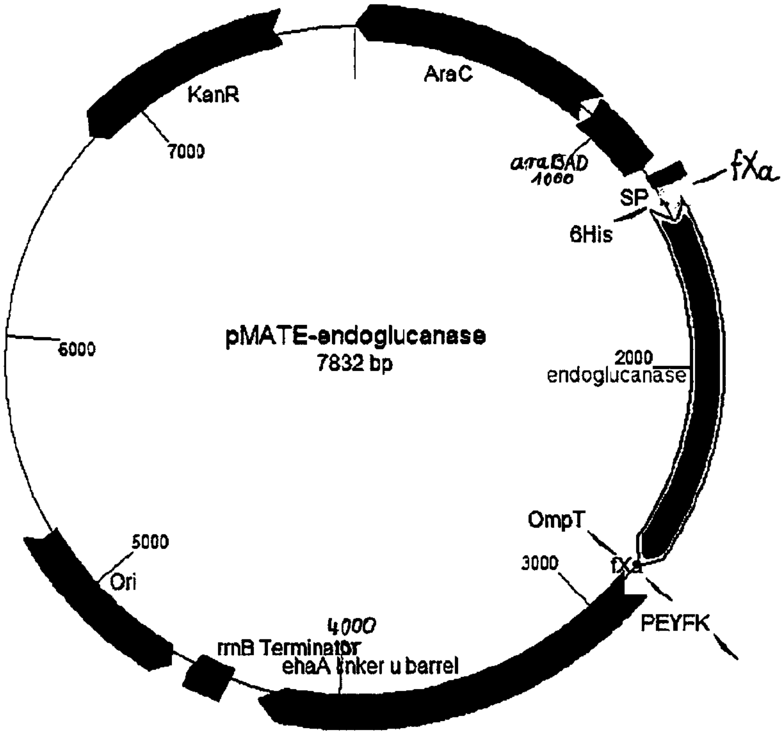

FIG. 39: Plasmid map of pMATE-endoglucanase. Annotation of the pMATE-endoglucanase plasmid:

| Feature | position |
|---|---|
| AraC | 4-902 bp |
| araBAD promoter | 912-1184 bp |
| CtxB SP sequence | 1227-1307 bp |
| 6xHis | 1308-1325 bp |
| fXa cleavage site | 1326-1337 bp |
| endoglucanase | 1338-2759 bp |
| OmpT cleavage site | 2760-2771 bp |
| fXa cleavage site (2.nd) | 2772-2783 bp |
| PEYFK epitope | 2787-2801 bp |
| MATE linker and β-barrel | 2802-4268 bp |
| pBBR1 rep gene (broad host rep) | 4590-5252 bp |
| KanR (kanamycine resistence cassette) | 6786-7580 bp |

Figure 40:
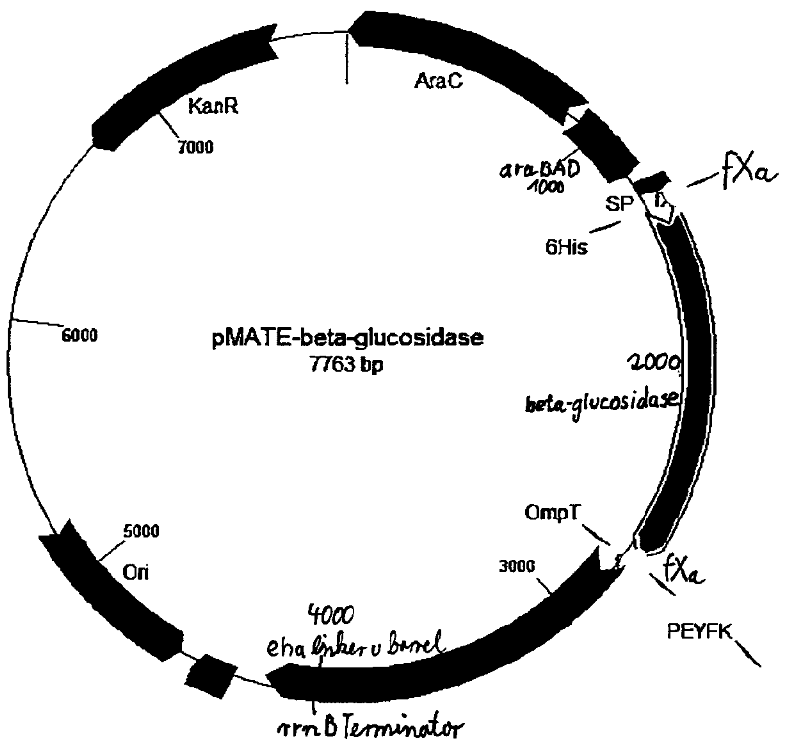

FIG. 40: Plasmid map of pMATE-β-glucosidase. Annotation of the pMATE-beta-glucosidase plasmid:

| Feature | position |
|---|---|
| AraC | 4-902 bp |
| araBAD promoter | 912-1184 bp |
| CtxB SP sequence | 1227-1307 bp |
| 6xHis | 1308-1325 bp |
| fXa cleavage site | 1326-1337 bp |
| β-glucosidase | 1338-2690 bp |
| OmpT cleavage site | 2691-2702 bp |
| fXa cleavage site (2.nd) | 2703-2714 bp |
| PEYFK epitope | 2718-2732 bp |
| MATE linker and β-barrel | 2733-4199 bp |
| pBBR1 rep gene (broad host rep) | 4521-5183 bp |
| KanR (kanamycine resistence cassette) | 6717-7511 bp |

EXAMPLE 1

Surface Expression of 6×His in *E. coli* using the MATE System

In this example, the MATE system is used to display a short peptide (6×His) on the surface of *E. coli.*

Bacterial Strains

*E. coli* BL21 (8, $\overline{F}$, dcm, ompT, Ion, hsdS($rB^-$ $mB^-$), gal) and *E. coli* BL21 (DE3) (B, $\overline{F}$, dcm, ompT, Ion, hsdS($rB^-$ $mB^-$), gal □(DE3)) were used for expression experiments.

Plasmid Construction

The gene encoding the pMATE autotransporter fusion protein was synthesised commercially in the pJexpress-401 plasmid vector (DNA2.0, USA) to create pMATEMT004. The pJExpress401 plasmid backbone contained an rrnB1/B2 terminator, kanamycin resistance gene, LacI repressor, pUC on as well as rpn and bla terminators. Expression of the fusion protein was under the transcriptional control of an Isopropyl β-D-1-thiogalactopyranoside (IPTG) inducible T5 promoter.

The fusion protein included an N-terminal signal peptide from the cholera toxin B subunit (CtxB), a 6×His tag, a multiple cloning site, and the autotransporter domain, which consists of a linker and Pbarrel region.

Protease cleavage sites (Factor Xa and OmpT) were incorporated after the multiple cloning site. A second Factor Xa cleavage site was inserted after the 6×His, for removal of this affinity tag after purification. An epitope (PEYFK) for a monoclonal antibody (Dü142) was inserted after the protease cleavage sites.

The pMATE contains the EhaA autotransporter domain (GenBank Accession No. Q8X6C1). This autotransporter domain has never before been used for the display of recombinant proteins in bacteria; however the full native protein is known to increase cell-cell interactions when overexpressed in *E. coli* (Wells et al. 2008). To define the border between the original passenger and the autotransporter domain, we aligned the EhaA polypeptide sequence against the Cterminal AIDAI fragment used for Autodisplay (GenBank Accession No. Q03155, Maurer et al. 1997). The sequence encoding the signal peptide and EhaA fragment was codon optimised for *E. coli* according the algorithm of Welch et al. (2009). The codon usage was further altered to remove some restriction sites, and to minimise predicted RNA 2° structure in the region encoding the CtxB signal peptide.

SDS-PAGE and Western Blot 40 ml of LB media was inoculated with 1 ml from an overnight culture of *E. coli* BL21 or BL21 (DE3) containing the plasmid of interest. The cultures were then incubated at 37° C., 200 rpm until they reached an $OD_{600}$ of 0.5. Protein expression was induced by the addition of 1 mM IPTG, and the cells harvested one hour after induction. Outer membrane proteins were prepared according to the rapid isolation protocol of Hantke (1981) with modifications as described previously (Jose and von Schwichow, 2004). Proteins were separated with 10% sodium-dodecyl-sulfate polyacrylamide gel electrophoresis (SDS-PAGE) (Laemmli 1970). Proteins were visualised after SDS-PAGE by staining with Coomassie Brilliant Blue R250. For Western blots, proteins were transferred onto a nitrocellulose membrane using standard electroblotting techniques (Mini-trans blot, Bio-Rad, USA). For the 1° antibody we used a mouse monoclonal anti-6-His IgG (Dianova, Germany). For the 2° antibody we used a horseradish peroxidase-conjugated anti-mouse IgG (Antibodies-online, USA). All solutions for Western blotting were based on Tris/Cl buffered saline (TBS, pH 7.4). The membrane was first blocked with 3% BSA, and incubated with a 1:1000 of 1° antibody for 3 hours. The membrane was then washed in TBS, and incubated for 2 hours with a 1:6000 dilution of 2° antibody. The blot was then washed and incubated with Pierce enhanced chemiluminescent (ECL) western blotting substrate (Thermo Scientific, USA), exposed to X-ray film.

Results and Discussion

SDS-PAGE and Western blots revealed a protein of 60-65 kDa in the outer membrane of *E. coli* containing pMATE-MT004 (FIG. 1). The nucleotide sequence of pMATE-MT004 is described by SEQ ID NO:3 (FIG. 18). The predicted size of the autotransporter fusion protein with 6×His as a passenger was 57.6 kDa after cleavage of the N-terminal signal peptide. The autotransporter fusion protein encoded by pMATE-MT004 is described by SEQ ID NO:4. The fusion protein was visible in all cases as a single band after SDS-PAGE, confirming that the MATE system did not suffer from limitations in the sec secretion or signal peptidase cleavage. The fusion protein was also visible from cells without the induction of protein expression (no IPTG). This suggests some "leaky" expression of the T5 promoter under these conditions, although the protein band seen after SDS-PAGE was much more intense after induction with IPTG.

Overall, this example shows that the MATE system can transfer a peptide to the outer membrane of *E. coli*. It shows that the 6×His is a suitable epitope for Western blotting, in order to detect the location of the fusion protein after SDS-PAGE.

EXAMPLE 2

Surface Expression of GFP in *E. coli* using the MATE System

In this example, the MATE system is used to display a fulllength protein (GFP) on the surface of *E. coli.*

Bacterial Strains

*E. coli* Stellar cells were used for cloning experiments [F−, endA1, supE44, thi-1, recA1, relA1, gyrA96, phoA, ϕ80d lacZΔ M15, Δ (lacZYA—argF) U169, Δ (mrr—hsdRMS—mcrBC), ΔmcrA, λ—] (Clontech, USA). Expression experiments were carried out in *Escherichia coli* UT5600 [$F^-$, ara-14, leuB6, secA6, lacY1, proC14, tsx-67, Δ(ompT-fepC)266, entA403, trpE38, rfbD1, rpsL109($Str^r$), xyl-5, mtl-1, thi-1] (Grodberg and Dunn, 1988).

Plasmid Construction

The gene encoding GFP (GFPmut2) was inserted into pMT004 to form pMATE-MT006 (FIG. 19) using ligation independent cloning techniques (In-Fusion Eco-Dry kit, Clontech). The nucleotide sequence of pMATE-MT006 is described by SEQ ID NO:5. The autotransporter fusion protein encoded by pMATE-MT004 is described by SEQ ID NO:6. The GFP insert was amplified from the plasmid pKE19 using the primers MT15 (GCTCGTCGTGCTATTGAGGGCCGCATCCCGG) and MT16 (ACGACCTTCGATATGATGGTGATGGTGGTGGGT) and polymerase chain reaction (PCR). The backbone plasmid was amplified with PCR using the primers MT17 (CATATCGAAGGTCGTatgagtaaaggagaagaacttttc) and MT18 (AATAGCACGACGAGCgcctttgtatagttcatccatgcc), which contained a 15 by overlap to the PCR product of GFP, as required for InFusion cloning. The two PCR Products were joined to form the plasmid pMATE-MT006 using standard In-Fusion techniques (Eco-Dry kit, Clontech) and transformed into *E. coli* Stellar chemically competent cells (Clontech).

Protease Accessibility Assay

*E. coli* UT5600 cells containing pMATE-MT006 were grown in LB medium to $OD_{600}$ of 0.5. Protein expression was induced by the addition of 1 mM IPTG, and the cells were harvested after 1 hour. For trypsin treatment, cells were incubated with 1.2 $\mu g \cdot ml^{-1}$ of Trypsin (6000 $NFU.ml^1$) while shaking for 1 hour at 37° C. Outer membrane proteins were isolated, and proteins were separated by 12.5% SDS-PAGE. Gels were stained for total protein with Coomassie Brilliant Blue R-250. For Western blots, proteins were transferred to PVDF membranes (Mini-trans blot, Bio-Rad, USA). The blot was blocked in TBS containing 5% milk powder, and incubated with a 1:2000 dilution of polyclonal rabbit anti-GFP IgG (GeneTex #GTX26556) overnight at 4° C. while shaking. The membrane was then washed with 0.1% Tween in TBS, and incubated for 2 hours with a 1:10 000 dilution of 2° antibody, horseradish peroxidase coupled anti-rabbit IgG (Promega #W401B). Horseradish peroxidase activity was detected with luminol reagent (sc-2048, Santa-Cruz Biotechnology, USA) and a chemiluminescence imager (Chemocam, Intas).

Pierce enhanced chemiluminescent (ECL) western blotting substrate (Thermo Scientific, USA), and viewed with an ECL imager.

Results and Discussion

A protein of approximately 105 kDa was found in the outer membrane in cells expressing GFP in the MATE system in *E. coli*. The apparent molecular weight is higher than the expected size of the fusion protein after cleavage of the Nterminal signal peptide (84 kDa). The 105 kDa band was detected with the antiGFP antibody (FIG. 2), confirming that it corresponded to the GFPautotransporter fusion protein.

We conducted a protease accessibility test to confirm the passenger domain was exposed to the surface. The protease trypsin is too large to enter the cell, therefore the trypsin accessibility of an Nterminal passenger domain demonstrates surface exposure. In contrast, Nterminal regions that are inaccessible to trypsin are presumed to be translocation intermediates, or misfolded proteins in the cytoplasm.

The band corresponding to the MATE fusion protein was significantly reduced after trypsin treatment (FIG. 2). This is strong evidence that the passenger was exposed to the surface. The OmpA band at 37 kDa was unaffected by protease treatment, ensuring that the protease digestion did not affected membrane integrity. Overall, the data confirms that GFP was transported to the cell surface with high efficiency using the MATE system.

EXAMPLE 3

Secretion of a Recombinant Protein into the Medium using the MATE System

In this example, the MATE system utilises the OmpT protease to enable the secretion of a fulllength protein.

In this example, we show that GFP is secreted into the growth media after when expressed in OmpT positive strains using the MATE system.

Materials and Methods pMATE-MT006 was transformed into *E. coli* UT2300 [$F^-$, ara-14, leuB6, secA6, lacY1, proC14, tsx-67, entA403, trpE38, rfbD1, rpsL109(Str), xyl-5, mtl-1, thi-1] and its OmpT deficient derivate *E. coli* UT5600 [$F^-$, ara-14, leuB6, secA6, lacY1, proC14, tsx-67, Δ(ompT-fepC)266, entA403, trpE38, rfbD1, rpsL109($Str^r$), xyl-5, mtl-1, thi-1] (Grodberg and Dunn, 1988). 40 ml of LB medium was inoculated with 0.4 ml of an overnight culture, and grown until $OD_{600}$ 0.5 at 37° C., 200 rpm. 1 mM of IPTG was added, and the cells were incubated for another 1.5 hours. Cells were then removed by centrifugation (3750 g, 30 min, 4° C.) followed by vacuum filtration (0.45 μm HVLP membrane, Millipore).

Proteins secreted into the LB media were concentrated by TCA/Acetone precipitation. TCA (80% w/v) was added to the 40 ml of LB medium to a final concentration of 8.5%. The sample was then incubated for 1 h at 4° C., followed by centrifugation (3750 g, 30 min, 4° C.). The supernatant was then discarded except for a small amount (3 ml) which was used to resuspend the pellet and transfer to 1.5 ml tubes. After centrifugation at 18 000 g for 30 min, the pellet was resuspended in 1 ml of icecold acetone and followed by centrifugation. The pellet was then resuspended in icecold acetone in water (80% v/v) followed by centrifugation. The pellet was then dried for 20 min on a 37° C. heating block, and resuspended in 200 μl of 1×SDS sample buffer containing 100 mM of dithiothreitol (DTT). Proteins were dissolved by heating at 96° C. for 50 min with vigorous vortexing.

Proteins were separated by 12.5% SDS-PAGE and proteins visualised with Coomassie Brilliant Blue R250. Western blotting was conducted using a 1° antibody against GFP (rabbit polyclonal anti-GFP, #GTX26556, GeneTex) and a 2° goat anti-rabbit IgG antibody, coupled with horseradish peroxidase (#W401B, Promega). After SDS-PAGE, proteins were transferred onto a PVDF membrane using standard electroblotting techniques (Mini-trans blot, Bio-Rad). All solutions for Western blotting were based on Tris/Cl buffered saline (TBS, pH 7.4). The membrane was blocked for 1 h with 5% milk powder (blotting grade, Roth). It was then incubated for overnight in a 1:1000 dilution of 1° antibody, at 4° C. while shaking. The membrane was then washed with 0.1% Tween in TBS and incubated for 1.5 hours with a 1:6000 dilution of 2° antibody. Horseradish peroxidase activity was detected with luminol reagent (sc-2048, Santa-Cruz Biotechnology, USA) and a chemiluminescence imager (Chemocam, Intas).

Results and Discussion

To facilitate secretion via OmpT cleavage, we inserted an artificial OmpT cleavage site (Ala-Arg-Arg-Ala) into the MATE autotransporter in between the passenger and the linker. Because the EhaA autotransporter region has never before been used for surface display of a recombinant passenger, we were unsure whether OmpT would facilitate cleavage, and we were also unsure if the autotransporter domain would facilitate self-proteolysis as seen for autotransporters in the SPATE family.

To test if this artificial OmpT cleavage site could allow protein secretion, we transferred the plasmid pMATE-MT006 into OmpT positive strain UT2300 and looked for the presence of GFP in the growth media. Western blotting clearly showed the presence of GFP in the growth media of *E. coli* UT2300 pMATE-MT006 (FIG. 3). In contrast, we did not detect any GFP in the growth media after expression in the OmpT deficient derivate strain *E. coli* UT5600. The GFP visualised by Western blotting was visible as a single band with an apparent molecular weight of ~30 kDa. The size of the GFP fragment detected by Western blotting strongly suggests that OmpT indeed cleaved at the artificial Ala-Arg-Arg-Ala site within the fusion protein. We did not see this band after SDS-PAGE followed by Coomassie staining, suggesting the amount of secreted protein was low. Nevertheless, we confirmed the ability to secrete proteins using this system, which should allow purification of the 6×His containing passengers, followed by cleavage of the 6×His region with Factor Xa.

When testing a new autotransporter system, it is important to determine if the surface displayed passengers are naturally released into the media by self-proteolysis. Self-proteolysis would reduce the amount of protein at the surface, and therefore reduce efficiency in biocatalysis or screening. In the MATE system we found no evidence that the passengers are released into the growth media by self-proteolysis. After surface expression in an OmpT negative strain (*E. coli* UT5600), GFP could be detected clearly in the outer membrane (see FIG. 2) but not in the growth media (FIG. 3). This reaffirms the efficiency of the MATE system for surface display in OmpT negative strains of *E. coli*. Since we did not detect any alternative OmpT fragments, it might be possible that the EhaA autotransporter linker does not contain any natural OmpT cleavage sites. This might allow the efficient surface expression using the MATE system in OmpT positive strains of *E. coli*.

Overall, our experiments show the feasibility of OmpT mediated secretion of recombinant passengers using the MATE system. OmpT did not cleave the passenger protein GFP, despite the presence of a typical OmpT recognition site within the primary sequence. We show for the first time that an artificial OmpT cleavage site can be used for the release of surface displayed passengers. In comparison to SPATE-like autoproteolytic cleavage, release by OmpT has the advantage that the same plasmid can be used for both surface display and secretion by simply varying the expression strain. This might have advantages in high-throughput approaches for protein expression and screening.

EXAMPLE 4

Secretion and Purification of Functional mCherry Protein using the MATE System in *E. coli*

Introduction

In this example, we show that mCherry is secreted into the growth media after expression in OmpT positive strains using the MATE system. The outer membrane protein T (OmpT) of *E. coli* is a surface membrane serine protease and is the prototypical member of the omptin family of gram-negative bacteria (Mangel, Toledo et al. 1994). Recombinant passengers have previously been shown to be secreted into the media, after surface display using autotransporters in OmpT containing *E. coli* strains. In all previous cases, an OmpT cleavage site was found within the autotransporter linker region. In our case it was unknown whether OmpT would facilitate cleavage, as the autotransporter within the MATE system (EhaA) has not been previously tested for the recombinant expression of passenger proteins. For this reason, we inserted an artificial OmpT cleavage site (Ala-Arg-Arg-Ala) to the Cterminal region of the recombinant passenger. Sevastsyanovich et al. already described the secretion of red fluorescent protein (RFP) mCherry by utilization of a serine protease autotransporter of the *Enterobacteriaceae* (SPATEs, Sevastsyanovich et al. 2012). In comparison to the cleavage procedure of the passenger domain of SPATES, the passenger of the MATE system is released by the endogenous protease OmpT by recognition of the artificial OmpT cleavage site within the plasmid.

Materials and Methods

Construction of pMATE-SI015

A ligation independent cloning was used for construction of pMATE-SI015

(In-Fusion Eco-Dry Kit, Clontech). The nucleotide sequence of pMATE-SI015 is described by SEQ ID NO:13 (FIG. 24). The autotransporter fusion protein encoded by pMATE-SI015 is described by SEQ ID NO:14. Therefore the pMATE-MT004 plasmid backbone was amplified with PCR using the primers S1020 (GCTCGTCGTGCTATT-GAGGGCCGCATCCC) and PQ019

(ATGATGGTGATGGTGGTGGGTGATGTTCTG). The gene encoding mCherry was amplified using the primers SI021 (AATAGCACGACGAGCcttgtacagctcgtccatgccgccg-gtgg) and PQ024 (CACCATCACCATCATATGGTGAG-CAAGGGCGAGGAGGATAACATG), which contained a 15 by overlap to the PCR product of the pMATE-MT004 plasmid backbone, as required for InFusion cloning. The two PCR Products were joined to form the plasmid pMATE-SI015 using standard In-Fusion techniques (Eco-Dry kit, Clontech) and transformed into *E. coli* Stellar chemically competent cells.

Bacterial Strains and Purification of mCherry pMATE-SI015 was transformed into *E. coli* UT5600 and its OmpT positive parent strain *E. coli* UT2300 (Grodberg and Dunn, 1988).

800 ml of LB medium was inoculated with 8 ml of an overnight culture, and grown until $OD_{600}$ 0.5 at 37° C., 200 rpm. 1 mM of IPTG was added, and the cells were incubated for 24 hours. Cells were then removed by centrifugation (10,000 g, 20 min, 4° C.).

Proteins secreted into the LB media were purified via the 6×His epitope present in the secreted heterologous mCherry passenger. Therefore the obtained supernatant was loaded on a Ni-NTA column, which was before equilibrated with 10 column volumes of binding buffer containing 20 mM sodium phosphate, 0.5 M sodium chloride and 20 mM imidazole (pH 7.0). The column was washed once with 10 column volumes binding buffer and with 30 ml washing buffer, containing 20 mM sodium phosphate, 0.5 M sodium chloride and 100 mM imidazole (pH 7.0). Elution of the protein was carried out by addition of three times 2 ml Elution buffer containing 20 mM sodium phosphate, 0.5 M sodium chloride and 500 mM imidazole (pH 7.0). The eluted protein fractions were concentrated in microcon centrifugal filter devices with a cut-off size of 10 kDA (Merck Millipore). All steps were carried out at 4° C.

The concentrated protein was resuspended in 40 μl of 100 mM sodium phosphate buffer pH 7.0 plus 40 μl of 2×SDS sample buffer containing 200 mM of dithiothreitol (DTT). Protein samples were heated at 96° C. for 10 min.

Equal amounts of protein samples were analysed by 10% SDS-PAGE and visualised by Coomassie stain.

Results and Discussion

The outer membrane protein T (OmpT) of *E. coli* is a surface membrane serine protease and is the prototypical member of the omptin family of gram-negative bacteria (Mangel, Toledo et al. 1994).

As described for the secretion of GFP using the MATE system in example 3a), we also tested the artificial OmpT cleavage site for the secretion of monomeric red flourescent protein (RFP) mCherry. Therefore we transferred the plasmid pMATE-SI015 into OmpT positive strain *E. coli* UT2300 and looked for the presence of mCherry in the growth media.

Supernatants from cultures of both *E. coli* UT2300 and *E. coli* UT5600 showed no visible difference. We then attempted to purify mCherry from the supernatant using a Ni-NTA column. After applying the supernatant to the Ni-NTA column and elution with 500 mM imidazole the sample of OmpT-positive strain *E. coli* UT2300 was indeed pink. In constrast, repeating this procedure with the supernatant from OmpT-negative cells resulted in an eluate which was clear. This suggests that mCherry was indeed displayed at the surface and then released by the OmpT protease in the OmpT (FIG. 4).

The putative mCherry visualised by SDS-PAGE and subsequent Coomassie staining was visible as a single band with an apparent molecular weight of ~30 kDa. In contrast, after expression and purification of the 6×His proteins from the OmpT negative derivate strain *E. coli* UT5600 we did not detect any RFP in the growth media, suggesting by the absence of a band at the same molecular weight as it is the case for the OmpT positive strain (FIG. 5).

The presence of a band with an apparent molecular weight of ~100 kDa for both, the OmpT positive and OmpT negative strain protein samples, suggests the co-purification of the full autotransporter fusion protein either after cell lysis or by occurrence of vesicles containing the autotransporter fusion protein (FIG. 5).

The size of the band from the eluate from *E. coli* UT2300 detected by SDS-PAGE with subsequent Coomassie stain strongly suggests that OmpT indeed cleaved at the artificial Ala-Arg-Arg-Ala site within the fusion protein and released the putative mCherry passenger. Overall, our experiments show the feasibility of OmpT mediated secretion of recombinant passengers using the MATE system. As it is described in Example 3a) for the GFP passenger, we did not detect any undesired cleavage of the mCherry passenger by OmpT. This example gives a further proof that the artificial OmpT cleavage site can be used for the release of surface displayed passengers. The OmpT mediated release has the advantage that the same plasmid can be used for both surface display and secretion. This allows greater flexibility than self-proteolysis, where it would be necessary to construct a second plasmid for surface display in which the residues necessary for self-proteolysis are removed.

EXAMPLE 5

Release of Recombinant Passenger using Factor Xa, after Surface Display using the MATE System In this example, the MATE system is shown to enable the release of a fulllength protein using the specific protease Factor Xa.

We showed earlier that the MATE system could be used for the constitutive secretion of a recombinant passenger in OmpT positive strains (Example 3). The secretome of *E. coli* is known to be relatively simple, reducing the costs associated with purification in comparison to intracellularly expressed proteins. However protein purification is still required to separate the recombinant protein of interest from other secreted proteins. For high-throughput screening, it would be beneficial to obtain small amounts of the protein of interest at higher purity. This could be achieved by first displaying the protein of interest on the cell surface, washing the cells in buffer, and then releasing the protein of interest into the buffer by the activity of a specific protease. The protein of interest can then be immediately assayed for functional activity. Optimally, the protease used to release the passenger is highly specific. In this example, we show that the protease Factor Xa can successfully release passengers displayed on the cell surface with the MATE system.

*E. coli* UT5600 cells containing pMATE-MT006 were grown in an overnight culture in LB medium. 20 ml of LB medium was inoculated with 0.5 ml of overnight culture, and grown at 37° C., 200 rpm to $OD_{600}$ of 0.5. Protein expression was induced by the addition of 1 mM IPTG, and the cells were harvested after 1.5 hour. Cells were washed in buffer consisting of 100 mM Tris/Cl pH 8, 50 mM NaCl, 1 mM $CaCl_2$, and incubated for 16 h with 100 $\mu g \cdot ml^{-1}$ of bovine Factor Xa protease (#33233, QIAGEN). Cells were removed by centrifugation at 14 000 g, and proteins within the supernatant were concentrated by TCA precipitation (final TCA concentration of 8%). Concentrated proteins from the supernatant were separated by 12.5% SDS-PAGE. Western blots were performed with polyclonal rabbit anti-GFP and horseradish peroxidase-coupled anti-rabbit IgG as described in Example 3.

Soluble GFP (~28 kDa) was detected in the supernatant after Factor Xa treatment of *E. coli* pMATE-MT006 (FIG. 6). No significant amounts of GFP were released without the addition of Factor Xa, suggesting that the MATE autotransporter does not undergo self-proteolysis as seen in SPATE autotransporters. The addition of the Factor Xa cleavage site after the passenger therefore allows the selective release of passengers from the cell surface.

In combination with the 6×His on the Nterminal region of the passenger, the selective release in the MATE system allows the rapid purification of proteins. As shown here, the cells can be washed before the release of the passenger into a buffer. This yields a purer form of the protein in comparison to a constitutive secretion system such as auto-proteolysis, where the passenger is released into the growth media and must be separated from other secreted proteins.

The Factor Xa mediated release also allows a more rapid protease-accessibility assay in the MATE system. Usually a nonspecific protease such as trypsin or proteinase K is used, whereby the incubation time must be optimised for each system. Proteins transported to the surface with Autodisplay have also been released with purified Iga1 protease (Klauser 1992), however this enzyme is not commercially available and the mode of action is not extensively researched. Only recently has this been attempted with a commercially available, highly specific protease (Nla-TEV, Ko et al. 2012). Here, we show the detection of the passenger in the supernatant after incubation of the cells with Factor Xa, a rapid and simple method of proving surface display, without the need for antibodies or extensive optimisation of protease digestion. When optimised, it may be also possible to detect the decrease in cell-associated passenger after Factor Xa treatment. This technique allows rapid and simple protein purification, and may be compatible with highthroughput screening approaches for protein improvement or inhibitor detection.

EXAMPLE 6

Functional Display of *B. gladioli* EstA Esterase on the Surface of *E. coli* with the MATE System In this example the EstA catalytic domain was functionally expressed on the surface of *E. coli* using the new MATE system.

Plasmid Construction

The plasmid pMATE-SI005 (FIG. 20, SEQ ID NO:7) was designed for the surface expression of proteins using the MATE system in a broad range of Gram negative bacteria. To create the plasmid, PCR products from three plasmids were combined using ligation independent cloning methods (In-Fusion, Clontech, USA). These fragments included the MATE autotransporter from pMATE-MT004, the rep and kanamycin resistance genes (aph) from pBBR1MCS-2 (Kovach et al. 1995), and two fragments from pBAD/gIII. The first fragment from pBAD/gIII contained the araBAD promoter and araC gene. The second fragment from pBAD/gIIl contained the rrnB transcription terminator.

The fusion protein encoded by pMATE-SI005 (SEQ ID NO:8) included a CtxB signal peptide, a small peptide passenger (6×His), a multiple cloning site, OmpT and Factor Xa cleavage sites and a PEYFK epitope. The Cterminus contains the EhaA autotransporter linker and n-barrel.

For the surface display of a functional esterase, the coding region of the catalytic domain of estA from *Burkholderia gladioli* was excised from pES01 (Schultheiss et al. 2002) via XhoI and KpnI and subsequently inserted in pMATE-SI005 to create pMATE-SI010 (FIG. 7, and see plasmid map in FIG. 22).

We conducted activity tests to determine if EstA catalytic domain was expressed in a functional form. For this purpose cells of *E. coli* UT5600 pMATE-SI010 and *E. coli* BL21 (DE3) pES01 were cultivated at 30° C. *E. coli* UT5600 without any plasmid served as a control. *E. coli* UT5600 cells were induced with 0.5% (w/v) L-arabinose for 2 hours. Cells of *E. coli* BL21 (DE3) pES01 were also cultivated for 2 hours. Since pES01 plasmid encodes a promoter facilitating a constitutive gene expression there was no need for any induction. Photometric activity assays were performed with pnitrophenyl acetate as a model esterase substrate. To obtain standard conditions $OD_{600}$ was adjusted to 0.2 for every measurement. In comparison to pES01 the MATE system gives vastly improved activity of surface-displayed esterase (FIG. 8).

EXAMPLE 7

Functional Surface Display of EstA Catalytic Domain in *Salmonella enterica* using the MATE System In this example the MATE system was used for expression of the estA catalytic domain in a second non *E. coli* strain, namely *S. enterica* serovar Typhimurium. Autotransporter-mediated surface display has been previously conducted in *Salmonella* strains (van Gerven et al. 2009), which are genetically closely related to *E. coli*. However this provides the first confirmation that the vector is compatible in non *E. coli* strains.

The broad host range plasmid pMATE-SI010 (FIG. 22, SEQ ID NO:9), encoding the new autotransporter EhaA and the catalytic domain of EstA (SEQ ID NO:10) was transferred to cells of *S. enterica*. Protein expression was induced with 0.5% (w/v) L-arabinose for two hours at 30° C., 200 rpm. To find out whether the EstA catalytic domain of the fusion protein was indeed exposed at the cell surface, proteinase K was added the whole cells.

Proteinase K is too large to enter the cell envelope of *S. enterica*. This means, if the EstA catalytic domain is degraded by proteinase K, it must be accessible at the cell surface.

Activity assays with pnitrophenyl acetate as a substrate were performed with either proteinase K treated or untreated whole cells containing *S. enterica* pMATE-SI010. Protein expression was induced for 2 h with 0.5% L-arabinose at 30° C. The final $OD_{600}$ in the assay was adjusted to 0.2. We used *S. enterica*, without any plasmid as a negative control. Cells of *S. enterica* pMATE-SI010 exhibited similar activity in comparison to *E. coli* cells harbouring pMATE-SI010 plasmid (FIG. 9).

The decrease in esterase activity at the surface after proteinase K treatment confirms that the estA catalytic domain was exposed to the surface. This confirmed that the MATE system functions not only in *E. coli*, but also in a closely related non *E. coli* species. The use of the MATE system in *S. enterica* may help in the development of vaccines. To our knowledge, this is the first time that surface display of a recombinant protein with an autotransporter has been successfully achieved in a *Salmonella* species.

EXAMPLE 8

Functional Surface Display of EstA Catalytic Domain in *Pseudomonas putida* KT2440 with the MATE System In this example the MATE system was used for the functional expression of and enzyme in a Gram negative species more distantly related to *E. coli*.

Functional surface display of estA in *E. coli* was carried out as described in Example 4. The broad host range plasmid pMATE-SI010, encoding the catalytic domain of the esterase EstA, was transferred to cells of *P. putida* KT2440 using standard chemical transformation techniques.

Functional activity was first tested using continuous esterase microplate assays. Esterase activity in *P. putida* cells containing pMATE-SI010 was significantly higher than cells containing the control plasmid, pMATE-SI005 (FIG. 10). When adjusted to an equal OD600, activity was higher in *E. coli* than in *P. putida*.

To confirm that this functional activity was at the cell surface, the esterase microplate assays were conducted with whole cells after incubation with proteinase K. Proteinase K is too large to cross the outer membrane. The loss of activity in whole cells after addition of proteinase K givesstrong evidence that the esterase is located at the cell surface. Using pnitrophenyl acetate as a substrate, activity assays were performed with either proteinase K treated or untreated whole cells of *P. putida* pMATE-SI010.

*P. putida* cells expressing an esterase at the surface using the MATE system completely lost their esterase activity after treatment with proteinase K (FIG. 11). In comparison, approximately half of the esterase activity was lost in *E. coli* cells under the same conditions. This implies that the EstA esterase had a better accessibility to the protease in *P. putida* than in *E. coli*.

We conducted flow cytometry analysis to confirm that the fusion protein containing the EstA fragment was exposed at the surface. The results are described in FIG. 12. *P. putida* KT2440 cells were grown in LB medium to an early exponential growth phase ($OD_{600}$ of 0.5). After cell harvest and resuspension in phosphate buffered saline (PBS), expression of EstA was induced for 18 hours by adding Larabinose to a final concentration of 0.5%. Cells were then incubated for 18 hours at 30° C., 200 rpm. Cells were harvested by centrifugation, washed twice with PBS and resuspended to a final $OD_{600}$ of 0.4. 1 ml of the cell suspension was centrifuged (90 s at 13.400 g), resuspended in 100 μL of a solution that contained a monoclonal mouse anti-6×His antibody (20 $\mu g \cdot ml^{-1}$ in PBS, Thermo Scientific) and incubated for 60 min at 22° C. Cells were then washed twice with 500 μL of PBS. The second incubation step was conducted in the dark (60 min, 22° C.) using 100 μL of a rabbit antimouse IgG antibody conjugated with fluorescein (20 $\mu g \cdot ml^{-1}$ in PBS). After washing twice in PBS, the cell pellet was resuspended in 1 ml of PBS for analysis. Samples were then analysed using a BD FacsAria III Cell Sorter (BD Biosciences, Heidelberg, Germany) at an excitation wavelength of 488 nm.

The fully processed, surface-displayed EstA fusion protein was predicted to have an N-terminus consisting of a 6×His affinity tag, the EstA fragment and MATE autotransporter domain. Using an antibody against the 6×His epitope, approximately 50% of the cells were found in a population with high fluorescence and could be judged to contain the fusion protein at the surface. To determine whether non-stained cells represented incomplete surface expression, or simply sub-optimal antibody binding, we conducted further analyses of cellular and outer membrane proteins.

As with many other esterases, EstA can be refolded after SDS-PAGE and functional activity measured using an ingel activity stain (Schultheiss et al. 2002). Briefly, proteins were heated for 30 min in loading buffer that contained DTT, and separated by 10% SDS-PAGE as per standard techniques (Laemmli 1970). The gels were then incubated in buffer containing 2.5% Triton-X100 until the esterase had refolded into an active form. The gels were then stained for esterase activity using 1naphthyl acetate as a substrate and Fast Blue RR as a conjugate dye.

In the analysis of whole cells expressing EstA at the surface, SDS-PAGE followed by esterase staining revealed a band at approximately 105 kDa in both *E. coli* and *P. putida* (FIG. 13B). The expected size of the fusion protein after cleavage of the signal peptide was 91.2 kDa. As expected, this band was not visible after Coomassie staining, as it comprised only a small proportion of total cellular protein. A single esterase band was visible in *P. putida*, however esterase activity at the apparent molecular weight of ~38 kDa and ~60 kDa were also visible in *E. coli*.

A further SDS-PAGE analysis was conducted to confirm the surface exposure of the EstA esterase in *P. putida*, when expressed using the MATE system. To find out whether the EstA catalytic domain of the fusion protein was indeed exposed at the cell surface, proteinase K was added the whole cells containing pMATE-SI010 after protein induction with 0.5% (w/v) L-arabinose for two hours at 30° C. Proteinase K is too large of a molecule to enter the cell envelope of *E. coli*, the decrease in bands associated with the fusion protein after Coomassie or esterase staining indicates the surface exposure of the esterase. SDS-PAGE with Coomassie stain allows a further control: OmpA has a Nterminal extension in the periplasm that is proteinase K sensitive, therefore the detection of intact OmpA indicates that the protease has not entered the periplasm due to cell leakiness.

After isolation of membrane proteins from *P. putida*, the EstAautotransporter fusion protein was visible after SDS-PAGE with both Coomassie and esterase staining (FIG. 14). As we showed previously for the GFP fusion protein, the apparent molecular weight (MW) of the EstA-autotransporter fusion protein after SDS-PAGE (~105 kDa) was higher than the molecular weight predicted from the primary sequence after accounting for signal peptide cleavage (91.2 kDa). It is not unusual for βbarrel proteins to show an altered apparent molecular weight after SDS-PAGE, as they remain partially folded and in some cases catalytically active in conditions that are strongly denaturing for other proteins. There was no difference in the apparent MW between the fusion protein expressed in *E. coli* and *P. putida.*

Confirming the results from microplate assays (FIG. 11), proteinase K treatment of *P. putida* cells expressing EstA at the surface completely removed all esterase activity, as judged by the disappearance of the esterase band after SDS-PAGE (FIG. 14). In contrast, protease treatment gave only a partial decrease in the intensity of the esterase band from *E. coli*. This strongly supports the results from microplate assays (FIG. 11), where only a proportion of the *E. coli* esterase activity was susceptible to external protease treatment (FIG. 11). Overall, this strongly suggests that a proportion of the esterase molecules in *E. coli* were intracellular, and therefore inaccessible to the protease. This hypothesis is supported by the undesired 38 kDa and 60 kDa esterase fragments seen in the analysis of *E. coli* whole cells. These fragments cannot be located at the cell surface, because they are not visible in the analysis of outer membrane proteins (FIG. 14).

In comparison to *E. coli*, the vast majority of esterase activity in *P. putida* pMATE-SI010 was protease accessible. This could suggest that *P. putida* has unexpected advantages for use with surface display. Another surprising benefit within *P. putida* was the absence of of the undesired intracellular fragments, which may indicate a small amount of the fusion protein is improperly folded in *E. coli*. These factors suggest that *P. putida* is highly suitable to screening of surface displayed enzymes or fluorescent molecules where intracellular activity is detrimental.

When we directly compared the surface-exposed (i.e. protease accessible) esterase activity of *E. coli* and *P. putida*, the overall activity in *E. coli* was higher (FIG. 15). Nevertheless, *P. putida* clearly showed some advantages over *E. coli* for surface display—not only is the strain chemical resistant and compatible with industrial processes, but a higher proportion of the passenger was found at the surface. This highlights the advantage of the MATE system, whereby the surface display of recombinant proteins can be rapidly tested in a broad range of bacterial hosts.

EXAMPLE 9

Functional Surface Display of *B. gladioli* Esterase EstA Catalytic Domain in *Zymomonas mobilis* with the MATE System

Introduction

*Zymomonas mobilis* is of big interest for the commercial production of biomass-derived ethanol as it produces ethanol with high yields and has a higher growth rate than the presently used Sacharomyces cerevisiae. The exposure of recombinant proteins on the surface of *Z. mobilis* offers considerable advantages in the industrial application of this organism. For instance, the surface display of cellulose degrading enzymes (cellulases) on *Z. mobilis* cells can provide a whole-cell catalytic system which is able to breakdown cellulose and ferment the formed monomeric sugars to ethanol in a single step. As cellulose cannot penetrate the cell membrane, elaborate and expensive enzyme purification steps become necessary when the cellulases are expressed intracellularly. Surface exposed cellulases could circumvent these difficulties as they have direct access to their substrates and do not have to be extracted from the cells prior to their use. A further benefit of a whole-cell catalyst is given by its reusability, since bacterial cells can easily be separated from a reaction mixture by centrifugation.

To our knowledge no surface display system for *Z. mobilis* has been established so far. This example presents the functional expression of *B. gladioli* esterase EstA catalytic domain on the surface of *Z. mobilis* using the new MATE system.

Materials and Methods

Construction of Plasmid pMATE-SI012 and Transfer to *Z. mobilis*

For the construction of pMATE-SI012 (FIG. 23, SEQ ID NO:11) genes encoding the estA catalytic domain were excised from plasmid pMATE-SI010 via XhoI/KpnI restriction endonucleases and ligated into plasmid pMATE-SI009 (FIG. 21). This plasmid contains a mob gene which is necessary for plasmid replication in *Z. mobilis*. pMATE-SI012 was transferred to cells of *Z. mobilis* ATCC 29191 using a standard electroporation procedure. The fusion protein is described in SEQ ID NO:12).

Cultivation of *Z. mobilis* and Induction of Protein Expression 200 mL of ZM Medium (10 g/L bacto peptone, 10 g/L yeast extract, 20 g/L glucose; Roth, Germany, when needed kanamycine 150 mg/mL; Sigma Aldrich, USA) were inoculated with an overnight-culture of *Z. mobilis* (1:1000 dilution) and incubated at 30° C., 60 rpm until the cultures reached an OD578 of 0.6. Induction of protein expression was performed by incubation with 0.2% (w/v) L-arabinose (Roth, Germany) in ZM Medium for two hours at 30° C., 60 rpm.

Trypsin Digestion

*Z. mobilis* cells were harvested by centrifugation and resuspended in 0.2 mol/L Tris-HCl pH 8.0. Porcine pancreatic trypsin was added to a final concentration of 2.5% and incubated for one hour at 37° C., 200 rpm. Digestion was stopped by washing three times with 10% fetal calf serum (FCS) in 0.2 mol/L Tris-HCl pH 8.0.

Outer Membrane Protein Isolation

Outer membrane protein isolation was carried out according to a modified protocol of Hantke (Hantke 1981, Jose and von Schwichow, 2004).

Protein Separation

Proteins were heated for 40 min at 95° C. in two-fold sample buffer (100 mM Tris-HCl, pH 6.8 containing 4% sodium dodecyl sulfate, 0.2% bromophenole blue, 20% glycerol and 30 mg dithiothreitol) and separated by means of sodium-dodecyl-sulfate polyacrylamide gel electrophoresis (SDS-PAGE) in a 10% resolving gel (Laemmli 1970). Proteins were then stained either with Coomassie Brilliant Blue or esterase activity stain (see below). Pictures were taken using an Intas Gel iX Imager (Intas, Germany).

Western Blot

Standard blotting techniques were used to transfer proteins from polyacrylamide-gels to nitrocellulose membranes (Mini-trans blot, Bio-Rad, USA). The membranes were blocked with 3% bovine serum albumine (BSA) in phosphate-buffered saline (PBS, pH 7.4) and incubated with mouse anti-6×His mAb IgG1 (Dianova, Germany) in PBS (1:1000 dilution). Subsequently the membranes were washed three times with PBS and incubated with horseradish peroxidase-conjugated anti-mouse IgG (Antibodies-online, USA) in PBS (1:5000 dilution). The membranes were then washed twice with PBS and treated with Pierce enhanced chemiluminescent (ECL) western blotting substrate (Thermo Scientific, USA). Pictures were taken using an Intas ChemoCam Imager (Intas, Germany).

Esterase Activity Staining

Esterase activity staining was carried out using a modified protocol of Schultheiss et al. (Schultheiss 2002). For the renaturation of the esterase SDS was removed by incubation of the polyacrylamide gels in 10 mmol/L Tris-HCl, pH 7.5 containing 2.5% Triton-X100 (AppliChem, Germany) for three hours. The gels were then stained for esterase activity with 10 mmol/L Tris-HCl, pH 7.5 containing 0.1% (w/v) FastBlueRR (Sigma Aldrich, USA) and 2% (v/v) α-naphtyl-acetate-solution (1% w/v in 50% v/v acetone; Sigma Aldrich, USA).

Results

SDS-PAGE Coomassie Staining

Outer membrane proteins of *Z. mobilis* cells without plasmid pMATE-SI012, cells with plasmid and cells with plasmid and aforegoing trypsin treatment were isolated and separated by SDS-PAGE. Coomassie staining of proteins isolated from cells with plasmid did not show any additional bands assignable to the EstA-autotransporter fusion protein. This is attributed to the small proportion of fusion protein in relation to the total outer membrane protein amount. Coomassie staining of proteins isolated from cells that were treated with trypsin prior to the outer membrane protein isolation revealed the disappearing of most protein bands except of four bands, which are visible at apparent molecular weights of <25 kDa (a), 25-35 kDa (b) and 35-40 kDa (c and d) (see FIG. 16A). The proteins within these bands seem to be resistant to Trypsin degradation. We excised the bands from the gel and analysed them by LC-MS/MS in order to identify the proteins within each band. 15 to 17 different *Z. mobilis* proteins were identified in each band. It is not possible to obtain quantitative information, however, OmpA/MotB domain containing proteins (Uniprot accession number: I6YFM2) could be shown to be present in bands b, c and d. Both OmpA and MotB are known to be integral membrane components. As Trypsin is too large to penetrate the outer membrane and therefore digests only proteins that are located on the cell surface, this is good evidence that the outer membrane remained undamaged by trypsin treatment and that only exterior proteins were degraded.

Western Blot

Western Blot analysis of outer membrane protein isolates with anti-6×His antibodies showed the presence of the EstA-autotransporter fusion protein at an apparent molecular weight of about 105 kDa, which is slightly higher than expected from the primary sequence (91.2 kDa). This is not unusual for beta-barrel containing proteins as they are not completely denatured under normal SDS-PAGE conditions. Neither in the outer membrane protein isolates of *Z. mobilis* cells without plasmid nor in the protein isolates of cells with plasmid but without L-arabinose induction a band was visible. Protein isolates of cells which were treated with trypsin prior to protein isolation also did not show any band. The absence of the fusion protein in the outer membrane proteins of trypsin-digested cells confirms the actual exposure of the esterase on the surface of the *Z. mobilis* cells (see FIG. 16B).

Esterase Activity Stain

In-gel esterase activity staining revealed an activity band at about 105 kDa in outer membrane proteins of arabinose treated *Z. mobilis* cells with plasmid. This is consistent with the presented Western Blot results, which identified this band as the EstA-autotransporter fusion protein. Besides this band, three other esterase activity bands between 55 and 100 kDa were visible in the same protein isolate. It is believed that these activity bands are unspecific degradation products. Esterase activity bands could neither be detected in protein isolates of cells without plasmid nor in protein isolates of cells with plasmid but without arabinose induction. Outer membrane proteins of cells that were trypsin digested also showed no esterase activity at all (see FIG. 17). This strongly supports the assumption that EstA is functionally active on the surface of *Z. mobilis* cells Conclusion Besides the successful establishment of the MATE system in *P. putida* and *S. enterica*, these experiments confirm the proper functionining of the MATE system in a third *Zymomonas mobilis*, a natural ethanol producer.

EXAMPLE 10

Surface Display of an Active Endoglucanase Obtained from *Bacillus subtilis* on the Ethanologenic Bacteria *Zymobacter palmae* and *Zymomonas mobilis* using Maximized Autotransporter Expression (MATE) System Introduction The biocatalytic conversion of cellulose to ethanol as a doorway to alternative fuel production is to date limited by the absence of a catalytic system applicable to economic large scale processes. The biocatalyst of choice combines the ability to break down cellulose and simultaneously ferment the released sugars to ethanol. The high growth and ethanol production rates of the Gram-negative bacteria *Zymobacter palmae* and *Zymomonas mobilis* make them promising host organisms for such an approach. Since they cannot degrade cellulose naturally, it is necessary to add extracellular (i.e. secreted or cell-bound) endoglucanase, exoglucanase and beta-glucosidase functionalities to these organisms. In this example we describe the expression of a recombinant fusion protein consisting of an endoglucanase obtained from *Bacillus subtilis* and the maximized autotransporter expression (MATE) translocation unit in *Z. palmae* and *Z. mobilis*, resulting in the exposure of functional active endoglucanase on the cell surface of of both species.

Construction of Plasmid pMATE-PT004

The plasmid pMATE-PT004 was constructed based on the previously described pMATE-SI010 (SEQ ID NO:9). Plasmid pMATE-SI010 encodes a fusion protein consisting of an N-terminal CtxB signal peptide, *Burkholderia gladioli* esterase EstA catalytic domain and the C-terminal EhaA autotransporter domain. The expression of the fusion protein is controlled by an arabinose inducible promoter (araBAD). For detection and purification purposes, 6×His and PEYFK-epitopes are incorporated N- and C-terminal of the esterase domain, respectively. The plasmid encodes a Kanamycin resistance gene for transformant selection (FIG. 22).

The esterase EstA catalytic domain of pMATE-SI010 was removed by restriction enzyme digestion with XhoI and KpnI, while the endoglucanase domain was obtained by an identical restriction enzyme digestion of pMATE-endoglucanase and inserted into pMATE-SI010 to generate pMATE-PT004. Furthermore, a mob gene was inserted into pMATE-PT004 using ligation independent cloning methods (In-Fusion Cloning Kit HD, Clontech, USA) to enable plasmid replication in *Z. mobilis* and *Z. palmae* (FIG. 26).

Cultivation and Transformation of used Bacterial Strains

*Z. mobilis* (DSM No. 3580) was cultured at 30° C., 80 rpm in culture medium containing 10 g/L bacto peptone, 10 g/L yeast extract and 20 g/L D-glucose. *Z. palmae* (DSM No. 10491) was cultured at 30° C., 200 rpm in growth medium containing 10 g/L yeast extract, 2 g/L potassium dihydrogen phosphate and 5 g/L sodium chloride, adjusted to pH=6.0. Insertion of plasmids was conducted according to standard electroporation procedure, electroporated cells were regenerated in culture medium for 6 h (*Z. mobilis*) and 2 h (*Z. palmae*), before transferring them to Kanamycin selection plates.

Sodiumdodecylsulfate Polyacrylamide Gel Electrophoresis (SDS PAGE)

Overnight cultures of *Z. mobilis/Z. palmae* containing pMATE-PT004 were used to inoculate 100 ml of the respective culture medium (1:100 dilution), and were incubated until the cultures reached $OD_{578}$ of 0.5. Protein expression was induced by the addition of 0.2% L-arabinose, and the cells harvested one hour after induction. Outer membrane proteins were prepared according to the rapid isolation protocol of Hantke (Hantke 1981) with modifications as described previously (Jose and von Schwichow, 2004).

Proteins were separated with 12.5% sodium-dodecylsulfate polyacrylamide gel electrophoresis (SDS-PAGE) (Laemmli 1970). Proteins were stained with Coomassie Brilliant Blue R250.

Fluorescence-Activated Cell Sorting (FACS)

Cells were cultivated as described above and adjusted to an $OD_{578}$ of 0.4. After washing three times with cold, particle-free PBS, cells were resuspended in PBS containing 1° antibody against 6×His (THE HisTag, mouse, GenScript, USA) in a dilution of 1:500. After 30 min incubation at 4° C., cells were washed three times with PBS and incubated 30 min with 2° antibody (goat anti-mouse IgG (H+L), Dylight 633 conjugated, Thermo Scientific Pierce Antibodies, Germany) at room temperature in the dark. Cells were washed again three times and cell fluorescence measured by FACS Aria III flow cytometer (BD Biosciences, USA) using a red laser for excitation at 633 nm and a 660/20 bandpass filter for detection.

Whole Cell CMC Hydrolysis Activity Assay

For the whole cell endoglucanase activity assay cells were cultivated as described above and adjusted to an OD of 25. Cells were incubated 10 min with 1% Carboxymethylcellulose (CMC) in sodium-citrate buffer, pH 6 at temperatures between 30° C. and 80° C. After cell removal, released reducing sugars were determined photometrically (absorption at 540 nm) using a modified 3,5-dinitrosalicylic (DNS) assay protocol of King et al. (2008). The absorption values of blank samples (buffer and substrate) were subtracted from the measured absorption values of the cell samples.

Expression of Fusion Protein

To confirm the expression of the endoglucanase fusion protein, outer membrane proteins of *Z. palmae* were isolated and separated by SDS-PAGE (FIG. 27). While in the outer membrane isolates of *Z. palmae* wildtype (lane 2) and non-induced *Z. palmae* pMATE-PT004 (lane 3) no band between 100 kDa and 130 kDa is visible, a strong band can be seen in the outer membrane isolate of induced *Z. palmae* pMATE-PT004 (lane 4) between 100 kDa and 130 kDa, which is consistent with the expected molecular weight of the endoglucanase fusion protein. To further check the localization of the protein on the cell surface, induced *Z. palmae* pMATE-PT004 cells were treated with trypsin prior to the outer membrane isolation (lane 5). Since trypsin is too large to penetrate the outer cell membrane, it can exclusively degrade surface-exposed proteins. The disappearance of the band assigned to the fusion protein in lane 5 suggests that the expressed protein is accessible to trypsin and therefore located on the cell surface.

Whole Cell CMC Hydrolysis Activity Assay

*Z. palmae* wildtype cells, *Z. palmae* cells with pMATE-esterase (negative controls) and cells with pMATE-PT004 were analysed in terms of their CMC hydrolysis activity. Induced *Z. palmae* cells containing the pMATE-PT004 plasmid show high CMC hydrolysis activity compared to negative controls.

CMC hydrolysis activity could be observed within a temperature range of 30° C. to 80° C. Non-induced cells with pMATE-PT004 show slightly higher activity than the negative controls, explained by the known effect of low basal protein expression level when using an arabinose promoter (FIG. 28).

Whole cell CMC hydrolysis activity assay was also performed with *Z. mobilis* wildtype and *Z. mobilis* pMATE-PT004 cells. *Z. mobilis* pMATE-PT004 cells showed high activity in a temperature range of 30° C. to 80° C. compared to *Z. mobilis* wild type cells (FIG. 29). Although an expression of the protein could not be confirmed by SDS-PAGE, the determined activity proves the existence of the enzyme on the cell surface.

Since CMC is a large polymer which is not able to pass the cell wall, neither by diffusion nor by active transport, the observed hydrolysis of CMC represents strong evidence for the localisation of the enzyme on the cell surface.

FACS

FACS-histogram of *Z. palmae* pMATE-PT004 cells expressing the endoglucanase fusion protein (FIG. 31) shows a total increase of cell fluorescence compared to *Z. palmae* wildtype cells (FIG. 30). As antibodies cannot penetrate the cell membrane and thus only bind to surface exposed epitopes, this experiment gives strong evidence that the endoglucanase is located on the surface of *Z. palmae* cells expressing the endoglucanase fusion protein. This supports the results of the described SDS-PAGE and activity assays.

Conclusion

We could successfully apply the MATE system to express a surface-displayed, active endoglucanase in the ethanologenic bacteria *Zymomonas mobilis* and *Zymobacter palmae*. This example illustrates the broad applicability of our invention to bacterial strains with prospective industrial use, in particular in combination with cellulose-degrading enzymes and ethanol-producing bacteria, forming a whole-cell biocatalyst for the production of second generation biofuels.

EXAMPLE 11

Functional Display of Bacterial Cellulases on the Surface of *Pseudomonas putida* with the pMATE System In this example an endoglucanase obtained from *Bacillus subtilis*, an exoglucanase obtained from *Clostridium thermocellum* and a 3-glucosidase obtained from *Clostridium thermocellum* were functionally expressed on the surface of *P. putida* using the new pMATE system. Plasmids used for transformation of *P. putida* are described in FIGS. 38, 39 and 40.

SEQ ID NO:20 describes the nucleotide sequence of the autotransporter fusion gene encoded by pMATE-exoglucanase, for the surface display of an exoglucanase using the pMATE system.

SEQ ID NO:21 describes the polypeptide sequence of the autotransporter fusion protein encoded by pMATE-exoglucanase, for the surface display of an exoglucanase using the pMATE system.

SEQ ID NO:22 describes the nucleotide sequence of the autotransporter fusion gene encoded by pMATE-endoglucanase, for the surface display of an endoglucanase using the pMATE system.

SEQ ID NO:23 describes the polypeptide sequence of the autotransporter fusion protein encoded by pMATE-endoglucanase, for the surface display of an endoglucanase using the pMATE system.

SEQ ID NO:24 describes the nucleotide sequence of the autotransporter fusion gene encoded by pMATE-β-glucosidase, for the surface display of a β-glucosidase using the pMATE system.

SEQ ID NO:25 describes the polypeptide sequence of the autotransporter fusion protein encoded by pMATE-β-glucosidase, for the surface display of a β-glucosidase using the pMATE system.

The expression was tested by isolation of the outer membrane proteins and following separation by 10% SDS-PAGE (FIG. 32). Proteins were visualized with Coomassie Brilliant Blue R250. For this purpose cells were cultivated at 30° C. in LB medium until they reached an $OD_{578}$ of 0.5. Protein expression was induced with 0.2% (w/v) L-arabinose for 4 h at 30° C. P. putida without the pMATE-plasmid served as control. The exo- and endoglucanase fusion proteins were visible as a single band at the predicted size (ca. 147 kDa and 110 kDa, respectively after cleavage of the N-terminal signal peptide). As expected the fusion proteins were not visible from cells without induction of protein expression or control cells without plasmid. In case of the β-glucosidase, a very weak expression of the fusion protein was detected at the predicted size (ca. 109 kDa).

For activity assays cells were cultivated as described above. The exoglucanase activity was measured at pH 6 and 55° C. using 5 mM p-nitrophenyl-3-D-cellobioside as substrate. $OD_{578}$ were adjusted to 0.5. After different incubation times cells were removed by centrifugation and the liberated p-nitrophenol in the supernatant was detected colorimetrically at 400 nm in order to determine the hydrolysis rate. In comparison to control cells, *P. putida* cells, expressing the exoglucanase, show continuous p-nitrophenol release within 4 min (FIG. 33).

The endoglucanase activity was measured by determining reducing sugars released of enzyme reaction with 1% carboxymethylcellulose (CMC) at pH 6 and 55°. $OD_{578}$ were adjusted to 20. After cell removal reducing sugars were detected in the supernatant colorimetrically at 540 nm using the 3,5-dinitrosalicylic acid (DNS) assay, modified by King et al (2008). In comparison to control cells, endoglucanase expressing *P. putida* cells show CMC-hydrolysis (FIG. 34).

The β-glucosidase activity was measured at pH 6 and 55° C. using 5 mM p-nitrophenyl-β-D-glucopyranoside as substrate. $OD_{578}$ were adjusted to 20.

After different incubation times cells were removed by centrifugation and the liberated p-nitrophenol in the supernatant was detected colorimetrically at 400 nm in order to determine the hydrolysis rate. In comparison to control cells, *P. putida* cells, expressing the β-glucosidase, show p-nitrophenol within 10 min (FIG. 35).

These examples show that the pMATE system can be used for functional display of cellulases on the surface of *P. putida*.

The most common total cellulase activity assay is the filter paper assay (FPA) using Whatman No 1 filter paper as the substrate, which was established and published by the International Union of Pure and Applied Chemistry (IUPAC) (Ghose 1987). To measure total pMATE-cellulase activity, exoglucanase, endoglucanase and β-glucosidase were mixed in equal parts. $OD_{578}$ of total cells were adjusted to 50. The FPA was performed at pH 6 and 55° C., modified by Xiao et al (2004). Reducing sugars, released by degradation of filter paper were detected in the supernatant colorimetrically at 540 nm using the 3,5-dinitrosalicylic acid (DNS) assay, modified by King et al (2008). In comparison to control cells, the mix of cellulase expressing *P. putida* cells show filter paper hydrolysis. Using glucose as standard the amount of released sugar equivalents (RSE) from filter paper after 4 days is 0.2 mg/ml (FIG. 36).

To determine the hydrolysis of a real lignocellulosic substrate by pMATE-cellulases, pretreated empty fruit punches (EFP) were used as substrate (2.5% dry weight). Exoglucanase, endoglucanase and β-glucosidase expressing cells were mixed in equal parts. $OD_{578}$ of total cells were adjusted to 20. The reaction was performed at pH 6 and 55° C. for 4 days. Reducing sugars (in particular glucose, cellubiose or/and cellulose-polysaccharide chains of variable length), released by EFB hydrolysis were detected in the supernatant colorimetrically at 540 nm using the 3,5-dinitrosalicylic acid (DNS) assay, modified by King et al (2008). In comparison to control cells, the mix of cellulase expressing *P. putida* cells show EFB degradation. Using glucose as standard the amount of released sugar equivalents (RSE) from from EFB after 4 days is 6.4 mg/ml (FIG. 37).

REFERENCES

Grodberg J, Dunn J J (1988) ompT encodes the *Escherichia coli* outer membrane protease that cleaves T7 RNA polymerase during purification. J Bacteriol 170:1245-1253

Ghose T K (1987) Measurement of cellulase activities. Pure Appl Chem 59: 257-68.

Hantke K (1981) Regulation of ferric iron transport in *Escherichia coli* K12: Isolation of a constitutive mutant. Mol Gen Genet 182:288-292

Jong W S P, Ten Hagen-Jongman C M, Ruijter E, Orru R V A, Genevaux P, Luirink J (2010) YidC is involved in the biogenesis of the secreted autotransporter hemfoglobin protease. J Biol Chem 285:39682-39690

Jose J, Von Schwichow S (2004) Autodisplay of active sorbitol dehydrogenase (SDH) yields a whole cell biocatalyst for the synthesis of rare sugars. ChemBioChem 5:491-499

King B C et al (2009) An optimized microplate assay system for quantitative evaluation of plant cell wall-degrading enzyme activity of fungal culture extracts. *Biotechnol Bioeng* 102(4): 1033-1044.

Klauser T, Pohlner J, Meyer T F (1990) Extracellular transport of cholera toxin B subunit using Neisseria IgA protease β-domain: Conformation-dependent outer membrane translocation. EMBO J 9:1991-1999

Klauser T, Pohlner J, Meyer T F (1992) Selective extracellular release of cholera toxin B subunit by *Escherichia coli*: Dissection of Neisseria Iga(β)-mediated outer membrane transport. EMBO J 11:2327-2335

Ko H J et al. (2012) Functional cell surface display and controlled secretion of diverse Agarolytic enzymes by *Escherichia coli* with a novel ligation-independent cloning vector based on the autotransporter YfaL. Appl Environ Microbiol 78:3051-3058

Kovach M E et al. (1995) Four new derivatives of the broad-host-range cloning vector pBBR1MCS, carrying different antibiotic-resistance cassettes. Gene 166:175-176

Laemmli U K (1970) Cleavage of structural proteins during the assembly of the head of bacteriophage T4. Nature 227:680-685.

Mangel, W. F., D. L. Toledo, et al. (1994). "Omptin: an *Escherichia coli* outer membrane proteinase that activates plasminogen." Methods Enzymol 244: 384-399.

Maurer J, Jose J, Meyer T F (1997) Autodisplay: One-component system for efficient surface display and release of soluble recombinant proteins from *Escherichia coli*. J Bacteriol 179:794-804

Schultheiss E, Paar C, Schwab H, Jose J (2002) Functional esterase surface display by the autotransporter pathway in *Escherichia coli*. Journal of Molecular Catalysis B: Enzymatic 18:89-97

Sevastsyanovich Y R et al. (2012) A generalised module for the selective extracellular accumulation of recombinant proteins. Microb Cell Fact 11(1): 69.

Van Gerven N, Sleutel M, Deboeck F, De Greve H, Hernalsteens J P (2009)

Surface display of the receptor-binding domain of the F17a-G fimbrial adhesin through the autotransporter AIDA-I leads to permeability of bacterial cells. Microbiology 155: 468-476

Welch M et al. (2009) Design parameters to control synthetic gene expression in *Escherichia coli*. PLoS ONE 4:e7002

Wells T J et al. (2008) EhaA is a novel autotransporter protein of enterohemorrhagic *Escherichia coli* O157:H7 that contributes to adhesion and biofilm formation. Environmental Microbiology 10:589-604

Spohn et al. (1992) B-cell epitopes of the Nef protein. Research in Virology 143:70-81.

Jose J, Bernhardt R, Hannemann F (2002) Cellular surface display of dimeric Adx and whole cell P450-mediated steroid synthesis on *E. coli. J Biotechnol,* 95: 257-268.

Jose J, Meyer T F (2007) Microbiol Mol Biol 71, 600-619.

Xiao Z et al (2004) Microplate-based filter paper assay to measure total cellulase activity. Biotechnol Bioeng 88(7): 832-837.

The invention claimed is:

1. A method for displaying a recombinant polypeptide on the surface of a host cell, said method comprising the steps:

(a) providing a host cell transformed with a nucleic acid fusion operatively linked with an expression control sequence, said nucleic acid fusion comprising:

(i) a portion encoding a signal peptide allowing for transport into the periplasm through the inner cell membrane, (ii) a portion encoding the recombinant polypeptide to be displayed, (iii) a portion encoding a transmembrane linker, and (iv) a portion encoding the transporter domain of an EhaA protein, and (b) culturing the host cell under conditions wherein the nucleic acid fusion is expressed and the expression product comprising the recombinant polypeptide is displayed on the surface of the host cell, wherein the host cell is a Gram negative bacterium, with the proviso that the Gram negative bacterium is not *E coli,* wherein the transporter domain of the EhaA protein is encoded by a sequence comprising a sequence selected from the group consisting of:

(1) a nucleotide sequence comprising SEQ ID NO:18, (2) a nucleotide sequence encoding SEQ ID NO:19, (3) nucleotide sequences comprising a sequence being at least 95% identical to SEQ ID NO:18 or/and a sequence encoding SEQ ID NO: 19, and (4) nucleotide sequences which encode the polypeptides encoded by (1), (2) or/and (3) within the scope of the degeneracy of the genetic code;

wherein the transmembrane linker is encoded by a sequence comprising a sequence selected from the group consisting of (I) a nucleotide sequence comprising SEQ ID NO:16, (II) a nucleotide sequence encoding SEQ ID NO:17, (III) nucleotide sequences comprising a sequence being at least 95% identical to SEQ ID NO:16 or/and a sequence encoding SEQ ID NO: 17, and (IV) nucleotide sequences which encodes the polypeptides encoded by (I), (II) or/and (III) within the scope of the degeneracy of the genetic code.

2. The method of claim 1, wherein the nucleic acid fusion further comprises at least one nucleic acid sequence encoding an affinity tag.

3. The method of claim 2, wherein a nucleic acid sequence defined in claim 2 is flanking the portion (ii) encoding the recombinant polypeptide to be displayed.

4. The method of claim 3, wherein the nucleic acid sequence is separated from portion (ii) by a sequence encoding at least one protease recognition sequence.

5. The method of claim 4, wherein the at least one protease recognition sequence is independently selected from factor Xa cleavage site, OmpT cleavage site, and TEV protease cleavage site.

6. The method of claim 2, wherein the affinity tag is independently selected from $His_6$ and epitopes.

7. The method of claim 1, wherein the nucleic acid fusion comprises a nucleotide sequence encoding at least one protease recognition sequence, said nucleotide sequence being located between portions (ii) and portion (iii).

8. The method of claim 7, wherein the at least one protease recognition sequence is independently selected from factor Xa cleavage site, OmpT cleavage site, and TEV protease cleavage site.

9. The method of claim 1, wherein the portion (ii) encoding the recombinant polypeptide to be displayed is flanked by at least one sequence comprising a multiple cloning site.

10. The method according to claim 1 wherein the transporter domain of the EhaA protein forms a β-barrel structure.

11. The method of claim 1, wherein the transmembrane linker (ii) comprises a sequence selected from the group consisting of:

(a) an amino acid sequence comprising SEQ ID NO:17, and (b) sequences which are at least 95% identical to the sequences of (a).

12. The method of claim 1, wherein the transporter domain of the EhaA protein (iii) comprises a sequence selected from the group consisting of:

(a) an amino acid sequence comprising SEQ ID NO:19, and (b) sequences which are at least 95% identical to the sequence of (a).

13. The method of claim 1, wherein the sequence of the nucleic acid fusion has a codon usage adapted to the host cell.

14. The method of claim 1, wherein the amino acid sequences encoded by nucleic acid sequences (i) to (iv) are arranged from N terminal to C terminal.

15. The method of claim 1, wherein the nucleic acid sequences (i) to (iv) are arranged from 5' to 3'.

16. The method of claim 1, wherein the transporter domain of an EhaA protein is heterologous with respect to the host cell.

17. The method of claim 1, wherein the host cell is a bacterium.

18. The method of claim 1, wherein the bacterium is a Gram negative bacterium.

19. The method of claim 1, wherein the bacterium is selected from *Salmonella* spp., *Zymomonas* spp., *Zymobacter* spp., *Pseudomonas* spp., *Cupriavidus* spp., *Rhodobacter* spp., *Acinetobacter* spp., *Gluconobacter* spp., *Gluconacetobacter* spp., *Acidomonas* spp., *Acetobacter* spp., *Paracoccous* spp., *Rhizobium* spp., and *Xanthomonas* spp.

20. A recombinant vector comprising the nucleic acid fusion as defined in claim 1, operatively linked to an expression control sequence.

21. A recombinant vector comprising:

(i) a portion encoding a signal peptide allowing for transport into the periplasm through the inner cell membrane, (ii) a portion encoding a multiple cloning site, (iii) a portion encoding a transmembrane linker, and (iv) a portion encoding the transporter domain of an EhaA protein, wherein the transporter domain of the EhaA protein is encoded by a sequence comprising a sequence selected from the group consisting of:

(1) a nucleotide sequence comprising SEQ ID NO:18, (2) a nucleotide sequence encoding SEQ ID NO:19, (3) nucleotide sequences comprising a sequence being at least 95% identical to SEQ ID NO:18 or/and a sequence encoding SEQ ID NO: 19, and (4) nucleotide sequences which encode the polypeptides encoded by (1), (2) or/and (3) within the scope of the degeneracy of the genetic code, and wherein the transmembrane linker is encoded by a sequence comprising a sequence selected from the group consisting of:

(I) a nucleotide sequence comprising SEQ ID NO:16,
(II) a nucleotide sequence encoding SEQ ID NO:17,
(III) nucleotide sequences comprising a sequence being at least 95% identical to SEQ ID NO:16 or/and a sequence encoding SEQ ID NO: 17, and
(IV) nucleotide sequences which encodes the polypeptides encoded by (I), (II) or/and (III) within the scope of the degeneracy of the genetic code.

22. The vector of claim 21, wherein the multiple cloning site is suitable for integration of a nucleic acid sequence encoding a recombinant polypeptide in frame with portions (i), (ii) and (iv).

23. The vector of claim 21, wherein the nucleic acid sequences (i) to (iv) are arranged from 5' to 3'.

24. A recombinant host cell comprising the recombinant vector as claimed in claim 21.

25. A method for producing a host cell capable of displaying a recombinant polypeptide on the surface, said method comprising the steps
(a) providing a vector comprising:
(i) a portion encoding a signal peptide allowing for transport into the periplasm through the inner cell membrane,
(ii) a portion encoding a multiple cloning site,
(iii) a portion encoding a transmembrane linker, and
(iv) a portion encoding the transporter domain of an EhaA protein
(b) inserting a sequence encoding the recombinant polypeptide to be displayed into the multiple cloning site (iv), and
(c) performing the method of claim 1,
wherein the transporter domain of the EhaA protein is encoded by a sequence comprising a sequence selected from the group consisting of:
(1) a nucleotide sequence comprising SEQ ID NO:18,
(2) a nucleotide sequence encoding SEQ ID NO:19,
(3) nucleotide sequences comprising a sequence being at least 95% identical to SEQ ID NO:18 or/and a sequence encoding SEQ ID NO: 19, and
(4) nucleotide sequences which encode the polypeptides encoded by (1), (2) or/and (3) within the scope of the degeneracy of the genetic code, and
wherein the transmembrane linker is encoded by a sequence comprising a sequence selected from the group consisting of:
(I) a nucleotide sequence comprising SEQ ID NO:16,
(II) a nucleotide sequence encoding SEQ ID NO:17,
(III) nucleotide sequences comprising a sequence being at least 95% identical to SEQ ID NO:16 or/and a sequence encoding SEQ ID NO: 17, and
(IV) nucleotide sequences which encodes the polypeptides encoded by (I), (II) or/and (III) within the scope of the degeneracy of the genetic code.

26. A method for displaying a recombinant polypeptide on the surface of a host cell, said method comprising the steps:
(a) providing a host cell transformed with a nucleic acid fusion operatively linked with an expression control sequence, said nucleic acid fusion comprising:
(i) a portion encoding a signal peptide allowing for transport into the periplasm through the inner cell membrane,
(ii) a portion encoding the recombinant polypeptide to be displayed,
(iii) a portion encoding a transmembrane linker, and
(iv) a portion encoding the transporter domain of an EhaA protein, and
(b) culturing the host cell under conditions wherein the nucleic acid fusion is expressed and the expression product comprising the recombinant polypeptide is displayed on the surface of the host cell,
wherein the recombinant polypeptide to be displayed is selected from an endoglucanase, an exoglucanase and a β-glucosidase, and combinations thereof, wherein the host cell is a Gram negative bacterium, and
wherein the transporter domain of the EhaA protein is encoded by a sequence comprising a sequence selected from the group consisting of:
(1) a nucleotide sequence comprising SEQ ID NO:18,
(2) a nucleotide sequence encoding SEQ ID NO:19,
(3) nucleotide sequences comprising a sequence being at least 95% identical to SEQ ID NO:18 or/and a sequence encoding SEQ ID NO: 19, and
(4) nucleotide sequences which encode the polypeptides encoded by (1), (2) or/and (3) within the scope of the degeneracy of the genetic code, and
wherein the transmembrane linker is encoded by a sequence comprising a sequence selected from the group consisting of:
(I) a nucleotide sequence comprising SEQ ID NO:16,
(II) a nucleotide sequence encoding SEQ ID NO:17,
(III) nucleotide sequences comprising a sequence being at least 95% identical to SEQ ID NO:16 or/and a sequence encoding SEQ ID NO: 17, and
(IV) nucleotide sequences which encodes the polypeptides encoded by (I), (II) or/and (III) within the scope of the degeneracy of the genetic code.

27. A method for displaying a recombinant polypeptide on the surface of a host cell according to claim 1, wherein the sequence of the nucleic acid fusion has a codon usage adapted to the host cell.

28. A method for displaying a recombinant polypeptide on the surface of a host cellusing a Maximized Autotransporter Expression System, said method comprising:
(a) providing a host cell transformed with a nucleic acid fusion operatively linked with an expression control sequence, said nucleic acid fusion comprising:
(i) a portion encoding a signal peptide which is a cholera toxin B subunit signal peptide,
(ii) a portion encoding the recombinant polypeptide to be displayed, wherein said recombinant polypeptide is selected from the group consisting of an endoglucanase, an exoglucanase and a β-glucosidase,
(iii) a portion encoding a transmembrane linker, wherein said transmembrane linker is encoded by a sequence comprising a sequence selected from the group consisting of:
(1) a nucleotide sequence comprising SEQ ID NO:16,
(2) a nucleotide sequence encoding SEQ ID NO:17,
(3) a nucleotide sequence comprising a sequence which is at least 95% identical to SEQ ID NO:16 and/or a sequence encoding SEQ ID NO: 17, and
(4) nucleotide sequences which encode the polypeptides encoded by (1) or/and (2) within the scope of the degeneracy of the genetic code,
(iv) a portion encoding the transporter domain of an EhaA protein, wherein the transporter domain of the EhaA protein is encoded by a sequence comprising a sequence selected from the group consisting of:
(A) a nucleotide sequence comprising SEQ ID NO:18, (B) a nucleotide sequence encoding SEQ ID NO:19, (C) a nucleotide sequence comprising a sequence which is at least 95% identical to SEQ ID NO:18 and/or a sequence encoding SEQ ID NO: 19, and (D) a nucleotide sequence which encodes the polypeptides encoded by (A), (B) or/and (C) within the scope of the degeneracy of the genetic code, and (b) culturing the host cell under conditions wherein the nucleic acid fusion is expressed and the expression product comprising the recombinant polypeptide is displayed on the surface of the host cell, wherein the host cell is a Gram negative bacterium, with the proviso that the Gram negative bacterium is not *E coli.*

29. The method according to claim 1, wherein said recombinant polypeptide is encoded by a nucleotide sequence selected from the group consisting of SEQ ID NO: 20, SEQ ID NO:21, SEQ ID NO: 22, SEQ ID NO:23, SEQ ID NO: 24, and SEQ ID NO:25.

30. The method of claim 1, wherein the signal peptide is a CtxB signal peptide.

31. The method of claim 1, wherein the signal peptide is obtained from a gram-negative bacterium.

* * * * *

UNITED STATES PATENT AND TRADEMARK OFFICE

CERTIFICATE OF CORRECTION

PATENT NO. : 10,683,509 B2
APPLICATION NO. : 14/774973
DATED : June 16, 2020
INVENTOR(S) : Joachim Jose et al.

It is certified that error appears in the above-identified patent and that said Letters Patent is hereby corrected as shown below:

On the Title Page

Item (22) PCT Filed should read: March 6, 2014

Signed and Sealed this
Twenty-second Day of December, 2020

Andrei Iancu
*Director of the United States Patent and Trademark Office*